(12) United States Patent
Goya et al.

(10) Patent No.: US 10,577,360 B2
(45) Date of Patent: Mar. 3, 2020

(54) ARYLAMIDE DERIVATIVES HAVING MULTIMODAL ACTIVITY AGAINST PAIN

(71) Applicant: ESTEVE PHARMACEUTICALS, S.A., Barcelona (ES)

(72) Inventors: Pilar Goya, Madrid (ES); Antoni Torrens-Jover, Terrassa (ES); Carmen Almansa-Rosales, Barcelona (ES); Jose-Luis Diaz-Fernández, Manresa (ES); Ana-Maria Caamaño-Moure, Santiago de Compostela (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/090,403

(22) PCT Filed: Apr. 12, 2017

(86) PCT No.: PCT/EP2017/058736
§ 371 (c)(1),
(2) Date: Oct. 1, 2018

(87) PCT Pub. No.: WO2017/178510
PCT Pub. Date: Oct. 19, 2017

(65) Prior Publication Data
US 2019/0127357 A1    May 2, 2019

(30) Foreign Application Priority Data

Apr. 12, 2016 (EP) ..................... 16382166

(51) Int. Cl.
| | | |
|---|---|---|
| *C07D 413/10* | (2006.01) |
| *C07D 401/14* | (2006.01) |
| *C07D 413/14* | (2006.01) |
| *C07D 401/12* | (2006.01) |
| *C07D 409/12* | (2006.01) |
| *C07D 409/14* | (2006.01) |
| *C07D 417/14* | (2006.01) |
| *C07D 407/14* | (2006.01) |
| *C07D 405/14* | (2006.01) |
| *A61P 25/04* | (2006.01) |

(52) U.S. Cl.
CPC ......... *C07D 413/10* (2013.01); *C07D 401/12* (2013.01); *C07D 401/14* (2013.01); *C07D 405/14* (2013.01); *C07D 407/14* (2013.01); *C07D 409/12* (2013.01); *C07D 409/14* (2013.01); *C07D 413/14* (2013.01); *C07D 417/14* (2013.01); *A61P 25/04* (2018.01)

(58) Field of Classification Search
None
See application file for complete search history.

(56) References Cited

U.S. PATENT DOCUMENTS 4,900,738 A    2/1990   Bagley

FOREIGN PATENT DOCUMENTS

EP           016022        11/1985

OTHER PUBLICATIONS

Girón, Rocio, et al., "Synthesis and opioid activity of new fentanyl analogs", Life Sciences, 71, 2002, pp. 1023-1034.
International Search Report for PCT/EP2017/058736 dated Apr. 28, 2007.

*Primary Examiner* — Heidi Reese
(74) *Attorney, Agent, or Firm* — Hueschen and Sage

(57) ABSTRACT

The present invention relates to arylamide derivatives having dual pharmacological activity towards both the α2δ subunit, in particular the α2δ-1 subunit, of the voltage-gated calcium channel and the μ-opioid receptor, to processes of preparation of such compounds, to pharmaceutical compositions comprising them, and to their use in therapy, in particular for the treatment of pain.

19 Claims, No Drawings

ARYLAMIDE DERIVATIVES HAVING MULTIMODAL ACTIVITY AGAINST PAIN

FIELD OF THE INVENTION

The present invention relates to compounds having dual pharmacological activity towards both the $\alpha_2\delta$ subunit of the voltage-gated calcium channel, and the µ-opioid receptor (MOR or mu-opioid receptor) and more particularly to arylamide derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved (Turk, D. C., Wilson, H. D., Cahana, A.; 2011; *Lancet* 377; 2226-2235). Pain affects a big portion of the population with an estimated prevalence of 20% and its incidence, particularly in the case of chronic pain, is increasing due to the population ageing. Additionally, pain is clearly related to comorbidities, such as depression, anxiety and insomnia, which leads to important productivity losses and socio-economical burden (Goldberg, D. S., McGee, S. J.; 2011; *BMC Public Health;* 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al., Pharmacol Rev. 2015 67:821-70). The VGCC are assembled through interactions of different subunits, namely $\alpha_1$ (Ca$_v\alpha_1$), β (Ca$_v\beta$) $\alpha_2\delta$ (Ca$_v\alpha_2\delta$) and γ (Ca$_v\gamma$). The $\alpha_1$ subunits are the key porous forming units of the channel complex, being responsible for the Ca$^{2+}$ conduction and generation of Ca$^{2+}$ influx. The $\alpha_2\delta$, β, and γ subunits are auxiliary, although very important for the regulation of the channel, since they increase the expression of the $\alpha_1$ subunits in the plasma membrane as well as modulate their function, resulting in functional diversity in different cell types. Based on their physiological and pharmacological properties, VGCC can be subdivided into low voltage-activated T-type (Ca$_v$3.1, Ca$_v$3.2, and Ca$_v$3.3), and high voltage-activated L-(Ca$_v$1.1 through Ca$_v$1.4), N—(Ca$_v$2.2), P/Q-(Ca$_v$2.1), and R-(Ca$_v$2.3) types, depending on the channel forming Ca$_v\alpha$ subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo, Neurotherapeutics. 2009 6:679-92; Zamponi et al., 2015 supra; Neumaier et al., Prog Neurobiol. 2015 129:1-36.). A large body of data has clearly indicated that VGCC are implicated in mediating various disease states including pain processing. Drugs interacting with the different calcium channel subtypes and subunits have been developed. Current therapeutic agents include drugs targeting L-type Ca$_v$1.2 calcium channels, particularly 1,4-dihydropyridines, which are widely used in the treatment of hypertension. T-type (Ca$_v$3) channels are the target of ethosuximide, widely used in absence epilepsy. Ziconotide, a peptide blocker of N-type (Ca$_v$2.2) calcium channels, has been approved as a treatment of intractable pain. (Perret and Luo, 2009, supra; Vink and Alewood, Br J Pharmacol. 2012 167:970-89.).

The Ca$_v$1 and Ca$_v$2 subfamilies contain an auxiliary $\alpha_2\delta$ subunit, which is the therapeutic target of the gabapentinoid drugs of value in certain epilepsies and chronic neuropathic pain. To date, there are four known $\alpha_2\delta$ subunits, each encoded by a unique gene and all possessing splice variants. Each $\alpha_2\delta$ protein is encoded by a single messenger RNA and is posttranslationally cleaved and then linked by disulfide bonds. Four genes encoding $\alpha_2\delta$ subunits have now been cloned. $\alpha_2\delta$-1 was initially cloned from skeletal muscle and shows a fairly ubiquitous distribution. The $\alpha_2\delta$-2 and $\alpha_2\delta$-3 subunits were subsequently cloned from brain. The most recently identified subunit, $\alpha_2\delta$-4, is largely nonneuronal. The human $\alpha_2\delta$-4 protein sequence shares 30, 32 and 61% identity with the human $\alpha_2\delta$-1, $\alpha_2\delta$-2 and $\alpha_2\delta$-3 subunits, respectively. The gene structure of all $\alpha_2\delta$ subunits is similar. All $\alpha_2\delta$ subunits show several splice variants (Davies et al., Trends Pharmacol Sci. 2007 28:220-8; Dolphin A C, Nat Rev Neurosci. 2012 13:542-55, Biochim Biophys Acts. 2013 1828:1541-9.).

The Ca$_v\alpha_2\delta$-1 subunit may play an important role in neuropathic pain development (Perret and Luo, 2009, supra; Vink and Alewood, 2012, supra). Biochemical data have indicated a significant Ca$_v\alpha_2\delta$-1, but not Ca$_v\alpha_2\delta$-2, subunit upregulation in the spinal dorsal horn, and DRG (dorsal root ganglia) after nerve injury that correlates with neuropathic pain development. In addition, blocking axonal transport of injury-induced DRG Ca$_v\alpha_2$-1 subunit to the central presynaptic terminals diminishes tactile allodynia in nerve injured animals, suggesting that elevated DRG Ca$_v\alpha_2\delta$-1 subunit contributes to neuropathic allodynia.

The Ca$_v\alpha_2\delta$-1 subunit (and the Ca$_v\alpha_2\delta$-2, but not Ca$_v\alpha_2\delta$-3 and Ca$_v\alpha_2\delta$-4, subunits) is the binding site for gabapentin which has anti-allodynic/hyperalgesic properties in patients and animal models. Because injury-induced Ca$_v\alpha_2\delta$-1 expression correlates with neuropathic pain development and maintenance, and various calcium channels are known to contribute to spinal synaptic neurotransmission and DRG neuron excitability, injury-induced Ca$_v\alpha_2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the Ca$_v\alpha_2$-1 subunit can block nerve injury-induced Ca$_v\alpha_2\delta$-1 upregulation and prevent the onset of allodynia and reserve established allodynia.

As mentioned above, the $\alpha_2\delta$ subunits of VGCC form the binding site for gabapentin and pregabalin, which are structural derivatives of the inhibitory neurotransmitter GABA although they do not bind to GABAA, GABAB, or benzodiazepine receptors, or alter GABA regulation in animal brain preparations. The binding of gabapentin and pregabalin to the Ca$_v\alpha_2\delta$ subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009, supra; Vink and Alewood, 2012, supra, Zamponi et al., 2015, supra).

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the µ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies*. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al., Nat Biotechnol 2009; 27: 659-666.).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al., Lancet Neurol. 2013 November; 12(11):1084-95.). In fact, positive synergistic interaction for several compounds, including analgesics, has been described (Schröder et al., J Pharmacol Exp Ther. 2011; 337:312-20. Erratum in: J Pharmacol Exp Ther. 2012; 342:232; Zhang et al., Cell Death Dis. 2014; 5:e1138; Gilron et al., 2013, supra).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins, Nat Chem Biol. 2008; 4:682-90.).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008, supra).

Thus, the present application, relates to the advantages of having dual activity, for µ-receptor and the $\alpha_2\delta$-1 subunit of voltage-gated calcium channels, in the same molecule to treat chronic pain.

In this way, the present invention relates to compounds having a complementary dual mechanism of action (µ-receptor agonist and blocker of the $\alpha_2\delta$ subunit, in particular the $\alpha_2\delta$-1 subunit, of voltage-gated calcium channels) which implies a better profile of tolerability than the strong opioids (morphine, oxycodone, fentanyl etc) and/or better efficacy and tolerability than gabapentinoids (pregabalin and gabapentin).

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies (Mao, J., Gold, M. S., Backonja, M.; 2011; J. Pain; 12; 157-166).

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

The authors of the present invention, have found a series of compounds that show dual pharmacological activity towards both the $\alpha_2\delta$ subunit, in particular the $\alpha_2\delta$-1 subunit, of the voltage-gated calcium channel, and the µ-opioid receptor (MOR or mu-opioid receptor) resulting in an innovative, effective and alternative solution for the treatment of pain.

In view of the existing results of the currently available therapies and clinical practices, the present invention offers a solution by combining in a single compound binding to two different targets relevant for the treatment of pain.

This was mainly achieved by providing the compounds according to the invention that bind both to the µ-opioid receptor and to the $\alpha_2\delta$ subunit, in particular the $\alpha_2\delta$-1 subunit, of the voltage-gated calcium channel.

SUMMARY OF THE INVENTION

In this invention a family of structurally distinct arylamide derivatives, encompassed by formula (I), which have a dual pharmacological activity towards both the $\alpha_2$ subunit, in particular the $\alpha_2\delta$-1 subunit, of the voltage-gated calcium channel, and the $\mu$-opioid receptor was identified thus solving the above problem of identifying alternative or improved pain treatments by offering such dual compounds.

The main object of the invention is directed to a compound having a dual activity binding to the $\alpha_2\delta$ subunit, in particular the $\alpha_2\delta$-1 subunit, of the voltage-gated calcium channel and the $\mu$-opioid receptor for use in the treatment of pain.

As this invention is aimed at providing a compound or a chemically related series of compounds which act as dual ligands of the $\alpha_2\delta$ subunit, in particular the $\alpha_2\delta$-1 subunit, of the voltage-gated calcium channel and the $\mu$-opioid receptor it is a very preferred embodiment if the compound has a binding expressed as $K_i$ responding to the following scales:

$K_i(\mu)$ is preferably <1000 nM, more preferably <500 nM, even more preferably <100 nM.

$K_i(\alpha_2\delta$-1) is preferably <10000 nM, more preferably <5000 nM, even more preferably <500 nM or even more preferably <100 nM.

More particularly, the main aspect of the invention refers to a compound of general Formula (I),

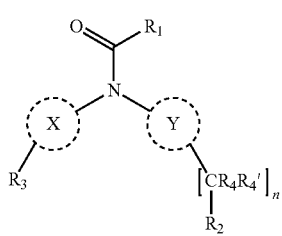

(I)

wherein $R_1$, $R_2$, $R_3$, $R_4$, $R_{4'}$, n, X and Y are as defined below in the detailed description.

A further object of the invention refers to the processes for preparation of compounds of general formula (I).

A still further object of the invention refers to the use of some intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct arylamide derivatives which have a dual pharmacological activity towards both the $\alpha_2\delta$ subunit, in particular the $\alpha_2\delta$-1 subunit, of the voltage-gated calcium channel and the $\mu$-opioid receptor.

The invention is directed to compounds having a dual activity binding to the $\alpha_2\delta$ subunit, in particular the $\alpha_2\delta$-1 subunit, of the voltage-gated calcium channel and the $\mu$-opioid receptor for use in the treatment of pain.

As this invention is aimed at providing a compound or a chemically related series of compounds which act as dual ligands of the $\alpha_6$ subunit, in particular the $\alpha_2\delta$-1 subunit, of the voltage-gated calcium channel and the $\mu$-opioid receptor it is a preferred embodiment if the compound has a binding expressed as $K_i$ responding to the following scales:

$K_i(\mu)$ is preferably <1000 nM, more preferably <500 nM, even more preferably <100 nM.

$K_i(\alpha_2\delta$-1) is preferably <10000 nM, more preferably <5000 nM, even more preferably <500 nM or even more preferably <100 nM.

The applicant has surprisingly found that the problem of providing a new effective and alternative for treating pain and pain related disorders can be solved by using a multimodal balanced analgesic approach combining two different synergistic activities in a single drug (i.e., dual ligands which are bifunctional and bind to $\mu$-opioid receptor and to $\alpha_2\delta$ subunit, in particular the $\alpha_2\delta$-1 subunit, of the voltage-gated calcium channel), thereby enhancing through the $\alpha_2\delta$ blockade without increasing the undesirable side effects. This supports the therapeutic value of a dual agent, whereby the $\alpha_2\delta$ binding component acts as an intrinsic adjuvant of the MOR binding component.

A dual compound that possess binding to both the $\mu$-opioid receptor and to the $\alpha_2\delta$ subunit of the voltage-gated calcium channel shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention show the following functionalities: blockade of the $\alpha_2\delta$ subunit, in particular the $\alpha_2\delta$-1 subunit, of the voltage-gated calcium channel and $\mu$-opioid receptor agonism It has to be noted, though, that functionalities "antagonism" and "agonism" are also sub-divided in their effect into subfunctionalities like partial agonism or inverse agonism. Accordingly, the functionalities of the compound should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

In addition, the two mechanisms complement each other since MOR agonists are only marginally effective in the treatment of neuropathic pain, while the blockers of the $\alpha_2\delta$ subunit, in particular the $\alpha_2\delta$-1 subunit, of voltage-gated calcium channels show outstanding effects in preclinical neuropathic pain models. Thus, the $\alpha_2\delta$ component, in particular the $\alpha_2\delta$-1 component, adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In its broader aspect, the present invention is directed to compounds of general Formula (I):

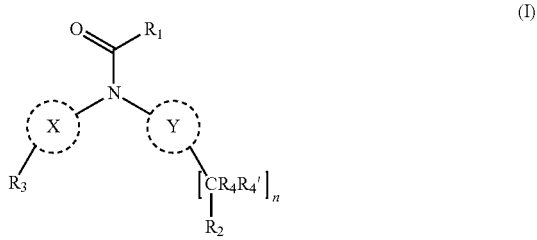

wherein
n is 0, 1, 2, 3, 4 or 5;
X is an unsubstituted aromatic heterocyclyl containing one or more nitrogen atoms as only heteroatom;
Y is selected from

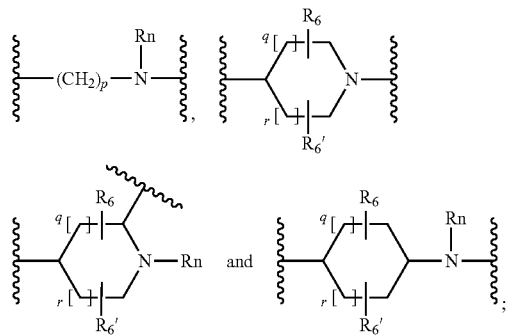

wherein
p is 2 or 3;
q is 0, 1, 2 or 3;
r is 0, 1, 2 or 3;
$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from substituted or unsubstituted aryl and substituted or unsubstituted aromatic heterocycyl;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl;
$R_3$ is selected from substituted or unsubstituted monocyclic aryl and substituted or unsubstituted monocyclic aromatic heterocyclyl;
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

These compounds according to the invention are optionally in form of one of the stereoisomer, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a particular aspect, the present invention is directed to compounds of general Formula (I):

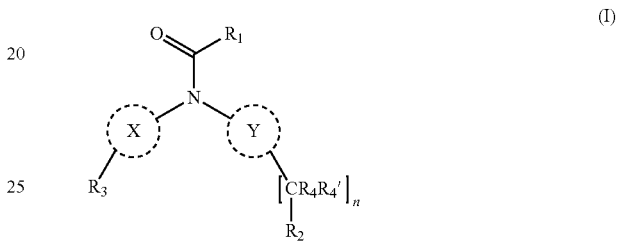

wherein
n is 0, 1, 2, 3, 4 or 5;
wherein X is selected from

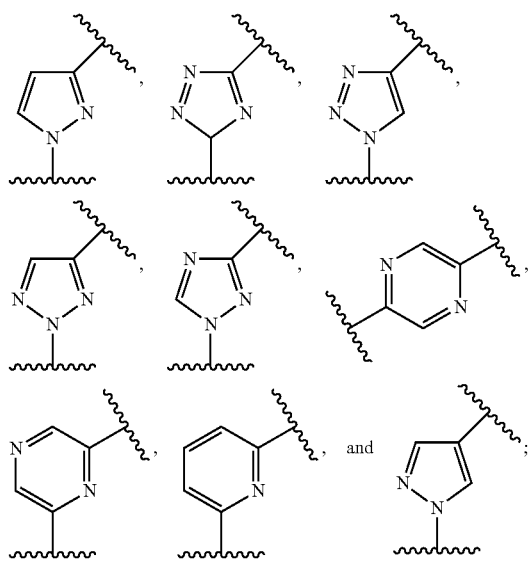

Y is selected from

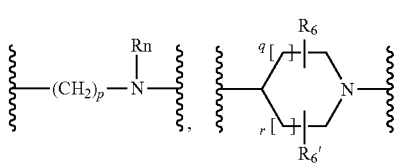

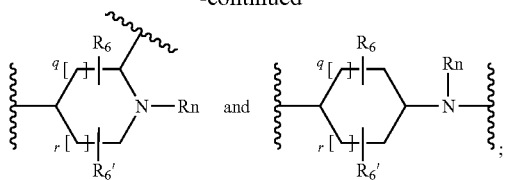

wherein p is 2 or 3;

q is 0, 1, 2 or 3;

r is 0, 1, 2 or 3;

$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from substituted or unsubstituted aryl and substituted or unsubstituted aromatic heterocycyl;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl, $R_3$ is selected from substituted or unsubstituted aryl and substituted or unsubstituted aromatic heterocyclyl, $R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

These compounds according to the invention are optionally in form of one of the stereoisomer, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention is a compound of general Formula (I')

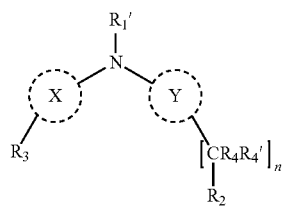

(I')

wherein, $R_2$, $R_3$, X, Y and n are as defined in the description, and $R_{1'}$ represents —C(O)$R_1$ as defined in the description or hydrogen, preferably $R_{1'}$ is hydrogen. Compounds of formula (I') wherein $R_1$' is hydrogen are not encompassed by general formula (I) but they are intermediates for the synthesis thereof.

In a further embodiment the compound according to the invention is a compound of general Formula (I$^{2'}$)

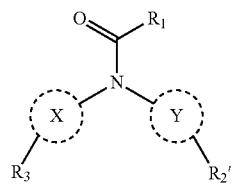

(I$^{2'}$)

wherein, $R_1$, $R_3$, X and Y are as defined in the description, and $R_{2'}$ represents —[CR$_4$R$_{4'}$]$_n$R$_2$ as defined in the description or hydrogen, preferably $R_{2'}$ is hydrogen.

In a further embodiment the compound according to the invention is a compound of general Formula (I$^{3'}$)

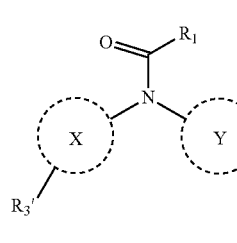

(I$^{3'}$)

wherein, $R_1$, $R_2$, X, Y and n are as defined in the description, and $R_{3'}$ represents $R_3$ as defined in the description or hydrogen, preferably $R_{3'}$ is hydrogen.

In a further embodiment the compound according to the invention is a compound of general Formula (I$^{4'}$)

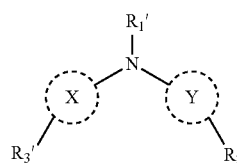

(I$^{4'}$)

wherein X and Y are as defined in the description, $R_{1'}$ represents —C(O)$R_1$ as defined in the description or hydrogen, $R_{2'}$ represents —[CR$_4$R$_{4'}$]$_n$R$_2$ as defined in the description or hydrogen and $R_{3'}$ represents $R_3$ as defined in the description or hydrogen, preferably $R_{1'}$ is hydrogen while $R_{2'}$ is —[CR$_4$R$_{4'}$]$_n$R$_2$ and $R_{3'}$ is $R_3$; or $R_{2'}$ is hydrogen while $R_{1'}$ is —C(O)$R_1$ and $R_{3'}$ is $R_3$; or $R_{3'}$ is hydrogen while $R_{1'}$ is —C(O)$R_1$ and $R_{2'}$ is —[CR$_4$R]$_n$R$_2$; or $R_{1'}$ is hydrogen while $R_{2'}$ is —[CR$_4$R$_{4'}$]$_n$R$_2$ and $R_{3'}$ is $R_3$; or $R_{1'}$ and $R_{2'}$ are both hydrogen while $R_{3'}$ is $R_3$; or $R_{1'}$ and $R_{3'}$ are both hydrogen while $R_{2'}$ is —[CR$_4$R$_{4'}$]$_n$R$_2$; or $R_{3'}$ and $R_{2'}$ are both hydrogen while $R_{1'}$ is —C(O)$R_1$; or $R_{1'}$, $R_{2'}$ and $R_{3'}$ are all hydrogen.

In a further embodiment the compound according to the invention is a compound of general Formula (I$^{5'}$)

(I⁵')

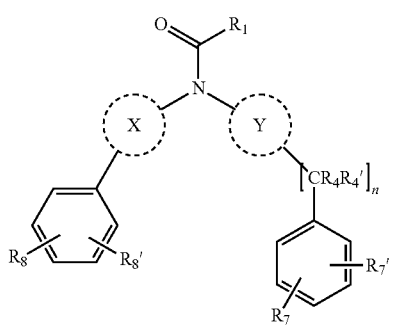

wherein R₇ and R₇' are independently selected from hydrogen, halogen, —R₁₂, —OR₁₂, —NO₂, —NR₁₂R₁₂''', NR₁₂C(O)R₁₂', —NR₁₂S(O)₂R₁₂', —S(O)₂NR₁₂R₁₂', —NR₁₂C(O)NR₁₂'R₁₂''', —SR₁₂, —S(O)R₁₂, S(O)₂R₁₂, —CN, haloalkyl, haloalkoxy, —C(O)OR₁₂, —C(O)NR₁₂R₁₂', —OCH₂CH₂OH, —NR₁₂S(O)₂NR₁₂'R₁₂'' and C(CH₃)₂OR₁₂;

R₈ and R₈' are independently selected from hydrogen, halogen, —R₁₃, —OR₁₃, —NO₂, —NR₁₃R₁₃''', NR₁₃C(O)R₁₃', —NR₁₃S(O)₂R₁₃', —S(O)₂NR₁₃R₁₃', —NR₁₃C(O)NR₁₃'R₁₃''', —SR₁₃, —S(O)R₁₃, S(O)₂R₁₃, —CN, haloalkyl, haloalkoxy, —C(O)OR₁₃, —C(O)NR₁₃R₁₃', —OCH₂CH₂OCH₃, —NR₁₃S(O)₂NR₁₃'R₁₃''', C(CH₃)₂OR₁₃ and substituted or unsubstituted five membered aromatic heterocyclyl;

and wherein R₁, R₄, R₄', R₁₂, R₁₂', R₁₂'', R₂''', R₁₃, R₁₃', R₁₃''', R₁₃'''', X, Y and n are as defined in the description.

In a further embodiment the compound according to the invention is a compound of general Formula (I⁶ᵃ')

(I⁶ᵃ')

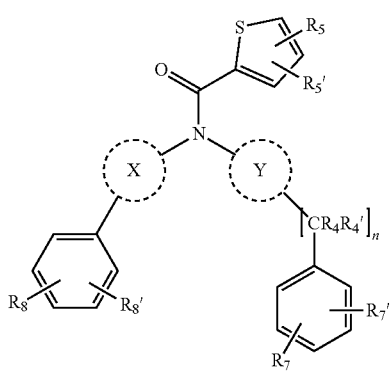

wherein R₅ and R₅' are independently selected from hydrogen, halogen, —R₁₁, —OR₁₁, —NO₂, —NR₁₁R₁₁''', NR₁C(O)R₁₁', —NR₁₁S(O)₂R₁₁', —S(O)₂NR₁₁R₁₁', —NR₁₁C(O)NR₁₁'R₁₁''', —SR₁₁, —S(O)R₁₁, S(O)₂R₁₁, —CN, haloalkyl, haloalkoxy, —C(O)OR₁₁, —C(O)NR₁₁R₁₁', —OCH₂CH₂OH, —NR₁₁S(O)₂NR₁₁'R₁₁''C(CH₃)₂ OR₁₁, and substituted or unsubstituted five membered aromatic heterocyclyl;

wherein R₈ and R₈' are independently selected from hydrogen, halogen, —R₁₃, —OR₁₃, —NO₂, —NR₁₃R₁₃''', NR₁₃C(O)R₁₃', —NR₁₃S(O)₂R₁₃', —S(O)₂NR₁₃R₁₃', —NR₁₃C(O)NR₁₃'R₁₃''', —SR₁₃, —S(O)R₁₃, S(O)₂R₁₃, —CN, haloalkyl, haloalkoxy, —C(O)OR₁₃, —C(O)NR₁₃R₁₃', —OCH₂CH₂OCH₃, —NR₁₃S(O)₂NR₁₃'R₁₃''', C(CH₃)₂OR₁₃ and substituted or unsubstituted five membered aromatic heterocyclyl;

and wherein R₂, R₄, R₄', R₁₁, R₁₁', R₁₁''', R₁₃, R₁₃', R₁₃''', R₁₃'''', X, Y and n are as defined in the description.

In a further embodiment the compound according to the invention is a compound of general Formula (I⁶ᵇ')

(I⁶ᵇ')

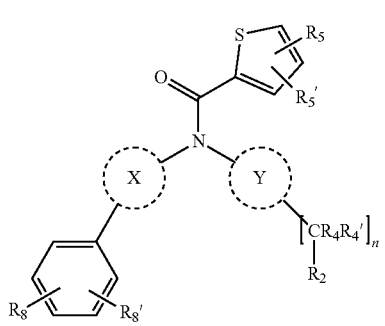

wherein R₅ and R₅' are independently selected from hydrogen, halogen, —R₁₁, —OR₁₁, —NO₂, —NR₁₁R₁₁''', NR₁C(O)R₁₁', —NR₁₁S(O)₂R₁₁', —S(O)₂NR₁₁R₁₁', —NR₁₁C(O)NR₁₁'R₁₁''', —SR₁₁, —S(O)R₁₁, S(O)₂R₁₁, —CN, haloalkyl, haloalkoxy, —C(O)OR₁₁, —C(O)NR₁₁R₁₁', —OCH₂CH₂OH, —NR₁₁S(O)₂NR₁₁'R₁₁'' C(CH₃)₂OR₁₁, and substituted or unsubstituted five membered aromatic heterocyclyl;

wherein R₇ and R₇' are independently selected from hydrogen, halogen, —R₁₂, —OR₁₂, —NO₂, —NR₁₂R₁₂''', NR₁₂C(O)R₁₂', —NR₁₂S(O)₂R₁₂', —S(O)₂NR₁₂R₁₂', —NR₁₂C(O)NR₁₂'R₁₂''', —SR₁₂, —S(O)R₁₂, S(O)₂R₁₂, —CN, haloalkyl, haloalkoxy, —C(O)OR₁₂, —C(O)NR₁₂R₁₂', —OCH₂CH₂OH, —NR₁₂S(O)₂NR₁₂'R₁₂'' and C(CH₃)₂OR₁₂;

R₈ and R₈' are independently selected from hydrogen, halogen, —R₁₃, —OR₁₃, —NO₂, —NR₁₃R₁₃''', NR₁₃C(O)R₁₃', —NR₁₃S(O)₂R₁₃', —S(O)₂NR₁₃R₁₃', —NR₁₃C(O)NR₁₃'R₁₃''', —SR₁₃, —S(O)R₁₃, S(O)₂R₁₃, —CN, haloalkyl, haloalkoxy, —C(O)OR₁₃, —C(O)NR₁₃R₁₃', —OCH₂CH₂OCH₃, —NR₁₃S(O)₂NR₁₃'R₁₃''', C(CH₃)₂OR₁₃ and substituted or unsubstituted five membered aromatic heterocyclyl;

and wherein R₄, R₄', R₁₁, R₁₁', R₁₁''', R₁₂, R₁₂', R₁₂'', R₁₂''', R₁₃, R₁₃', R₁₃''', R₁₃'''', X, Y and n are as defined in the description.

In a further embodiment the compound according to the invention is a compound of general Formula (I⁹')

(I⁹')

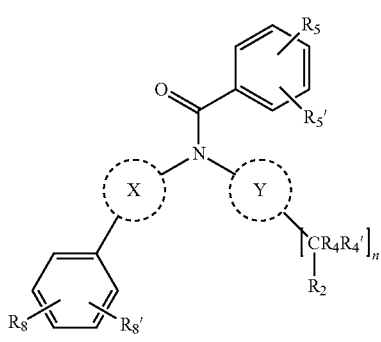

wherein R$_5$ and R$_5$' are independently selected from hydrogen, halogen, —R$_{11}$, —OR$_{11}$, —NO$_2$, —NR$_{11}$R$_{11}$''', NR$_1$C(O)R$_{11}$', —NR$_{11}$S(O)$_2$R$_{11}$', —S(O)$_2$NR$_{11}$R$_{11}$', —NR$_{11}$C(O)NR$_{11}$'R$_{11}$''', —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11}$', —OCH$_2$CH$_2$OH, —NR$_{11}$S(O)$_2$NR$_{11}$'R$_{11}$''' C(CH$_3$)$_2$OR$_{11}$, and substituted or unsubstituted five membered aromatic heterocyclyl;

wherein R$_8$ and R$_8$' are independently selected from hydrogen, halogen, —R$_{13}$, —OR$_{13}$, —NO$_2$, —NR$_{13}$R$_{13}$''', NR$_{13}$C(O)R$_{13}$', —NR$_{13}$S(O)$_2$R$_{13}$', —S(O)$_2$NR$_{13}$R$_{13}$', —NR$_{13}$C(O)NR$_{13}$'R$_{13}$''', —SR$_{13}$, —S(O)R$_{13}$, S(O)$_2$R$_{13}$, —CN, haloalkyl, haloalkoxy, —C(O)OR$_{13}$, —C(O)NR$_{13}$R$_{13}$', —OCH$_2$CH$_2$OCH$_3$, —NR$_{13}$S(O)$_2$NR$_{13}$'R$_{13}$''', C(CH$_3$)$_2$OR$_{13}$ and substituted or unsubstituted five membered aromatic heterocyclyl;

and wherein R$_2$, R$_4$, R$_4$', R$_{11}$, R$_{11}$', R$_{11}$''', R$_{13}$, R$_{13}$', R$_{13}$''', R$_{13}$'''', X, Y and n are as defined in the description.

For clarity purposes, R$_5$ and R$_5$' corresponds to the substitution pattern on any aryl and aromatic heterocyclyl moieties defined in R$_1$, and are not restricted to the thiophen or phenyl moieties shown in general formulae I$^{6a'}$, I$^{6b'}$ and I$^{9'}$ For clarity purposes, R$_7$ and R$_7$' corresponds to the substitution pattern on any cycloalkyl, aryl and aromatic heterocyclyl moieties defined in R$_2$; and are not restricted to the phenyl moieties shown in general formulae I$^{5'}$ and I$^{6b'}$ For clarity purposes, R$_8$ and R$_8$' corresponds to the substitution pattern on any aryl and aromatic heterocycyl moieties defined in R$_3$; and are not restricted to the phenyl moieties shown in general formulae I$^{5'}$, I$^{6a'}$, I$^{6b'}$ and I$^{9'}$.

For clarity purposes, reference is also made to the following statements below in the definitions of substitutions on alkyl etc. or aryl etc. that "wherein when different radicals R$_1$ to R$_{15}$''' are present simultaneously in Formula (I) they may be identical or different". This statement is reflected in the below general Formula (I$^{7'}$) being derived from and falling into general Formula (I).

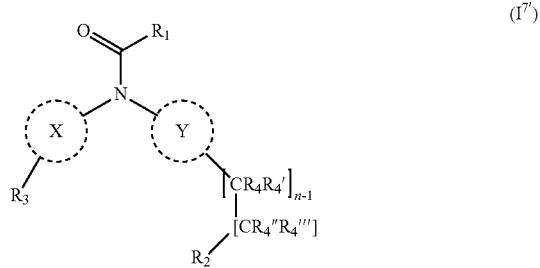

(I$^{7'}$)

wherein R$_1$, R$_2$, R$_3$, R$_4$'', R$_4$''', X and Y and n are as defined in the description. In addition, (n being different from 0), R$_4$'' and R$_4$''' are added. As said above, this statement is thus reflected in that R$_4$'' and R$_4$''' are or could be different from R$_4$ and R$_4$' or not.

The same would be applicable mutatis mutandis for general Formulas like general Formula (I) as well as the other general Formulas (I') to (I$^{9'}$) above.

For clarity purposes, all groups and definitions described in the description and referring to compounds of general Formula (I), also apply to compounds of general Formulae (I'), (I$^{2'}$), (I$^{3'}$), (I$^{4'}$), (I$^{5'}$), (I$^{6a'}$), (I$^{6b'}$), (I$^{7'}$), and (I$^{9'}$), when those groups are present in the mentioned general Markush formulae.

For clarity purposes, all groups and definitions described in the description and referring to compounds of general Formula (I), also apply to compounds of general Formulae (I$^{5'}$), (I$^{6a'}$), (I$^{6b'}$), (I$^{7'}$) and (I$^{9'}$), when those groups are present in the mentioned general Markush formulae, since compounds of general Formula (I$^{5'}$), (I$^{6a'}$), (I$^{6b'}$), (I$^{7'}$) and (I$^{9'}$), are included in the general Formula (I).

For clarity purposes, the expression "X is an unsubstituted aromatic heterocyclyl containing one or more nitrogen atoms as only heteroatom", means that the aromatic heterocycyl in X contains only one or more nitrogen atoms as heteroatom and no other heteroatom like oxygen or sulfur.

In a further embodiment the compound according to the invention is a compound of general Formula (I) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I') having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I$^{2'}$) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I$^{3'}$) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I$^{4'}$) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I$^{5'}$) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formulae (I$^{6a'}$) or (I$^{6b'}$) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I$^{7'}$) having dual pharmacological activity towards both the α$_2$δ subunit of the voltage-gated calcium channel and the μ-opioid receptor for use in therapy, in particular for the treatment of pain.

In a further embodiment the compound according to the invention is a compound of general Formula (I$^{9'}$) having dual pharmacological activity towards both the α$_2$δ subunit of the voltage-gated calcium channel and the μ-opioid receptor for use in therapy, in particular for the treatment of pain.

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, C$_{1-2}$-alkyl represents C1- or C2-alkyl, C$_{1-3}$-alkyl represents C1-, C2- or C3-alkyl, C$_{1-4}$-alkyl represents C1-, C2-, C3- or C4-alkyl, C$_{1-5}$-alkyl represents C1-, C2-, C3-, C4-, or C5-alkyl, C$_{1-6}$-alkyl represents C1-, C2-, C3-, C4-, C5- or C6-alkyl, C$_{1-7}$-alkyl represents C1-, C2-, C3-, C4-, C5-, C6- or C7-alkyl, C$_{1-8}$-alkyl represents C1-, C2-, C3-, C4-, C5-, C6-, C7- or C8-alkyl, C$_{1-10}$-alkyl represents C1-, C2-, C3-, C4-, C5-, C6-, C7-, C8-, C9- or C10-alkyl and C$_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF$_2$, CF$_3$ or CH$_2$OH etc. Preferably alkyl is understood in the context of this invention as C$_{1-8}$alkyl like methyl, ethyl, propyl, butyl, pentyl, hexyl, heptyl, or octyl; preferably is C$_{1-6}$alkyl like methyl, ethyl, propyl, butyl, pentyl, or hexyl; more preferably is C$_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—CH$_3$. The alkenyl radicals are preferably vinyl (ethenyl), allyl (2-propenyl). Preferably in the context of this invention alkenyl is C$_{2-10}$-alkenyl or C$_{2-8}$-alkenyl like ethylene, propylene, butylene, pentylene, hexylene, heptylene or octylene; or is C$_{2-6}$-alkenyl like ethylene, propylene, butylene, pentylene, or hexylene; or is C$_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH$_3$ (1-propinyl). Preferably alkynyl in the context of this invention is C$_{2-10}$-alkynyl or C$_{2-8}$-alkynyl like ethyne, propyne, butyne, pentyne, hexyne, heptyne, or octyne; or is C$_{2-6}$-alkynyl like ethyne, propyne, butyne, pentyne, or hexyne; or is C$_{2-4}$-alkynyl like ethyne, propyne, butyne, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —NR$_c$R$_{c'''}$, —SR$_c$, —S(O)R$_c$, —S(O)$_2$R$_c$, —OR$_c$, —C(O)OR$_c$, —C(O)R$_c$, —CN, —C(O)NR$_c$R$_{c'}$, haloalkyl, haloalkoxy, being R$_c$ represented by R$_{12}$ or R$_{14}$ (being R$_{c'}$ represented by R$_{12'}$ or R$_{14'}$; being R$_{c''}$ represented by R$_{12''}$ or R$_{14''}$; being R$_{c'''}$ represented by R$_{12'''}$ or R$_{14'''}$). R$_1$ to R$_{15'''}$ are as defined in the description, and when different radicals R$_1$ to R$_{15'''}$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which, if substituted, is substituted with one or more of halogen (F, Cl, Br, I), —NR$_c$R$_{c'''}$, —OR$_c$, —CN, —SR$_c$, —S(O)R$_c$, —S(O)$_2$R$_c$, —C(O)R$_c$, haloalkyl, haloalkoxy, being R$_c$ represented by R$_{12}$ or R$_{14}$ (being R$_{c'}$ represented by R$_{12'}$ or R$_{14'}$; being R$_{c''}$ represented by R$_{12''}$ or R$_{14''}$; being R$_{c'''}$ represented by R$_{12'''}$ or R$_{14'''}$). R$_1$ to R$_{15'''}$ are as defined in the description, and when different radicals R$_1$ to R$_{15'''}$ are present simultaneously in Formula I, they may be identical or different.

More than one replacement on the same molecule and also on the same carbon atom is possible with the same or different substituents. This includes for example 3 hydrogens being replaced on the same C atom, as in the case of CF$_3$, or at different places of the same molecule, as in the case of e.g. —CH(OH)—CH═CH—CHCl$_2$.

In the context of this invention haloalkyl is understood as meaning an alkyl being substituted once or several times by a halogen (selected from F, Cl, Br, I). It encompasses e.g. —CH$_2$Cl, —CH$_2$F, —CHCl$_2$, —CHF$_2$, —CCl$_3$, —CF$_3$ and —CH$_2$—CHCl$_2$. Preferably haloalkyl is understood in the context of this invention as halogen-substituted C$_{1-4}$-alkyl representing halogen substituted C1-, C2-, C3- or C4-alkyl. The halogen-substituted alkyl radicals are thus preferably methyl, ethyl, propyl, and butyl. Preferred examples include —CH$_2$Cl, —CH$_2$F, —CHCl$_2$, —CHF$_2$, and —CF$_3$.

In the context of this invention haloalkoxy is understood as meaning an —O-alkyl being substituted once or several times by a halogen (selected from F, Cl, Br, I). It encompasses e.g. —OCH$_2$Cl, —OCH$_2$F, —OCHCl$_2$, —OCHF$_2$, —OCCl$_3$, —OCF$_3$ and —OCH$_2$—CHCl$_2$. Preferably haloalkyl is understood in the context of this invention as halogen-substituted —OC$_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —OCH$_2$Cl, —OCH$_2$F, —OCHCl$_2$, —OCHF$_2$, and —OCF$_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, C$_{3-4}$-cycloalkyl represents C3- or C4-cycloalkyl, C$_{3-5}$-cycloalkyl represents C3-, C4- or C5-cycloalkyl, C$_{3-6}$-cycloalkyl represents C3-, C4-, C5- or C6-cycloalkyl, C$_{3-7}$-cycloalkyl represents C3-, C4-, C5-, C6- or C7-cycloalkyl, C$_{3-8}$-cycloalkyl represents C3-, C4-, C5-, C6-, C7- or C8-cycloalkyl, C$_{4-5}$-cycloalkyl represents C4- or C5-cycloalkyl, C$_{5-7}$-cycloalkyl represents C4-, C5- or C6-cycloalkyl, C$_{4-7}$-cycloalkyl represents C4-, C5-, C6- or C7-cycloalkyl, C$_{5-6}$-cycloalkyl represents C5- or C6-cycloalkyl and C$_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is C$_{3-8}$cycloalkyl like cyclopropyl, cyclobutyl, cyclopentyl, cyclohexyl, cycloheptyl, or cyclooctyl; or is C$_{3-7}$cycloalkyl like cyclopropyl, cyclobutyl, cyclopentyl, cyclohexyl, or cycloheptyl; or is C$_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl, indanyl, 9H-fluorenyl or anthracenyl radicals, which can be unsubstituted or once or several times substituted. Most preferably aryl is understood in the context of this invention as phenyl, naphthyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms selected from the group consisting of nitrogen, oxygen and/or sulfur in the ring. A heterocyclic group can also be substituted once or several times.

Examples include non-aromatic heterocyclyls such as tetrahydropyran, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, isothiazole, imidazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered heterocyclic ring system of one or more rings of which at least one aromatic ring contains one or more heteroatoms selected from the group consisting of nitrogen, oxygen and/or sulfur in the ring; preferably is an aromatic heterocyclic ring system of one or two rings of which at least one aromatic ring contains one or more heteroatoms selected from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, isothiazole, imidazole, pyrazole, oxazole, thiophene and benzimidazole;

the non-aromatic heterocyclyl is a 5 to 18 membered heterocyclic ring system of one or more rings of which at least one ring—with this (or these) ring(s) then not being aromatic—contains one or more heteroatoms selected from the group consisting of nitrogen, oxygen and/or sulfur in the ring; preferably is a heterocyclic ring system of one or two rings of which one or both rings—with this one or two rings then not being aromatic—contain/s one or more heteroatoms selected from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, oxetane, especially is benzodioxane, morpholine, tetrahydropyran, piperidine, oxopyrrolidine, oxetane and pyrrolidine.

Preferably, in the context of this invention heterocyclyl is defined as a heterocyclic ring system of one or more saturated or unsaturated rings of which at least one ring contains one or more heteroatoms selected from the group consisting of nitrogen, oxygen and/or sulfur in the ring. Preferably it is a heterocyclic ring system of one or two saturated or unsaturated rings of which at least one ring contains one or more heteroatoms selected from the group consisting of nitrogen, oxygen and/or sulfur in the ring.

Preferred examples of heterocyclyls include oxetane, oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, isothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyran, pyrazole, imidazole, piperidine, thiophene, indole, benzimidazole, pyrrolo[2,3b]pyridine, benzoxazole, oxopyrrolidine, pyrimidine, oxazepane, oxetane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_{c'}$, —$C(O)NR_cR_{c'}$, —$NR_cS(O)_2R_{c'}$, =O, —$OCH_2CH_2OH$, —$NR_cC(O)NR_cR_{c''}$, —$S(O)_2NR_cR_{c'}$, —$NR_cS(O)_2NR_cR_{c''}$, haloalkyl, haloalkoxy, —$SR_c$, —$S(O)R_c$, —$S(O)_2$ or $C(CH_3)OR_c$ or substituted or unsubstituted five membered aromatic heterocyclyl; with $R_c$, $R_{c'}$, $R_{c''}$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$ alkyl (alkoxy); a saturated or unsaturated, linear or branched, substituted or unsubstituted —S—$C_{1-6}$ alkyl; a saturated or unsaturated, linear or branched, substituted or unsubstituted —C(O)—$C_{1-6}$ alkyl-group; a saturated or unsaturated, linear or branched, substituted or unsubstituted —C(O)—O—$C_{1-6}$ alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$, $R_{13}$ or $R_{15}$, (being $R_{c'}$ one of $R_{11'}$, $R_{12'}$, $R_{13'}$ or $R_{15'}$; being $R_{c''}$ one of $R_{11''}$, $R_{12''}$, $R_{13''}$ or $R_{15''}$; being $R_{c'''}$ one of $R_{11'''}$, $R_{12'''}$, $R_{13'''}$ or $R_{15'''}$. $R_1$ to $R_{15'''}$ are as defined in the description, and when different radicals $R_1$ to $R_{15'''}$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_c(O)R_{c'}$, —$NR_cS(O)_2R_{c'}$, =O, haloalkyl, haloalkoxy, $C(CH_3)OR_c$ or substituted or unsubstituted five membered aromatic heterocyclyl or —$OC_{1-4}$ alkyl being unsubstituted or substituted with one or more of $OR_c$ or halogen (F, Cl, I, Br), —CN, or —$C_{1-4}$alkyl being unsubstituted or substituted with one or more of $OR_0$ or halogen (F, Cl, I, Br), being $R_c$ one of $R_{11}$, $R_{12}$, $R_{13}$ or $R_{15}$, (being $R_{c'}$ one of $R_{11'}$, $R_{12'}$, $R_{13'}$ or $R_{15'}$; being $R_{c''}$ one of $R_{11''}$, $R_{12''}$, $R_{13''}$ or $R_{15''}$; being $R_{c'''}$ one of $R_{11'''}$, $R_{12'''}$, $R_{13'''}$ or $R_{15'''}$). $R_1$ to $R_{15'''}$ are as defined in the description, and when different radicals $R_1$ to $R_{15'''}$ are present simultaneously in Formula I they may be identical or different.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

(leading to a spiro structure) or =O, preferably substitution with =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound

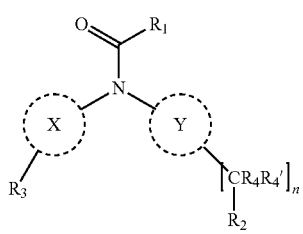

(I)

wherein n is 0, 1, 2, 3, 4 or 5;

X is an unsubstituted aromatic heterocyclyl containing one or more nitrogen atoms as only heteroatom;

Y is selected from

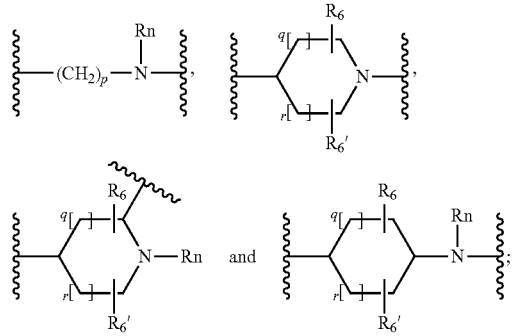

wherein p is 2 or 3;

q is 0, 1, 2 or 3;

r is 0, 1, 2 or 3;

$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from substituted or unsubstituted aryl and substituted or unsubstituted aromatic heterocycyl;

wherein said aryl or aromatic heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$, and substituted or unsubstituted five membered aromatic heterocyclyl;

wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl, wherein said cycloalkyl, aryl or aromatic heterocyclyl in $R_2$, if substituted, is substituted with one or more substituents selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

wherein the alkyl, alkenyl or alkynyl in $R_2$, if substituted, is substituted with one or more substituent/s selected from —$OR_{12}$, halogen, —CN, haloalkyl, haloalkoxy and —$NR_{12}R_{12'''}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{1-6}$ alkenyl, unsubstituted $C_{2-6}$ alkynyl and -Boc;

$R_3$ is selected from substituted or unsubstituted monocyclic aryl and substituted or unsubstituted monocyclic aromatic heterocyclyl, wherein said aryl or aromatic heterocyclyl in $R_3$, if substituted, is substituted with one or more substituent/s selected from halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

the alkyl, alkenyl or alkynyl, other than those defined in $R_2$, if substituted, is substituted with one or more substituent/s selected from —$OR_{14}$, halogen, —CN, haloalkyl, haloalkoxy and —$NR_{14}R_{14'''}$;

wherein $R_{14}$ is selected from hydrogen, unsubstituted $C_{1-6}$ alkyl, unsubstituted $C_{2-6}$ alkenyl, and unsubstituted $C_{2-6}$ alkynyl;

$R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

the aryl, heterocyclyl or cycloalkyl other than those defined in $R_1$, $R_2$ or $R_3$, if substituted, is substituted with one or more substituent/s selected from halogen, —$R_{15}$, —$OR_{15}$, —$NO_2$, —$NR_{15}R_{15'''}$, $NR_{15}C(O)R_{15'}$, —$NR_{15}S(O)_2R_{15'}$, —$S(O)_2NR_{15}R_{15'}$, —$NR_{15}C(O)NR_{15'}R_{15''}$, —$SR_{15}$, —$S(O)R_{15}$, $S(O)_2R_{15}$, —CN, haloalkyl, haloalkoxy, —$C(O)OR_{15}$, —$C(O)NR_{15}R_{15'}$, —$OCH_2CH_2OH$, —$NR_{15}S(O)_2NR_{15'}R_{15''}$ and $C(CH_3)_2 OR_{15}$;

wherein $R_{15}$, $R_{15'}$ and $R_{15''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{15'''}$ is selected from hydrogen, unsubstituted $C_{1-6}$ alkyl, unsubstituted $C_{2-6}$ alkenyl, unsubstituted $C_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound

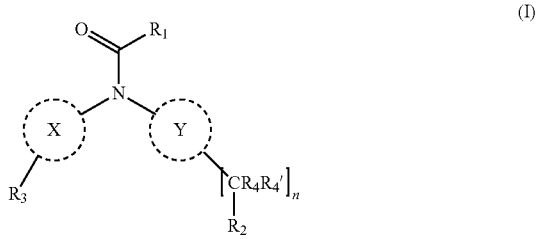

(I)

wherein
n is 0, 1, 2, 3, 4 or 5;
wherein X is selected from

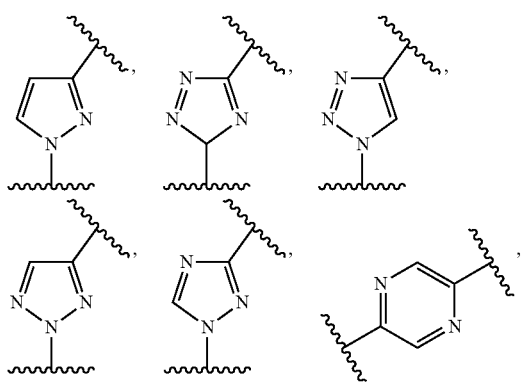

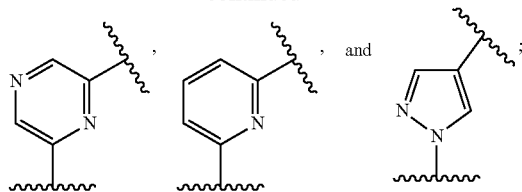

Y is selected from

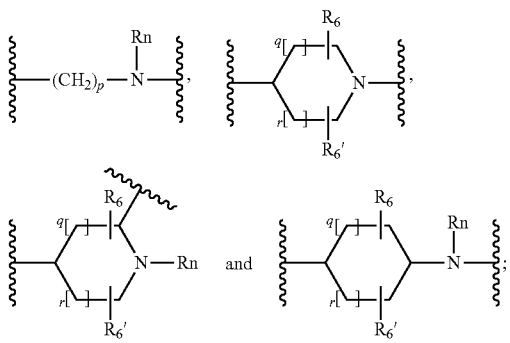

wherein
p is 2 or 3;
q is 0, 1, 2 or 3;
r is 0, 1, 2 or 3;
$R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from substituted or unsubstituted aryl and substituted or unsubstituted aromatic heterocycyl;
wherein said aryl or aromatic heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$, and substituted or unsubstituted five membered aromatic heterocyclyl;
wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl,
wherein said cycloalkyl, aryl or aromatic heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —C(O)OR$_{12}$, —C(O)NR$_{12}$R$_{12'}$, —OCH$_2$CH$_2$OH, —NR$_{12}$S(O)$_2$NR$_{12'}$R$_{12''}$ and C(CH$_3$)$_2$OR$_{12}$;
  wherein the alkyl, alkenyl or alkynyl in R$_2$, if substituted, is substituted with one or more substituent/s selected from —OR$_{12}$, halogen, —CN, haloalkyl, haloalkoxy and —NR$_{12}$R$_{12'''}$;
  wherein R$_{12}$, R$_{12'}$ and R$_{12''}$ are independently selected from hydrogen, unsubstituted C$_{1-6}$ alkyl, unsubstituted C$_{2-6}$ alkenyl and unsubstituted C$_{2-6}$ alkynyl;
  and wherein R$_{12'''}$ is selected from hydrogen, unsubstituted C$_{1-6}$ alkyl, unsubstituted C$_{2-6}$ alkenyl, unsubstituted C$_{2-6}$ alkynyl and -Boc;
R$_3$ is selected from substituted or unsubstituted aryl and substituted or unsubstituted aromatic heterocyclyl,
  wherein said aryl or aromatic heterocyclyl in R$_3$, if substituted, is substituted with one or more substituent/s selected from halogen, —R$_{13}$, —OR$_{13}$, —NO$_2$, —NR$_{13}$R$_{13'''}$, NR$_{13}$C(O)R$_{13'}$, —NR$_{13}$S(O)$_2$R$_{13'}$, —S(O)$_2$NR$_{13}$R$_{13'}$, —NR$_{13}$C(O)NR$_{13'}$R$_{13''}$, —SR$_{13}$, —S(O)R$_{13}$, S(O)$_2$R$_{13}$, —CN, haloalkyl, haloalkoxy, —C(O)OR$_{13}$, —C(O)NR$_{13}$R$_{13'}$, —OCH$_2$CH$_2$OCH$_3$, —NR$_{13}$S(O)$_2$NR$_{13'}$R$_{13''}$, C(CH$_3$)$_2$OR$_{13}$ and substituted or unsubstituted five membered aromatic heterocyclyl;
  wherein R$_{13}$, R$_{13'}$ and R$_{13''}$ are independently selected from hydrogen, unsubstituted C$_{1-6}$ alkyl, unsubstituted C$_{2-6}$ alkenyl, and unsubstituted C$_{2-6}$ alkynyl;
  R$_{13'''}$ is selected from hydrogen, unsubstituted C$_{1-6}$ alkyl, unsubstituted C$_{2-6}$ alkenyl, unsubstituted C$_{2-6}$ alkynyl and -Boc;
R$_4$ and R$_{4'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
  the alkyl, alkenyl or alkynyl, other than those defined in R$_2$, if substituted, is substituted with one or more substituent/s selected from —OR$_{14}$, halogen, —CN, haloalkyl, haloalkoxy and —NR$_{14}$R$_{14'''}$;
    wherein R$_{14}$ is selected from hydrogen, unsubstituted C$_{1-6}$ alkyl, unsubstituted C$_{2-6}$ alkenyl, and unsubstituted C$_{2-6}$ alkynyl;
    R$_{14'''}$ is selected from hydrogen, unsubstituted C$_{1-6}$ alkyl, unsubstituted C$_{2-6}$ alkenyl, unsubstituted C$_{2-6}$ alkynyl and -Boc;
  the aryl, heterocyclyl or cycloalkyl other than those defined in R$_1$, R$_2$ or R$_3$, if substituted, is substituted with one or more substituent/s selected from halogen, —R$_{15}$, —OR$_{15}$, —NO$_2$, —NR$_{15}$R$_{15'''}$, NR$_{15}$C(O)R$_{15'}$, —NR$_{15}$S(O)$_2$R$_{15'}$, —S(O)$_2$NR$_{15}$R$_{15'}$, —NR$_{15}$C(O)NR$_{15'}$R$_{15''}$, —SR$_{15}$, —S(O)R$_{15}$, S(O)$_2$R$_{15}$, —CN, haloalkyl, haloalkoxy, —C(O)OR$_{15}$, —C(O)NR$_{15}$R$_{15}$, —OCH$_2$CH$_2$OH, —NR$_{15}$S(O)$_2$NR$_{15'}$R$_{15''}$ and C(CH$_3$)$_2$OR$_{15}$;
    wherein R$_{15}$, R$_{15'}$ and R$_{15''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted cycloalkyl and unsubstituted heterocyclyl;
    and wherein R$_{15'''}$ is selected from hydrogen, unsubstituted C$_{1-6}$ alkyl, unsubstituted C$_{2-6}$ alkenyl, unsubstituted C$_{2-6}$ alkynyl and -Boc;
These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  n is 0, 1, 2, 3, 4 or 5;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  p is 2 or 3;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  q is 0, 1, 2 or 3;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  r is 0, 1, 2 or 3;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  X is an unsubstituted aromatic heterocyclyl containing one or more nitrogen atoms as only heteroatom;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  X is a substituted or unsubstituted aromatic heterocyclyl containing one or more nitrogen atoms as only heteroatom;
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
  X is a 5 or 6 members substituted or unsubstituted aromatic heterocyclyl containing one or more nitrogen atoms as only heteroatom.
  optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein X is a 5 or 6 members unsubstituted aromatic heterocyclyl containing one or more nitrogen atoms as only heteroatom.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is selected from

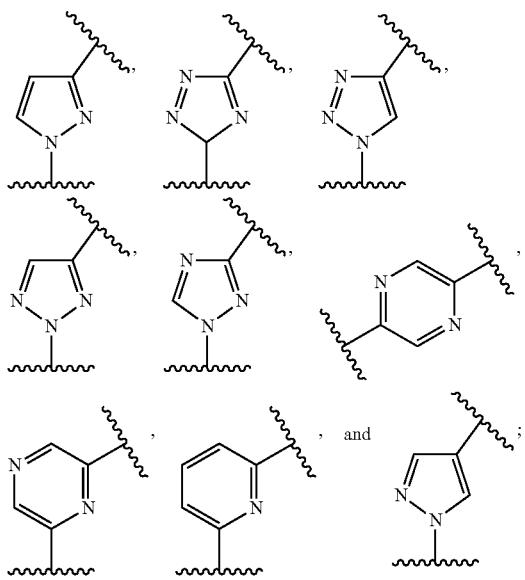

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

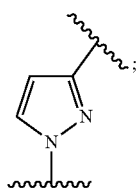

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is

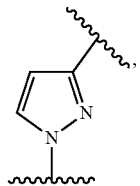

leading to compounds of formulae (Ia$_1$)

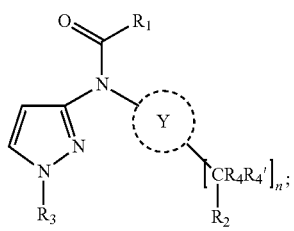

(Ia$_1$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

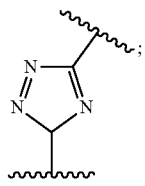 [SMILES: *C1=NC(*)N=N1]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

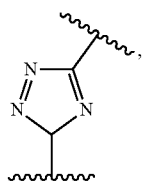 [SMILES: *C1=NC(*)N=N1]

leading to compounds of formula (Ia₉)

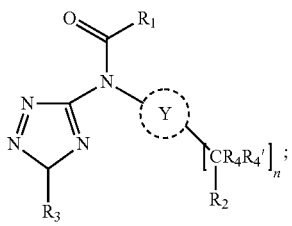

(Ia₉)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

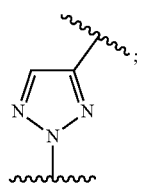

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

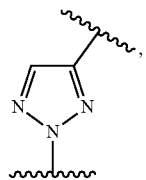

leading to compounds of formula (Ia₃)

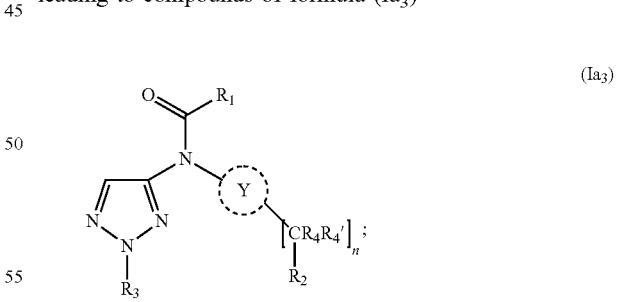

(Ia₃)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

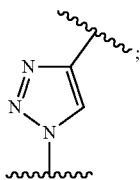 [SMILES: *c1cn(*)nn1]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

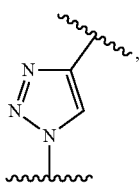 [SMILES: *c1cn(*)nn1]

leading to compounds of formula (Ia₂)

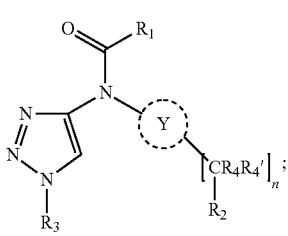

(Ia₂)

In another preferred embodiment of the compound according to the invention of general Formula (I) is a compound wherein X is

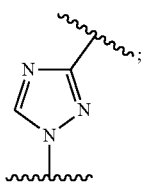

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

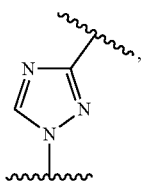 [SMILES: *c1ncn(*)n1]

leading to compounds of formula (Ia$_4$)

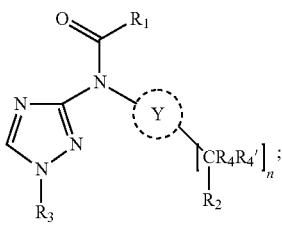

(Ia$_4$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

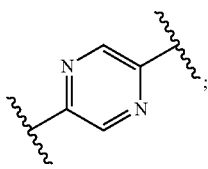 [SMILES: *c1cnc(*)cn1]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

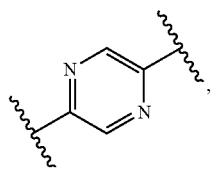 [SMILES: *c1cnc(*)cn1]

leading to compounds of formula (Ia$_5$)

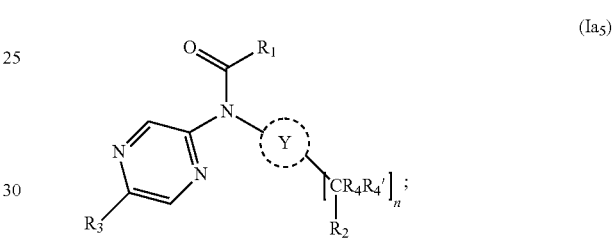

(Ia$_5$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

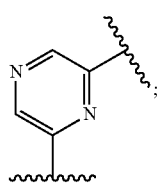

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein X is

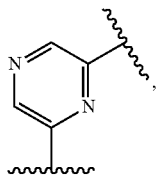

leading to compounds of formula (Ia$_6$)

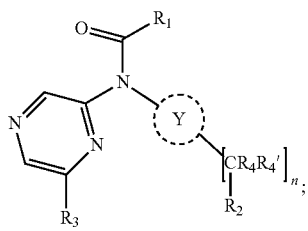
(Ia$_6$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

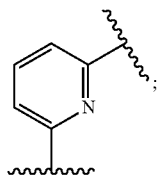 [SMILES: *c1cccc(*)n1]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

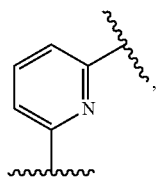

leading to compounds of formula (Ia$_7$)

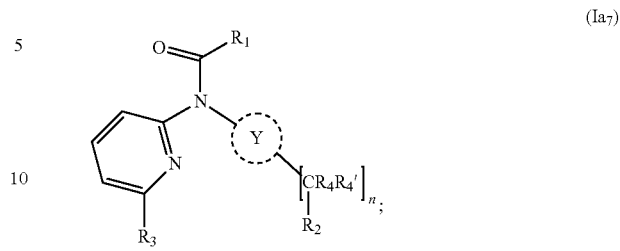
(Ia$_7$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

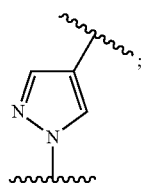 [SMILES: *c1cnn(*)c1]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is

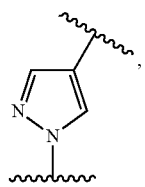

leading to compounds of formula (Ia$_8$)

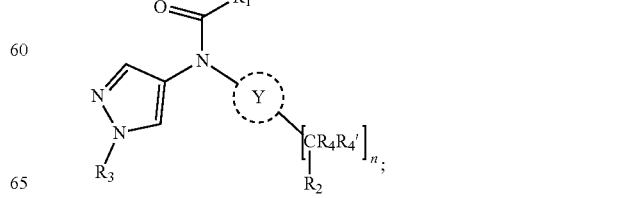
(Ia$_8$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
Y is

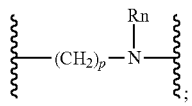

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
Y is

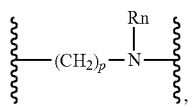

leading to compounds of formula ($Ib_1$)

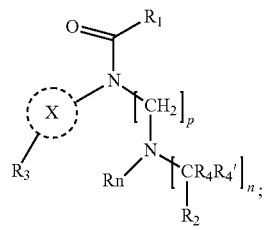

(Ib$_1$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

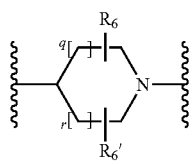

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
Y is

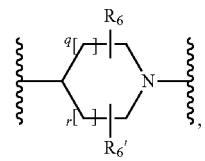

leading to compounds of formula ($Ib_2$)

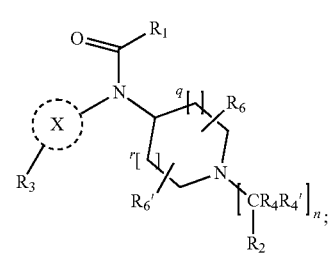

(Ib$_2$)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
Y is

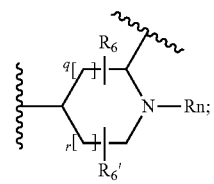

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein Y is

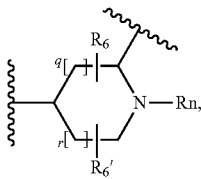

leading to compounds of formula (Ib$_3$)

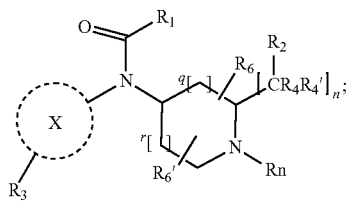

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
Y is

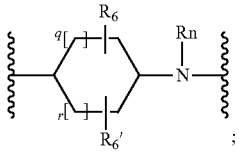

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
Y is

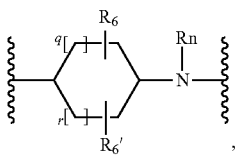

leading to compounds of formula (Ib$_4$)

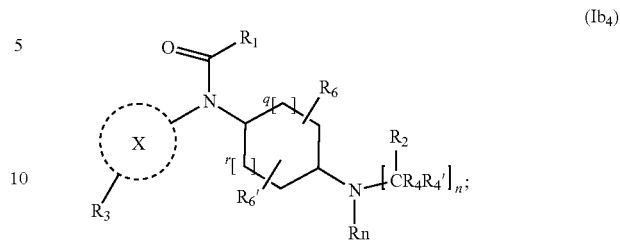

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound of formula (Ib$_{11}$)

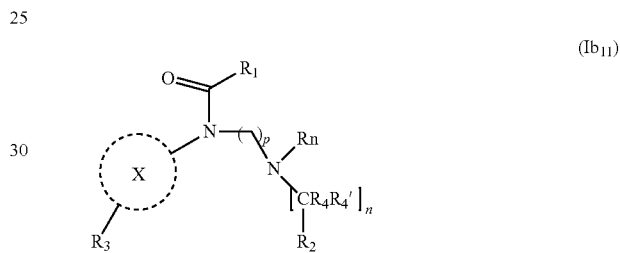

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound of formula (Ib$_{21}$)

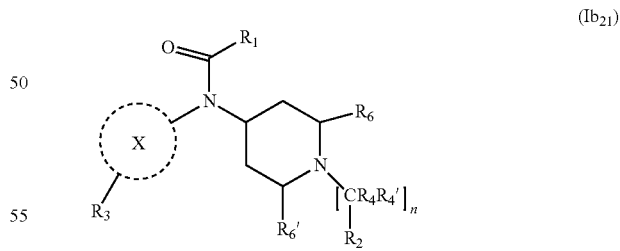

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound of formula (Ib$_{22}$)

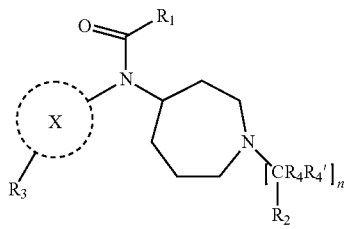

(Ib22)

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound of formula (Ib23)

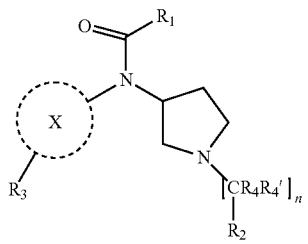

(Ib23)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound of formula (Ib24)

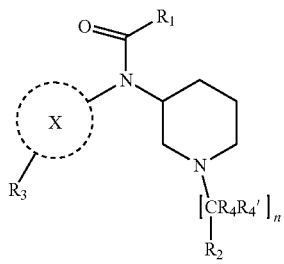

(Ib24)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound of formula (Ib31)

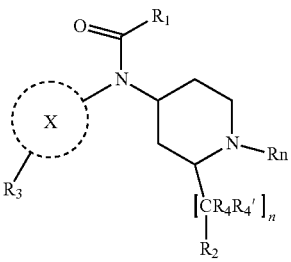

(Ib31)

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound of formula (Ib41)

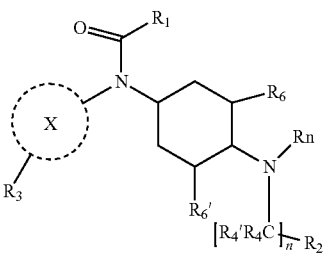

(Ib41)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_1$ is selected from substituted or unsubstituted aryl and substituted or unsubstituted aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl and substituted or unsubstituted aromatic heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is selected from hydrogen, substituted or unsubstituted $C_{1-6}$ alkyl, substituted or unsubstituted aryl and substituted or unsubstituted aromatic heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_3$ is selected from substituted or unsubstituted monocyclic aryl and substituted or unsubstituted monocyclic aromatic heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_3$ is selected from substituted or unsubstituted aryl and substituted or unsubstituted aromatic heterocyclyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ and $R_{4'}$ are independently selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ and $R_{4'}$ are independently selected from hydrogen, —$OR_{14}$, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_4$ and $R_{4'}$ are independently selected from hydrogen, —$OR_{14}$ and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_5$ and $R_5'$ are independently selected from hydrogen, halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11}R_{11'''}$ $C(CH_3)_2OR_{11}$, and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_5$ and $R_5'$ are independently selected from hydrogen, halogen, —$R_{11}$, —$OR_{11}$, and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_5$ and $R_5'$ are independently selected from hydrogen, halogen, —$R_{11}$, —$OR_{11}$, —$NR_{11}S(O)_2R_{11'}$ and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according the invention of general Formula (I) is a compound wherein $R_6$ and $R_{6'}$ are independently selected from hydrogen and unsubstituted $C_{1-6}$ alkyl, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula ($I^{5'}$) or ($I^{b'}$) is a compound wherein $R_7$ and $R_7'$ are independently selected from hydrogen, halogen, $-R_{12}$, $-OR_{12}$, $-NO_2$, $-NR_{12}R_{12'''}$, $NR_{12}C(O)R_{12'}$, $-NR_{12}S(O)R_{12'}$, $-S(O)_2NR_{12}R_{12'}$, $-NR_{12}C(O)NR_{12}R_{12'''}$, $-SR_{12}$, $-S(O)R_{12}$, $S(O)_2R_{12}$, $-CN$, haloalkyl, haloalkoxy, $-C(O)OR_{12}$, $-C(O)NR_{12}R_{12'}$, $-OCH_2CH_2OH$, $-NR_{12}S(O)_2NR_{12}R_{12''}$ and $C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula ($I^{5'}$) or ($I^{6b'}$) is a compound wherein $R_7$ and $R_7'$ are independently selected from hydrogen, halogen and haloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula ($I^{5'}$), ($I^{6a'}$), ($I^{6b'}$) or ($I^{9'}$) is a compound wherein $R_8$ and $R_{8'}$ are independently selected from hydrogen, halogen, $-R_{13}$, $-OR_{13}$, $-NO_2$, $-NR_{13}R_{13'''}$, $NR_{13}C(O)R_{13'}$, $-NR_{13}S(O)_2R_{13'}$, $-S(O)_2NR_{13}R_{13'}$, $-NR_{13}C(O)NR_{13'}R_{13'''}$, $-SR_{13}$, $-S(O)R_{13}$, $S(O)_2R_{13}$, $-CN$, haloalkyl, haloalkoxy, $-C(O)OR_{13}$, $-C(O)NR_{13}R_{13'''}$, $-OCH_2CH_2OCH_3$, $-NR_{13}S(O)_2NR_{13'}R_{13'''}$, $C(CH_3)_2OR_{13}$ and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula ($I^{5'}$), ($I^{6a'}$), ($I^{6b'}$) or ($I^{9'}$) is a compound wherein $R_8$ and $R_{8'}$ are independently selected from selected from hydrogen, halogen, $-R_{13}$, $-OR_{13}$, $-NR_{13}R_{13'''}$, $NR_{13}C(O)R_{13'}$, $-NR_{13}S(O)_2R_{13'}$, CN, haloalkoxy, and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl; and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$, $R_{13'}$ and $R_{13''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, and unsubstituted $C_{2-6}$ alkynyl;

$R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$ is selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{15}$, $R_{15'}$ and $R_{15''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{15'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{15}$, $R_{15'}$ and $R_{15''}$ is are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein and wherein $R_{15'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_n$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_n$ is selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein n is 0, 1, 2, 3, 4 or 5;
p is 2 or 3;
q is 0, 1, 2 or 3;
r is 0, 1, 2 or 3;
X is an unsubstituted aromatic heterocyclyl containing one or more nitrogen atoms as only heteroatom;
Y is selected from

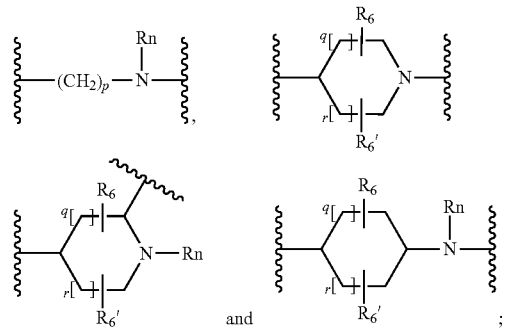

$R_1$ is selected from substituted or unsubstituted aryl and substituted or unsubstituted aromatic heterocyclyl;

wherein the aryl is selected from phenyl, naphthyl, or anthracene; preferably is napthyl and phenyl; more preferably the aryl is phenyl;

the heterocycyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is thiophene, furane, isoxazole, thiazole, pyrrole, oxazole, pyridine or isothiazole, even more preferably, preferably the heterocycle is thiophen;

and/or $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl, wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl, ethyl, isopropyl or isobutyl; even more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphthyl, or anthracene; preferably is napthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_3$ is selected from substituted or unsubstituted monocyclic aryl and substituted or unsubstituted monocyclic aromatic heterocyclyl, wherein the aryl is selected from phenyl, naphthyl, or anthracene; preferably is napthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is pyridine or pyrazole; even more preferably the heterocycle is pyridine;

and/or $R_4$ and $R_{4'}$ are independently selected from hydrogen, substituted or unsubstituted $C_{1-6}$ alkyl, substituted or unsubstituted C24 alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_5$ and $R_5{'}$ are independently selected from hydrogen, halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11'''}$ $C(CH_3)_2OR_{11}$, and substituted or unsubstituted five membered aromatic heterocyclyl;

wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is imidazole or 2-methyl-1,3,4-oxadiazole;

the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

and/or $R_6$ and $R_{6'}$ are independently selected from hydrogen, unsubstituted $C_{1-6}$ alkyl, unsubstituted $C_{2-6}$ alkenyl and unsubstituted $C_{2-6}$ alkynyl; preferably the $C_{1-6}$ alkyl is methyl;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_7$ and $R_{7'}$ are independently selected from hydrogen, halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12}R_{12''}$ and $C(CH_3)_2OR_{12}$;

wherein the haloalkyl is $C_{1-4}$ haloalkyl, preferably $C_{1-3}$ haloalkyl, more preferably $C_{1-2}$ haloalkyl, even more preferably $C_1$ haloalkyl, preferably, the haloalkyl is —$CF_3$;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

$R_8$ and $R_{8'}$ are independently selected from hydrogen, halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13}R_{13'''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'''}$, —$OCH_2CH_2OCH_3$, —$NR_{13}S(O)_2NR_{13}R_{13''}$, $C(CH_3)_2OR_{13}$ and substituted or unsubstituted five membered aromatic heterocyclyl;

wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is 2-methyl-1,3,4-oxadiazole;

and/or the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy, preferably, the haloalkoxy is —$OCF_3$;

and/or $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

$R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

$R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

$R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{14}$ is selected from hydrogen, unsubstituted $C_{1-6}$ alkyl, unsubstituted $C_{2-6}$ alkenyl, and unsubstituted $C_{2-6}$ alkynyl;

$R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{15}$, $R_{15'}$ and $R_{15''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{15'''}$ is selected from hydrogen, unsubstituted $C_{1-6}$ alkyl, unsubstituted $C_{2-6}$ alkenyl, unsubstituted $C_{2-6}$ alkynyl and -Boc; wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphthyl, or anthracene; preferably is napthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline;

the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein $R_4$ and $R_{4'}$ are independently selected from hydrogen, $-OR_{14}$, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein wherein n is 0, 1, 2, 3, 4 or 5;

p is 2 or 3;

q is 0, 1, 2 or 3;

r is 0, 1, 2 or 3;

X is selected from

[chemical structures]

Y is selected from

[chemical structures]

-continued

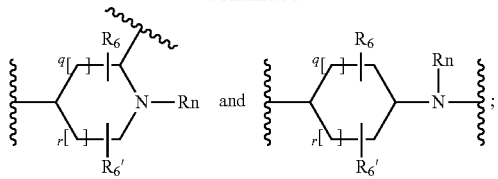

$R_1$ is selected from substituted or unsubstituted aryl and substituted or unsubstituted aromatic heterocyclyl;
wherein
the aryl is selected from phenyl, naphthyl, or anthracene; preferably is napthyl and phenyl; more preferably the aryl is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is thiophene, furane, isoxazole, thiazole, pyrrole, oxazole, pyridine or isothiazole, even more preferably, preferably the heterocycle is thiophen;
and/or
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl,
wherein
the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl, ethyl, isopropyl or isobutyl; even more preferably the $C_{1-6}$ alkyl is methyl;
and/or
the $C_{2-6}$-alkenyl is preferably selected from ethylene, propylene, butylene, pentylene, hexylene, isopropylene and isobutylene;
the $C_{2-6}$-alkynyl is preferably selected from ethyne, propyne, butyne, pentyne, hexyne, isopropyne and isobutyne;
and/or
the aryl is selected from phenyl, naphthyl, or anthracene; preferably is napthyl and phenyl; more preferably the aryl is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is pyridine;
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_3$a cycloalkyl like cyclopropyl, cyclobutyl, cyclopentyl or cyclohexyl;
and/or
$R_3$ is selected from substituted or unsubstituted monocyclic aryl and substituted or unsubstituted monocyclic aromatic heterocyclyl,
wherein
the aryl is selected from phenyl, naphthyl, or anthracene; preferably is napthyl and phenyl; more preferably the aryl is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is pyridine or pyrazole; even more preferably the heterocycle is pyridine;
and/or
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl, isobutyl and 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
$R_5$ and $R_5'$ are independently selected from hydrogen, halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)$ $NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$, and substituted or unsubstituted five membered aromatic heterocyclyl;

wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is imidazole or 2-methyl-1,3,4-oxadiazole;

and/or the haloalkyl is $C_{1-4}$ haloalkyl, preferably $C_{1-3}$ haloalkyl, more preferably $C_{1-2}$ haloalkyl, even more preferably $C_1$ haloalkyl;

the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

and/or $R_6$ and $R_{6'}$ are independently selected from hydrogen, unsubstituted $C_{1-6}$ alkyl, unsubstituted $C_{2-6}$ alkenyl and unsubstituted $C_{2-6}$ alkynyl;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_7$ and $R_7'$ are independently selected from hydrogen, halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{42}S(O)_2NR_{12'}R_{12''}$ and $C(CH_3)_2OR_{12}$;

wherein the haloalkyl is $C_{1-4}$ haloalkyl, preferably $C_{1-3}$ haloalkyl, more preferably $C_{1-2}$ haloalkyl, even more preferably $C_1$ haloalkyl, preferably, the haloalkyl is —$CF_3$;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

and/or $R_8$ and $R_{8'}$ are independently selected from hydrogen, halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)$ $NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is 2-methyl-1,3,4-oxadiazole;

and/or the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy, preferably, the haloalkoxy is —$OCF_3$;

and/or $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

$R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

$R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

$R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;

$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{14}$ is selected from hydrogen, unsubstituted $C_{1-6}$ alkyl, unsubstituted $C_{2-6}$ alkenyl, and unsubstituted $C_{2-6}$ alkynyl;

$R_{14}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{15}$, $R_{15'}$ and $R_{15''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{15'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphthyl, or anthracene; preferably is napthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_n$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention, the aryl is selected from phenyl, naphthyl, or anthracene; preferably is napthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is thiophene, furane, isoxazole, thiazole, pyrrole, oxazole, pyridine or isothiazole, even more preferably, preferably the heterocycle is thiophen;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the invention according to general Formula (I) the compound is a compound, wherein in $R_2$ as defined in any of the embodiments of the present invention, the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl, ethyl, isopropyl or isobutyl; even more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphthyl, or anthracene; preferably is napthyl and phenyl; more preferably the aryl is phenyl;

the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, the aryl is selected from phenyl, naphthyl, or anthracene; preferably is napthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is pyridine or pyrazole; even more preferably the heterocycle is pyridine;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the invention according to general Formula (I) the compound is a compound, wherein in $R_4$ as defined in any of the embodiments of the present invention, the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{4'}$ as defined in any of the embodiments of the present invention, the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula ($I^{6a'}$), ($I^{6b'}$) or ($I^{9'}$) the compound is a compound, wherein in $R_5$ and $R_{5'}$ as defined in any of the embodiments of the present invention, the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is imidazole or 2-methyl-1,3,4-oxadiazole;

and/or the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments of the present invention, the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula $(I^{5'})$ or $(I^{6b'})$ the compound is a compound, wherein in $R_7$ and $R_{7'}$ as defined in any of the embodiments of the present invention, wherein the haloalkyl is $C_{1-4}$ haloalkyl, preferably $C_{1-3}$ haloalkyl, more preferably $C_{1-2}$ haloalkyl, even more preferably $C_1$ haloalkyl; preferably the haloalkyl is —CF3;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula $(I^{5'})$, $(I^{6a'})$, $(I^{6b'})$ or $(I^{9'})$ the compound is a compound, wherein in $R_8$ and $R_{8'}$ as defined in any of the embodiments of the present invention, wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline, more preferably the heterocycle is 2-methyl-1,3,4-oxadiazole; and/or the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy, preferably, the haloalkoxy is —OCF$_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$, $R_{11''}$ and $R_{11'''}$ as defined in any of the embodiments of the present invention, wherein the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$, $R_{12''}$ and $R_{12'''}$ as defined in any of the embodiments of the present invention, the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$, $R_{13'}$, $R_{13''}$ and $R_{13'''}$ as defined in any of the embodiments of the present invention, the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diasteromers, in any mixing ratio, or a corresponding salt thereof, or a corresponding solvate thereof.

In another preferred embodiment of the invention according to general Formula (I) the compound is a compound, wherein in $R_{14}$, $R_{14'}$, $R_{14''}$ and $R_{14'''}$ as defined in any of the embodiments of the present invention, the $C_{1-6}$ alkyl is preferably selected from methyl, ethyl, propyl, butyl, pentyl, hexyl, isopropyl, isobutyl and 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diasteromers, in any mixing ratio, or a corresponding salt thereof, or a corresponding solvate thereof.

In another preferred embodiment of the invention according to general Formula (I) the compound is a compound, wherein in $R_{15}$, $R_{15'}$, $R_{15''}$ and $R_{15'''}$ as defined in any of the embodiments of the present invention, the $C_{1-6}$ alkyl is preferably selected from methyl, ethyl, propyl, butyl, pentyl, hexyl, isopropyl, isobutyl and 2-methylpropyl; more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphthyl, or anthracene; preferably is napthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from isothiazole, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole, 2-methyl-1,3,4-oxadiazole and quinazoline;

and/or the cycloalkyl is $C_3$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the haloalkyl is $C_{1-4}$ haloalkyl, preferably $C_{1-3}$ haloalkyl, more preferably $C_{1-2}$ haloalkyl, even more preferably $C_1$ haloalkyl;

and/or the haloalkoxy is $C_{1-4}$ haloalkoxy, preferably $C_{1-3}$ haloalkoxy, more preferably $C_{1-2}$ haloalkoxy, even more preferably $C_1$ haloalkoxy;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in R as defined in any of the embodiments of the present invention, the $C_{1-6}$ alkyl is preferably selected from methyl, ethyl, propyl, butyl, pentyl, hexyl, isopropyl, isobutyl and 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the invention according to general Formula (I) the compound is a compound, wherein n is 0, 1, 2, 3, 4 or 5; preferably n is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein q is 0, 1, 2 or 3; preferably q is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein r is 0, 1, 2 or 3; preferably r is 0, 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is an unsubstituted aromatic heterocyclyl containing one or more nitrogen atoms as only heteroatom;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is an unsubstituted aromatic heterocyclyl containing one or more nitrogen atoms as only heteroatom; preferably pyrazole, triazole, pyridine or pyrazine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from

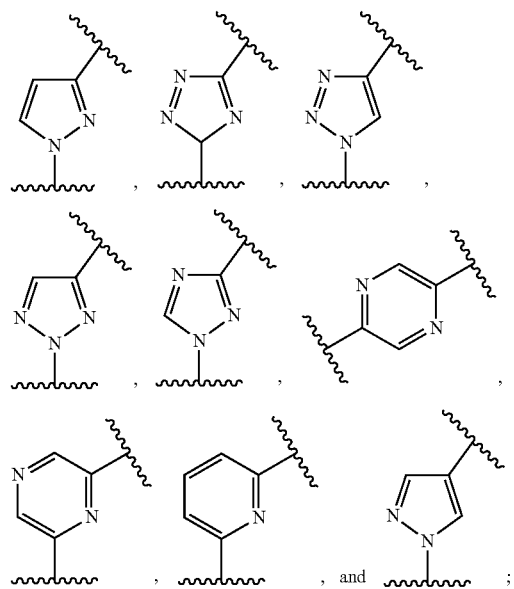

preferably

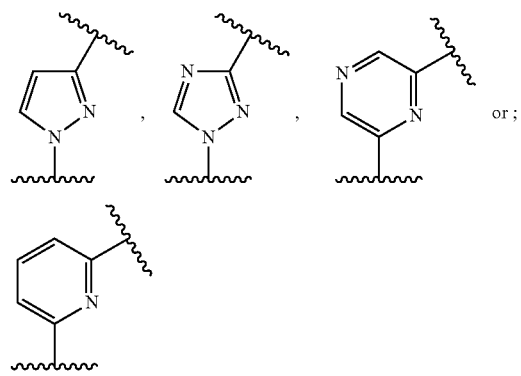

or;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from

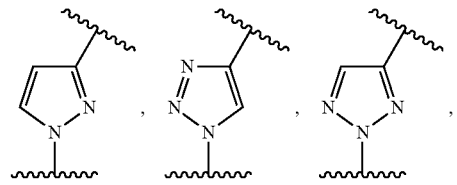

-continued

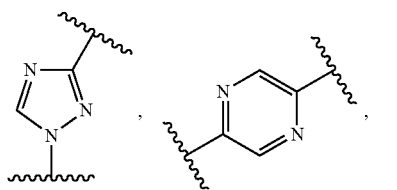

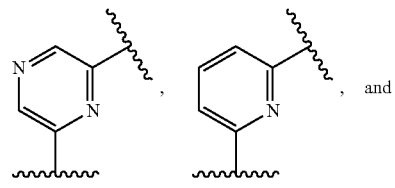

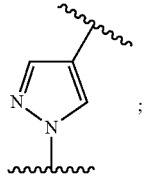;

preferably

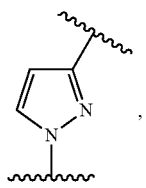, 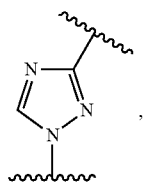, 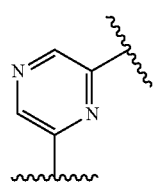 or;

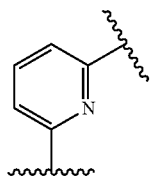

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

X is selected from an unsubstituted group selected from

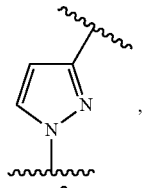, 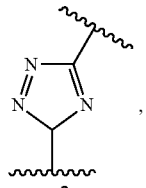, 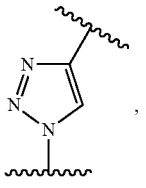,

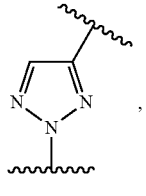, 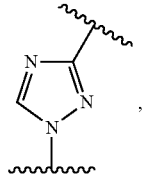, 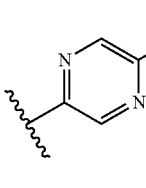,

-continued

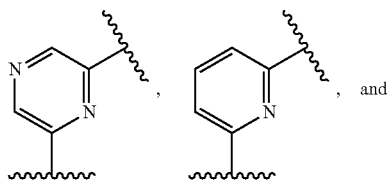, and

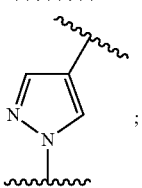;

preferably

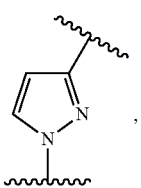, 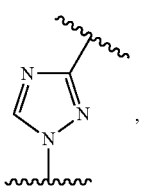, 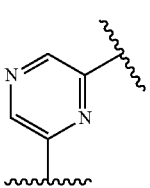 or;

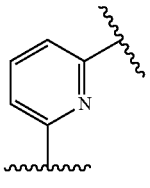

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

X is selected from an unsubstituted group selected from

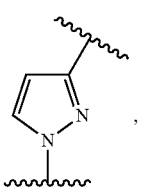 [SMILES: *c1ccn(*)n1], 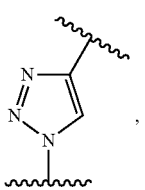, 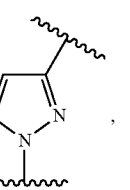,

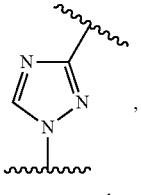, 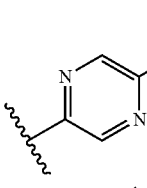,

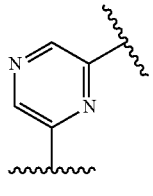, 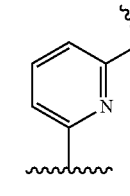, and

-continued

[structure: pyrazole attached via C4, N1]

preferably

[structures: pyrazole, triazole, pyrazine] or;

[structure: pyridine (2,6-disubstituted)]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

X is a substituted or unsubstituted group selected from

[structures: pyrazole, triazole, triazole],

[structures: pyrazole, triazole, pyrazine],

[structures: pyrazine, pyridine], and

[structure: pyrazole];

preferably a substituted or unsubstituted group selected from

[structures: pyrazole, triazole, pyrazine] or;

[structure: pyridine];

more preferably a substituted or unsubstituted group

[structure: pyrazole], even more preferably unsubstituted or methyl substituted

[structure: pyrazole];

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

X is a substituted or unsubstituted group selected from

[structures: pyrazole, triazole, triazole],

[structures: triazole, pyrazine],

-continued

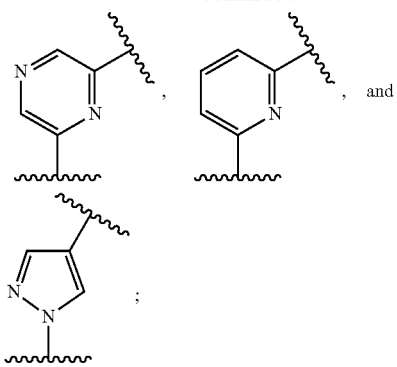

preferably a substituted or unsubstituted group selected from

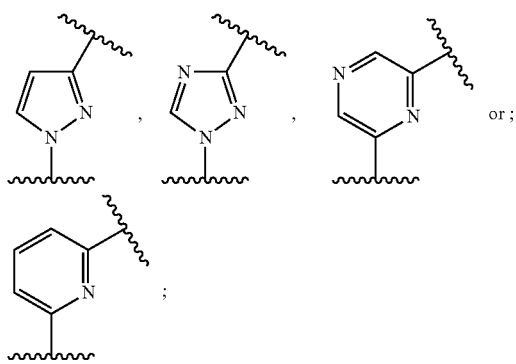

more preferably a substituted or unsubstituted group

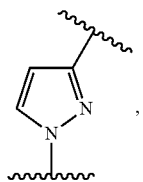 [SMILES: *c1ccn(*)n1], even more preferably unsubstituted or methyl substituted

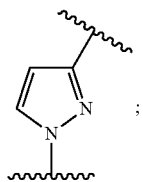;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein Y is selected from

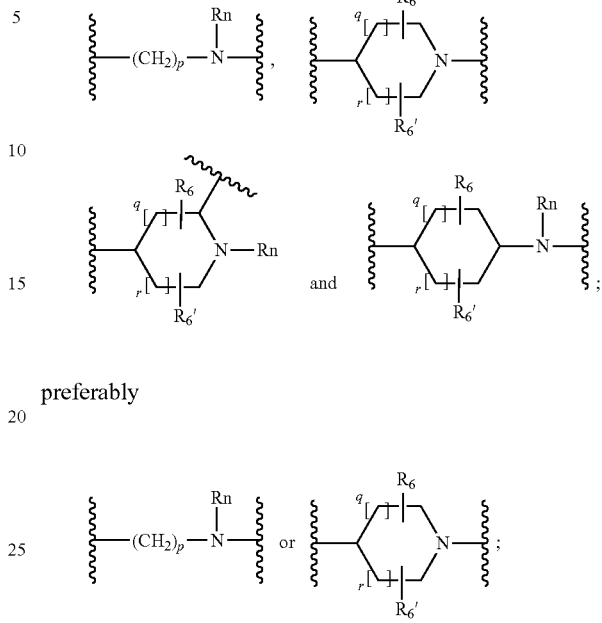

preferably

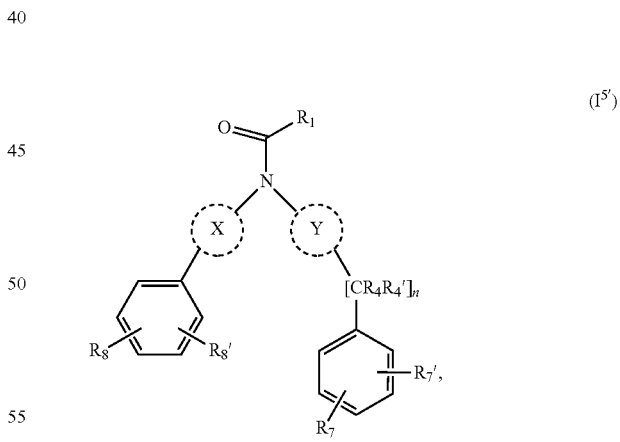

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula ($I^{5'}$)

$$(I^{5'})$$

[structure of Formula ($I^{5'}$) showing R₁, X, Y, [CR₄R₄']ₙ, R₇, R₇', R₈, R₈' substituents]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula ($I^{5'}$)

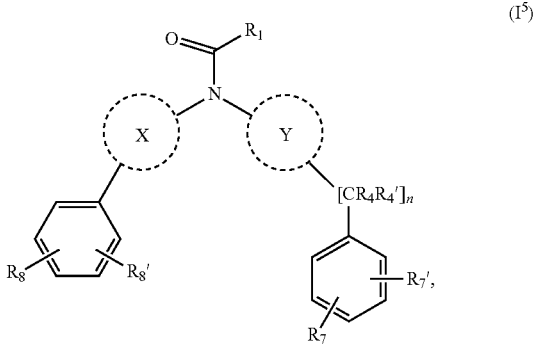

(I⁵)

wherein
X and Y are as defined in the description;
n is 0, 1, 2, 3, 4 or 5;
$R_1$ is selected from substituted or unsubstituted aryl and substituted or unsubstituted aromatic heterocyclyl;
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_7$ and $R_{7'}$ are independently selected from hydrogen, halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
$R_8$ and $R_{8'}$ are independently selected from hydrogen, halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I⁶ᵃ'),

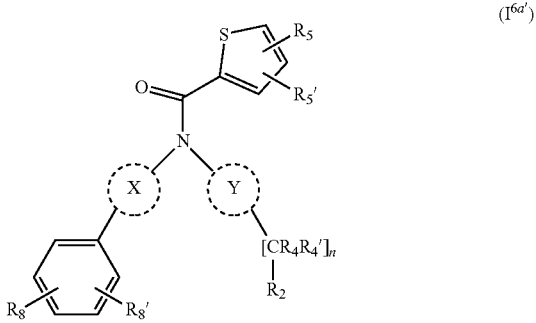

(I⁶ᵃ')

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I⁶ᵃ'),

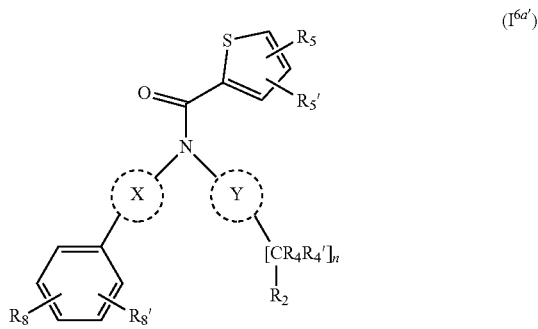

(I⁶ᵃ')

wherein
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl,
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from hydrogen, halogen, —$R_{11}$, —$OR_{11}$, —$NO_2$, —$NR_{11}R_{11'''}$, $NR_1C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$, and substituted or unsubstituted five membered aromatic heterocyclyl;
$R_8$ and $R_{8'}$ are independently selected from selected from hydrogen, halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

and wherein $R_{11}$, $R_{11'}$, $R_{11''}$, $R_{11'''}$, $R_{13}$, $R_{13'}$, $R_{13''}$, $R_{13'''}$, X, Y and n are as defined in the description.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula (I⁶ᵇ'),

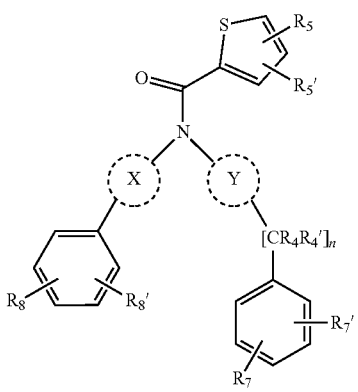

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula ($I^{6b'}$),

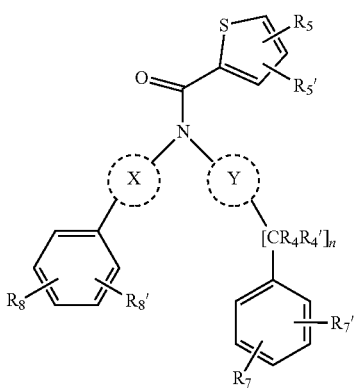

$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_5$ and $R_5'$ are independently selected from hydrogen, halogen, —$R_{11}$, —$OR_{11}$, —$NO_2$, —$NR_{11}R_{11'''}$, $NR_1C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$, $C(CH_3)_2OR_{11}$, and substituted or unsubstituted five membered aromatic heterocyclyl;

$R_7$ and $R_{7'}$ are independently selected from hydrogen, halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

$R_8$ and $R_{8'}$ are independently selected from hydrogen, halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

and wherein $R_{11}$, $R_{11'}$, $R_{11''}$, $R_{11'''}$, $R_{12}$, $R_{12'}$, $R_{12''}$, $R_{12'''}$, $R_{13}$, $R_{13'}$, $R_{13''}$, $R_{13'''}$, X, Y and n are as defined in the description.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula ($I^{9'}$),

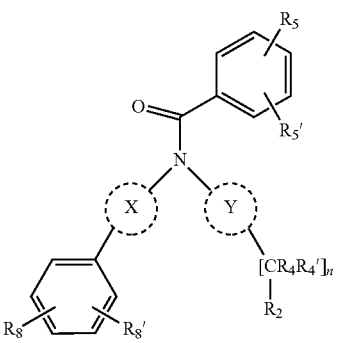

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula ($I^{9'}$),

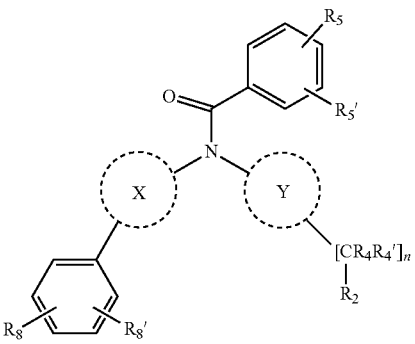

wherein $R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl, $R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_5$ and $R_5'$ are independently selected from hydrogen, halogen, —$R_{11}$, —$OR_{11}$, —$NO_2$, —$NR_{11}R_{11'''}$, $NR_1C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$, $C(CH_3)_2OR_{11}$, and substituted or unsubstituted five membered aromatic heterocyclyl;

$R_8$ and $R_{8'}$ are independently selected from hydrogen, halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

and wherein $R_{11}$, $R_{11'}$, $R_{11''}$, $R_{11'''}$, $R_{13}$, $R_{13'}$, $R_{13''}$, $R_{13'''}$, X, Y and n are as defined in the description.

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
$R_1$ is a substituted or unsubstituted group selected from thiophen, furane, isoxazole, thiazole, pyrrole, oxazole, pyridine, isothiazole and phenyl preferably is a substituted or unsubstituted group selected from thiophen, furane, thiazole, pyridine and phenyl, even more preferably is a substituted or unsubstituted thiophen.

In a preferred embodiment
$R_1$ is substituted or unsubstituted thiophen.

In a preferred embodiment
$R_1$ is substituted or unsubstituted phenyl.

In a preferred embodiment
$R_2$ is hydrogen or a substituted or unsubstituted group selected from methyl, ethyl, isopropyl, isobutyl, phenyl and pyridine.

In a preferred embodiment
$R_3$ is a substituted or unsubstituted group selected from phenyl, pyridine or pyrazole.

In a preferred embodiment
$R_3$ is substituted or unsubstituted benzyl.

In a preferred embodiment
$R_4$ is hydrogen.

In a preferred embodiment
$R_4$ is OH.

In a preferred embodiment
$R_{4'}$ is hydrogen.

In a preferred embodiment
$R_4$ and $R_{4'}$ are both hydrogen.

In a preferred embodiment
$R_4$ is OH while $R_{4'}$ is hydrogen.

In a preferred embodiment
$R_5$ is hydrogen or a substituted or unsubstituted group selected from methyl, hydroxy, methoxy, fluorine, chlorine or 2-methyl-1,3,4-oxadiazole.

In a preferred embodiment
$R_5$ is hydrogen or an unsubstituted group selected from methyl, hydroxy, methoxy, fluorine, chlorine or 2-methyl-1,3,4-oxadiazole.

In a preferred embodiment
$R_5$ is hydrogen, fluorine, chlorine or a substituted or unsubstituted group selected from methyl, hydroxy, methoxy, ethoxy, —$NHS(O)_2$-methyl, imidazole or 2-methyl-1,3,4-oxadiazole.

In a preferred embodiment
$R_5$ is hydrogen, fluorine, chlorine or an unsubstituted group selected from methyl, hydroxyl, methoxy, ethoxy, —$NHS(O)_2$-methyl, imidazole or 2-methyl-1,3,4-oxadiazole.

In a preferred embodiment
$R_5$ is a substituted or unsubstituted group selected from ethoxy, —$NHS(O)_2$-methyl or imidazole.

In a preferred embodiment
$R_5$ is an unsubstituted group selected from ethoxy, —$NHS(O)_2$-methyl or imidazole.

In a preferred embodiment
$R_{5'}$ is hydrogen.

In a preferred embodiment
$R_5$ is hydrogen or a substituted or unsubstituted group selected from methyl, hydroxyl, methoxy, fluorine, chlorine or 2-methyl-1,3,4-oxadiazole, while $R_{5'}$ is hydrogen.

In a preferred embodiment
$R_5$ is hydrogen or a unsubstituted group selected from methyl, hydroxyl, methoxy, fluorine, chlorine or 2-methyl-1,3,4-oxadiazole, while $R_{5'}$ is hydrogen.

In a preferred embodiment
$R_5$ is hydrogen, fluorine, chlorine or a substituted or unsubstituted group selected from methyl, hydroxyl, methoxy, ethoxy, —$NHS(O)_2$-methyl, imidazole or 2-methyl-1,3,4-oxadiazole, while $R_{5'}$ is hydrogen.

In a preferred embodiment
$R_5$ is hydrogen, fluorine, chlorine or an unsubstituted group selected from methyl, hydroxyl, methoxy, ethoxy, —$NHS(O)_2$-methyl, imidazole or 2-methyl-1,3,4-oxadiazole, while $R_{5'}$ is hydrogen.

In a preferred embodiment
$R_5$ and $R_{5'}$ are both hydrogen.

In a preferred embodiment
$R_6$ is hydrogen or substituted or unsubstituted methyl, preferably $R_6$ is hydrogen or unsubstituted methyl.

In a preferred embodiment
$R_{6'}$ is hydrogen or substituted or unsubstituted methyl, preferably $R_{6'}$ is hydrogen or unsubstituted methyl In a preferred embodiment
$R_6$ and $R_{6'}$ are both hydrogen.

In a preferred embodiment
$R_6$ and $R_{6'}$ are both substituted or unsubstituted methyl, preferably $R_6$ and $R_{6'}$ are both unsubstituted methyl In a preferred embodiment
$R_7$ is hydrogen, fluorine or —$CF_3$, preferably hydrogen.

In a preferred embodiment
$R_{7'}$ is hydrogen or fluorine, preferably hydrogen.

In a preferred embodiment
$R_7$ is hydrogen, fluorine or —$CF_3$, while $R_{7'}$ is hydrogen or fluorine.

In a preferred embodiment
$R_7$ and $R_{7'}$ are both hydrogen.

In a preferred embodiment
$R_6$ is hydrogen, chlorine, fluorine, —CN, —OH, —$OCH2CH2OCH3$, —$OCF3$, —$N(methyl)_2$. —NHC(O)-methyl, —$NHS(O)_2$-methyl or a substituted or unsubstituted group selected from methyl, methoxy, ethoxy and 2-methyl-1,3,4-oxadiazole.

In a preferred embodiment
$R_{8'}$ is hydrogen, chlorine, —OH or substituted or unsubstituted methoxy.

In a preferred embodiment

R$_8$ is hydrogen, chlorine, fluorine, —CN, —OH, —OCH2CH2OCH3, —OCF3, —N(methyl)$_2$, —NHC(O)-methyl, —NHS(O)$_2$-methyl or a substituted or unsubstituted group selected from methyl, methoxy, ethoxy and 2-methyl-1,3,4-oxadiazole, while R$_{8'}$ is hydrogen, chlorine, —OH or substituted or unsubstituted methoxy.

In a preferred embodiment

R$_8$ and R$_{8'}$ are both hydrogen.

In a preferred embodiment

R$_8$ is substituted or unsubstituted methoxy, preferably unsubstituted methoxy, while R$_{8'}$ is hydrogen.

In a preferred embodiment

R$_8$ is substituted or unsubstituted 2-methyl-1,3,4-oxadiazole, preferably unsubstituted 2-methyl-1,3,4-oxadiazole, while R$_{8'}$ is hydrogen.

In a preferred embodiment

R$_8$ is fluorine, while R$_{8'}$ is hydrogen.

In a preferred embodiment

R$_{11}$ is hydrogen or substituted or unsubstituted methyl; preferably, R$_{11}$ is hydrogen or unsubstituted methyl.

In a preferred embodiment

R$_{11}$ is hydrogen, substituted or unsubstituted methyl or substituted or unsubstituted ethyl; preferably, R$_{11}$ is hydrogen, unsubstituted methyl or unsubstituted ethyl.

In a preferred embodiment

R$_{11'}$ is substituted or unsubstituted methyl, preferably unsubstituted methyl.

In a preferred embodiment

R$_{11}$ is hydrogen, substituted or unsubstituted methyl or substituted or unsubstituted ethyl; preferably, R$_{11}$ is hydrogen, unsubstituted methyl or unsubstituted ethyl, while R$_{11'}$ is substituted or unsubstituted methyl, preferably unsubstituted methyl.

In a preferred embodiment

R$_{11}$ is hydrogen, while R$_{11'}$ is substituted or unsubstituted methyl, preferably unsubstituted methyl.

In a preferred embodiment

R$_{13}$ is hydrogen or a substituted or unsubstituted group selected from methyl and ethyl; preferably, R$_{13}$ is hydrogen or a unsubstituted group selected from methyl and ethyl, In a preferred embodiment R$_{13'}$ is substituted or unsubstituted methyl, preferably, R$_{13}$ is unsubstituted methyl, In a preferred embodiment R$_{13'''}$ is substituted or unsubstituted methyl, preferably, R$_{13}$ is unsubstituted methyl, In a preferred embodiment R$_{13}$ is hydrogen or substituted or unsubstituted methyl, while R$_{13'}$ or R$_{13'''}$ are substituted or unsubstituted methyl; preferably, R$_{13}$ is hydrogen or unsubstituted methyl, while R$_{13'}$ or R$_{13'''}$ are unsubstituted methyl;

In a preferred embodiment

R$_{13}$ is hydrogen, while R$_{13'}$ is substituted or unsubstituted methyl; preferably, R$_{13}$ is hydrogen, while R$_{13'}$ unsubstituted methyl;

In a preferred embodiment

R$_{13}$ is substituted or unsubstituted methyl, while R$_{13'''}$ is substituted or unsubstituted methyl; preferably, R$_{13}$ is unsubstituted methyl, while R$_{13'}$ or R$_{13'''}$ are unsubstituted methyl;

In a preferred embodiment

R$_{14}$ is hydrogen.

In a preferred embodiment

R$_{15}$ is substituted or unsubstituted methyl, more preferably unsubstituted methyl;

In a preferred embodiment

R$_n$ is hydrogen or substituted or unsubstituted methyl, preferably is hydrogen or unsubstituted methyl.

In another preferred embodiment n is 1, 2 or 3;

In another preferred embodiment p is 2 or 3;

In another preferred embodiment r is 0, 1 or 2

In an particular embodiment the halogen is fluorine or chlorine, bromine or iodine, preferably is fluorine or chlorine.

In an particular embodiment

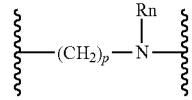

is —[CH$_2$]$_2$—N(Rn)— or —[CH$_2$]$_3$—N(Rn)—; wherein R$_n$ is hydrogen or substituted or unsubstituted methyl, preferably R$_n$ is hydrogen or unsubstituted methyl.

In an particular embodiment

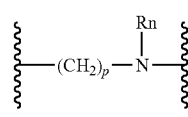

is —[CH$_2$]$_2$—N(Rn)—; wherein R$_n$ is hydrogen or substituted or unsubstituted methyl, preferably R$_n$ is hydrogen or unsubstituted methyl.

In an particular embodiment

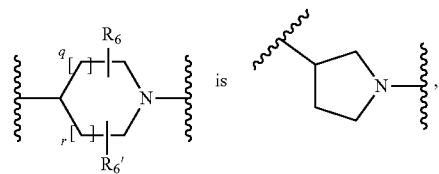

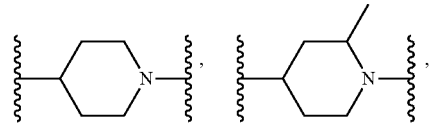

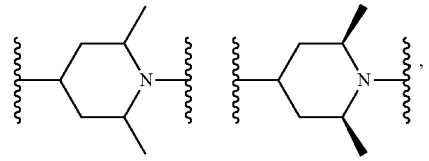

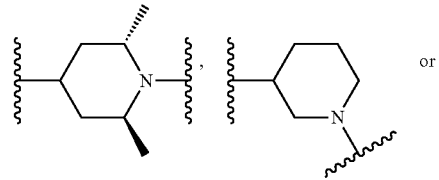

or

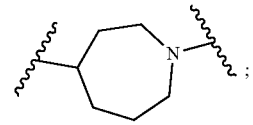

;

more preferably is

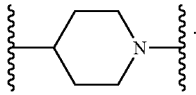

In an particular embodiment

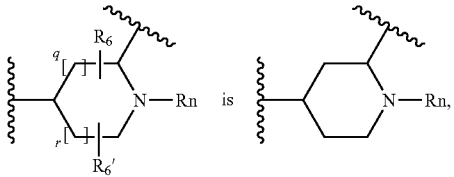 is wherein $R_n$ is hydrogen or substituted or unsubstituted methyl, preferably $R_n$ is hydrogen or unsubstituted methyl, more preferably $R_n$ is unsubstituted methyl.

In an particular embodiment

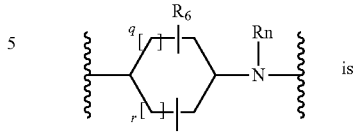 is

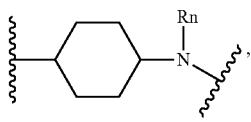, wherein $R_n$ is hydrogen or substituted or unsubstituted methyl, preferably $R_n$ is hydrogen or unsubstituted methyl, more preferably $R_n$ is hydrogen.

In a preferred further embodiment, the compounds of the general Formula (I) are selected from

| EX | Chemical name |
|---|---|
| 1 | N-(1-Benzylpiperidin-4-yl)-N-[1-(4-fluorophenyl)-1H-pyrazol-3-yl]thiophene-2-carboxamide |
| 2 | N-(1-Benzylpiperidin-4-yl)-N-[1-(4-fluorophenyl)-1H-pyrazol-3-yl]furan-2-carboxamide |
| 3 | N-(1-Benzylpiperidin-4-yl)-N-[1-(4-fluorophenyl)-1H-pyrazol-3-yl]isoxazole-5-carboxamide |
| 4 | N-(1-Benzylpiperidin-4-yl)-N-[1-(4-fluorophenyl)-1H-pyrazol-3-yl]furan-3-carboxamide |
| 5 | N-(1-Benzylpiperidin-4-yl)-N-[1-(4-fluorophenyl)-1H-pyrazol-3-yl]thiazole-2-carboxamide |
| 6 | N-(1-Benzylpiperidin-4-yl)-N-[1-(4-fluorophenyl)-1H-pyrazol-3-yl]-1-methyl-1H-pyrrole-2-carboxamide |
| 7 | N-(1-Benzylpiperidin-4-yl)-N-[1-(4-fluorophenyl)-1H-pyrazol-3-yl]oxazole-5-carboxamide |
| 8 | N-[1-(4-Fluorophenyl)-1H-pyrazol-3-yl]-N-(1-phenethylpiperidin-4-yl)thiophene-2-carboxamide |
| 9 | N-[1-(4-Fluorophenyl)-1H-pyrazol-3-yl]-N-(1-phenethylpiperidin-4-yl)isoxazole-5-carboxamide |
| 10 | N-(1-Benzylpiperidin-4-yl)-N-[5-(4-fluorophenyl)pyrazin-2-yl]thiophene-2-carboxamide |
| 11 | N-(1-Benzylpiperidin-4-yl)-N-[6-(4-fluorophenyl)pyrazin-2-yl]thiophene-2-carboxamide |
| 12 | N-(1-Benzylpiperidin-4-yl)-N-(6-phenylpyrazin-2-yl)thiophene-2-carboxamide |
| 13 | N-(1-Benzylpiperidin-4-yl)-N-[6-(4-ethoxyphenyl)pyrazin-2-yl]thiophene-2-carboxamide |
| 14 | N-(1-Benzylpiperidin-4-yl)-N-[1-(4-ethoxyphenyl)-1H-pyrazol-3-yl]thiophene-2-carboxamide |
| 15 | N-(1-Benzylpiperidin-4-yl)-N-[1-(4-ethoxyphenyl)-1H-pyrazol-3-yl]thiazole-2-carboxamide |
| 16 | N-(1-Phenethylpiperidin-4-yl)-N-(1-phenyl-1H-pyrazol-3-yl) thiophene-2-carboxamide |
| 17 | N-(1-Benzylpiperidin-4-yl)-N-(1-phenyl-1H-pyrazol-3-yl)thiophene-2-carboxamide |
| 18 | N-(1-Benzylpiperidin-4-yl)-N-(1-phenyl-1H-pyrazol-3-yl)furan-2-carboxamide |
| 19 | N-(1-Benzylpiperidin-4-yl)-N-(1-phenyl-1H-pyrazol-3-yl)thiazole-2-carboxamide |
| 20 | N-(1-Benzylpiperidin-4-yl)-N-(1-phenyl-1H-pyrazol-3-yl)picolinamide |
| 21 | N-(1-Benzylpiperidin-4-yl)-N-(1-phenyl-1H-pyrazol-3-yl)thiazole-5-carboxamide |
| 22 | N-(1-Benzylpiperidin-4-yl)-5-fluoro-N-(1-phenyl-1H-pyrazol-3-yl)thiophene-2-carboxamide |
| 23 | N-(1-Benzylpiperidin-4-yl)-5-chloro-N-(1-phenyl-1H-pyrazol-3-yl)thiophene-2-carboxamide |
| 24 | N-(1-Benzylpiperidin-4-yl)-3-chloro-N-(1-phenyl-1H-pyrazol-3-yl)thiophene-2-carboxamide |
| 25 | N-(1-Benzylpiperidin-4-yl)-N-(1-phenyl-1H-pyrazol-3-yl)isothiazole-5-carboxamide |
| 26 | N-(1-Benzylpiperidin-4-yl)-4-methoxy-N-(1-phenyl-1H-pyrazol-3-yl)benzamide |
| 27 | N-(1-Methylpiperidin-4-yl)-N-(1-phenyl-1H-pyrazol-3-yl)thiophene-2-carboxamide |
| 28 | 3-Methoxy-N-(1-methyl-piperidin-4-yl)-N-(1-phenyl-1H-pyrazol-3-yl)-benzamide |
| 29 | 3-(5-Methyl-[1,3,4]oxadiazol-2-yl)-N-(1-methyl-piperidin-4-yl)-N-(1-phenyl-1H-pyrazol-3-yl)-benzamide |
| 30 | N-(1-Methylpiperidin-4-yl)-N-(1-phenyl-1H-pyrazol-3-yl)benzamide |
| 31 | 2-Methoxy-N-(1-methylpiperidin-4-yl)-N-(1-phenyl-1H-pyrazol-3-yl)benzamide |

| EX | Chemical name |
|---|---|
| 32 | 3-Fluoro-N-(1-methylpiperidin-4-yl)-N-1-phenyl-1H-pyrazol-3-yl)picolinamide |
| 33 | N-(1-Methylpiperidin-4-yl)-N-(1-phenyl-1H-pyrazol-3-yl)nicotinamide |
| 34 | 2-Fluoro-6-methyl-N-(1-methylpiperidin-4-yl)-N-(1-phenyl-1H-pyrazol-3-yl)benzamide |
| 35 | 4-Methyl-N-(1-methylpiperidin-4-yl)-N-(1-phenyl-1H-pyrazol-3-yl)thiazole-2-carboxamide |
| 36 | 6-Methyl-N-(1-methylpiperidin-4-yl)-N-(1-phenyl-1H-pyrazol-3-yl)nicotinamide |
| 37 | N-(1-Methylpiperidin-4-yl)-N-(1-phenyl-1H-pyrazol-3-yl)-1H-pyrrole-2-carboxamide |
| 38 | N-(1-Methylpyrrolidin-3-yl)-N-(1-phenyl-1H-pyrazol-3-yl)thiophene-2-carboxamide |
| 39 | N-(1-Methylazepan-4-yl)-N-(1-phenyl-1H-pyrazol-3-yl)thiophene-2-carboxamide |
| 40 | N-(1-Benzyl-2,6-dimethylpiperidin-4-yl)-N-(1-phenyl-1H-pyrazol-3-yl)thiophene-2-carboxamide |
| 41 | N-(1-Phenyl-1H-pyrazol-3-yl)-N-(1,2,6-trimethylpiperidin-4-yl)thiophene-2-carboxamide |
| 42 | N-[1-(3,4-Dichlorophenyl)-1H-pyrazol-3-yl]-N-(1-phenethylpiperidin-4-yl)furan-2-carboxamide |
| 43 | N-(1-Benzylpiperidin-4-yl)-N-{1-[3-(5-methyl-1,3,4-oxadiazol-2-yl)phenyl]-1H-pyrazol-3-yl}-1,3-thiazole-2-carboxamide |
| 44 | N-(1-Benzylpiperidin-4-yl)-N-{1-[3-(5-methyl-1,3,4-oxadiazol-2-yl)phenyl]-1H-pyrazol-3-yl}-isothiazole-5-carboxamide |
| 45 | N-{1-[3-(5-Methyl-1,3,4-oxadiazol-2-yl)phenyl]-1H-pyrazol-3-yl}-N-{1-[2-pyridin-2-yl)ethyl]piperidin-4-yl}thiophene-2-carboxamide |
| 46 | N-[1-(3-Methoxyphenyl)-1H-pyrazol-3-yl]-N-[1-(pyridin-3-ylmethyl)piperidin-4-yl]thiophene-2-carboxamide |
| 47 | N-(1-benzylpiperidin-4-yl)-N-(1-phenyl-1H-1,2,4-triazol-3-yl)thiophene-2-carboxamide |
| 48 | N-(1-benzylpiperidin-4-yl)-N-(1-phenyl-1H-1,2,4-triazol-3-yl)furan-2-carboxamide |
| 49 | N-(1-phenethylpiperidin-4-yl)-N-(1-phenyl-1H-1,2,4-triazol-3-yl)thiophene-2-carboxamide |
| 50 | 3-Hydroxy-N-{1-[3-(5-methyl-1,3,4-oxadiazol-2-yl)phenyl]-1H-pyrazol-3-yl}-N-(1-methylpiperidin-4-yl)benzamide |
| 51 | N-(1-Benzylpiperidin-4-yl)-3-hydroxy-N-{1-[3-(5-methyl-1,3,4-oxadiazol-2-yl)phenyl]-1H-pyrazol-3-yl}benzamide |
| 52 | N-(1-Phenyl-1H-pyrazol-3-yl)-N-piperidin-4-ylthiophene-2-carboxamide |
| 53 | N-(1-Phenyl-1H-pyrazol-3-yl)-N-(piperidin-3-yl)thiophene-2-carboxamide |
| 54 | N-(2-Benzylpiperidin-4-yl)-N-(1-phenyl-1H-pyrazol-3-yl)thiophene-2-carboxamide |
| 55 | N-[2-(Benzylamino)ethyl]-N-(1-phenyl-1H-pyrazol-3-yl)thiophene-2-carboxamide |
| 56 | N-[3-(Benzylamino)propyl]-N-(1-phenyl-1H-pyrazol-3-yl)thiophene-2-carboxamide |
| 57 | N-[2-(Methylamino)ethyl]-N-(1-phenyl-1H-pyrazol-3-yl)thiophene-2-carboxamide |
| 58 | N-(1-Isobutylpiperidin-4-yl)-N-(1-phenyl-1H-pyrazol-3-yl)thiophene-2-carboxamide |
| 59 | N-(1-Ethylpiperidin-4-yl)-N-(1-phenyl-1H-pyrazol-3-yl)thiophene-2-carboxamide |
| 60 | N-(1-Isopropylpiperidin-4-yl)-N-(1-phenyl-1H-pyrazol-3-yl)thiophene-2-carboxamide |
| 61 | N-{2-[Benzyl(methyl)amino]ethyl}-N-(1-phenyl-1H-pyrazol-3-yl)thiophene-2-carboxamide |
| 62 | N-{3-[Benzyl(methyl)amino]propyl}-N-(1-phenyl-1H-pyrazol-3-yl)thiophene-2-carboxamide |
| 63 | N-{2-[Benzyl(methyl)amino]ethyl}-N-(1-phenyl-1H-pyrazol-3-yl)thiophene-2-carboxamide |
| 64 | N-{2-[Methyl(pyridin-4-ylmethyl)amino]ethyl}-N-(1-phenyl-1H-pyrazol-3-yl)thiophene-2-carboxamide |
| 65 | N-{2-[Methyl(pyridin-4-ylmethyl)amino]ethyl}-N-(1-phenyl-1H-py-razol-3-yl)thiophene-2-carboxamide |
| 66 | N-{2-[Methyl(pyridin-4-ylmethyl)amino]ethyl}-N-(1-phenyl-1H-pyrazol-3-yl)thiophene-2-carboxamide |
| 67 | N-(1-Methylpiperidin-3-yl)-N-(1-phenyl-1H-pyrazol-3-yl)thiophene-2-carboxamide |
| 68 | N-[2-(Ethylamino)ethyl]-N-(1-phenyl-1H-pyrazol-3-yl)thiophene-2-carboxamide |
| 69 | N-{2-[Benzyl(methyl)amino]ethyl}-N-{1-[3-(5-methyl-1,3,4-oxadiazol-2-yl)phenyl]-1H-pyrazol-3-yl}thiophene-2-carboxamide |
| 70 | N-(1-Methylpiperidin-4-yl)-N-(1-pyridin-2-yl-1H-pyrazol-3-yl)thiophene-2-carboxamide |
| 71 | N-(1-Methylpiperidin-4-yl)-N-[1-(pyridin-3-yl)-1H-pyrazol-3-yl]thiophene-2-carboxamide |
| 72 | N-[1-(3-Fluoropyridin-4-yl)-1H-pyrazol-3-yl]-N-(1-methylpiperidin-4-yl)thiophene-2-carboxamide |
| 73 | N-(1-Methylpiperidin-4-yl)-N-[1-(3-methylpyridin-4-yl)-1H-pyrazol-3-yl]thiophene-2-carboxamide |
| 74 | N-(1-Methylpiperidin-4-yl)-N-[1-(o-tolyl)-1H-pyrazol-3-yl]thiophene-2-carboxamide |
| 75 | N-{1-[3-(2-Methoxyethoxy)phenyl]-1H-pyrazol-3-yl}-N-(1-methylpiperidin-4-yl)thiophene-2-carboxamide |
| 76 | N-[1-(3-Methoxy-5-methylphenyl)-1H-pyrazol-3-yl]-N-(1-methylpiperidin-4-yl)thiophene-2-carboxamide |
| 77 | N-(1-Benzylpiperidin-4-yl)-N-[1-(3,5-dichloropyridin-4-yl)-1H-pyrazol-3-yl]thiophene-2-carboxamide |
| 78 | N-(1-Benzylpiperidin-4-yl)-N-[1-(pyridin-4-yl)-1H-pyrazol-3-yl]thiophene-2-carboxamide |
| 79 | N-(1-Benzylpiperidin-4-yl)-N-[1-(pyridin-3-yl)-1H-pyrazol-3-yl]thiophene-2-carboxamide |

| EX | Chemical name |
|---|---|
| 80 | N-(1-Benzylpiperidin-4-yl)-N-[1-(pyridin-2-yl)-1H-pyrazol-3-yl]thiophene-2-carboxamide |
| 81 | N-(1-Benzylpiperidin-4-yl)-N-[1-(o-tolyl)-1H-pyrazol-3-yl]thiophene-2-carboxamide |
| 82 | N-(1-Benzylpiperidin-4-yl)-N-[1-(3-fluoropyridin-4-yl)-1H-pyrazol-3-yl]thiophene-2-carboxamide |
| 83 | N-(1-Benzylpiperidin-4-yl)-N-[1-(3-chloropyridin-4-yl)-1H-pyrazol-3-yl]thiophene-2-carboxamide |
| 84 | N-[1-(3,4-Difluorobenzyl)piperidin-4-yl]-N-(1-[3-(5-methyl-1,3,4-oxadiazol-2-yl)phenyl]-1H-pyrazol-3-yl}thiophene-2-carboxamide |
| 85 | N-{1-[3-(5-Methyl-1,3,4-oxadiazol-2-yl)phenyl]-1H-pyrazol-3-yl}-N-(1-phenethylpiperidin-4-yl)thiophene-2-carboxamide |
| 86 | N-{1-[3-(5-Methyl-1,3,4-oxadiazol-2-yl)phenyl]-1H-pyrazol-3-yl}-N-(1-pyridin-2-ylmethyl)piperidin-4-yl)thiophene-2-carboxamide |
| 87 | N-[1-(4-Ethoxyphenyl)-1H-pyrazol-3-yl]-N-(1-methylpiperidin-4-yl)thiophene-2-carboxamide |
| 88 | N-[1-(3-Ethoxyphenyl)-1H-pyrazol-3-yl]-N-(1-methylpiperidin-4-yl)thiophene-2-carboxamide |
| 89 | N-[1-(4-Cyanophenyl)-1H-pyrazol-3-yl]-N-(1-methylpiperidin-4-yl)thiophene-2-carboxamide |
| 90 | N-[1-(3-Cyanophenyl)-1H-pyrazol-3-yl]-N-(1-methylpiperidin-4-yl)thiophene-2-carboxamide |
| 91 | N-[1-(4-Fluorophenyl)-1H-pyrazol-3-yl]-N-(1-methylpiperidin-4-yl)thiophene-2-carboxamide |
| 92 | N-[1-(3-Fluorophenyl)-1H-pyrazol-3-yl]-N-(1-methylpiperidin-4-yl)thiophene-2-carboxamide |
| 93 | N-[1-(2-Fluorophenyl)-1H-pyrazol-3-yl]-N-(1-methylpiperidin-4-yl)thiophene-2-carboxamide |
| 94 | N-(1-Methylpiperidin-4-yl)-N-[1-(pyridin-4-yl)-1H-pyrazol-3-yl]thiophene-2-carboxamide |
| 95 | N-[1-(3,4-Dimethoxyphenyl)-1H-pyrazol-3-yl]-N-(1-methylpiperidin-4-yl)thiophene-2-carboxamide |
| 96 | N-[1-(2-Chloro-4-methoxyphenyl)-1H-pyrazol-3-yl]-N-(1-methylpiperidin-4-yl)thiophene-2-carboxamide |
| 97 | N-[1-(6-Methoxypyridin-3-yl)-1H-pyrazol-3-yl]-N-(1-methylpiperidin-4-yl)thiophene-2-carboxamide |
| 98 | N-[1-(2,4-Dichlorophenyl)-1H-pyrazol-3-yl]-N-(1-methylpiperidin-4-yl)thiophene-2-carboxamide |
| 99 | N-[1-(4-Fluoro-3-methoxyphenyl)-1H-pyrazol-3-yl]-N-(1-methylpiperidin-4-yl)thiophene-2-carboxamide |
| 100 | N-[1-(2-Chloro-5-methoxyphenyl)-1H-pyrazol-3-yl]-N-(1-methylpiperidin-4-yl)thiophene-2-carboxamide |
| 101 | N-[1-(3,5-Dimethoxyphenyl)-1H-pyrazol-3-yl]-N-(1-methylpiperidin-4-yl)thiophene-2-carboxamide |
| 102 | N-[1-(3-Chloro-5-methoxyphenyl)-1H-pyrazol-3-yl]-N-(1-methylpiperidin-4-yl)thiophene-2-carboxamide |
| 103 | N-(1-Methylpiperidin-4-yl)-N-{1-[3-(trifluoromethoxy)phenyl]-1H-pyrazol-3-yl}thiophene-2-carboxamide |
| 104 | N-[1-(3-Fluoro-5-methoxyphenyl)-1H-pyrazol-3-yl]-N-(1-methylpiperidin-4-yl)thiophene-2-carboxamide |
| 105 | N-[1-(2-Methoxypyridin-4-yl)-1H-pyrazol-3-yl]-N-(1-methylpiperidin-4-yl)thiophene-2-carboxamide |
| 106 | N-{1-[3-(Dimethylamino)phenyl]-1H-pyrazol-3-yl}-N-(1-methylpiperidin-4-yl)thiophene-2-carboxamide |
| 107 | N-[1-(3-Acetamidophenyl)-1H-pyrazol-3-yl]-N-(1-methylpiperidin-4-yl)thiophene-2-carboxamide |
| 108 | N-(1-Methylpiperidin-4-yl)-N-{1-[3-(methylsulfonamido)phenyl]-1H-pyrazol-3-yl}thiophene-2-carboxamide |
| 109 | N-(2'-Methyl-2'H-[1,3'-bipyrazol]-3-yl)-N-(1-methylpiperidin-4-yl)thiophene-2-carboxamide |
| 110 | N-[1-(3-Methoxyphenyl)-1H-pyrazol-3-yl]-N-(1-methylpiperidin-4-yl)thiophene-3-carboxamide |
| 111 | 3-Hydroxy-N-[1-(3-methoxyphenyl)-1H-pyrazol-3-yl]-N-(1-methylpiperidin-4-yl)benzamide |
| 112 | N-[1-(3-Methoxyphenyl)-1H-pyrazol-3-yl]-N-(1-methylpiperidin-4-yl)thiophene-2-carboxamide |
| 113 | N-{1-[3-(5-Methyl-1,3,4-oxadiazol-2-yl)phenyl]-1H-pyrazol-3-yl}-N-(1-methylpiperidin-4-yl)thiophene-2-carboxamide |
| 114 | N-[1-(3-Hydroxyphenyl)-1H-pyrazol-3-yl]-N-(1-methylpiperidin-4-yl)thiophene-2-carboxamide |
| 115 | N-(5-Methyl-1-phenyl-1H-pyrazol-3-yl)-N-(1-methylpiperidin-4-yl)thiophene-2-carboxamide |
| 116 | N-(1-Benzylpiperidin-4-yl)-N-[1-(4-cyanophenyl)-1H-pyrazol-3-yl]thiophene-2-carboxamide |
| 117 | N-(1-Benzylpiperidin-4-yl)-N-[1-(3-cyanophenyl)-1H-pyrazol-3-yl]thiophene-2-carboxamide |
| 118 | N-(1-Benzylpiperidin-4-yl)-N-{1-[3-(5-methyl-1,3,4-oxadiazol-2-yl)phenyl]-1H-pyrazol-3-yl}-thiophene-2-carboxamide |

| EX | Chemical name |
|---|---|
| 119 | N-(1-Benzylpiperidin-4-yl)-N-[1-(3-fluorophenyl)-1H-pyrazol-3-yl]thiophene-2-carboxamide |
| 120 | N-(1-Benzylpiperidin-4-yl)-N-{1-3-(5-methyl-1,3,4-oxadiazol-2-yl)phenyl]-1H-pyrazol-3-yl}-2-furamide |
| 121 | N-[1-(3-Methoxyphenyl)-1H-pyrazol-3-yl]-N-[1-(pyridin-2-ylmethyl)piperidin-4-yl]thiophene-2-carboxamide |
| 122 | N-[1-(3-Methoxyphenyl)-1H-pyrazol-3-yl]-N-[1-{[6-(trifluoromethyl)pyridin-3-yl]methyl}piperidin-4-yl)thiophene-2-carboxamide |
| 123 | N-[1-(2-Chloro-4-hydroxyphenyl)-1H-pyrazol-3-yl]-N-(1-methylpiperidin-4-yl]thiophene-2-carboxamide |
| 124 | N-[1-(4-Fluoro-3-hydroxyphenyl)-1H-pyrazol-3-yl]-N-(1-methylpiperidin-4-yl]thiophene-2-carboxamide |
| 125 | N-[1-(2-Chloro-5-hydroxyphenyl)-1H-pyrazol-3-yl]-N-(1-methylpiperidin-4-yl]thiophene-2-carboxamide |
| 126 | N-(1-Isobutylpiperidin-4-yl)-N-{1-[3-(5-methyl-1,3,4-oxadiazol-2-yl)phenyl]-1H-pyrazol-3-yl}-thiophene-2-carboxamide |
| 127 | N-[4-(Dimethylamino)cyclohexyl]-N-(1-phenyl-1H-pyrazol-3-yl)thiophene-2-carboxamide |
| 128 | N-{4-[Benzyl(methyl)amino]cyclohexyl}-N-(1-phenyl-1H-pyrazol-3-yl)thiophene-2-carboxamide |
| 129 | N-[6-(4-Fluorophenyl)pyrazin-2-yl]-N-(1-methylpiperidin-4-yl)thiophene-2-carboxamide |
| 130 | N-{6-[3-(5-Methyl-1,3,4-oxadiazol-2-yl)phenyl]pyridin-2-yl]-N-(1-methylpiperidin-4-yl)thiophene-2-carboxamide |
| 131 | N-[6-(3-Methoxyphenyl)pyrazin-2-yl]-N-(1-methylpiperidin-4-yl)thiophene-2-carboxamide |
| 132 | N-[6-(4-Methoxyphenyl)pyrazin-2-yl]-N-(1-methylpiperidin-4-yl)thiophene-2-carboxamide |
| 133 | N-[6-(4-Fluorophenyl)pyrazin-2-yl]-N-(piperidin-4-yl)thiophene-2-carboxamide |
| 134 | N-[6-(4-Fluorophenyl)pyrazin-2-yl]-N-(1-methylpiperidin-4-yl)thiophene-2-carboxamide |
| 135 | N-(1-benzylpiperidin-4-yl)-N-(1-(4-fluorophenyl)-1H-1,2,3-triazol-4-yl)thiophene-2-carboxamide |
| 136 | N-(1-benzylpiperidin-4-yl)-N-(1-phenyl-1H-1,2,3-triazol-4-yl)thiophene-2-carboxamide |
| 137 | N-(1-benzylpiperidin-4-yl)-N-(2-phenyl-2H-1,2,3-triazol-4-yl)thiophene-2-carboxamide | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| EX | Structure | Chemical name |
|---|---|---|
| 138 | 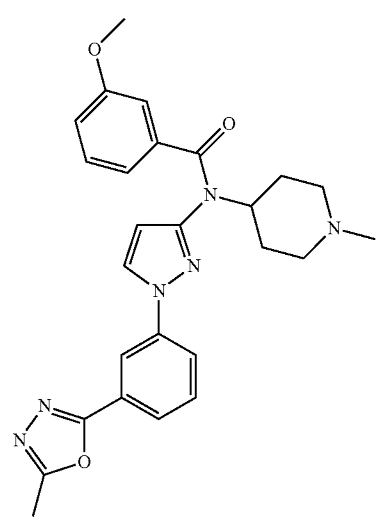 [SMILES: COc1cccc(C(=O)N(c2ccn(-c3cccc(-c4nnc(C)o4)c3)n2)C2CCN(C)CC2)c1] | 3-Methoxy-N-{1-[3-(5-methyl-1,3,4-oxadiazol-2-yl)phenyl]-1H-pyrazol-3-yl}-N-(1-methylpiperidin-4-yl)benzamide |

| EX | Structure | Chemical name |
| --- | --- | --- |
| 139 | 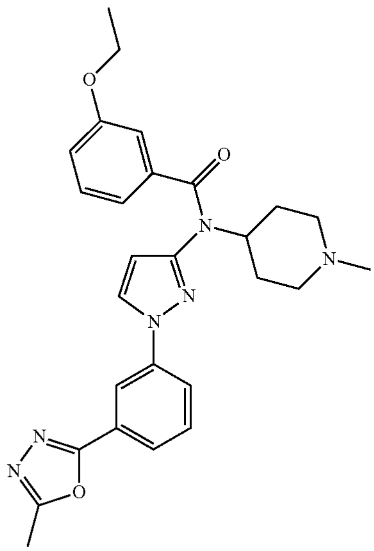 [SMILES: CCOc1cccc(C(=O)N(c2ccn(-c3cccc(-c4nnc(C)o4)c3)n2)C2CCN(C)CC2)c1] | 3-Ethoxy-N-{1-[3-(5-methyl-1,3,4-oxadiazol-2-yl)phenyl]-1H-pyrazol-3-yl}-N-(1-methylpiperidin-4-yl)benzamide |
| 140 | 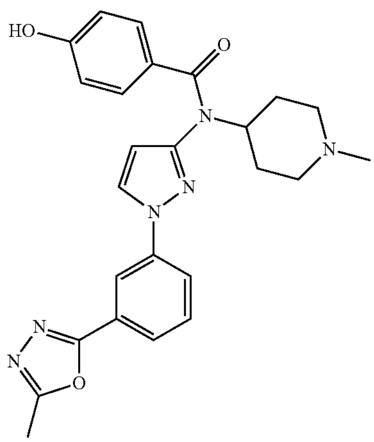 [SMILES: Cc1nnc(-c2cccc(-n3ccc(N(C(=O)c4ccc(O)cc4)C4CCN(C)CC4)n3)c2)o1] | 4-Hydroxy-N-{1-[3-(5-methyl-1,3,4-oxadiazol-2-yl)phenyl]-1H-pyrazol-3-yl}-N-(1-methylpiperidin-4-yl)benzamide |
| 141 | 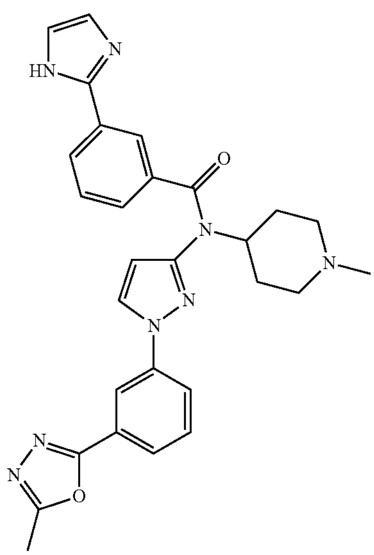 [SMILES: Cc1nnc(-c2cccc(-n3ccc(N(C(=O)c4cccc(-c5ncc[nH]5)c4)C4CCN(C)CC4)n3)c2)o1] | 3-(1H-Imidazol-2-yl)-N-{1-[3-(5-methyl-1,3,4-oxadiazol-2-yl)phenyl]-1H-pyrazol-3-yl}-N-(1-methylpiperidin-4-yl)benzamide |

| EX | Structure | Chemical name |
|---|---|---|
| 142 | 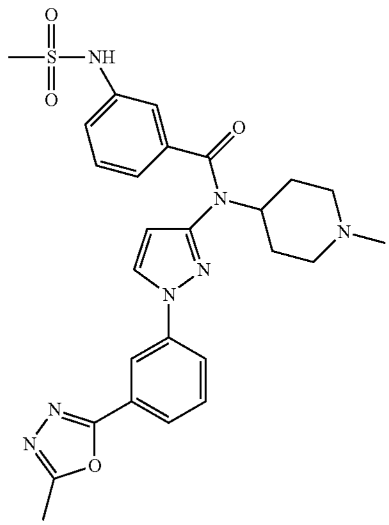 | N-{1-[3-(5-Methyl-1,3,4-oxadiazol-2-yl)phenyl]-1H-pyrazol-3-yl}-N-(1-methylpiperidin-4-yl)-3-(methylsulfonamido)benzamide |
| 143 | 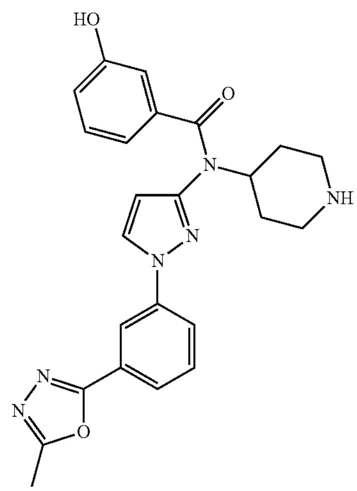 [SMILES: Cc1nnc(-c2cccc(-n3ccc(N(C(=O)c4cccc(O)c4)C4CCNCC4)n3)c2)o1] | 3-Hydroxy-N-{1-[3-(5-methyl-1,3,4-oxadiazol-2-yl)phenyl]-1H-pyrazol-3-yl}-N-(piperidin-4-yl)benzamide |
| 144 | 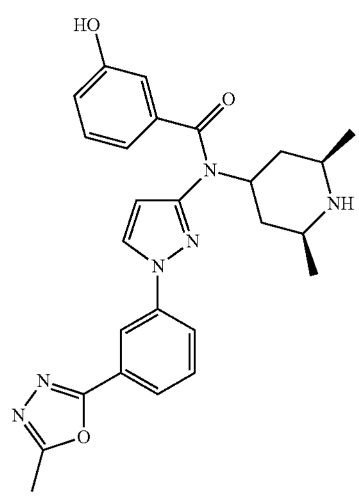 [SMILES: Cc1nnc(-c2cccc(-n3ccc(N(C(=O)c4cccc(O)c4)C4C[C@@H](C)N[C@@H](C)C4)n3)c2)o1] | N-[(2S,6R)-2,6-Dimethylpiperidin-4-yl]-3-hydroxy-N-{1-[3-(5-methyl-1,3,4-oxadiazol-2-yl)phenyl]-1H-pyrazol-3-yl}benzamide |

-continued

| EX | Structure | Chemical name |
|---|---|---|
| 145 | 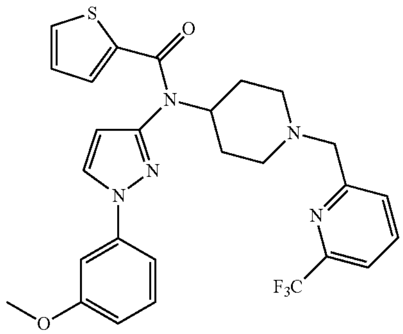 [SMILES: COc1cccc(-n2ccc(N(C(=O)c3cccs3)C3CCN(Cc4cccc(C(F)(F)F)n4)CC3)n2)c1] | N-[1-(3-Methoxyphenyl)-1H-pyrazol-3-yl]-N-(1-{[6-(trifluoromethyl)pyridin-2-yl]methyl}piperidin-4-yl)thiophene-2-carboxamide |
| 146 | 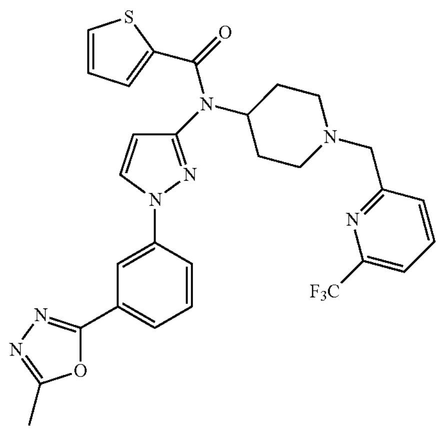 [SMILES: Cc1nnc(-c2cccc(-n3ccc(N(C(=O)c4cccs4)C4CCN(Cc5cccc(C(F)(F)F)n5)CC4)n3)c2)o1] | N-{1-[3-(5-Methyl-1,3,4-oxadiazol-2-yl)phenyl]-1H-pyrazol-3-yl}-N-(1-{[6-(trifluoromethyl)pyridin-2-yl]methyl}piperidin-4-yl)thiophene-2-carboxamide |
| 147 | 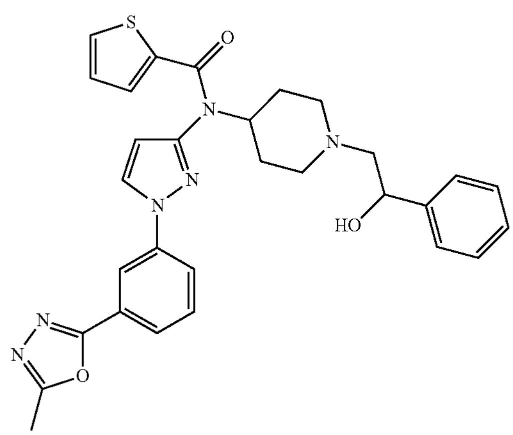 [SMILES: Cc1nnc(-c2cccc(-n3ccc(N(C(=O)c4cccs4)C4CCN(CC(O)c5ccccc5)CC4)n3)c2)o1] | N-[1-(2-Hydroxy-2-phenylethyl)piperidin-4-yl]-N-{1-[3-(5-methyl-1,3,4-oxadiazol-2-yl)phenyl]-1H-pyrazol-3-yl}thiophene-2-carboxamide |
| 149 | 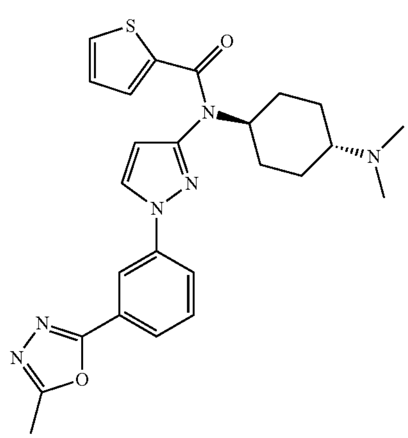 [SMILES: Cc1nnc(-c2cccc(-n3ccc(N(C(=O)c4cccs4)[C@H]4CC[C@H](N(C)C)CC4)n3)c2)o1] | N-[(1r,4r)-4-(Dimethylamino)cyclohexyl]-N-{1-[3-(5-methyl-1,3,4-oxadiazol-2-yl)phenyl]-1H-pyrazol-3-yl}thiophene-2-carboxamide |

-continued

| EX | Structure | Chemical name |
|---|---|---|
| 150 | 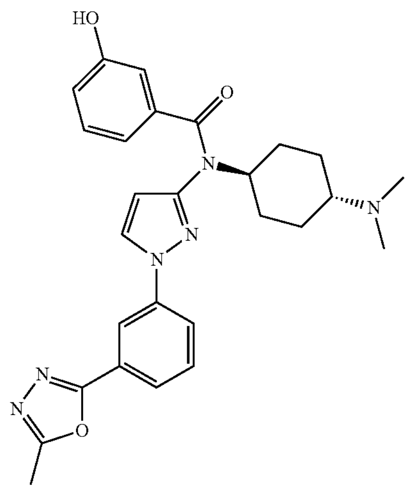 [SMILES: Cc1nnc(-c2cccc(-n3ccc(N(C(=O)c4cccc(O)c4)[C@H]4CC[C@H](N(C)C)CC4)n3)c2)o1] | N-[(1r,4r)-4-(Dimethylamino)cyclohexyl]-3-hydroxy-N-{1-[3-(5-methyl-1,3,4-oxadiazol-2-yl)phenyl]-1H-pyrazol-3-yl}benzamide |
| 151 | 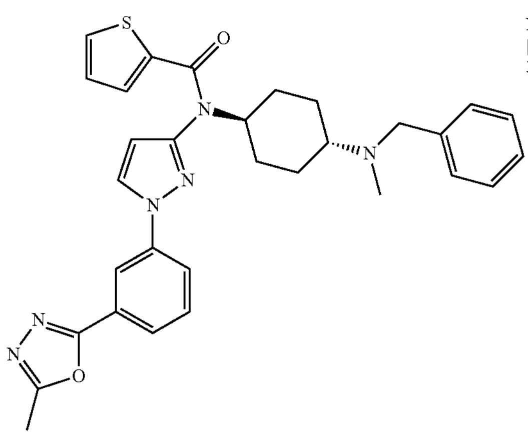 [SMILES: Cc1nnc(-c2cccc(-n3ccc(N(C(=O)c4cccs4)[C@H]4CC[C@H](N(C)Cc5ccccc5)CC4)n3)c2)o1] | N-{(1r,4r)-4-[Benzyl(methyl)amino]cyclohexyl}-N-{1-[3-(5-methyl-1,3,4-oxadiazol-2-yl)phenyl]-1H-pyrazol-3-yl}thiophene-2-carboxamide |
| 152 | 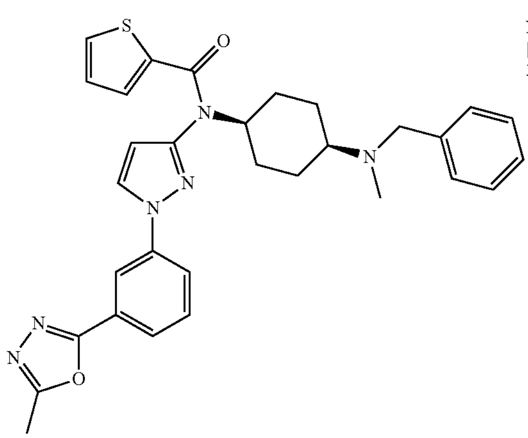 [SMILES: Cc1nnc(-c2cccc(-n3ccc(N(C(=O)c4cccs4)[C@H]4CC[C@@H](N(C)Cc5ccccc5)CC4)n3)c2)o1] | N-{(1s,4s)-4-[Benzyl(methyl)amino]cyclohexyl}-N-{1-[3-(5-methyl-1,3,4-oxadiazol-2-yl)phenyl]-1H-pyrazol-3-yl}thiophene-2-carboxamide |

-continued

| EX | Structure | Chemical name |
|---|---|---|
| 153 | 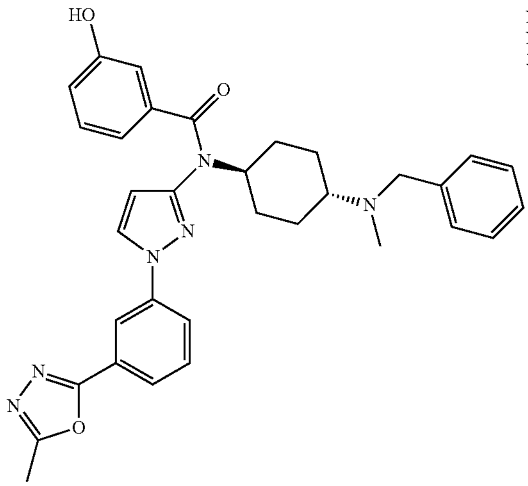 [SMILES: Cc1nnc(-c2cccc(-n3ccc(N(C(=O)c4cccc(O)c4)[C@H]4CC[C@H](N(C)Cc5ccccc5)CC4)n3)c2)o1] | N-{(1r,4r)-4-[Benzyl(methyl)amino]cyclohexyl}-3-hydroxy-N-{1-[3-(5-methyl-1,3,4-oxadiazol-2-yl)phenyl]-1H-pyrazol-3-yl}benzamide |
| 154 | 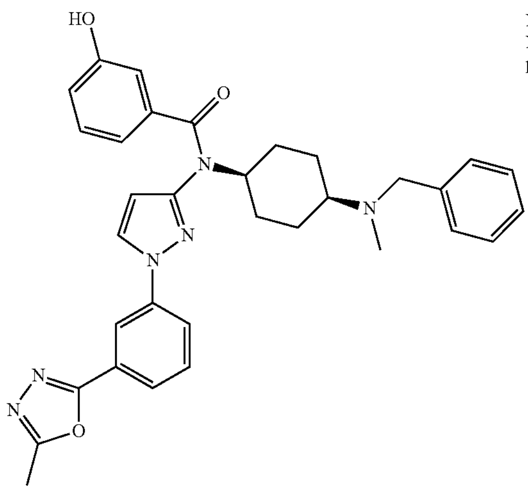 [SMILES: Cc1nnc(-c2cccc(-n3ccc(N(C(=O)c4cccc(O)c4)[C@H]4CC[C@@H](N(C)Cc5ccccc5)CC4)n3)c2)o1] | N-{(1s,4s)-4-[Benzyl(methyl)amino]cyclohexyl}-3-hydroxy-N-{1-[3-(5-methyl-1,3,4-oxadiazol-2-yl)phenyl]-1H-pyrazol-3-yl}benzamide |
| 155 | 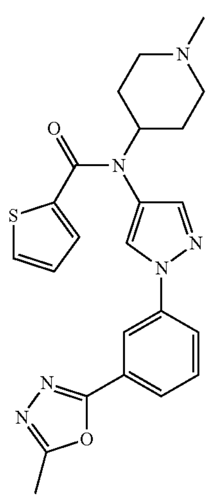 [SMILES: Cc1nnc(-c2cccc(-n3cc(N(C(=O)c4cccs4)C4CCN(C)CC4)cn3)c2)o1] | N-{1-[3-(5-Methyl-1,3,4-oxadiazol-2-yl)phenyl]-1H-pyrazol-4-yl}-N-(1-methylpiperidin-4-yl)thiophene-2-carboxamide |

-continued

| EX | Structure | Chemical name |
|---|---|---|
| 156 | 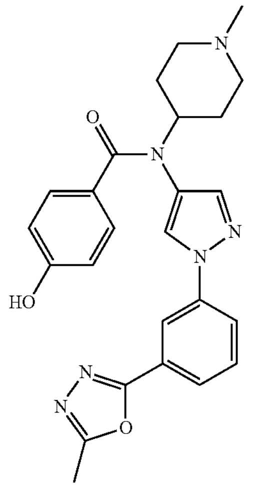 [SMILES: Cc1nnc(-c2cccc(-n3cc(N(C(=O)c4ccc(O)cc4)C4CCN(C)CC4)cn3)c2)o1] | 4-Hydroxy-N-{1-[3-(5-methyl-1,3,4-oxadiazol-2-yl)phenyl]-1H-pyrazol-4-yl}-N-(1-methylpiperidin-4-yl)benzamide |
| 157 | 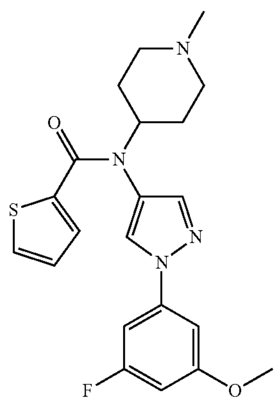 [SMILES: COc1cc(F)cc(-n2cc(N(C(=O)c3cccs3)C3CCN(C)CC3)cn2)c1] | N-[1-(3-Fluoro-5-methoxyphenyl)-1H-pyrazol-4-yl]-N-(1-methylpiperidin-4-yl)thiophene-2-carboxamide |
| 158 | | N-(1-Benzylpiperidin-4-yl)-N-{1-[3-(5-methyl-1,3,4-oxadiazol-2-yl)phenyl]-1H-pyrazol-4-yl}thiazole-2-carboxamide | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_1$ is selected from substituted or unsubstituted aryl and substituted or unsubstituted aromatic heterocyclyl;

wherein said aryl or aromatic heterocyclyl in $R_1$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$, and substituted or unsubstituted five membered aromatic heterocyclyl;
wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
$R_2$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted aromatic heterocyclyl,
wherein said cycloalkyl, aryl or aromatic heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;
wherein the alkyl, alkenyl or alkynyl in $R_2$, if substituted, is substituted with one or more substituent/s selected from —$OR_{12}$, halogen, —CN, haloalkyl, haloalkoxy and —$NR_{12}R_{12'''}$;
wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_3$ is selected from substituted or unsubstituted monocyclic aryl and substituted or unsubstituted monocyclic aromatic heterocyclyl,
wherein said aryl or aromatic heterocyclyl in $R_3$, if substituted, is substituted with one or more substituent/s selected from halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;
wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;
$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
$R_3$ is selected from substituted or unsubstituted aryl and substituted or unsubstituted aromatic heterocyclyl,
wherein said aryl or aromatic heterocyclyl in $R_3$, if substituted, is substituted with one or more substituent/s selected from halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;
wherein $R_{13}$, $R_{13'}$ and $R_{13''}$ are independently selected from hydrogen, unsubstituted $C_{1-6}$ alkyl, unsubstituted $C_{2-6}$ alkenyl, and unsubstituted $C_{2-6}$ alkynyl;
$R_{13'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
the alkyl, alkenyl or alkynyl, other than those defined in $R_2$, if substituted, is substituted with one or more substituent/s selected from —$OR_{14}$, halogen, —CN, haloalkyl, haloalkoxy and —$NR_{14}R_{14'''}$;
wherein $R_{14}$ is selected from hydrogen, unsubstituted $C_{1-6}$ alkyl, unsubstituted $C_{2-6}$ alkenyl, and unsubstituted $C_{2-6}$ alkynyl;
$R_{14'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
the aryl, heterocyclyl or cycloalkyl other than those defined in $R_1$, $R_2$ or $R_3$, if from halogen, —$R_{15}$, —$OR_{15}$, —$NO_2$, —$NR_{15}R_{15'''}$, $NR_{15}C(O)R_{15'}$, —$NR_{15}S(O)_2R_{15'}$, —$S(O)_2NR_{15}R_{15'}$, —$NR_{15}C(O)NR_{15'}R_{15''}$, —$SR_{15}$, —$S(O)R_{15}$, $S(O)_2R_{15}$, —CN, haloalkyl, haloalkoxy, —$C(O)OR_{15}$, —$C(O)NR_{15}R_{15'}$, —$OCH_2CH_2OH$, —$NR_{15}S(O)_2NR_{15'}R_{15''}$ and $C(CH_3)_2OR_{15}$;
wherein $R_{15}$, $R_{15'}$ and $R_{15''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{15'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the aryl or aromatic heterocyclyl in $R_1$ if substituted, is substituted with one or more substituent/s selected from halogen, $-R_{11}$, $-OR_{11}$, $-NO_2$, $-NR_{11}R_{11'''}$, $NR_{11}C(O)R_{11'}$, $-NR_{11}S(O)_2R_{11'}$, $-S(O)_2NR_{11}R_{11'}$, $-NR_{11}C(O)NR_{11'}R_{11'''}$, $-SR_{11}$, $-S(O)R_{11}$, $S(O)_2R_{11}$, $-CN$, haloalkyl, haloalkoxy, $-C(O)OR_{11}$, $-C(O)NR_{11}R_{11'}$, $-OCH_2CH_2OH$, $-NR_{11}S(O)_2NR_{11'}R_{11''}$ $C(CH_3)_2OR_{11}$, and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_1$ of any of the embodiments of the present invention, the aryl or aromatic heterocycyl in $R_1$ if substituted, is substituted with one or more substituent/s selected from halogen, $-R_{11}$, $-OR_{11}$, and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the aryl or aromatic heterocyclyl in $R_1$ if substituted, is substituted with one or more substituent/s selected from fluorine, chlorine, methyl, $-OH$, methoxy, ethoxy, $-NHS(O)_2$-methyl, 2-methyl-1,3,4-oxadiazole and imidazole;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the cycloalkyl, aryl or aromatic heterocyclyl in $R_2$, if substituted, is substituted with one or more substituents selected from halogen, $-R_{12}$, $-OR_{12}$, $-NO_2$, $-NR_{12}R_{12'''}$, $NR_{12}C(O)R_{12'}$, $-NR_{12}S(O)_2R_{12'}$, $-S(O)_2NR_{12}R_{12'}$, $-NR_{12}C(O)NR_{12'}R_{12'''}$, $-SR_{12}$, $-S(O)R_{12}$, $S(O)_2R_{12}$, $-CN$, haloalkyl, haloalkoxy, $-C(O)OR_{12}$, $-C(O)NR_{12}R_{12'}$, $-OCH_2CH_2OH$, $-NR_{12}S(O)_2NR_{12'}R_{12''}$ and $C(CH_3)_2OR_{12}$;
the alkyl, alkenyl or alkynyl in $R_2$, if substituted, is substituted with one or more substituent/s selected from $-OR_{12}$, halogen, $-CN$, haloalkyl, haloalkoxy and $-NR_{12}R_{12'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the cycloalkyl, aryl or aromatic heterocyclyl in $R_2$, if substituted, is substituted with one or more substituent/s selected from halogen and haloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the cycloalkyl, aryl or aromatic heterocyclyl in $R_2$, if substituted, is substituted with one or more substituent/s selected from fluorine and $-CF3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_3$ of any of the embodiments of the present invention,
the aryl or aromatic heterocyclyl in $R_3$, if substituted, is substituted with one or more substituent/s selected from halogen, $-R_{13}$, $-OR_{13}$, $-NO_2$, $-NR_{13}R_{13'''}$, $NR_{13}C(O)R_{13'}$, $-NR_{13}S(O)_2R_{13'}$, $-S(O)_2NR_{13}R_{13'}$, $-NR_{13}C(O)NR_{13'}R_{13'''}$, $-SR_{13}$, $-S(O)R_{13}$, $S(O)_2R_{13}$, $-CN$, haloalkyl, haloalkoxy, $-C(O)OR_{13}$, $-C(O)NR_{13}R_{13'}$, $-OCH_2CH_2OCH_3$, $-NR_{13}S(O)_2NR_{13'}R_{13'''}$, $C(CH_3)_2OR_{13}$ and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_3$ of any of the embodiments of the present invention,
the aryl or aromatic heterocyclyl in $R_3$, if substituted, is substituted with one or more substituent/s selected from halogen, $-R_{13}$, $-OR_{13}$, $-NR_{13}R_{13'''}$, $NR_{13}C(O)R_{13'}$, $-NR_{13}S(O)_2R_{13'}$, $-CN$, haloalkoxy, $-OCH_2CH_2OCH_3$ and substituted or unsubstituted five membered aromatic heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I),
the aryl or aromatic heterocyclyl in $R_3$, if substituted, is substituted with one or more substituent/s selected from fluorine, chlorine, methyl, $-OH$, methoxy, ethoxy, —CN, —OCH$_2$CH$_2$—OCH$_3$, —OCF$_3$, —N(methyl)$_2$, —NHC(O)— methyl, —NHS(O)$_2$-methyl and 2-methyl-1,3,4-oxadiazole;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), the alkyl, alkenyl or alkynyl, other than those defined in R$_2$, if substituted, is substituted with one or more substituent/s selected from —OR$_{14}$, halogen, —CN, haloalkyl, haloalkoxy and —NR$_{14}$R$_{14'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), the aryl, heterocyclyl or cycloalkyl other than those defined in R$_1$, R$_2$ or R$_3$, if substituted, is substituted with one or more substituent/s selected from halogen, —R$_{15}$, —OR$_{15}$, —NO$_2$, —NR$_{15}$R$_{15'''}$, NR$_{15}$C(O)R$_{15'}$, —NR$_{15}$S(O)$_2$R$_{15'}$, —S(O)$_2$NR$_{15}$R$_{15'}$, —NR$_{15}$C(O)NR$_{15'}$R$_{15'''}$, —SR$_{15}$, —S(O) R$_{15}$, S(O)$_2$R$_{15}$, —CN, haloalkyl, haloalkoxy, —C(O)OR$_{15}$, —C(O)NR$_{15}$R$_{15}$, —OCH$_2$CH$_2$OH, —NR$_{15}$S(O)$_2$NR$_{15'}$R$_{15}$" and C(CH$_3$)$_2$OR$_{15}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)

the halogen is fluorine or chlorine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the haloalkyl is —CF$_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I), the haloalkoxy is —OCF$_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the α2δ subunit, particularly the α2δ-1 subunit, of the voltage-gated calcium channel and the μ-opioid receptor it is a very preferred embodiment in which the compounds are selected which act as dual ligands of the α2δ subunit, particularly the α2δ-1 subunit, of the voltage-gated calcium channel and the μ-opioid receptor and especially compounds which have a binding expressed as K$_i$ responding to the following scales:

K$_i$(μ) is preferably <1000 nM, more preferably <500 nM, even more preferably <100 nM.

Ki(α2δ1) is preferably <10000 nM, more preferably <5000 nM, even more preferably <500 nM or even more preferably <100 nM.

In the following the phrase "compound of the invention" is used. This is to be understood as any compound according to the invention as described above according to general Formula (I), (I$^{5'}$) or (I$^{6a'}$), (I$^{6b'}$), (I$^{7'}$) or (I$^{9'}$) or to general Formula (I'), (I$^{2'}$), (I$^{3'}$) or (I$^{4'}$).

The compounds of the invention represented by the above described Formula (I) may include enantiomers depending on the presence of chiral centres or isomers depending on the presence of multiple bonds (e.g. Z, E).

The single isomers, enantiomers or diastereoisomers and mixtures thereof fall within the scope of the present invention.

For the sake of clarity the expression "a compound according to Formula (I), wherein R$_1$, R$_2$, R$_3$, R$_4$, etc. are as defined below in the detailed description" would (just like the expression e.g. "a compound of Formula (I) as defined in any one of claims 1 to 10" found in the claims) refer to "a compound according to Formula (I)", wherein the definitions of the respective substituents R$_1$ etc. (also from the cited claims) are applied. In addition, this would also mean, though (especially in regards to the claims) that also one or more disclaimers defined in the description (or used in any of the cited claims like e.g. claim 1) would be applicable to define the respective compound. Thus, a disclaimer found in e.g. claim 1 would be also used to define the compound "of Formula (I) as defined in any one of claims 1 to 10".

In general the processes are described below in the experimental part. The starting materials are commercially available or can be prepared by conventional methods.

A preferred aspect of the invention is also a process for the production of a compound according to Formula (I), following scheme 1.

A preferred embodiment of the invention is a process for the production of a compound according to Formula (I), wherein R$_1$, R$_2$, R$_3$, R$_4$, n, X and Y have the meanings defined in the description, following scheme 1.

In all processes and uses described underneath and in scheme 1, the values of R$_1$, R$_2$, R$_3$, R$_4$, p, q, r, n, X and Y are as defined in the description, wherein L is a leaving group such as halogen, mesylate, tosylate or triflate and Z is

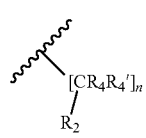

(the group indicated in a square in Scheme 1),

PG is a protecting group and A is (BOH)$_2$ or L.

In a particular embodiment there is a process for the production of a compound of Formula (I),

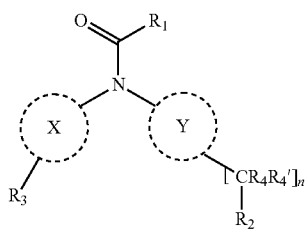
(I)

said process comprises the acylation of compounds of formula IVb

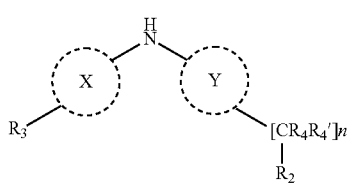
IVb with an acyl halide of formula V

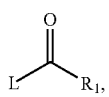
V following preferably the process as described under STEP 2 of scheme 1.

In a particular embodiment there is a process for the production of a compound of Formula (I),

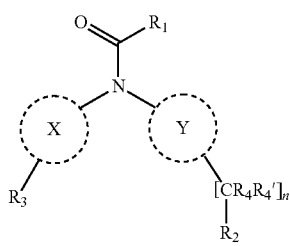
(I)

said process comprises the alkylation of a compound of Formula Ib,

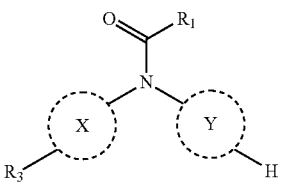
Ib with a compound of formula VIIa,

VIIa following preferably the process as described in STEP 4 of scheme 1.

In a particular embodiment there is a process for the production of a compound of Formula (I),

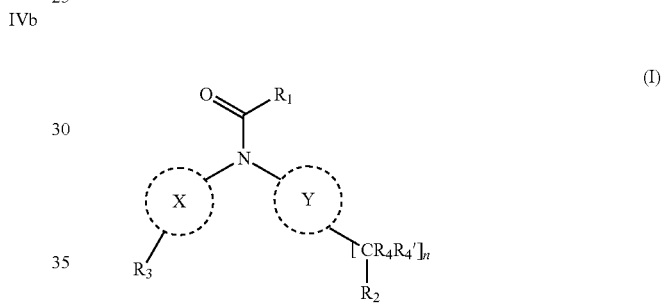
(I)

said process comprises the reductive amination reaction between a compound of formula Ib,

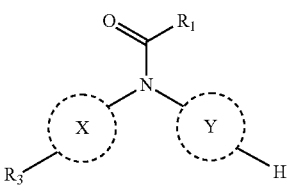
Ib and a compound of formula VIIb,

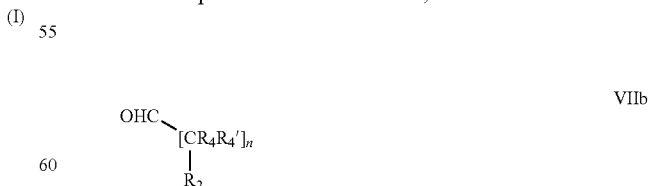
VIIb following preferably the process as described in STEP 4 of scheme 1.

In a particular embodiment there is a process for the production of a compound of Formula (I),

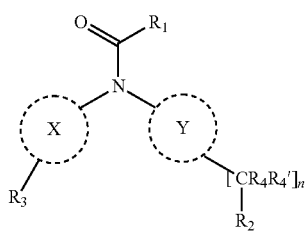
(I)

said process comprises the coupling between a compound of formula XIb

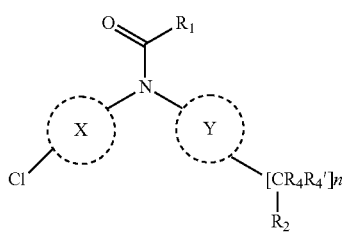
XIb with a compound of formula IX

R₃—A.
IX

In a particular embodiment there is a process for the production of a compound of Formula (I),

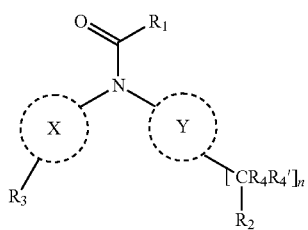
(I)

said process comprises the acylation of compounds of formula IVb

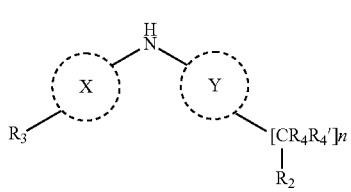
IVb with an acyl halide of formula V

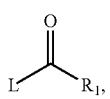
V or
the alkylation of a compound of Formula Ib,

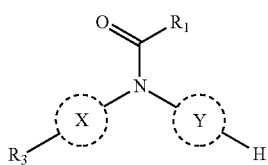
Ib with a compound of formula VIIa,

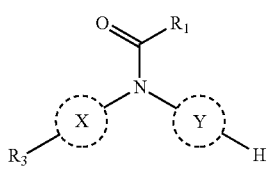
VIIa or
the reductive amination reaction between a compound of formula Ib,

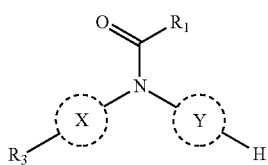
Ib and a compound of formula VIIb,

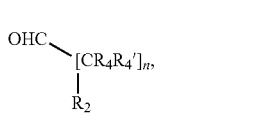
VIIb or
the coupling between a compound of formula XIb

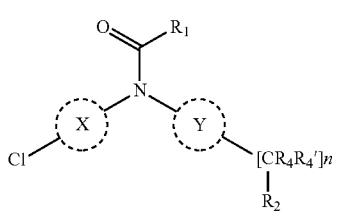
XIb with a compound of formula IX

R₃—A.   IX

In addition to the processes for the synthesis of compounds of formula (I), several processes for the preparation of the starting material of such synthesis and intermediates thereof are herein provided.

In particular, there is provided a process for the production of a compound (VIa) starting from a compound of formula (IVa),

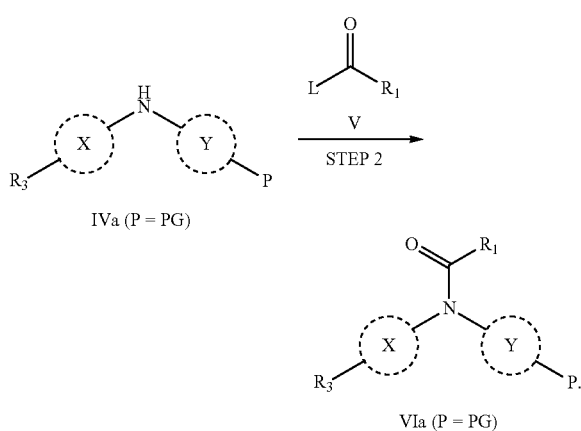

It is also provided a process for the production of a compound (IVa) starting with a compound (II),

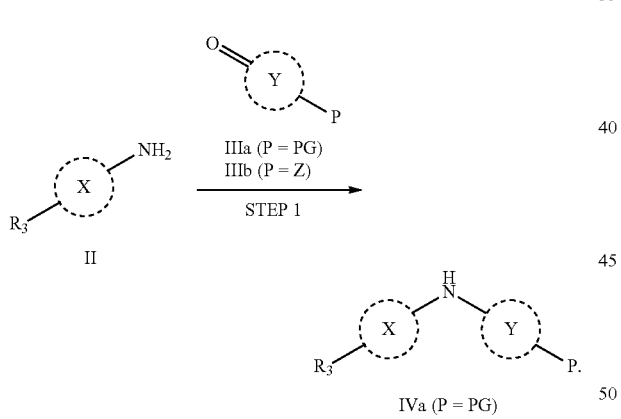

In a particular embodiment there is a process for the production of a compound (XIa) or (XIb) starting with a compound (Xa) or (Xb), respectively,

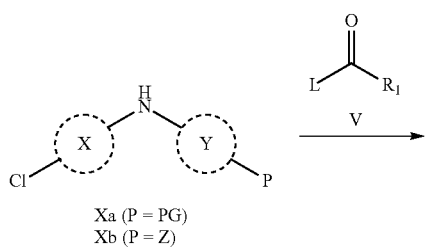

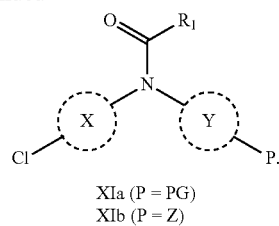

XIa (P = PG)
XIb (P = Z)

In a particular embodiment there is a process for the production of a compound (Xa) or (Xb) starting with a compound (VIII),

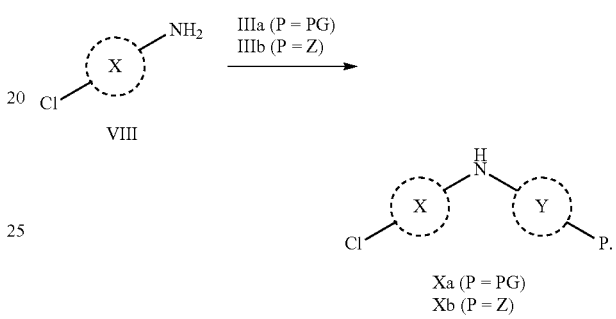

In a particular embodiment there is a process for the production of a compound (Ib) by deprotection of a compound of formula (VIa),

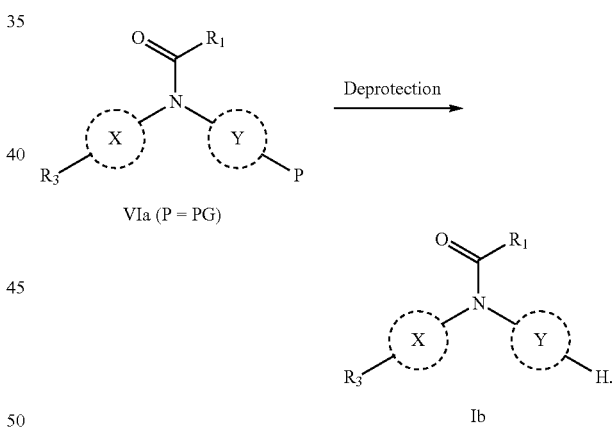

In a particular embodiment there is a process for the production of a compound (I) or (VIa) starting with a compound of formula (XIa) or (XIb), respectively

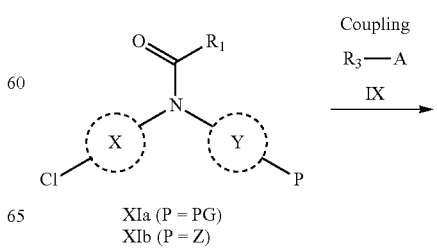

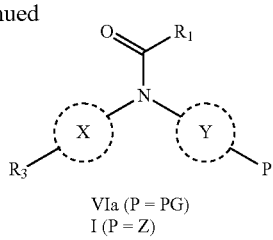

VIa (P = PG)
I (P = Z)

In a particular embodiment there is a process for the production of a compound (IVa) or (IVb) starting with a compound of formula (Xa) or (Xb), respectively

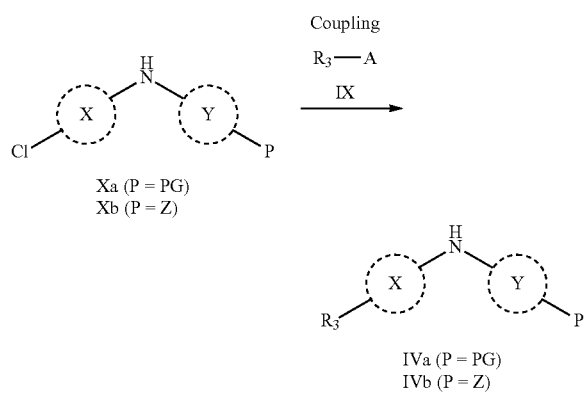

Xa (P = PG)
Xb (P = Z)

IVa (P = PG)
IVb (P = Z)

In a particular embodiment there is a process for the production of a compound (II) starting with a compound of formula (VIII),

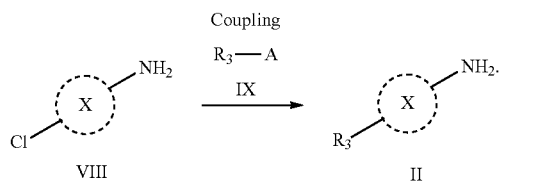

VIII

II

In a particular embodiment there is a process for the production of a compound (I) by deprotection of a compound (VIa) followed by either an alkylation of compound of formula (Ib) with compound of formula (VIIa) or a reductive amination reaction between a compound (Ib) and a compound (VIIb), In another particular embodiment a compound of Formula (II),

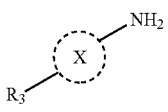

II is used for the preparation of a compound of Formula (I).

In another particular embodiment a compound of Formula (IIIa) or (IIIb),

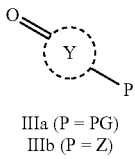

IIIa (P = PG)
IIIb (P = Z)

is used for the preparation of a compound of Formula (I).

In another particular embodiment a compound of Formula (IVa) or (IVb),

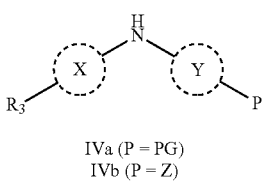

IVa (P = PG)
IVb (P = Z)

is used for the preparation of a compound of Formula (I).

In another particular embodiment a compound of Formula (V),

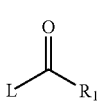

V is used for the preparation of a compound of Formula (I).

In another particular embodiment a compound of Formula (VIa),

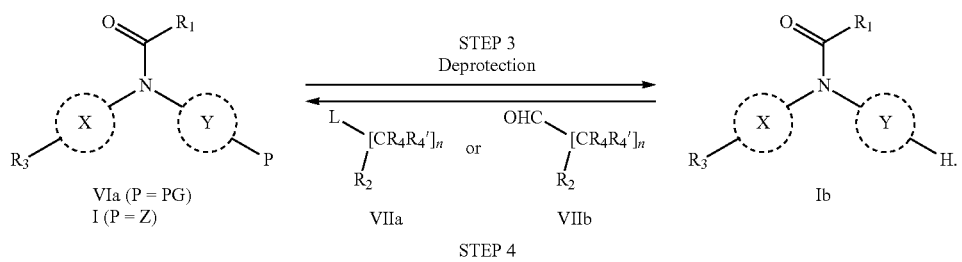

VIa (P = PG)
I (P = Z)

VIIa    VIIb

Ib

STEP 3 Deprotection

STEP 4

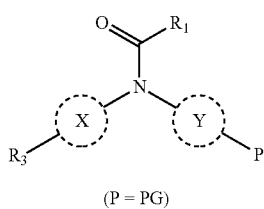

VIa (P = PG)

is used for the preparation of a compound of Formula (I).

In another particular embodiment a compound of Formula (VIIa) or (VIIb),

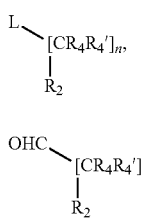

VIIa

VIIb is used for the preparation of a compound of Formula (I).

In another particular embodiment a compound of Formula (VIII),

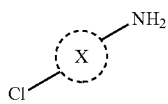

VIII is used for the preparation of a compound of Formula (I).

In another particular embodiment a compound of Formula (IX),

IX is used for the preparation of a compound of Formula (I).

In another particular embodiment a compound of Formula (Xa) or (Xb),

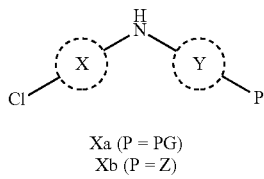

Xa (P = PG)
Xb (P = Z)

is used for the preparation of a compound of Formula (I).

In another particular embodiment a compound of Formula (XIa) or (XIb),

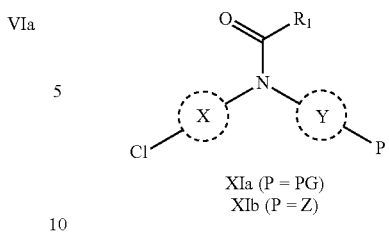

XIa (P = PG)
XIb (P = Z)

is used for the preparation of a compound of Formula (I).

In another particular embodiment compounds of Formula II, IIIa, IIIb, IVa, IVb, V, VIa, VIIa, VIIb, VIII, IX, Xa, Xb, XIa or XIb,

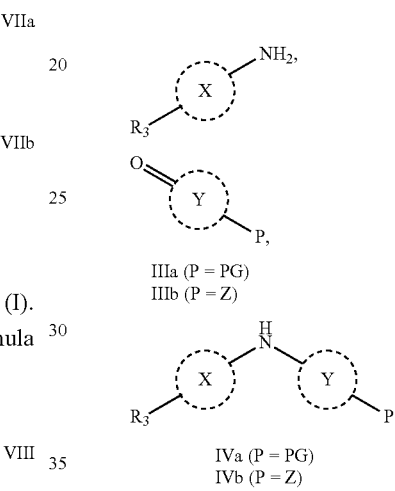

II

IIIa (P = PG)
IIIb (P = Z)

IVa (P = PG)
IVb (P = Z)

V

VIa (P = PG)

VIIa

VIIb

VIII

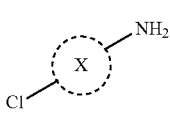

IX

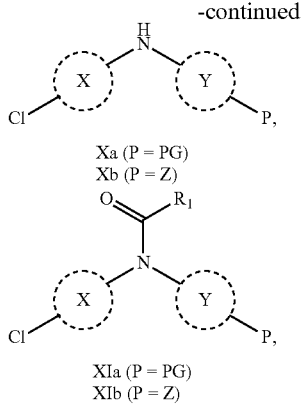

Xa (P = PG)
Xb (P = Z)

XIa (P = PG)
XIb (P = Z)

are used for the preparation of compounds of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or stereoisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art.

The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis
Method Description A process is described in Scheme 1 for the preparation of compounds of general formula I, wherein $R_1$, $R_2$, $R_3$, $R_4$, n, X and Y have the meanings defined above.

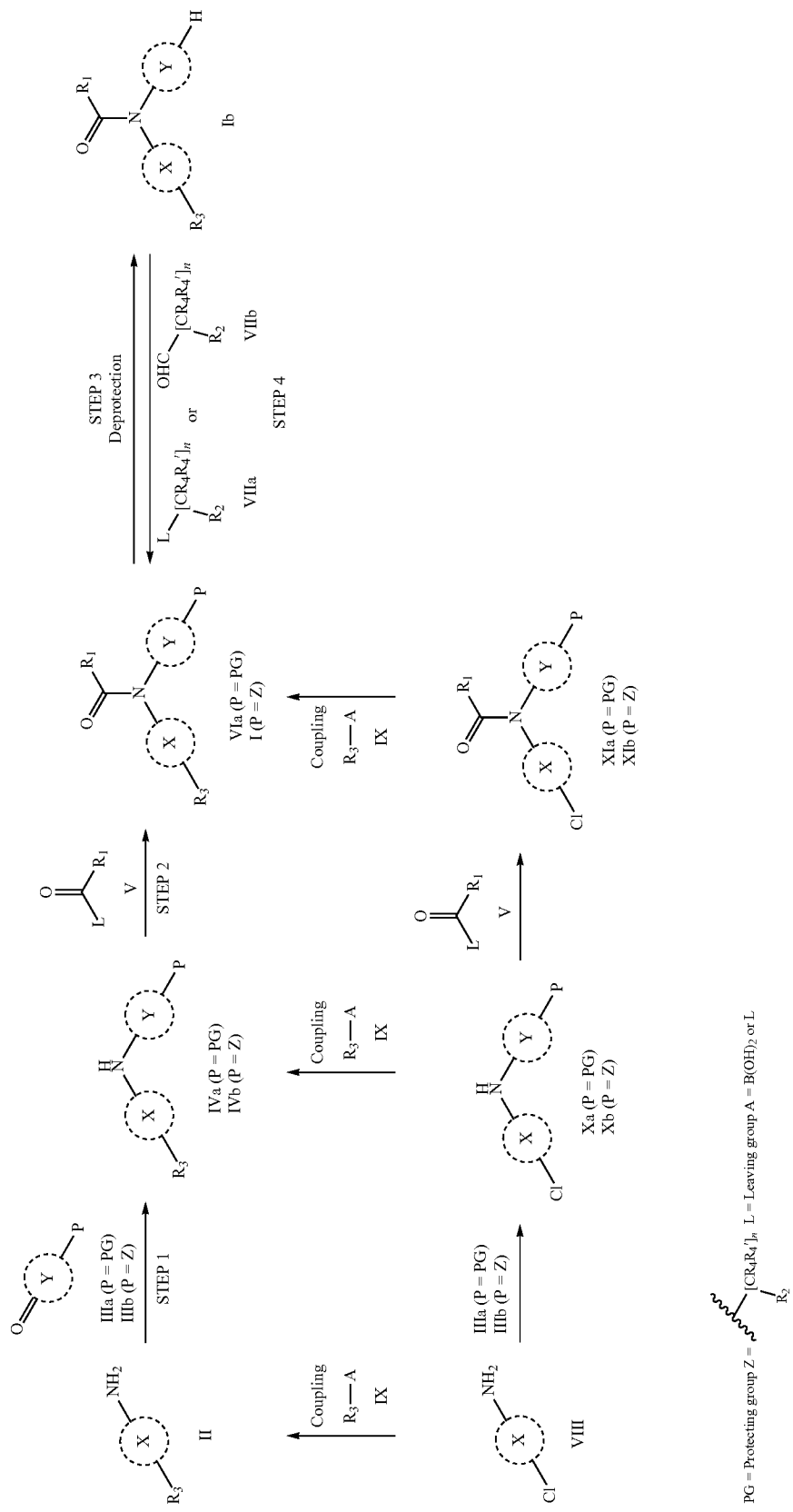

where, L is a leaving group such as halogen, mesylate, tosylate or triflate, A is B(OH)$_2$ or L and Z is the group indicated in a square in Scheme 1 and PG is a protecting group.

This process is carried out as described below:

Step 1:

The compounds of formula IVa or IVb are prepared by reductive amination of compounds of formula II with a compound of formula IIIa or IIIb, in the presence of a reductive reagent, preferably sodium triacetoxyborohydride, in a suitable solvent, preferably dichloromethane, at a suitable temperature comprised between room temperature and the solvent reflux temperature, preferably at room temperature.

Step 2:

Compounds of general formula VI or I are prepared by acylation of compounds of formula IVa or IVb with an acyl halide of formula V. This reaction is carried out in the presence of a suitable solvent, such as acetonitrile, dichloromethane, 1,4-dioxane, 1,2-didoroethane, toluene or dimethylformamide, in the presence of an organic base such as triethylamine, pyridine or diisopropylethylamine, at a suitable temperature comprised between room temperature and the solvent reflux temperature, or alternatively, the reactions can be carried out in a microwave reactor.

For compounds of general formula VI, wherein P is a protecting group, one or two additional steps are necessary to obtain compounds of formula I:

Step 3:

A compound of formula Ib is prepared by deprotection of a compound of formula VI. If the protecting group is benzyl, the deprotection is carried out with hydrogen at a pressure comprised between 1 and 10 bar, in the presence of Pd, in a suitable solvent such as methanol or ethanol, optionally in the presence of an acid such as acetic or hydrochloric acid at a suitable temperature comprised between room temperature and the solvent reflux temperature, preferably at room temperature. Optional deprotecting procedures involve the use of 1-chloroethyl chloroformate in a suitable solvent such as dichloromethane at a suitable temperature, such as reflux temperature. If the protecting group is Boc, the deprotection is carried out in the presence of an acid such as HCl or trifluoroacetic acid, in a suitable solvent such as dichloromethane, at a suitable temperature comprised between room temperature and the solvent reflux temperature.

Step 4:

From deprotected compounds of general formula Ib, compounds of general formula I can be prepared by reaction with suitable reagents, such as those of formula VIIa-b, using different conditions depending on the reagent nature. Thus:

The alkylation reaction with a compound of formula VIIa is carried out in a suitable solvent, such as acetonitrile, dichloromethane, 1,4-dioxane, ethanol or dimethylformamide, preferably in acetonitrile, in the presence of an inorganic base such as K$_2$CO$_3$ or Cs$_2$CO$_3$, or an organic base such as triethylamine or diisopropylethylamine, preferably K$_2$CO$_3$, at a suitable temperature comprised between room temperature and the solvent reflux temperature, preferably heating, or alternatively, this reaction can be carried out in a microwave reactor. Additionally, an activating agent such as NaI or KI can be used.

The reductive amination reaction between a compound of formula Ib and a compound of formula VIIb is carried out in the presence of a reductive reagent, preferably sodium triacetoxyborohydride, in a protic solvent, preferably methanol at a suitable temperature, preferably room temperature.

Alternatively, the reaction can be carried out in an aprotic solvent, preferably tetrahydrofuran or dichloroethane, in the presence of an acid, preferably acetic acid.

The process described by Steps 1 to 4 represents the general route for the preparation of compounds of formula I. Additionally, the functional groups present in any of the positions can be interconverted using reactions known to those skilled in the art.

For example for the preparation of compounds of formula II, IV, VI and I, different aromatic coupling reactions with compounds of formula IX and from the corresponding VIII, X and XI can be effected. These couplings involve different conditions depending on the reagent nature. Thus:

In the case where IX is a boronic acid the reaction is carried out in the presence of a copper salt, preferably copper acetate, in a basic solvent, preferably pyridine at a suitable temperature, preferably room temperature.

In the case where IX is an halide, the reaction is carried out in the presence of a chelating agent, such as N,N,N',N'-tetramethylethane-1,2-diamine, (±)-trans-1,2-diaminocyclohexane or N,N'-dimethylethane-1,2-diamine, in the presence of a base, such as cesium carbonate in a polar solvent, such as acetonitrile, at a suitable temperature, preferably reflux temperature.

Additionally, the different groups constituting the moieties

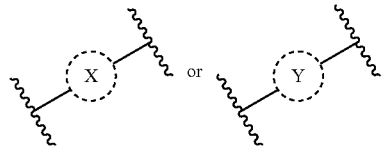

can be constructed along the synthesis. For instance the 1,2,3-triazole derivatives represented by example 137 can be obtained by a procedure that involves the preparation of protected ethynylamides, which provide the final compounds I upon deprotection and cyclization with the corresponding azide derivatives in the presence of a copper catalyst, an organic base such as triethylamine or diisopropylethylamine, preferably diisopropylethylamine, in suitable solvent, such as tetrahydrofuran, at a suitable temperature comprised between room temperature and the solvent reflux temperature, preferably at room temperature.

Compounds of formula II, IIIa, IIIb, V, VIIa, VIIb, VIII, and IX where $R_1$, $R_2$, $R_3$, $R_4$, n, L, X, Y and Z have the meanings as defined above, are commercially available or can be prepared by conventional methods described in the bibliography.

EXAMPLES

Intermediates and Examples

The following abbreviations are used in the examples:
Ac: Acetyl
Ar: Aryl
Bn: Benzyl
DIPEA: N,N-Diisopropylethylamine
DMF: Dimethylformamide
DMSO: Dimethyl sulfoxide
dppf: 1,1'-Bis(diphenylphosphino)ferrocene
ESI: Electrospray ionization
EtOH: Ethanol
Et$_2$O: Diethyl ether EtOAc: Ethyl acetate
Ex: Example
h: Hours
HPLC: High-performance liquid chromatography
INT: Intermediate
iPrOH: 2-Propanol
m/z: Mass-to-charge ratio
MeOH: Methanol
MeTHF: 2-Methyltetrahydrofuran
MS: Mass spectrometry
min: Minutes
MW: Microwaves
NMP: N-Methyl-2-pyrrolidone
Ret: Retention
TFA: Trifluoroacetic acid
THF: Tetrahydrofuran
wt: weight The following methods were used to obtain the HPLC-MS data:

A: Column: SunFire C18, 5 μm, 2.1×50 mm; flow rate: 0.30 mL/min; A: CH$_3$CN:MeOH (1:1); B: water; C: 100 mM ammonium acetate pH 7; gradient: 2 min in 10:85:5+from 10:85:5 to 95:0:5 in 6 min+7 min in 95:0:5.

B: Column: SunFire C18, 3.5 μm, 2.1×100 mm; flow rate: 0.30 mL/min; A: CH$_3$CN:MeOH (1:1); B: water; C: 100 mM ammonium acetate pH 7; gradient: 3 min in 10:85:5+from 10:85:5 to 95:0:5 in 17 min+10 min in 95:0:5.

C: Column: SunFire C18, 3.5 μm, 2.1×100 mm; flow rate: 0.30 mL/min; A: CH$_3$CN:MeOH (1:1); B: water; C: 100 mM ammonium formate pH 4; gradient: 3 min in 30:65:5+from 30:65:5 to 50:45:5 in 7 min+5 min in 50:45:5+from 50:45:5 to 65:30:5 in 5 min+5 min in 65:30:5+from 65:30:5 to 90:5:5 in 5 min.

D: Column Kinetex C18 5 μm, 2.1×50 mm; flow rate: 0.30 mL/min; A: CH$_3$CN:MeOH (1:1); B: water, C: 100 mM ammonium acetate pH 7; gradient A:B:C: 3 min in 10:85:5+from 10:85:5 to 95:0:5 in 6 min+86 min in 95:0:5.

E: Column XBridge C18 5 μm, 2.1×150 mm; flow rate: 0.30 mL/min; A: CH$_3$CN:MeOH (1:1); 8: water; C: 100 mM ammonium acetate pH 7; gradient A:B:C: 2 min in 10:85:5+from 10:85:5 to 95:0:5 in 6 min+7 min in 95:0:5.

F: Column Kinetex C18 5 μm, 2.1×150 mm; flow rate: 0.35 mL/min; A: CH$_3$CN:MeOH (1:1); B: water, C: 100 mM ammonium acetate pH 7; gradient A:B:C: 4 min in 10:85:5+from 10:85:5 to 95:0:5 in 14 min+12 min in 95:0:5.

G: Column Kinetex C18 5 μm, 2.1×150 mm; flow rate: 0.35 mL/min; A: CH$_3$CN:MeOH (1:1); B: water; C: 100 mM ammonium acetate pH 7; gradient A:B:C: 5 min in 5:90:5+from 5:90:5 to 95:0:5 in 15 min+10 min in 95:0:5.

H: Column Luna C18 (2) 5 μm, 2.0×50 mm; flow rate: 0.30 mL/min; A: CH$_3$CN:MeOH (1:1); 8: water: C: 100 mM ammonium acetate pH 7; gradient A:B:C: 3 min in 10:85:5+from 10:85:5 to 95:0:5 in 6 min+6 min in 95:0:5.

I: Column: SunFire C18, 5 μm, 2.1×50 mm; flow rate: 0.30 mL/min; A: CH$_3$CN:MeOH (1:1); B: water; C: 100 mM ammonium acetate pH 7; gradient: 3 min in 10:85:5+from 10:85:5 to 95:0:5 in 6 min+6 min in 95:0:5.

J: Column Luna PFP (2) 3 μm, 2.0×100 mm; flow rate: 0.35 mL/min; A: CH$_3$CN:MeOH (1:1); B: water; C: 100 mM ammonium acetate pH 7; gradient A:B:C: 7 min in 10:85:5+from 10:85:5 to 90:5:5 in 15 min+8 min in 90:5:5.

K: Column Kinetex C18 5 μm, 2.1×150 mm; flow rate: 0.35 ml/min; A: CH$_3$CN; B: water; C: 100 mM ammonium acetate pH 7; gradient A:B:C: 5 min in 25:70:5+from 25:70:5 to 75:20:5 in 13 min+12 min in 75:20:5.

L: Column XBridge C18 5 μm, 2.1×150 mm; flow rate: 0.30 ml/min; A: CH$_3$CN:MeOH (1:1); B: water; C: 100 mM ammonium acetate buffer pH 9 (NH$_4$OH); gradient A:B:C: 3 min in 5:90:5+from 5:90:5 to 95:0:5 in 6 min+6 min in 95:0:5.

M: Column Kinetex C18 5 μm, 2.1×150 mm; flow rate: 0.35 mL/min: A: CH$_3$CN:MeOH (1:1); B: water, C: 100 mM ammonium acetate pH 7; gradient A:B:C: 4 min in 35:60:5+from 35:60:5 to 95:0:5 in 12 min+14 min in 95:0:5.

N: Column Acquity UPLC BEH C18 2.1×50 mm, 1.7 μm; flow rate 0.61 mL/min; A: NH$_4$HCO$_3$ 10 mM; B: ACN; Gradient: 0.3 min in 98% A, 98% A to 5% A in 2.52 min, 1.02 min in 5% A, 5% A to 98% A in 0.34 min, 0.57 min in 98% A O: Column SunFire (C-18, 4.6×50 mm, 3.5 μm) and a 5 min gradient of solvents A (acetonitrile) and B (H$_2$O with 2% formic acid) visualizing at A=254 nm.

P: Column: SunFire C18, 3.5 μm, 2.1×100 mm; flow rate: 0.30 mL/min; A: CH$_3$CN:MeOH (1:1); B: water; C: 100 mM ammonium acetate pH 7; gradient: 5 min in 10:85:5+from 10:85:5 to 95:0:5 in 15 min+10 min in 95:0:5.

Intermediate A1.
1-(4-Fluorophenyl)-1H-pyrazol-3-amine

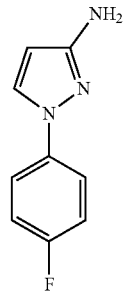 [SMILES: Nc1ccn(-c2ccc(F)cc2)n1]

NaOEt (21% weight in EtOH, 37 mL, 98.17 mmol) and 3-ethoxyacrylonitrile (6.50 mL, 63.10 mmol) were added to a suspension of (4-fluorophenyl)hydrazine hydrochloride (5.70 g, 35.06 mmol) in EtOH (45 mL) and the mixture was heated under reflux for 20 h. The reaction mixture was allowed to reach room temperature and water (35 mL) and HCl (6 N aqueous solution, pH 2) were added, stirring continued for additional 2 h. The reaction was basified with NaOH (40% aqueous solution, pH 8) and was extracted with EtOAc. The combined organic layers were dried over Na$_2$SO$_4$ (anhydrous), filtered and stirred in the presence of charcoal. After 2 h the mixture was filtered through a pad of Celite® and the solvent was removed. The crude residue was purified by flash chromatography on SiO$_2$ (40% to 70% EtOAc/hexanes) to afford the title compound (brown solid, 4.94 g, 74% yield).

HPLC-MS (Method A): Ret, 7.43 min; ESI$^+$-MS m/z: 178 (M+1).

This method was used for the preparation of intermediates A2-A3 using suitable starting materials:

| INT | Structure | Chemical name | Method | Ret (min) | MS (M + H) |
|---|---|---|---|---|---|
| A2 | 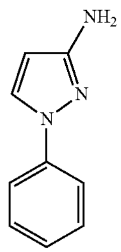 [SMILES: Nc1ccn(-c2ccccc2)n1] | 1-Phenyl-1H-pyrazol-3-amine | D | 6.96 | 160 |
| A3 | 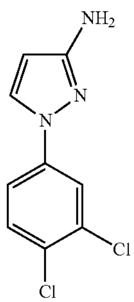 [SMILES: Nc1ccn(-c2ccc(Cl)c(Cl)c2)n1] | 1-(3,4-Dichlorophenyl)-1H-pyrazol-3-amine | | | |

Intermediate A4.
6-(4-Fluorophenyl)pyrazin-2-amine

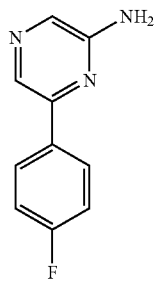 [SMILES: Nc1cncc(-c2ccc(F)cc2)n1]

6-Chloropyrazin-2-amine (0.96 g, 7.41 mmol) was added to a degassed suspension of $Na_2CO_3$ (2.0 M aqueous solution, 7.4 mL, 14.82 mmol), $Pd(dppf)Cl_2 \cdot CH_2Cl_2$ (0.49 g, 0.59 mmol) and (4-fluorophenyl)boronic acid (1.55 g, 11.11 mmol) in 1,4-dioxane (20 mL). The reaction was refluxed for 5 h and stirred at room temperature for 15 h. The mixture was poured into water (40 mL) and extracted with $Et_2O$. The combined organic layers were dried over $Na_2SO_4$ (anhydrous), filtered and concentrated. The crude residue was purified by flash chromatography on $SiO_2$ (20% to 40% EtOAc/hexanes) to give the title compound (off-white solid, 1.5 g, quantitative yield).

HPLC-MS (Method A): Ret, 8.01 min; $ESI^+$-MS m/z: 190 (M+1).

This method was used for the preparation of intermediates A5-A6 using suitable starting materials:

| INT | Structure | Chemical name | Method | Ret (min) | MS (M + H) |
|---|---|---|---|---|---|
| A5 | 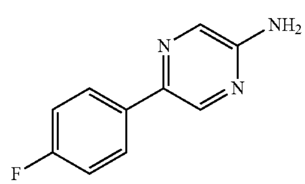 [SMILES: Nc1cnc(-c2ccc(F)cc2)cn1] | 5-(4-Fluorophenyl)pyrazin-2-amine | A | 8.01 | 190 |
| A6 | 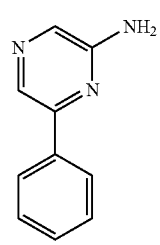 [SMILES: Nc1cncc(-c2ccccc2)n1] | 6-Phenylpyrazin-2-amine | E | 7.28 | 172 |

Intermediate A7.
6-(4-Ethoxyphenyl)pyrazin-2-amine

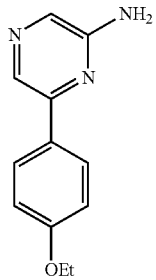 [SMILES: CCOc1ccc(-c2cncc(N)n2)cc1]

NaOEt (1.79 g, 26.4 mmol) was added to a solution of 6-(4-fluorophenyl)pyrazin-2-amine (0.50 g, 2.64 mmol) in NMP (20 mL). The reaction mixture was heated at 120° C. for 24 h. NaOEt (1.79 g, 26.4 mmol) was added and the reaction mixture was heated at 120° C. for 24 h. The mixture was allowed to reach room temperature, poured into water (50 mL) and extracted with EtOAc. The combined organic layers were dried over $Na_2SO_4$ (anhydrous), filtered and concentrated. The crude residue was purified by flash chromatography on $SiO_2$ (40% to 70% EtOAc/hexanes) to afford the title compound contaminated with NMP (orange oil, 2.70 g).

HPLC-MS (Method E): Ret, 8.04 min; $ESI^+$-MS m/z: 216 (M+1).

Intermediate B1. 1-Benzyl-N-[1-(4-fluorophenyl)-1H-pyrrol-3-yl]piperidin-4-amine

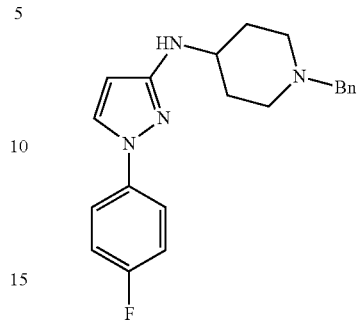

1-Benzylpiperidin-4-one (9.7 mL, 52.38 mmol) and AcOH (4.5 mL, 78.57 mmol) were added to a solution of 1-(4-fluorophenyl)-1H-pyrazol-3-amine (4.96 g, 26.19 mmol) in $CH_2Cl_2$ (60 mL). The reaction mixture was stirred at room temperature for 15 min, $NaBH(OAc)_3$ (11.10 g, 52.38 mmol) was added and the suspension was stirred at room temperature for 22 h. The reaction mixture was diluted with $CH_2Cl_2$ (200 mL) and was poured into $K_2CO_3$ (saturated aqueous solution, 50 mL) and water (100 mL). The organic layer was dried over $Na_2SO_4$ (anhydrous), filtered and concentrated. The crude residue was purified by flash chromatography on $SiO_2$ (70% to 100% EtOAc/hexanes) to afford the title compound (beige solid, 7.81 g, 85% yield).

HPLC-MS (Method A): Ret, 9.70 min; $ESI^+$-MS m/z: 351 (M+1).

This method was used for the preparation of intermediates B2-832 using suitable starting materials:

| INT | Structure | Chemical name | Method | Ret (min) | MS (M + H) |
|---|---|---|---|---|---|
| B2 | 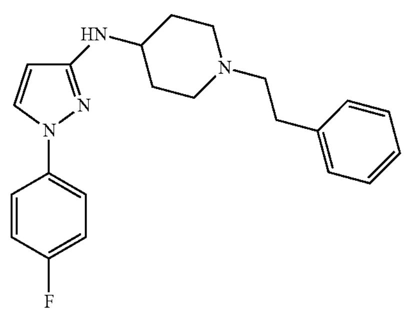 [SMILES: Fc1ccc(-n2ccc(NC3CCN(CCc4ccccc4)CC3)n2)cc1] | N-[1-(4-Fluorophenyl)-1H-pyrazol-3-yl]-1-phenethylpiperidin-4-amine | A | 9.45 | 365 |
| B3 | 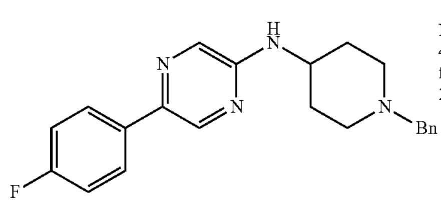 | N-(1-Benzylpiperidin-4-yl)-5-(4-fluorophenyl)pyrazin-2-amine | A | 10.20 | 363 |

| INT | Structure | Chemical name | Method | Ret (min) | MS (M + H) |
|---|---|---|---|---|---|
| B4 | 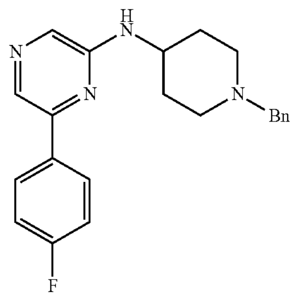 [SMILES: Fc1ccc(-c2cncc(NC3CCN(Cc4ccccc4)CC3)n2)cc1] | N-(1-Benzylpiperidin-4-yl)-6-(4-fluorophenyl)pyrazin-2-amine | A | 10.40 | 363 |
| B5 | 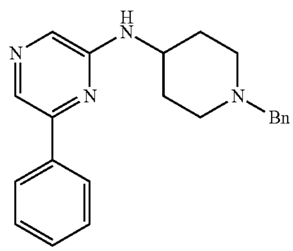 [SMILES: c1ccc(CN2CCC(Nc3cncc(-c4ccccc4)n3)CC2)cc1] | N-(1-Benzylpiperidin-4-yl)-6-phenylpyrazin-2-amine | E | 9.91 | 345 |
| B6 | 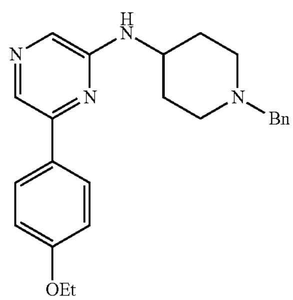 [SMILES: CCOc1ccc(-c2cncc(NC3CCN(Cc4ccccc4)CC3)n2)cc1] | N-(1-Benzylpiperidin-4-yl)-6-(4-ethoxyphenyl)pyrazin-2-amine | E | 10.17 | 389 |
| B7 | 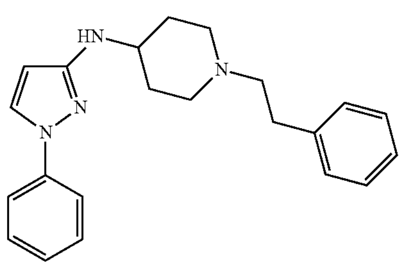 [SMILES: c1ccc(CCN2CCC(Nc3ccn(-c4ccccc4)n3)CC2)cc1] | 1-Phenethyl-N-(1-phenyl-1H-pyrazol-3-yl)piperidin-4-amine | B | 16.02 | 347 |
| B8 | 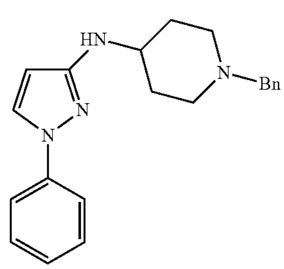 [SMILES: c1ccc(CN2CCC(Nc3ccn(-c4ccccc4)n3)CC2)cc1] | 1-Benzyl-N-(1-phenyl-1H-pyrazol-3-yl)piperidin-4-amine | E | 9.23 | 333 |

-continued

| INT | Structure | Chemical name | Method | Ret (min) | MS (M + H) |
|---|---|---|---|---|---|
| B9 | 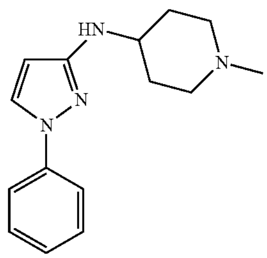 [SMILES: CN1CCC(Nc2ccn(-c3ccccc3)n2)CC1] | 1-Methyl-N-(1-phenyl-1H-pyrazol-3-yl)piperidin-4-amine | D | 7.70 | 257 |
| B10 | 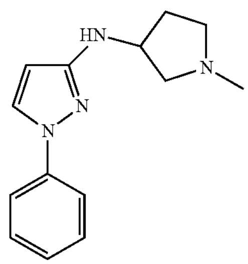 [SMILES: CN1CCC(Nc2ccn(-c3ccccc3)n2)C1] | N-(1-Methylpyrrolidin-3-yl)-1-phenyl-1H-pyrazol-3-amine | G | 13.24 | 243 |
| B11 | 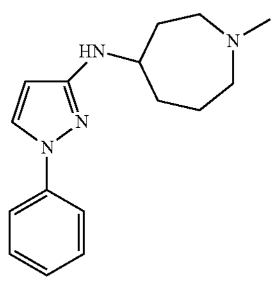 [SMILES: CN1CCCC(Nc2ccn(-c3ccccc3)n2)CC1] | 1-Methyl-N-(1-phenyl-1H-pyrazol-3-yl)azepan-4-amine | D | 7.75 | 271 |
| B12 | 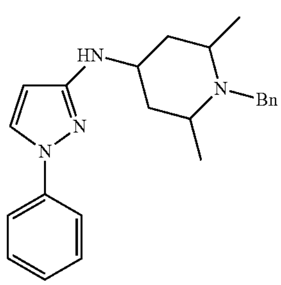 [SMILES: CC1CC(Nc2ccn(-c3ccccc3)n2)CC(C)N1Cc1ccccc1] | 1-Benzyl-2,6-dimethyl-N-(1-phenyl-1H-pyrazol-3-yl)piperidin-4-amine | D | 9.81 | 361 |
| B13 | 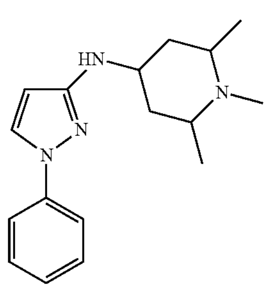 [SMILES: CC1CC(Nc2ccn(-c3ccccc3)n2)CC(C)N1C] | 1,2,6-Trimethyl-N-(1-phenyl-1H-pyrazol-3-yl)piperidin-4-amine | D | 8.25 | 285 |

-continued

| INT | Structure | Chemical name | Method | Ret (min) | MS (M + H) |
|---|---|---|---|---|---|
| B14 | 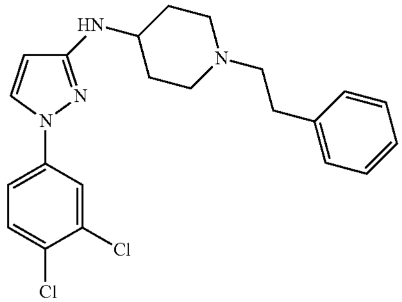 [SMILES: Clc1ccc(-n2ccc(NC3CCN(CCc4ccccc4)CC3)n2)cc1Cl] | N-[1-(3,4-Dichlorophenyl)-1H-pyrazol-3-yl]-1-phenethylpiperidin-4-amine | | | |
| B15 | 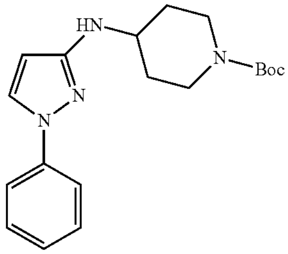 [SMILES: CC(C)(C)OC(=O)N1CCC(Nc2ccn(-c3ccccc3)n2)CC1] | tert-Butyl 4-[(1-phenyl-1H-pyrazol-3-yl)amino]piperidine-1-carboxylate | D | 10.32 | 343 |
| B16 | 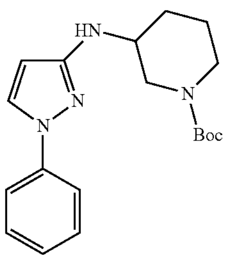 [SMILES: CC(C)(C)OC(=O)N1CCCC(Nc2ccn(-c3ccccc3)n2)C1] | tert-Butyl 3-[(1-phenyl-1H-pyrazol-3-yl)amino]piperidine-1-carboxylate | D | 10.25 | 343 |
| B17 | 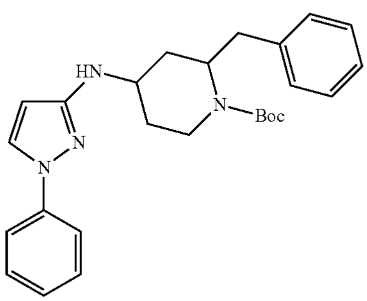 [SMILES: CC(C)(C)OC(=O)N1CCC(Nc2ccn(-c3ccccc3)n2)CC1Cc1ccccc1] | tert-Butyl 2-benzyl-4-[(1-phenyl-1H-pyrazol-3-yl)amino]piperidine-1-carboxylate | D | 11.11 | 433 |
| B18 | 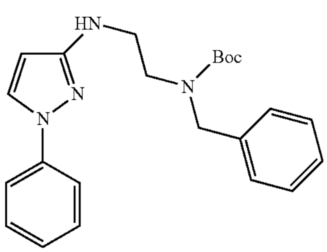 [SMILES: CC(C)(C)OC(=O)N(CCNc1ccn(-c2ccccc2)n1)Cc1ccccc1] | tert-Butyl benzyl{2-[(1-phenyl-1H-pyrazol-3-yl)amino]ethyl}carbamate | D | 10.82 | 393 |

-continued

| INT | Structure | Chemical name | Method | Ret (min) | MS (M + H) |
|---|---|---|---|---|---|
| B19 | 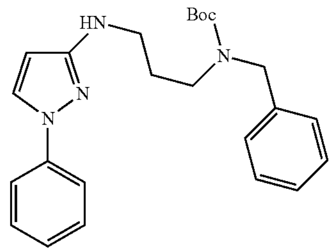 [SMILES: CC(C)(C)OC(=O)N(CCCNc1ccn(-c2ccccc2)n1)Cc1ccccc1] | tert-Butyl benzyl{3-[(1-phenyl-1H-pyrazol-3-yl)amino]propyl}carbamate | D | 10.95 | 407 |
| B20 | 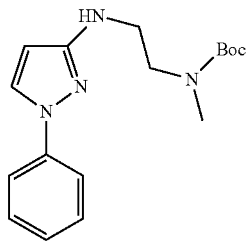 [SMILES: CN(CCNc1ccn(-c2ccccc2)n1)C(=O)OC(C)(C)C] | tert-Butyl methyl{2-[(1-phenyl-1H-pyrazol-3-yl)amino]ethyl}carbamate | D | 9.96 | 317 |
| B21 | 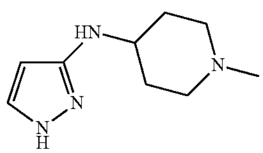 | 1-Methyl-N-(1H-pyrazol-3-yl)piperidin-4-amine | D | 1.22 | 181 |
| B22 | 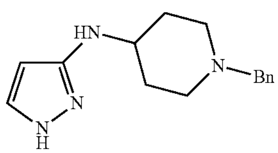 [SMILES: c1ccc(CN2CCC(Nc3cc[nH]n3)CC2)cc1] | 1-Benzyl-N-(1H-pyrazol-3-yl)piperidin-4-amine | D | 5.66 | 257 |
| B23 | 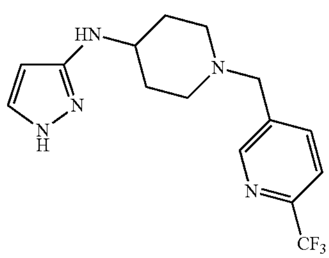 [SMILES: FC(F)(F)c1ccc(CN2CCC(Nc3cc[nH]n3)CC2)cn1] | N-(1H-Pyrazol-3-yl)-1-{[6-(trifluoromethyl)pyridin-3-yl]methyl}piperidin-4-amine | H | 8.94 | 326 |
| B24 | 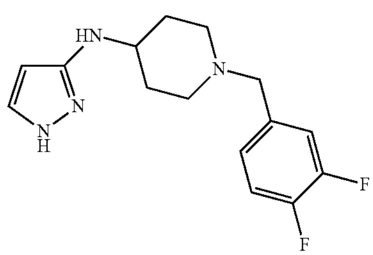 [SMILES: Fc1ccc(CN2CCC(Nc3cc[nH]n3)CC2)cc1F] | 1-(3,4-Difluorobenzyl)-H-(1H-pyrazol-3-yl)piperidin-4-amine | I | 8.78 | 293 |
| B25 | 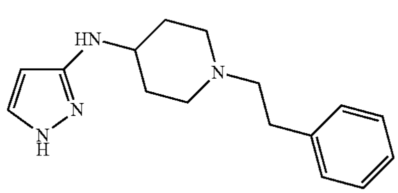 [SMILES: c1ccc(CCN2CCC(Nc3cc[nH]n3)CC2)cc1] | 1-Phenethyl-N-(1H-pyrazol-3-yl)piperidin-4-amine | H | 8.11 | 271 |

-continued

| INT | Structure | Chemical name | Method | Ret (min) | MS (M + H) |
|---|---|---|---|---|---|
| B26 | 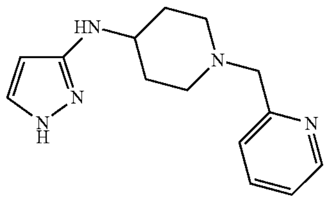 [SMILES: c1ccc(CN2CCC(Nc3cc[nH]n3)CC2)nc1] | N-(1H-Pyrazol-3-yl)-1-(pyridin-2-ylmethyl)piperidin-4-amine | H | 7.07 | 258 |
| B27 | 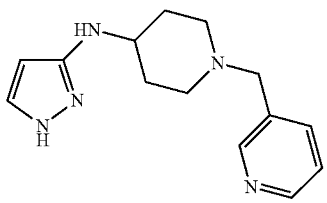 [SMILES: c1cncc(CN2CCC(Nc3cc[nH]n3)CC2)c1] | N-(1H-Pyrazol-3-yl)-1-(pyridin-3-ylmethyl)piperidin-4-amine | H | 7.26 | 258 |
| B28 | 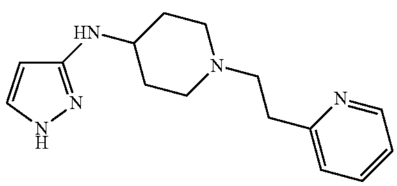 [SMILES: c1ccc(CCN2CCC(Nc3cc[nH]n3)CC2)nc1] | N-(1H-Pyrazol-3-yl)-1-[2-(pyridin-2-yl)ethyl]piperidin-4-amine | H | 6.98 | 272 |
| B29 | 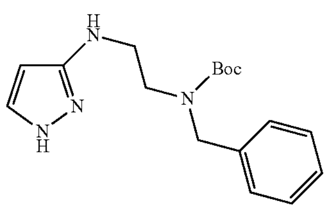 [SMILES: CC(C)(C)OC(=O)N(CCNc1cc[nH]n1)Cc1ccccc1] | tert-Butyl {2-[(1H-pyrazol-3-yl)amino]ethyl}(benzyl)carbamate | H | 10.27 | 317 |
| B30 | 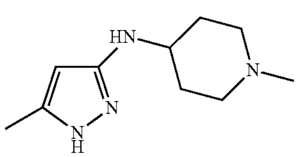 | 1-Methyl-N-(5-methyl-1H-pyrazol-3-yl)piperidin-4-amine | D | 1.13 and 2.04 | 195 |
| B31 | 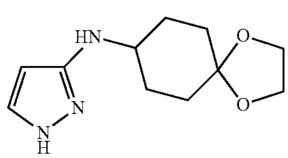 [SMILES: c1cc(NC2CCC3(CC2)OCCO3)n[nH]1] | N-(1,4-Dioxaspiro[4.5]decan-8-yl)-1H-pyrazol-3-amine | H | 7.29 | 224 |
| B32 | 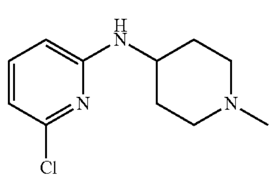 | 6-Chloro-N-(1-methylpiperidin-4-yl)pyridin-2-amine | D | 7.13 | 226 |
| B33 | 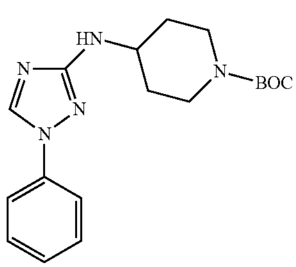 [SMILES: CC(C)(C)OC(=O)N1CCC(Nc2ncn(-c3ccccc3)n2)CC1] | tert-Butyl 4-(1-phenyl-1H-1,2,4-triazol-3-ylamino)piperidine-1-carboxylate | O | 4.8 | 344 |

| INT | Structure | Chemical name | Method | Ret (min) | MS (M + H) |
|---|---|---|---|---|---|
| B34 | 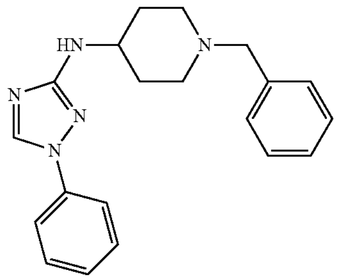 [SMILES: c1ccc(CN2CCC(Nc3ncn(-c4ccccc4)n3)CC2)cc1] | 1-Benzyl-N-(1-phenyl-1H-1,2,4-triazol-3-yl)-piperidin-4-amine | O | 2.4 | 334 |
| B35 | 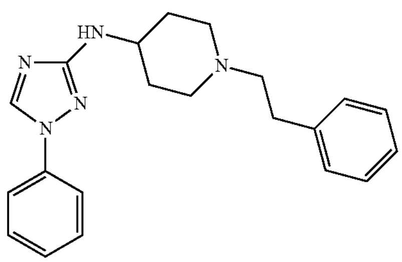 [SMILES: c1ccc(CCN2CCC(Nc3ncn(-c4ccccc4)n3)CC2)cc1] | 1-Phenethyl-N-(1-phenyl-1H-1,2,4-triazol-3-yl)piperidin-4-amine | O | 4.3 | 348 |

Intermediate B36. 1-Benzyl-N-[1-(4-ethoxyphenyl)-1H-pyrazol 3-yl]piperidin-4-amine

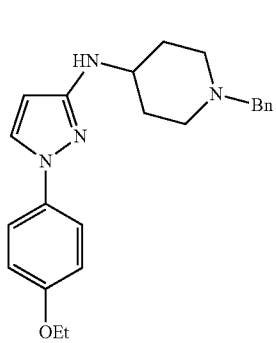 [SMILES: CCOc1ccc(-n2ccc(NC3CCN(Cc4ccccc4)CC3)n2)cc1]

NaOEt (0.39 g, 5.7 mmol) was added to a solution of 1-benzyl-N-[1-(4-fluorophenyl)-1H-pyrazol-3-yl]piperidin-4-amine (0.20 g, 0.57 mmol) in NMP (10 mL). The reaction mixture was stirred at 100° C. for 20 h and at 120° C. for 36 h, allowed to reach room temperature, poured into water (20 mL) and extracted with EtOAc. The combined organic layers were dried over $Na_2SO_4$ (anhydrous), filtered and concentrated. The crude residue was purified by flash chromatography on $SiO_2$ ($CH_2Cl_2$/MeOH/$NH_4OH$ 96:4:1 to 94:6:1) to afford the title compound (yellow oil, 0.27 g, 96% yield).

HPLC-MS (Method B): Ret, 17.12 min; $ESI^+$-MS m/z: 377 (M+1).

Intermediate B37. 1-Benzyl-N-{1-[3-(5-methyl-1,3,4-oxadiazol-2-yl)phenyl]-1H-pyrazol-3-yl}piperidin-4-amine

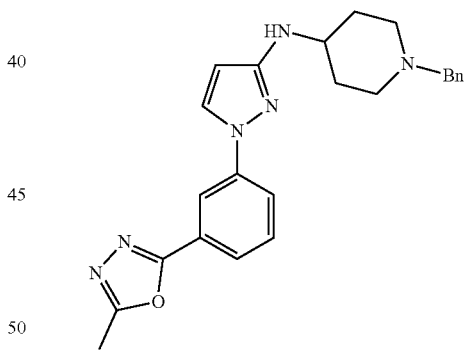

CuI (103 mg, 0.54 mmol) and $K_3PO_4$ (3.45 g, 16.26 mmol) were added to a solution of 1-benzyl-N-1H-pyrazol-3-ylpiperidin-4-amine (1.39 g, 5.42 mmol), N,N-dimethylethane-1,2-diamine (96 mg, 1.08 mmol) and 2-(3-iodophenyl)-5-methyl-1,3,4-oxadiazole (2.30 g, 8.13 mmol) in dioxane (20 mL) and the mixture was heated under reflux for 21 h. The reaction was allowed to reach room temperature; volatiles were removed and the residue was dissolved in EtOAc (70 mL) and washed with brine (100 mL). The organic layer was dried over $Na_2SO_4$ (anhydrous), filtered and concentrated. The crude residue was purified by flash chromatography on $SiO_2$ ($CH_2Cl_2$/MeOH/$NH_4OH$ 100:0:0 to 90:10:1) to afford the title compound (pale yellow foam, 1.60 g, 73% yield).

HPLC-MS (Method H): Ret, 9.96 min; $ESI^+$-MS m/z: 415 (M+1).

This method was used for the preparation of intermediates 838-B40 using suitable starting materials:

| INT | Structure | Chemical name | Method | Ret (min) | MS (M + H) |
|---|---|---|---|---|---|
| B38 | 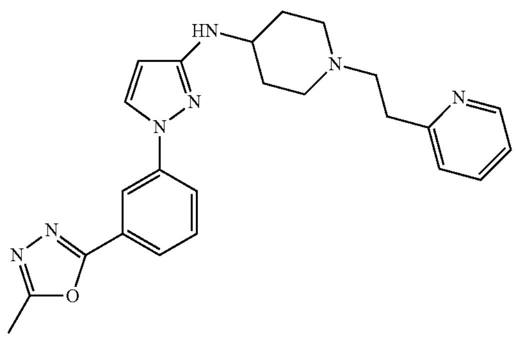 [SMILES: Cc1nnc(-c2cccc(-n3ccc(NC4CCN(CCc5ccccn5)CC4)n3)c2)o1] | N-{1-[3-(5-Methyl-1,3,4-oxadiazol-2-yl)phenyl]-1H-pyrazol-3-yl}-1-[2-(pyridin-2-yl)ethyl]piperidin-4-amine | H | 8.91 | 430 |
| B39 | 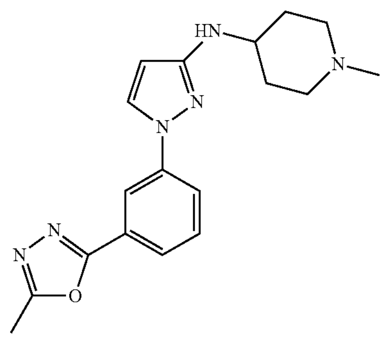 | 1-Methyl-N-{1-[3-(5-methyl-1,3,4-oxadiazol-2-yl)phenyl]-1H-pyrazol-3-yl}-piperidin-4-amine | H | 7.96 | 339 |
| B40 | 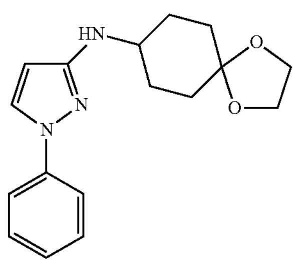 [SMILES: c1ccc(-n2ccc(NC3CCC4(CC3)OCCO4)n2)cc1] | 1-Phenyl-N-(1,4-dioxaspiro[4.5]decan-8-yl)-1H-pyrazol-3-amine | H | 10.07 | 300 |

Intermediate B41. N-[1-(3-Methoxyphenyl)-1H-pyrazol-3-yl]-1-(pyridin-3-ylmethyl)piperidin-4-amine

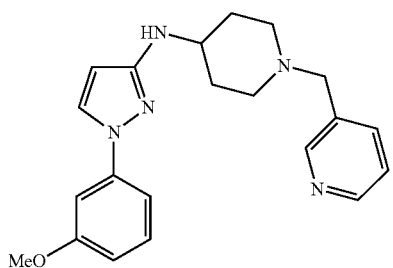 [SMILES: COc1cccc(-n2ccc(NC3CCN(Cc4cccnc4)CC3)n2)c1]

Pyridine (0.17 mL, 2.16 mmol) and Cu(OAc)₂ (0.26 g, 1.44 mmol) were added to a solution of (3-methoxyphenyl)boronic acid (0.16 g, 1.08 mmol) and N-(1H-pyrazol-3-yl)-1-(pyridin-3-ylmethyl)piperidin-4-amine (0.19 g, 0.72 mmol) in CH₂C (10 mL) and the mixture was stirred for 22 h in an open flask. The reaction was diluted with CH₂Cl (30 mL) and was washed with brine. The organic layer was dried over Na₂SO₄ (anhydrous), filtered and concentrated. The crude residue was purified by flash chromatography on SiO₂ (CH₂Cl₂/MeOH/NH₄OH 98:2:1 to 96:4:1) affording the title compound (pale yellow oil, 130 mg, 50% yield).

HPLC-MS (Method H): Ret, 9.31 min; ESI⁺-MS m/z: 364 (M+1).

Intermediate C1. N-(1-Methylpiperidin-4-yl)-N-(1H-pyrazol-3-yl)thiophene-2-carboxamide

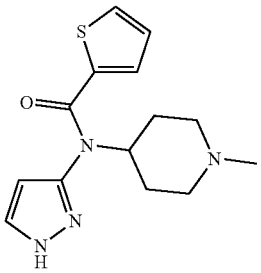 [SMILES: CN1CCC(N(C(=O)c2cccs2)c2cc[nH]n2)CC1]

Thiophene-2-carbonyl chloride (5.50 mL, 52.11 mmol) was added to a 0° C. cooled solution of 1-methyl-N-(1H-pyrazol-3-yl)piperidin-4-amine (4.27 g, 23.68 mmol) and DIPEA (8.90 ml, 52.09 mmol) in $CH_2Cl_2$ (60 mL). The reaction mixture was allowed to reach room temperature, stirred at this temperature for 20 min and heated under reflux for 16 h. The mixture was cooled down to room temperature poured into $NaHCO_3$ (saturated aqueous solution, 60 mL) and extracted with $CH_2Cl_2$. The combined organic layers were dried over $Na_2SO_4$ (anhydrous), filtered and concentrated. The crude residue was dissolved in THF (20 mL) and MeOH (20 mL) and $LiOH.H_2O$ (2 M aqueous solution, 6.0 mL, 12.05 mmol) was added, stirring continued for 6 h. Volatiles were removed by rotatory evaporation and the residue was dissolved in $CH_2Cl_2$ (60 mL) and washed with brine. The organic layer was dried over $Na_2SO_4$ (anhydrous), filtered and concentrated, obtaining an orange oil which was purified by flash chromatography on $SiO_2$ ($CH_2Cl_2$/MeOH/$NH_4OH$ 80:20:2) affording the title compound (1.60 g, yellow solid, 20% yield).

HPLC-MS (Method D): Ret 5.09 min; $ESI^+$-MS m/z: 291 (M+1).

This method was used for the preparation of intermediates C2-C11 using suitable starting materials:

| INT | Structure | Chemical name | Method | Ret (min) | MS (M + H) |
|---|---|---|---|---|---|
| C2 | 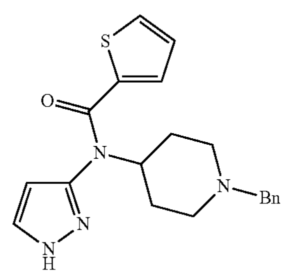 | N-(1-Benzylpiperidin-4-yl)-N-(1H-pyrazol-3-yl)thiophene-2-carboxamide | D | 5.65 | 367 |
| C3 | 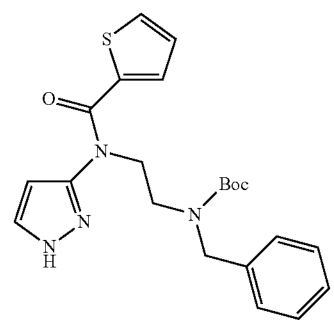 [SMILES: CC(C)(C)OC(=O)N(CCN(C(=O)c1cccs1)c1cc[nH]n1)Cc1ccccc1] | tert-Butyl {2-[N-(1H-pyrazol-3-yl)thiophene-2-carboxamido]ethyl}(benzyl)carbamate | H | 10.67 | 427 |
| C4 | 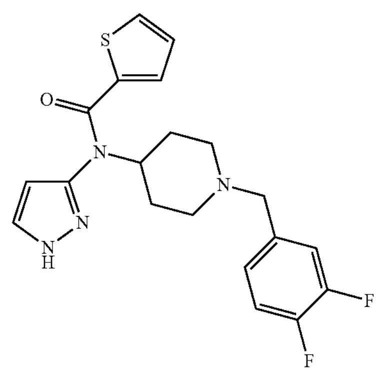 [SMILES: O=C(c1cccs1)N(c1cc[nH]n1)C1CCN(Cc2ccc(F)c(F)c2)CC1] | N-[1-(3,4-difluorobenzyl)piperidin-4-yl]-N-(1H-pyrazol-3-yl)thiophene-2-carboxamide | H | 10.28 | 403 |

| INT | Structure | Chemical name | Method | Ret (min) | MS (M + H) |
|---|---|---|---|---|---|
| C5 | 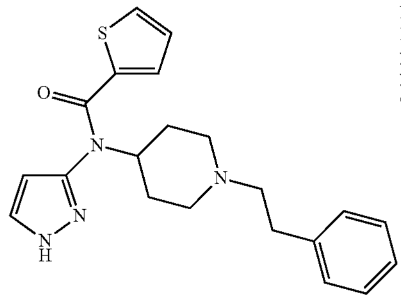 [SMILES: O=C(c1cccs1)N(c1cc[nH]n1)C1CCN(CCc2ccccc2)CC1] | N-(1-Phenethylpiperidin-4-yl)-N-(1H-pyrazol-3-yl)thiophene-2-carboxamide | H | 9.38 | 381 |
| C6 | 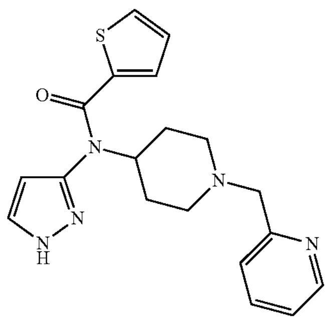 [SMILES: O=C(c1cccs1)N(c1cc[nH]n1)C1CCN(Cc2ccccn2)CC1] | N-(1H-pyrazol-3-yl)-N-[1-(pyridin-2-ylmethyl)piperidin-4-yl]thiophene-2-carboxamide | H | 8.63 | 368 |
| C7 | 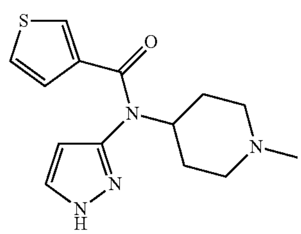 [SMILES: CN1CCC(N(C(=O)c2ccsc2)c2cc[nH]n2)CC1] | N-(1-Methylpiperidin-4-yl)-N-(1H-pyrazol-3-yl)thiophene-3-carboxamide | H | 6.44 | 291 |
| C8 | 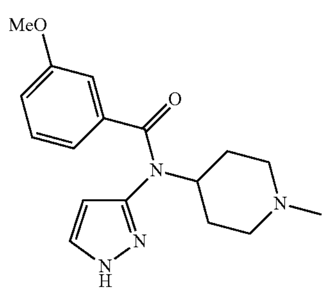 [SMILES: COc1cccc(C(=O)N(c2cc[nH]n2)C2CCN(C)CC2)c1] | 3-Methoxy-N-(1-methylpiperidin-4-yl)-N-(1H-pyrazol-3-yl)benzamide | I | 7.10 | 315 |
| C9 | 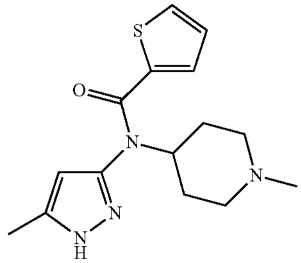 | N-(5-Methyl-1H-pyrazol-3-yl)-N-(1-methylpiperidin-4-yl)thiophene-2-carboxamide | D | 6.98 | 305 |

| INT | Structure | Chemical name | Method | Ret (min) | MS (M + H) |
|---|---|---|---|---|---|
| C10 | 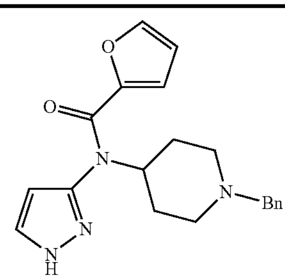 | N-(1-Benzylpiperidin-4-yl)-N-(1H-pyrazol-3-yl)furan-2-carboxamide | I | 8.83 | 351 |
| C11 | 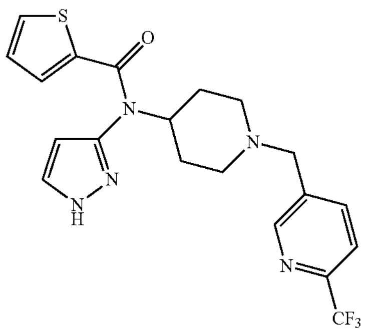 [SMILES: O=C(c1cccs1)N(c1cc[nH]n1)C1CCN(Cc2ccc(C(F)(F)F)nc2)CC1] | N-(1H-Pyrazol-3-yl)-N-(1-{[6-(trifluoromethyl)pyridin-3-yl]methyl}piperidin-4-yl)thiophene-2-carboxamide | H | 6.62 | 436 |

Intermediate C12. 3-Hydroxy-N-(1-methylpiperidin-4-yl)-N-1H-pyrazol-3-ylbenzamide

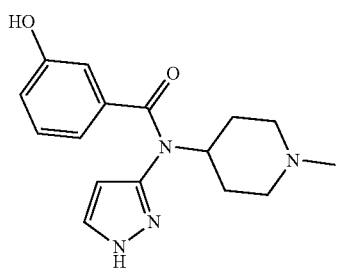 [SMILES: CN1CCC(N(C(=O)c2cccc(O)c2)c2cc[nH]n2)CC1]

BBr$_3$ (1 M solution in CH$_2$Cl$_2$, 13.85 mL, 13.85 mmol) was added to a solution of 3-methoxy-N-(1-methylpiperidin-4-yl)-N-1H-pyrazol-3-ylbenzamide (Intermediate C8, 650 mg, 2.07 mmol) in CH$_2$Cl$_2$ (15 mL) cooled at −5° C. and the mixture was stirred at room temperature for 42 h. Water (5 mL) was added dropwise, followed by the addition of NaOH (10% aqueous solution, 45 mL). After 30 min the mixture was extracted with EtOAc (3×30 mL) followed by MeTHF (3×30 mL); the combined organic layers were dried over Na$_2$SO$_4$ (anhydrous), filtered and concentrated, obtaining a yellow solid, which was triturated with Et$_2$O (5 mL) and CH$_2$Cl$_2$ (5 mL), affording the title compound (pale yellow solid, 315 mg, 51% yield).

HPLC-MS (Method L): Ret, 7.78 min; ESI$^+$-MS m/z: 301 (M+1).

Intermediate C13. N-(6-Chloropyridin-2-yl)-N-(1-methylpiperidin-4-yl)thiophene-2-carboxamide Thiophene-2-carbonyl chloride (1.50 mL, 14.28 mmol) was added to a 0° C. cooled solution of 6-chloro-N-(1-methylpiperidin-4-yl)pyridin-2-amine (1.24 g, 5.49 mmol) and DIPEA (2.82 mL, 16.47 mmol) in CH$_2$Cl$_2$ (20 mL) and the mixture was heated under reflux for 17 h. The reaction was allowed to reach room temperature poured into NaHCO$_3$ (saturated aqueous solution, 30 mL) and extracted with CH$_2$Cl$_2$. The combined organic layers were dried over Na$_2$SO$_4$ (anhydrous), filtered and concentrated. The crude residue was purified by flash chromatography on SiO$_2$ (CH$_2$Cl$_2$/MeOH/NH$_4$OH 90:10:1) followed by medium pressure flash chromatography (Combiflash, 0 to 100% MeOH/H$_2$O) affording the title compound (pale yellow solid, 0.72 g, 44% yield).

HPLC-MS (Method D): Ret, 8.07 min; ESI$^+$-MS m/z: 336 (M+1).

This method was used for the preparation of intermediate C14 using suitable starting materials:

| INT | Structure | Chemical name | Method | Ret (min) | MS (M + H) |
|---|---|---|---|---|---|
| C14 | 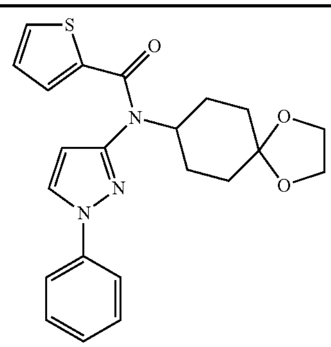 | N-(1-Phenyl-1H-pyrazol-3-yl)-N-(1,4-dioxaspiro[4.5]decan-8-yl)thiophene-2-carboxamide | H | 10.53 | 410 |

Intermediate D1.
N-(1-benzylpiperidin-4-yl)thiophene-2-carboxamide

Intermediate E1. N-(1-benzylpiperidin-4-yl)-N-((triisopropylsilyl)ethynyl)thiophene-2-carboxamide

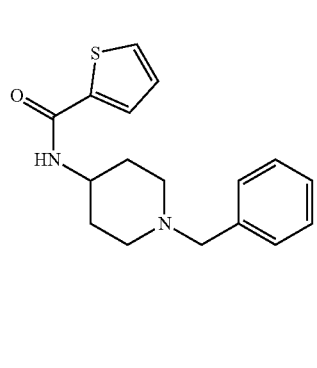 [SMILES: O=C(NC1CCN(Cc2ccccc2)CC1)c1cccs1]

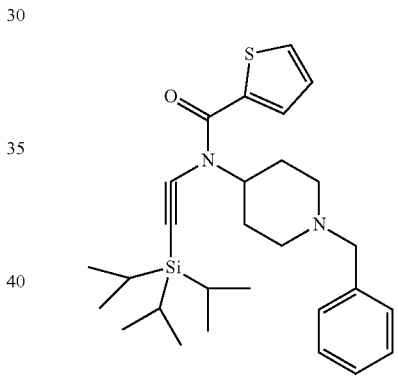

To a solution of 1-benzylpiperidin-4-amine (3.00 g, 15.8 mmol) in dry $CH_2Cl_2$ (40 mL) was added DIPEA (6.75 mL, 39.4 mmol) and the reaction stirred for 10 min at r.t., after which the mixture was cooled down to 0° C. At this temperature thiophene-2-carbonyl chloride (2.02 ml, 18.9 mmol) was added. The reaction was allowed to reach r.t. and stirred overnight. The reaction was diluted with $CH_2Cl_2$ and washed two times with sat. $NaHCO_3$ solution followed by sat. NaCl solution. The organic phase was dried over sodium sulphate and the solvent removed under reduced pressure after filtration. The residue was absorbed onto silica gel with the aid of ethyl acetate and purified by combiflash chromatography ($SiO_2$, $CH_2Cl$/MeOH up to 10%) to give the title compound as brown solid (3.91 g, 83%).

HPLC-MS (Method N): Ret, 6.08 min; $ESI^+$-MS m/z: 301 (M+1),

A three-neck Rb flask was charged with N-(1-benzylpiperidin-4-yl)thiophene-2-carboxamide (3.71 g, 12.3 mmol), 1,10-phenanthroline (445 mg, 2.47 mmol), $CuSO_4.5H_2O$ (307 mg, 1.23 mmol) and $K_3PO_4$ (5.24 g, 24.7 mmol) evacuated and backfilled with argon. Then (bromoethynyl)triisopropylsilane (3.55 g, 13.6 mmol) was added, followed by dry toluene. The reaction mixture was heated at 115° C. for 3 days. The solvent was removed under reduced pressure and the residue purified by combiflash chromatography ($SiO_2$, c-Hexane/ethyl acetate, then $CH_2Cl_2$/MeOH) to give the title compound as dark oil (308 mg, 5% yield).

HPLC-MS (Method N): Ret, 5.18 min; $ESI^+$-MS m/z: 481 (M+1).

Intermediate F1 N-(1-benzylpiperidin-4-yl)-N-(1H-1,2,3-triazol-4-yl)thiophene-2-carboxamide

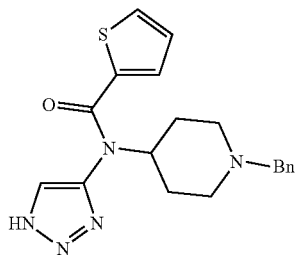 [SMILES: O=C(c1cccs1)N(c1c[nH]nn1)C1CCN(Cc2ccccc2)CC1]

N-(1-benzylpiperidin-4-yl)-N-(1-(4-methoxybenzyl)-1H-1,2,3-triazol-4-yl)thiophene-2-carboxamide (118 mg, 0242 mmol) was dissolved in TFA (ca. 6 mL) and heated at 60° C. overnight. The reaction was cooled down to r.t. and TFA was removed by co-evaporating with toluene. The residue was taken up in MeOH and then purified by cation-interchange chromatography (column: Agilent HF Mega BE-SCX 2 gm 12 mL 20/PK), eluating first with Methanol, then with $NH_3$/MeOH (2M). The fraction eluating with $NH_3$/MeOH (2M) was collected. Evaporation of the solvent of this fraction gave N-(1-benzylpiperidin-4-yl)-N-(1H-1,2,3-triazol-4-yl)thiophene-2-carboxamide (57 mg, 64% yield)

HPLC-MS (Method N): Ret, 4.12 min; $ESI^+$-MS m/z: 368 (M+1).

Example 1. N-(1-Benzylpiperidin-4-yl)-N-[1-(4-fluorophenyl)-1H-pyrazol-3-yl]thiophene-2-carboxamide

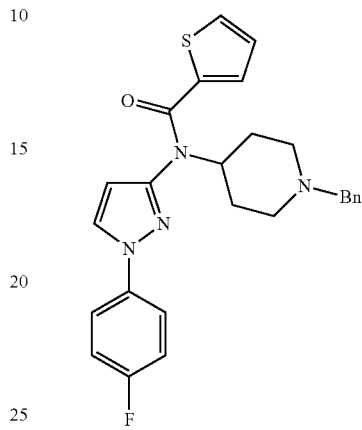

Thiophene-2-carbonyl chloride (125 mg, 0.85 mmol) was added to a solution of 1-benzyl-N-[1-(4-fluorophenyl)-1H-pyrazol-3-yl]piperidin-4-amine (150 mg, 0.42 mmol) and DIPEA (0.15 mL, 0.85 mmol) in $CH_2Cl_2$ (10 mL). The reaction mixture was stirred at room temperature for 23 h, poured into $NaHCO_3$ (20 mL, saturated aqueous solution) and extracted with $CH_2Cl_2$. The combined organic layers were dried over $Na_2SO_4$ (anhydrous), filtered and concentrated. The crude residue was purified by flash chromatography on $SiO_2$ (3% MeOH/$CH_2Cl_2$) to afford the title compound (white solid, 97 mg, 49% yield).

HPLC-MS (Method B): Ret, 19.04 min; $ESI^+$-MS m/z: 461 (M+1).

This method was used for the preparation of examples 2-49 using suitable starting materials:

| EX | Structure | Chemical name | Method | Ret (min) | MS (M + H) |
|---|---|---|---|---|---|
| 2 | 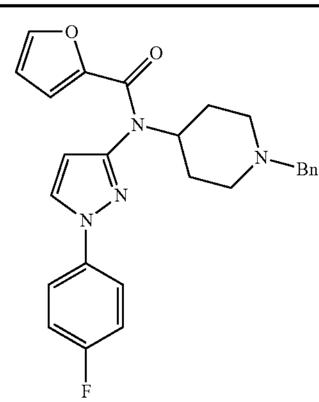 | N-(1-Benzylpiperidin-4-yl)-N-[1-(4-fluorophenyl)-1H-pyrazol-3-yl]furan-2-carboxamide | B | 19.01 | 445 |

-continued

| EX | Structure | Chemical name | Method | Ret (min) | MS (M + H) |
|---|---|---|---|---|---|
| 3 | 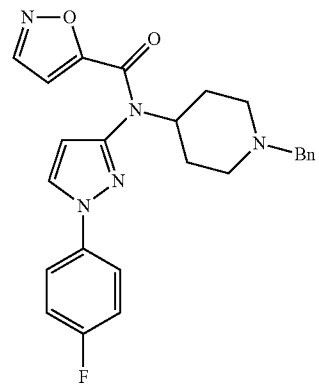 [SMILES: O=C(c1ccno1)N(c1ccn(-c2ccc(F)cc2)n1)C1CCN(Cc2ccccc2)CC1] | N-(1-Benzylpiperidin-4-yl)-N-[1-(4-fluorophenyl)-1H-pyrazol-3-yl]isoxazole-5-carboxamide | B | 18.94 | 446 |
| 4 | 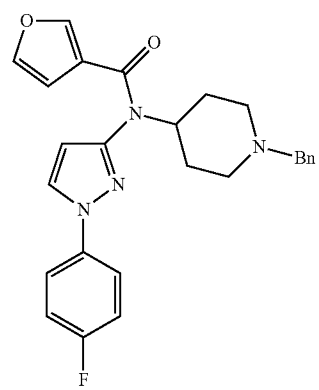 [SMILES: O=C(c1ccoc1)N(c1ccn(-c2ccc(F)cc2)n1)C1CCN(Cc2ccccc2)CC1] | N-(1-Benzylpiperidin-4-yl)-N-[1-(4-fluorophenyl)-1H-pyrazol-3-yl]furan-3-carboxamide | B | 19.30 | 445 |
| 5 | 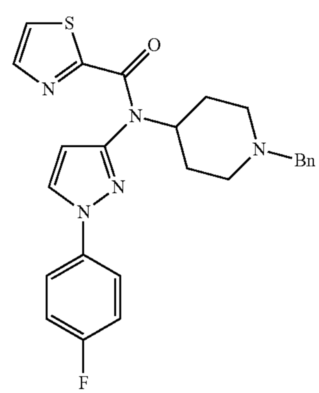 [SMILES: O=C(c1nccs1)N(c1ccn(-c2ccc(F)cc2)n1)C1CCN(Cc2ccccc2)CC1] | N-(1-Benzylpiperidin-4-yl)-N-[1-(4-fluorophenyl)-1H-pyrazol-3-yl]thiazole-2-carboxamide | B | 19.08 | 462 |
| 6 | 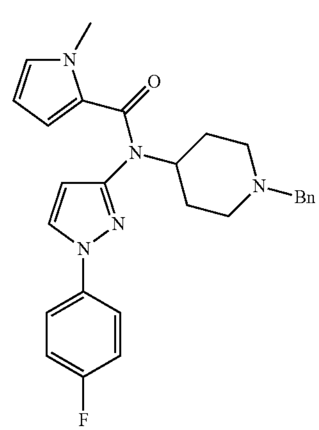 [SMILES: Cn1cccc1C(=O)N(c1ccn(-c2ccc(F)cc2)n1)C1CCN(Cc2ccccc2)CC1] | N-(1-Benzylpiperidin-4-yl)-N-[1-(4-fluorophenyl)-1H-pyrazol-3-yl]-1-methyl-1H-pyrrole-2-carboxamide | C | 12.35 | 458 |

| EX | Structure | Chemical name | Method | Ret (min) | MS (M + H) |
|---|---|---|---|---|---|
| 7 | 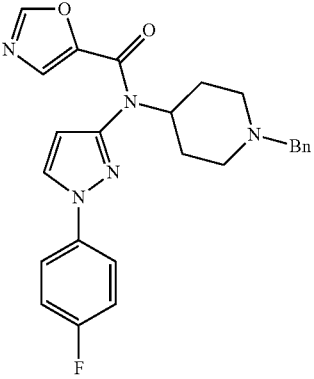 [SMILES: O=C(c1cnco1)N(c1ccn(-c2ccc(F)cc2)n1)C1CCN(Cc2ccccc2)CC1] | N-(1-Benzylpiperidin-4-yl)-N-[1-(4-fluorophenyl)-1H-pyrazol-3-yl)]oxazole-5-carboxamide | B | 18.42 | 446 |
| 8 | 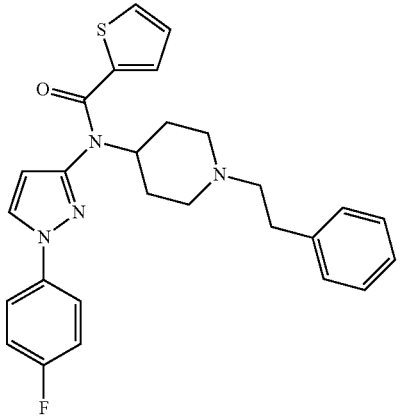 [SMILES: O=C(c1cccs1)N(c1ccn(-c2ccc(F)cc2)n1)C1CCN(CCc2ccccc2)CC1] | N-[1-(4-Fluorophenyl)-1H-pyrazol-3-yl]-N-(1-phenethylpiperidin-4-yl)thiophene-2-carboxamide | B | 18.36 | 475 |
| 9 | 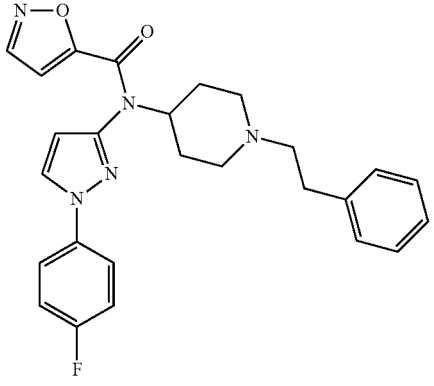 [SMILES: O=C(c1ccno1)N(c1ccn(-c2ccc(F)cc2)n1)C1CCN(CCc2ccccc2)CC1] | N-[1-(4-Fluorophenyl)-1H-pyrazol-3-yl]-N-(1-phenethylpiperidin-4-yl)isoxazole-5-carboxamide | B | 18.42 | 460 |
| 10 | 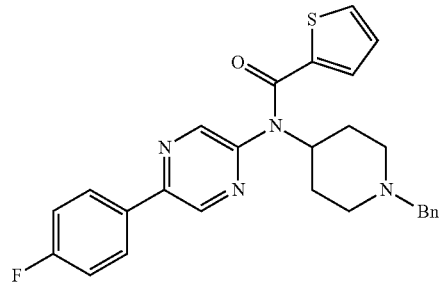 [SMILES: O=C(c1cccs1)N(c1cnc(-c2ccc(F)cc2)cn1)C1CCN(Cc2ccccc2)CC1] | N-(1-Benzylpiperidin-4-yl)-N-[5-(4-fluorophenyl)pyrazin-2-yl]thiophene-2-carboxamide | B | 20.09 | 473 |

-continued

| EX | Structure | Chemical name | Method | Ret (min) | MS (M + H) |
|---|---|---|---|---|---|
| 11 | 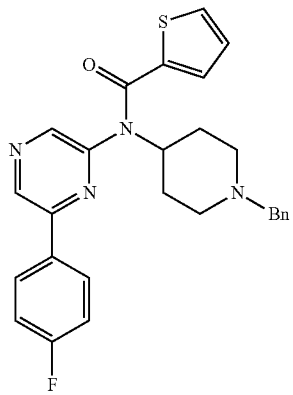 [SMILES: O=C(c1cccs1)N(c1cncc(-c2ccc(F)cc2)n1)C1CCN(Cc2ccccc2)CC1] | N-(1-Benzylpiperidin-4-yl)-N-[6-(4-fluorophenyl)pyrazin-2-yl]thiophene-2-carboxamide | B | 17.82 | 473 |
| 12 | 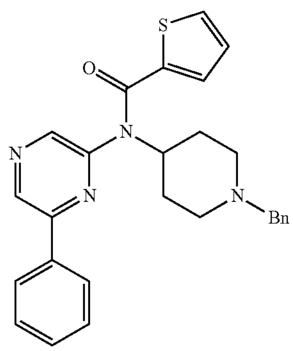 [SMILES: O=C(c1cccs1)N(c1cncc(-c2ccccc2)n1)C1CCN(Cc2ccccc2)CC1] | N-(1-Benzylpiperidin-4-yl)-N-(6-phenylpyrazin-2-yl)thiophene-2-carboxamide | F | 18.39 | 455 |
| 13 | 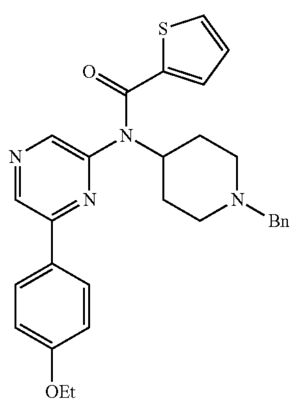 [SMILES: CCOc1ccc(-c2cncc(N(C(=O)c3cccs3)C3CCN(Cc4ccccc4)CC3)n2)cc1] | N-(1-Benzylpiperidin-4-yl)-N-[6-(4-ethoxyphenyl)pyrazin-2-yl]thiophene-2-carboxamide | F | 18.97 | 499 |
| 14 | 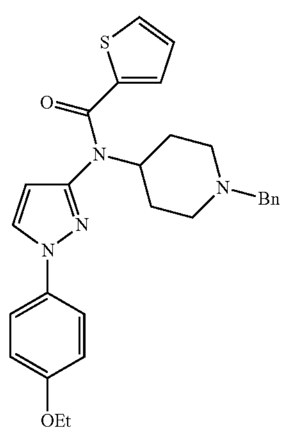 [SMILES: CCOc1ccc(-n2ccc(N(C(=O)c3cccs3)C3CCN(Cc4ccccc4)CC3)n2)cc1] | N-(1-Benzylpiperidin-4-yl)-N-[1-(4-ethoxyphenyl)-1H-pyrazol-3-yl]thiophene-2-carboxamide | B | 19.71 | 487 |

-continued
| EX | Structure | Chemical name | Method | Ret (min) | MS (M + H) |
|---|---|---|---|---|---|
| 15 | 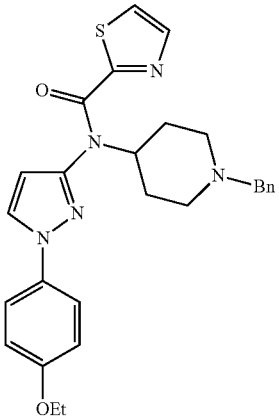 [SMILES: CCOc1ccc(-n2ccc(N(C(=O)c3nccs3)C3CCN(Cc4ccccc4)CC3)n2)cc1] | N-(1-Benzylpiperidin-4-yl)-N-[1-(4-ethoxyphenyl)-1H-pyrazol-3-yl]thiazole-2-carboxamide | B | 19.94 | 488 |
| 16 | 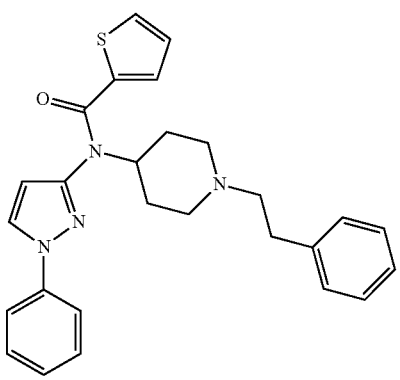 [SMILES: O=C(c1cccs1)N(c1ccn(-c2ccccc2)n1)C1CCN(CCc2ccccc2)CC1] | N-(1-Phenethylpiperidin-4-yl)-N-(1-phenyl-1H-pyrazol-3-yl)thiophene-2-carboxamide | B | 18.08 | 457 |
| 17 | 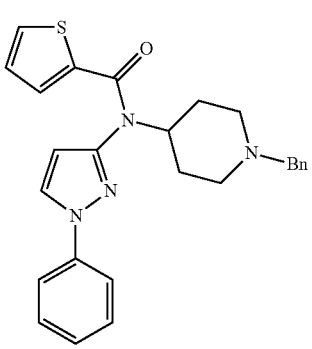 | N-(1-Benzylpiperidin-4-yl)-N-(1-phenyl-1H-pyrazol-3-yl)thiophene-2-carboxamide | G | 19.75 | 443 |
| 18 | 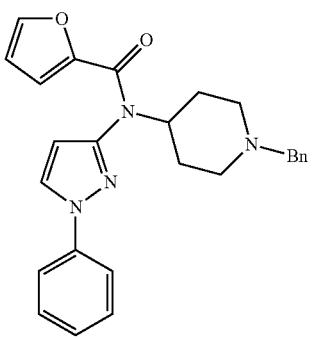 [SMILES: O=C(c1ccco1)N(c1ccn(-c2ccccc2)n1)C1CCN(Cc2ccccc2)CC1] | N-(1-Benzylpiperidin-4-yl)-N-(1-phenyl-1H-pyrazol-3-yl)furan-2-carboxamide | G | 18.14 | 427 |

-continued

| EX | Structure | Chemical name | Method | Ret (min) | MS (M + H) |
|---|---|---|---|---|---|
| 19 | 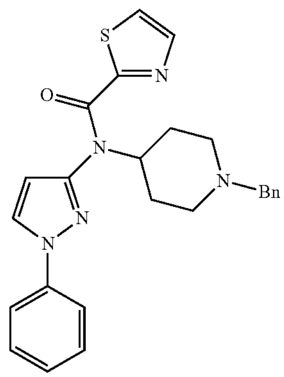 [SMILES: O=C(c1nccs1)N(c1ccn(-c2ccccc2)n1)C1CCN(Cc2ccccc2)CC1] | N-(1-Benzylpiperidin-4-yl)-N-(1-phenyl-1H-pyrazol-3-yl)thiazole-2-carboxamide | F | 17.18 | 444 |
| 20 | 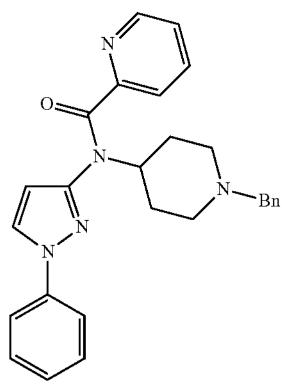 [SMILES: O=C(c1ccccn1)N(c1ccn(-c2ccccc2)n1)C1CCN(Cc2ccccc2)CC1] | N-(1-Benzylpiperidin-4-yl)-N-(1-phenyl-1H-pyrazol-3-yl)picolinamide | F | 14.31 | 438 |
| 21 | 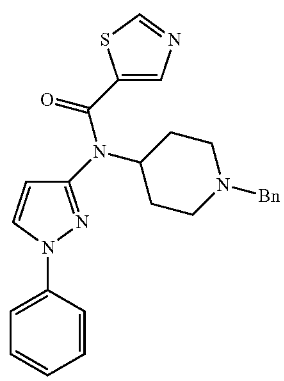 [SMILES: O=C(c1cncs1)N(c1ccn(-c2ccccc2)n1)C1CCN(Cc2ccccc2)CC1] | N-(1-Benzylpiperidin-4-yl)-N-(1-phenyl-1H-pyrazol-3-yl)thiazole-5-carboxamide | F | 18.84 | 444 |
| 22 | 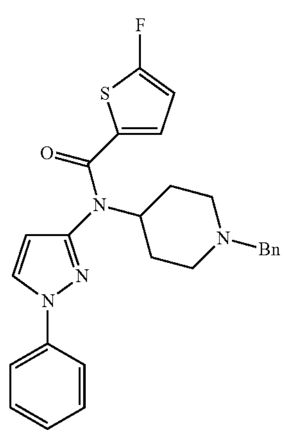 [SMILES: O=C(c1ccc(F)s1)N(c1ccn(-c2ccccc2)n1)C1CCN(Cc2ccccc2)CC1] | N-(1-Benzylpiperidin-4-yl)-5-fluoro-N-(1-phenyl-1H-pyrazol-3-yl)thiophene-2-carboxamide | F | 20.58 | 461 |

-continued

| EX | Structure | Chemical name | Method | Ret (min) | MS (M + H) |
|---|---|---|---|---|---|
| 23 | 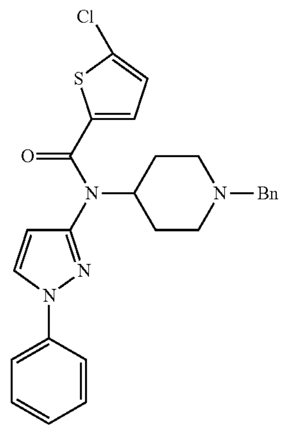 [SMILES: O=C(c1ccc(Cl)s1)N(c1ccn(-c2ccccc2)n1)C1CCN(Cc2ccccc2)CC1] | N-(1-Benzylpiperidin-4-yl)-5-chloro-N-(1-phenyl-1H-pyrazol-3-yl)thiophene-2-carboxamide | F | 21.09 | 477 |
| 24 | 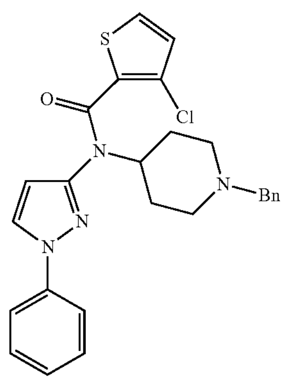 [SMILES: O=C(c1sccc1Cl)N(c1ccn(-c2ccccc2)n1)C1CCN(Cc2ccccc2)CC1] | N-(1-Benzylpiperidin-4-yl)-3-chloro-N-(1-phenyl-1H-pyrazol-3-yl)thiophene-2-carboxamide | F | 20.20 | 477 |
| 25 | 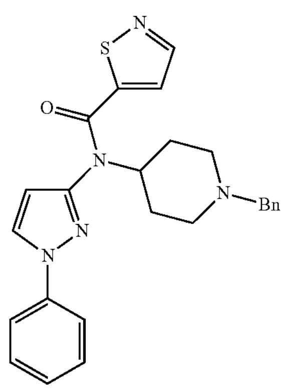 [SMILES: O=C(c1ccns1)N(c1ccn(-c2ccccc2)n1)C1CCN(Cc2ccccc2)CC1] | N-(1-Benzylpiperidin-4-yl)-N-(1-phenyl-1H-pyrazol-3-yl)isothiazole-5-carboxamide | F | 19.65 | 444 |
| 26 | 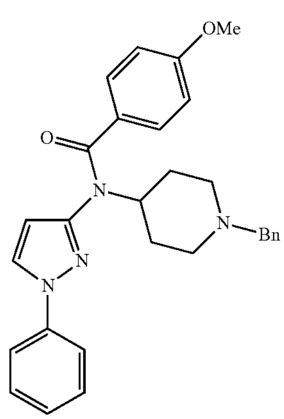 [SMILES: COc1ccc(C(=O)N(c2ccn(-c3ccccc3)n2)C2CCN(Cc3ccccc3)CC2)cc1] | N-(1-Benzylpiperidin-4-yl)-4-methoxy-N-(1-phenyl-1H-pyrazol-3-yl)benzamide | F | 19.76 | 467 |

| EX | Structure | Chemical name | Method | Ret (min) | MS (M + H) |
|----|-----------|---------------|--------|-----------|------------|
| 27 | 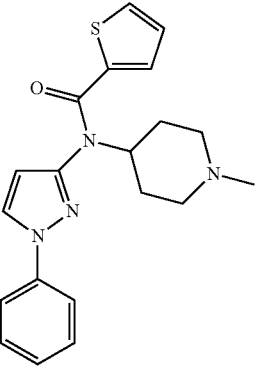 | N-(1-Methylpiperidin-4-yl)-N-(1-phenyl-1H-pyrazol-3-yl)thiophene-2-carboxamide | G | 15.27 | 367 |
| 28 | 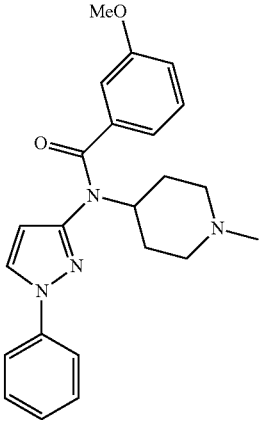 [SMILES: COc1cccc(C(=O)N(c2ccn(-c3ccccc3)n2)C2CCN(C)CC2)c1] | 3-Methoxy-N-(1-methyl-piperidin-4-yl)-N-(1-phenyl-1H-pyrazol-3-yl)-benzamide | G | 15.66 | 391 |
| 29 | 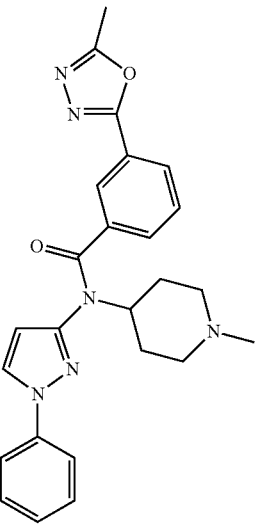 [SMILES: Cc1nnc(-c2cccc(C(=O)N(c3ccn(-c4ccccc4)n3)C3CCN(C)CC3)c2)o1] | 3-(5-Methyl-[1,3,4]oxadiazol-2-yl)-N-(1-methyl-piperidin-4-yl)-N-(1-phenyl-1H-pyrazol-3-yl)-benzamide | G | 14.86 | 443 |

-continued

| EX | Structure | Chemical name | Method | Ret (min) | MS (M + H) |
|---|---|---|---|---|---|
| 30 | 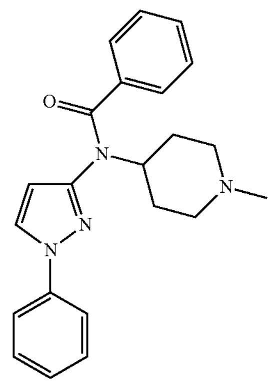 [SMILES: CN1CCC(N(C(=O)c2ccccc2)c2ccn(-c3ccccc3)n2)CC1] | N-(1-Methylpiperidin-4-yl)-N-(1-phenyl-1H-pyrazol-3-yl)benzamide | G | 15.49 | 361 |
| 31 | 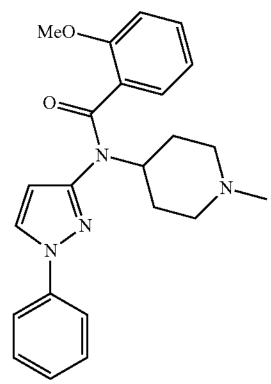 [SMILES: COc1ccccc1C(=O)N(c1ccn(-c2ccccc2)n1)C1CCN(C)CC1] | 2-Methoxy-N-(1-methylpiperidin-4-yl)-N-(1-phenyl-1H-pyrazol-3-yl)benzamide | G | 15.17 | 391 |
| 32 | 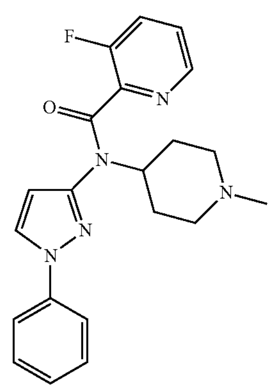 [SMILES: CN1CCC(N(C(=O)c2ncccc2F)c2ccn(-c3ccccc3)n2)CC1] | 3-Fluoro-N-(1-methylpiperidin-4-yl)-N-1-phenyl-1H-pyrazol-3-yl)picolinamide | G | 13.95 | 380 |
| 33 | 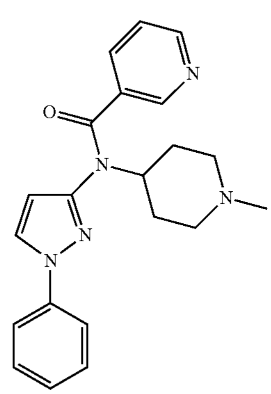 | N-(1-Methylpiperidin-4-yl)-N-(1-phenyl-1H-pyrazol-3-yl)nicotinamide | G | 13.52 | 362 |

-continued

| EX | Structure | Chemical name | Method | Ret (min) | MS (M + H) |
|---|---|---|---|---|---|
| 34 | 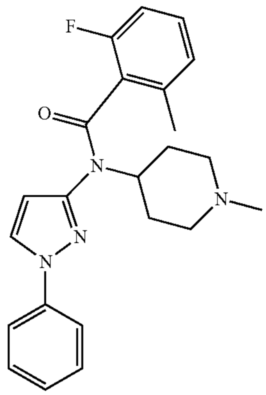 [SMILES: Cc1cccc(F)c1C(=O)N(c1ccn(-c2ccccc2)n1)C1CCN(C)CC1] | 2-Fluoro-6-methyl-N-(1-methylpiperidin-4-yl)-N-(1-phenyl-1H-pyrazol-3-yl) benzamide | G | 16.51 | 393 |
| 35 | 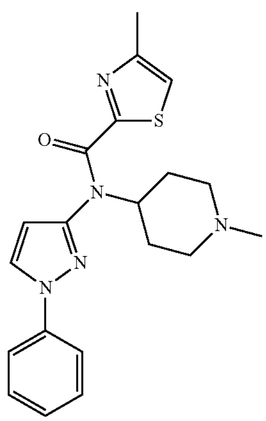 [SMILES: Cc1csc(C(=O)N(c2ccn(-c3ccccc3)n2)C2CCN(C)CC2)n1] | 4-Methyl-N-(1-methylpiperidin-4-yl)-N-(1-phenyl-1H-pyrazol-3-yl)thiazole-2-carboxamide | G | 15.02 | 382 |
| 36 | 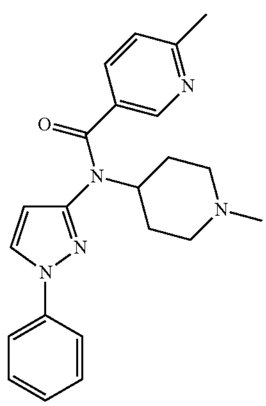 [SMILES: Cc1ccc(C(=O)N(c2ccn(-c3ccccc3)n2)C2CCN(C)CC2)cn1] | 6-Methyl-N-(1-methylpiperidin-4-yl)-N-(1-phenyl-1H-pyrazol-3-yl) nicotinamide | G | 14.32 | 376 |
| 37 | 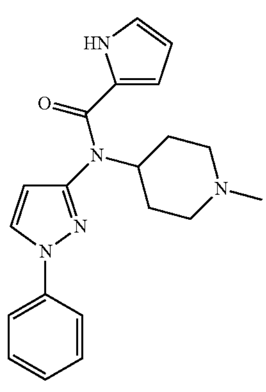 [SMILES: CN1CCC(N(C(=O)c2ccc[nH]2)c2ccn(-c3ccccc3)n2)CC1] | N-(1-Methylpiperidin-4-yl)-N-(1-phenyl-1H-pyrazol-3-yl)-1H-pyrrole-2-carboxamide | G | 14.86 | 350 |

-continued

| EX | Structure | Chemical name | Method | Ret (min) | MS (M + H) |
|---|---|---|---|---|---|
| 38 | 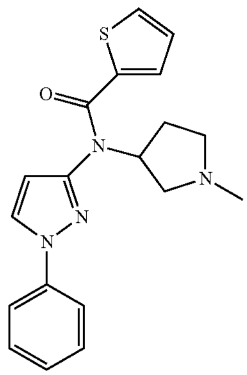 [SMILES: CN1CCC(N(C(=O)c2cccs2)c2ccn(-c3ccccc3)n2)C1] | N-(1-Methylpyrrolidin-3-yl)-N-(1-phenyl-1H-pyrazol-3-yl)thiophene-2-carboxamide | G | 15.69 | 353 |
| 39 | 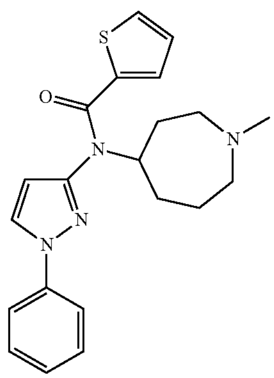 [SMILES: CN1CCCC(N(C(=O)c2cccs2)c2ccn(-c3ccccc3)n2)CC1] | N-(1-Methylazepan-4-yl)-N-(1-phenyl-1H-pyrazol-3-yl)thiophene-2-carboxamide | G | 15.59 | 381 |
| 40 | 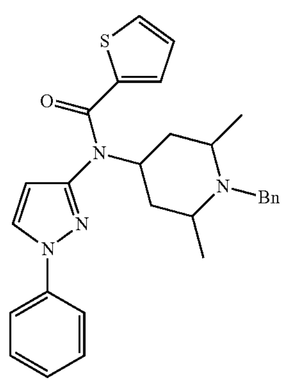 [SMILES: CC1CC(N(C(=O)c2cccs2)c2ccn(-c3ccccc3)n2)CC(C)N1Cc1ccccc1] | N-(1-Benzyl-2,6-dimethylpiperidin-4-yl)-N-(1-phenyl-1H-pyrazol-3-yl)thiophene-2-carboxamide | G | 18.24 | 471 |
| 41 | 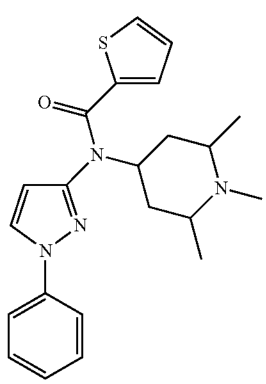 [SMILES: CC1CC(N(C(=O)c2cccs2)c2ccn(-c3ccccc3)n2)CC(C)N1C] | N-(1-Phenyl-1H-pyrazol-3-yl)-N-(1,2,6-trimethylpiperidin-4-yl)thiophene-2-carboxamide | G | 16.22 | 395 |

-continued

| EX | Structure | Chemical name | Method | Ret (min) | MS (M + H) |
|---|---|---|---|---|---|
| 42 | 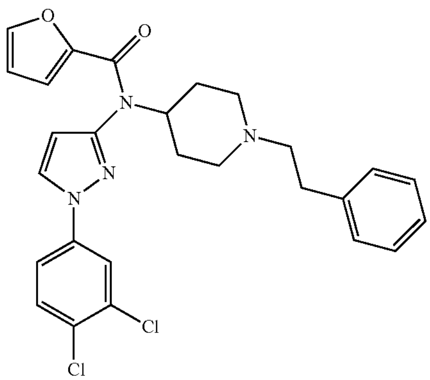 [SMILES: O=C(c1ccco1)N(c1ccn(-c2ccc(Cl)c(Cl)c2)n1)C1CCN(CCc2ccccc2)CC1] | N-[1-(3,4-Dichlorophenyl)-1H-pyrazol-3-yl]-N-(1-phenethylpiperidin-4-yl)furan-2-carboxamide | G | 17.14 | 509 |
| 43 | 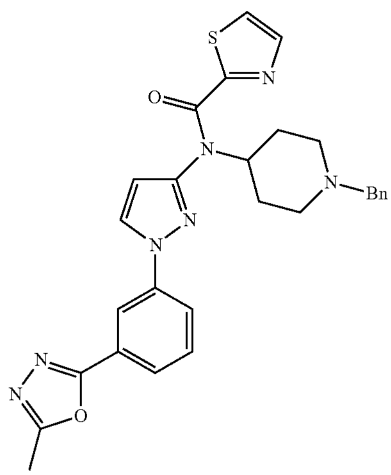 [SMILES: Cc1nnc(-c2cccc(-n3ccc(N(C(=O)c4nccs4)C4CCN(Cc5ccccc5)CC4)n3)c2)o1] | N-(1-Benzylpiperidin-4-yl)-N-{1-[3-(5-methyl-1,3,4-oxadiazol-2-yl)phenyl]-1H-pyrazol-3-yl}-1,3-thiazole-2-carboxamide | G | 18.27 | 526 |
| 44 | 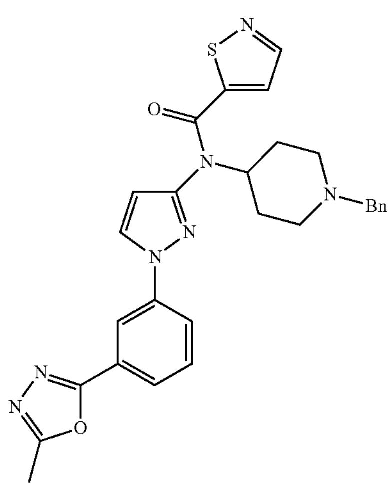 [SMILES: Cc1nnc(-c2cccc(-n3ccc(N(C(=O)c4ccns4)C4CCN(Cc5ccccc5)CC4)n3)c2)o1] | N-(1-Benzylpiperidin-4-yl)-N-{1-[3-(5-methyl-1,3,4-oxadiazol-2-yl)phenyl]-1H-pyrazol-3-yl}-isothiazole-5-carboxamide | G | 18.76 | 526 |

-continued

| EX | Structure | Chemical name | Method | Ret (min) | MS (M + H) |
|---|---|---|---|---|---|
| 45 | 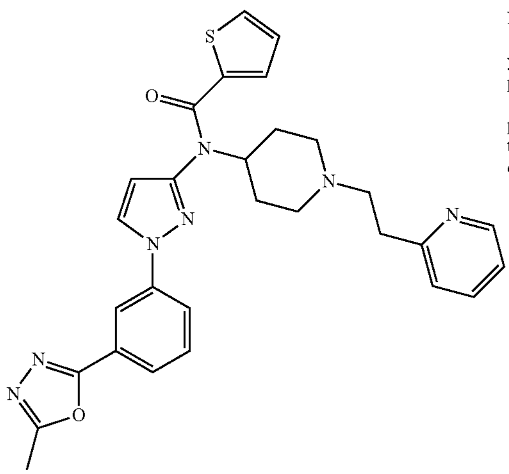 [SMILES: Cc1nnc(-c2cccc(-n3ccc(N(C(=O)c4cccs4)C4CCN(CCc5ccccn5)CC4)n3)c2)o1] | N-{1-[3-(5-Methyl-1,3,4-oxadiazol-2-yl)phenyl]-1H-pyrazol-3-yl}-N-{1-[2-(pyridin-2-yl)ethyl]piperidin-4-yl}thiophene-2-carboxamide | J | 20.24 | 540 |
| 46 | 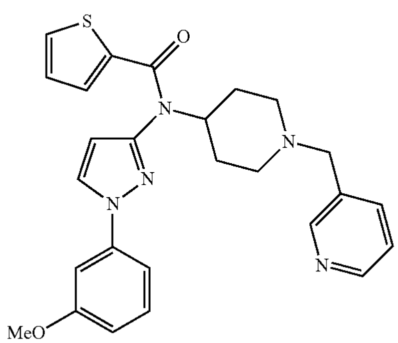 [SMILES: COc1cccc(-n2ccc(N(C(=O)c3cccs3)C3CCN(Cc4cccnc4)CC3)n2)c1] | N-[1-(3-Methoxyphenyl)-1H-pyrazol-3-yl]-N-[1-(pyridin-3-ylmethyl)piperidin-4-yl]thiophene-2-carboxamide | G | 17.74 | 474 |
| 47 | 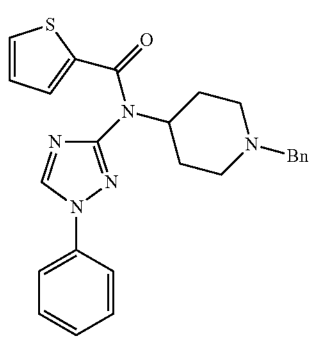 [SMILES: O=C(c1cccs1)N(c1ncn(-c2ccccc2)n1)C1CCN(Cc2ccccc2)CC1] | N-(1-benzylpiperidin-4-yl)-N-(1-phenyl-1H-1,2,4-triazol-3-yl)thiophene-2-carboxamide | O | 2.85 | 444 |
| 48 | 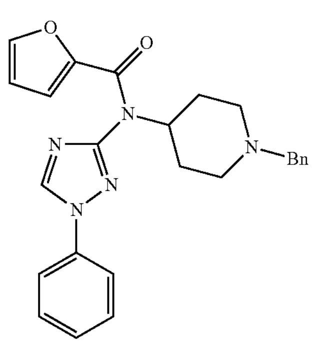 [SMILES: O=C(c1ccco1)N(c1ncn(-c2ccccc2)n1)C1CCN(Cc2ccccc2)CC1] | N-(1-benzylpiperidin-4-yl)-N-(1-phenyl-1H-1,2,4-triazol-3-yl)furan-2-carboxamide | O | 2.60 | 428 |

| EX | Structure | Chemical name | Method | Ret (min) | MS (M + H) |
|---|---|---|---|---|---|
| 49 | 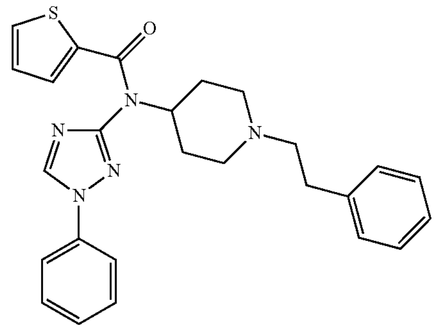 [SMILES: O=C(c1cccs1)N(c1ncn(-c2ccccc2)n1)C1CCN(CCc2ccccc2)CC1] | N-(1-phenethylpiperidin-4-yl)-N-(1-phenyl-1H-1,2,4-triazol-3-yl)thiophene-2-carboxamide | O | 2.95 | 458 |

Example 50. 3-Hydroxy-N-{1-[3-(5-methyl-1,3,4-oxadiazol-2-yl)phenyl]-1H-pyrazol-3-yl}-N-(1-methylpiperidin-4-yl)benzamide

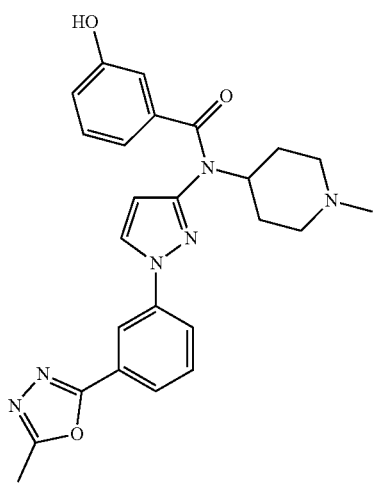 [SMILES: Cc1nnc(-c2cccc(-n3ccc(N(C(=O)c4cccc(O)c4)C4CCN(C)CC4)n3)c2)o1]

a) 3-[(1-[3-(5-Methyl-1,3,4-oxadiazol-2-yl)phenyl]-1H-pyrazol-3-yl)(1-methylpiperidin-4-yl)carbamoyl] phenyl acetate The title compound was obtained following the procedure described in Example 1 and using 1-methyl-N-{1-[3-(5-methyl-1,3,4-oxadiazol-2-yl)phenyl]-1H-pyrazol-3-yl}piperidin-4-amine and 3-(acetyloxy)benzoyl chloride as starting materials.

HPLC-MS (Method H): Ret, 8.80 min; ESI$^+$-MS m/z, 501 (M+1).

b) Title Compound

LiOH.H$_2$O (2 M aqueous solution, 0.19 mL, 0.37 mmol) was added to a solution of the compound obtained in step a) (0.19 g, 0.37 mmol) and the mixture was stirred at room temperature for 2 h. Volatiles were removed by rotatory evaporation and the residue was diluted with CH$_2$Cl$_2$ (30 mL) and washed with brine. The organic layer was dried over Na$_2$SO$_4$ (anhydrous), filtered and concentrated, obtaining a yellow oil which was purified by flash chromatography on SiO$_2$ (2% to 10% MeOH/CH$_2$Cl$_2$) to afford the title compound as a white solid (70 mg, 41% yield).

HPLC-MS (Method G): Ret, 14.11 min; ESI$^+$-MS m/z, 459 (M+1).

This method was used for the preparation of example 51 using suitable starting materials:

| Ex | Structure | Chemical name | Method | Ret (min) | MS (M + H) |
|---|---|---|---|---|---|
| 51 | 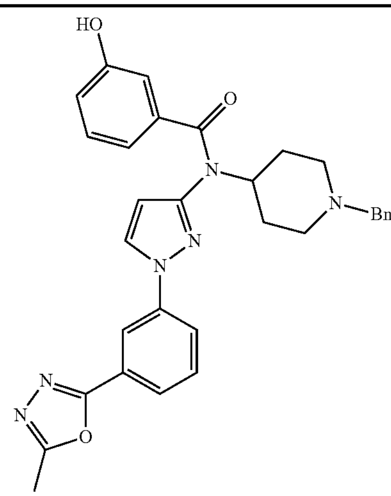 | N-(1-Benzylpiperidin-4-yl)-3-hydroxy-N-{1-[3-(5-methyl-1,3,4-oxadiazol-2-yl)phenyl]-1H-pyrazol-3-yl}benzamide | G | 17.78 | 535 |

Example 52. N-(1 Phenyl-1H-pyrazol-3-yl)-N-piperidin-4-ylthiophene-2-carboxamide

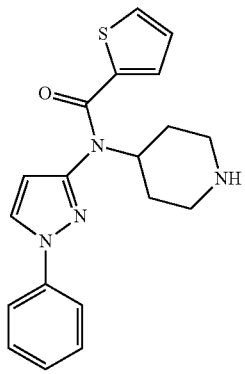 [SMILES: O=C(c1cccs1)N(c1ccn(-c2ccccc2)n1)C1CCNCC1]

a) tert-Butyl 4-[N-(1-phenyl-1H pyrazol-3-yl)thiophene-2-carboxamido]piperidine-1-carboxylate The title compound was obtained following the procedure described in Example 1 and using tert-butyl 4-[(1-phenyl-1H-pyrazol-3-yl)amino]piperidine-1-carboxylate as starting material.

HPLC-MS (Method D): Ret, 10.63 min; ESI$^+$-MS m/z, 453 (M+1).

b) Title Compound

TFA (0.30 mL, 3.90 mmol) was added to a solution of the compound obtained in step a) (320 mg, 0.71 mmol) in $CH_2Cl_2$ (6 mL). The reaction mixture was stirred at room temperature until full conversion was achieved (23 h). The mixture was poured into $NaHCO_3$ (saturated aqueous solution, 20 mL) and extracted with $CH_2Cl$. The combined organic layers were dried over $Na_2SO_4$ (anhydrous), filtered and concentrated. The crude residue was purified by flash chromatography on $SiO_2$ ($CH_2Cl_2$/MeOH/$NH_4OH$ 94:6:1 to 92:8:1) to afford the title compound (white solid, 221 mg, 89% yield).

HPLC-MS (Method G): Ret, 14.62 min; ESI$^+$-MS m/z, 353 (M+1).

This method was used for the preparation of examples 53-57 using suitable starting materials:

| Ex | Structure | Chemical name | Method | Ret (min) | MS (M + H) |
|---|---|---|---|---|---|
| 53 | 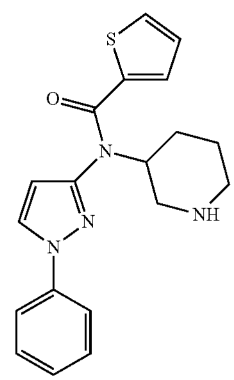 [SMILES: O=C(c1cccs1)N(c1ccn(-c2ccccc2)n1)C1CCCNC1] | N-(1-Phenyl-1H-pyrazol-3-yl)-N-(piperidin-3-yl)thiophene-2-carboxamide | D | 8.69 | 353 |
| 54 | 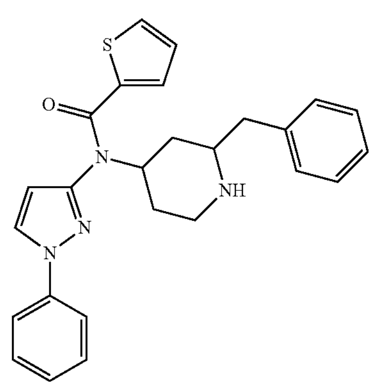 [SMILES: O=C(c1cccs1)N(c1ccn(-c2ccccc2)n1)C1CCNC(Cc2ccccc2)C1] | N-(2-Benzylpiperidin-4-yl)-N-(1-phenyl-1H-pyrazol-3-yl)thiophene-2-carboxamide | G | 17.58 | 443 |

-continued
| Ex | Structure | Chemical name | Method | Ret (min) | MS (M + H) |
|----|-----------|---------------|--------|-----------|------------|
| 55 | 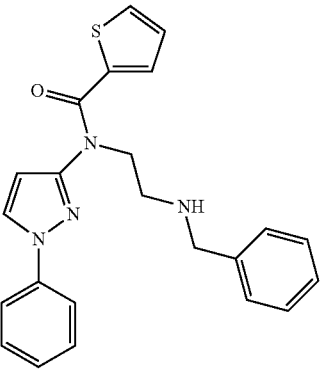 [SMILES: O=C(c1cccs1)N(CCNCc1ccccc1)c1ccn(-c2ccccc2)n1] | N-[2-(Benzylamino) ethyl]-N-(1-phenyl-1H-pyrazol-3-yl) thiophene-2-carboxamide | G | 17.86 | 403 |
| 56 | 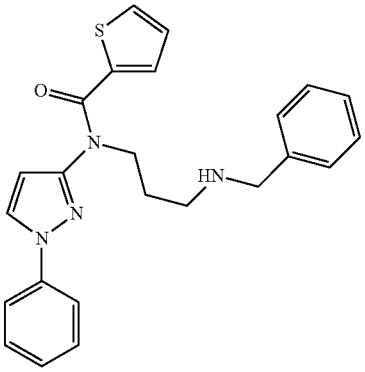 [SMILES: O=C(c1cccs1)N(CCCNCc1ccccc1)c1ccn(-c2ccccc2)n1] | N-[3-(Benzylamino) propyl]-N-(1-phenyl-1H-pyrazol-3-yl) thiophene-2-carboxamide | G | 17.16 | 417 |
| 57 | 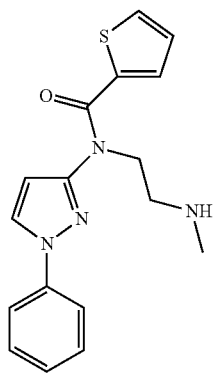 [SMILES: CNCCN(C(=O)c1cccs1)c1ccn(-c2ccccc2)n1] | N-[2-(Methylamino) ethyl]-N-(1-phenyl-1H-pyrazol-3-yl) thiophene-2-carboxamide | G | 14.61 | 327 |

Example 58. N-(1-Isobutylpiperidin-4-yl)-N-(1-phenyl-1H-pyrazol-3-yl)thiophene-2-carboxamide

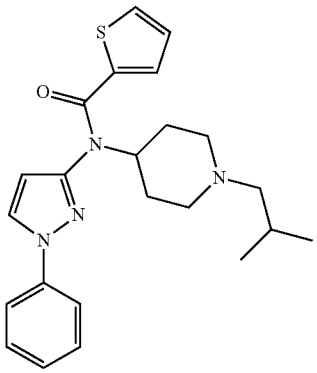 [SMILES: CC(C)CN1CCC(N(C(=O)c2cccs2)c2ccn(-c3ccccc3)n2)CC1]

K$_2$CO$_3$ (168 mg, 1.22 mmol) was added to a solution of N-(1-phenyl-1H-pyrazol-3-yl)-N-(piperidin-4-yl)thiophene-2 carboxamide (Example 52, 143 mg, 0.41 mmol) and 1-iodo-2-methylpropane (94 µL, 0.81 mmol) in CH$_3$CN (10 mL). The resulting suspension was stirred at 60° C. for 3 h, and 1-iodo-2-methylpropane (94 µL, 0.81 mmol) was further added. The mixture was warmed up to reflux and stirred at this temperature for 5 h and at room temperature for 15 h. The mixture was poured into water (10 mL) and extracted with EtOAc. The combined organic layers were dried over Na$_2$SO$_4$ (anhydrous), filtered and concentrated. The crude residue was purified by flash chromatography on SiO$_2$ (CH$_2$Cl$_2$/MeOH/NH$_4$OH 98:2:1 to 96:4:1) to obtain the title compound (pale yellow solid, 109 mg, 686% yield).

HPLC-MS (Method G): Ret, 18.03 min; ESI$^+$-MS m/z, 409 (M+1).

This method was used for the preparation of examples 59-60 using suitable starting materials:

| Ex | Structure | Chemical name | Method | Ret (min) | MS (M + H) |
|---|---|---|---|---|---|
| 59 | 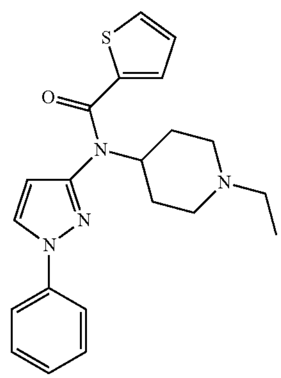 [SMILES: CCN1CCC(N(C(=O)c2cccs2)c2ccn(-c3ccccc3)n2)CC1] | N-(1-Ethylpiperidin-4-yl)-N-(1-phenyl-1H-pyrazol-3-yl)thiophene-2-carboxamide | G | 15.40 | 381 |
| 60 | 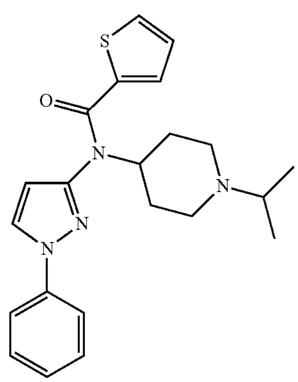 [SMILES: CC(C)N1CCC(N(C(=O)c2cccs2)c2ccn(-c3ccccc3)n2)CC1] | N-(1-Isopropyl-piperidin-4-yl)-N-(1-phenyl-1H-pyrazol-3-yl)thiophene-2-carboxamide | G | 15.53 | 395 |

Example 61. N-{2-[Benzyl(methyl)amino]ethyl}-N-(1-phenyl-1H-pyrazol-3-yl)thiophene-2-carboxamide

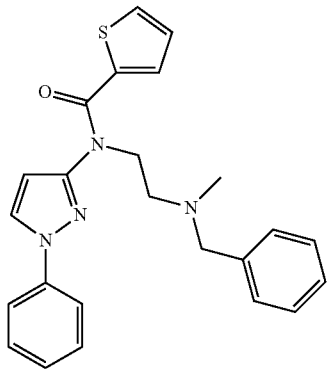 [SMILES: CN(CCN(C(=O)c1cccs1)c1ccn(-c2ccccc2)n1)Cc1ccccc1]

Formaldehyde (37% aqueous solution, 0.19 mL, 2.48 mmol) was added to a solution of N-[2-(methylamino)ethyl]-N-(1-phenyl-1H-pyrazol-3-yl)thiophene-2-carboxamide (Example 55, 0.10 g, 0.29 mmol) in MeOH (6 mL). The reaction mixture was stirred at room temperature for 10 min, NaBH(OAc)$_3$ (0.13 g, 0.62 mmol) was added and the mixture was stirred at room temperature for 6.5 h. The reaction mixture was poured into brine (15 mL) and extracted with CH$_2$Cl$_2$. The combined organic layers were dried over Na$_2$SO$_4$ (anhydrous), filtered and concentrated. The crude residue was purified by flash chromatography on SiO$_2$ (0 to 2% MeOH/CH$_2$Cl$_2$), to afford the title compound (yellow oil, 62 mg, 60% yield).

HPLC-MS (Method G): Ret, 19.59 min; ESI$^+$-MS m/z, 417 (M+1).

This method was used for the preparation of examples 62-67 using suitable starting materials:

| Ex | Structure | Chemical name | Method | Ret (min) | MS (M + H) |
|---|---|---|---|---|---|
| 62 | 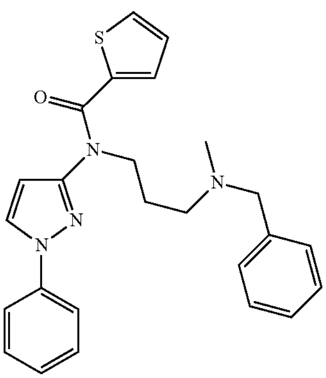 [SMILES: CN(CCCN(C(=O)c1cccs1)c1ccn(-c2ccccc2)n1)Cc1ccccc1] | N-{3-[Benzyl(methyl)amino]propyl}-N-(1-phenyl-1H-pyrazol-3-yl)thiophene-2-carboxamide | G | 18.85 | 431 |
| 63 | 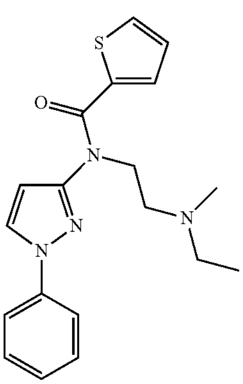 [SMILES: CCN(C)CCN(C(=O)c1cccs1)c1ccn(-c2ccccc2)n1] | N-{2-[Benzyl(methyl)amino]ethyl}-N-(1-phenyl-1H-pyrazol-3-yl)thiophene-2-carboxamide | G | 16.14 | 355 |

| Ex | Structure | Chemical name | Method | Ret (min) | MS (M + H) |
|---|---|---|---|---|---|
| 64 | 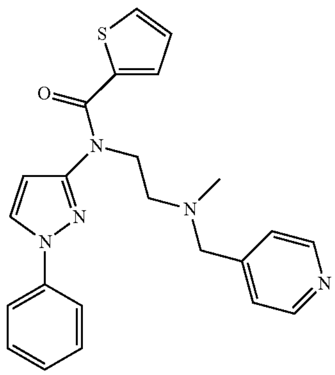 [SMILES: CN(CCN(C(=O)c1cccs1)c1ccn(-c2ccccc2)n1)Cc1ccncc1] | N-{2-[Methyl(pyridin-4-ylmethyl)amino]ethyl}-N-(1-phenyl-1H-pyrazol-3-yl)thiophene-2-carboxamide | G | 18.34 | 418 |
| 65 | 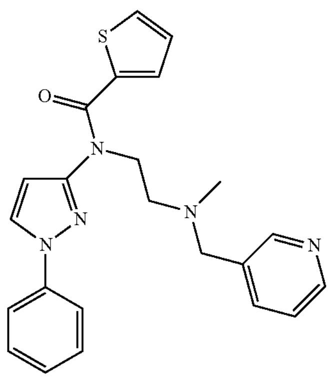 [SMILES: CN(CCN(C(=O)c1cccs1)c1ccn(-c2ccccc2)n1)Cc1cccnc1] | N-{2-[Methyl(pyridin-3-ylmethyl)amino]ethyl}-N-(1-phenyl-1H-pyrazol-3-yl)thiophene-2-carboxamide | G | 17.86 | 418 |
| 66 | 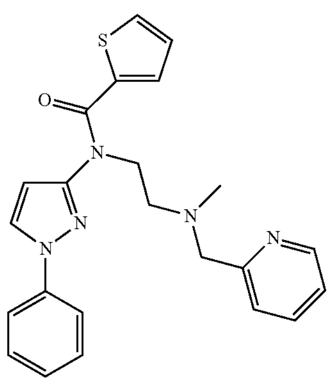 [SMILES: CN(CCN(C(=O)c1cccs1)c1ccn(-c2ccccc2)n1)Cc1ccccn1] | N-{2-[Methyl(pyridin-2-ylmethyl)amino]ethyl}-N-(1-phenyl-1H-pyrazol-3-yl)thiophene-2-carboxamide | G | 17.84 | 418 |
| 67 | 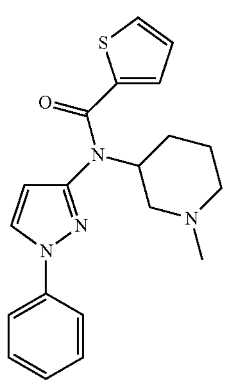 [SMILES: CN1CCCC(N(C(=O)c2cccs2)c2ccn(-c3ccccc3)n2)C1] | N-(1-Methylpiperidin-3-yl)-N-(1-phenyl-1H-pyrazol-3-yl)thiophene-2-carboxamide | G | 16.98 | 367 |

Example 68. N-[2-(Ethylamino)ethyl]-N-(1-phenyl-1H-pyrazol-3-yl)thiophene-2-carboxamide

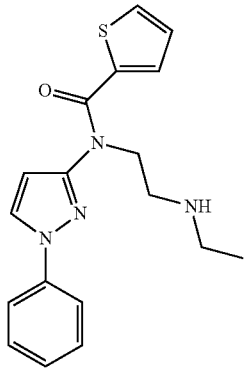 [SMILES: CCNCCN(C(=O)c1cccs1)c1ccn(-c2ccccc2)n1]

a) N-{2-[Benzyl(ethyl)amino]ethyl}-N-(1-phenyl-1H-pyrazol-3-yl)thiophene-2-carboxamide The title compound was obtained following the procedure described in example 58 and using N-[2-(benzylamino)ethyl]-N-(1-phenyl-1H-pyrazol-3-yl)thiophene-2-carboxamide (Example 55) and ethyl iodide as starting materials.

HPLC-MS (Method D): Ret, 10.81 min; ESI$^+$-MS m/z, 431 (M+1).

b) N-[2-(N-Benzyl-2-chloropropanamido)ethyl]-N-(1-phenyl-1H-pyrazol-3-yl)thiophene-2-carboxamide 1-Chloroethyl chloroformate (46 μL, 0.42 mmol) was added to a solution of the compound obtained in step a) (91 mg, 0.21 mmol) in CH$_2$Cl$_2$ (5 mL) and the mixture was refluxed for 3 h. The mixture was poured into NaHCO$_3$ (saturated aqueous solution, 15 mL) and extracted with CH$_2$Cl$_2$. The combined organic layers were dried over Na$_2$SO$_4$ (anhydrous), filtered and concentrated. The crude residue was purified by flash chromatography on SiO$_2$ (3% MeOH/CH$_2$Cl$_2$) to give the title compound (yellow oil, 83 mg, 88% yield).

c) Title Compound

A solution of the compound obtained in step b) (81 mg, 0.18 mmol) in MeOH (5 mL) was heated under reflux for 1 h. The solvent was concentrated off and the crude residue was purified by medium pressure flash chromatography (Combiflash, MeCN/H$_2$O) and preparative HPLC, to afford the title compound (white solid, 6 mg, 10% yield).

HPLC-MS (Method G): Ret, 14.96 min; ESI$^+$-MS m/z, 341 (M+1).

Example 69. N-{2-[Benzyl(methyl)amino]ethyl}-N-{1-[3-(S-methyl-1,3,4-oxadiazol-2-yl)phenyl]-1H-pyrazol-3-yl}thiophene-2-carboxamide

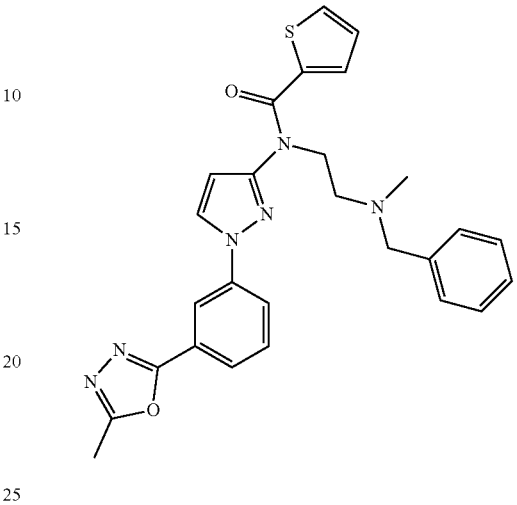

a) tert-Butyl benzyl[2-(N-{1-[3-(5-methyl-1,3,4-oxadiazol-2-yl)phenyl]-1H-pyrazol-3-yl}thiophene-2-carboxamido)ethyl]carbamate CuI (24 mg, 0.12 mmol) and K$_3$PO$_4$ (0.79 g, 3.72 mmol) were added to a solution of tert-butyl benzyl{2-[1H-pyrazol-3-yl(thien-2-ylcarbonyl)amino]ethyl}carbamate (0.53 g, 1.24 mmol), 2-(3-iodophenyl)-5-methyl-1,3,4-oxadiazole (0.44 g, 1.55 mmol) and N,N-dimethylethane-1,2-diamine (0.03 mL, 0.25 mmol) in dioxane (10 mL) and the mixture was heated at 100° C. for 24 h. The reaction was allowed to reach room temperature, was poured into NaHCO$_3$ (saturated aqueous solution, 40 mL) and extracted with EtOAc. The organic layer was washed with water, dried over Na$_2$SO$_4$ (anhydrous), filtered and concentrated. The crude residue was purified by flash chromatography on SiO$_2$ (5% MeOH/CH$_2$Cl$_2$) affording the title compound (reddish oil, 0.69 g, 95% yield), which was used without further purification.

HPLC-MS (Method H): Ret, 11.31 min; ESI$^+$-MS m/z, 585 (M+1).

b) N-[2-(Benzylamino)ethyl]-N-{1-[3-(5-methyl-1,3,4-oxadiazol-2-yl)phenyl]-1H-pyrazol-3-yl}thiophene-2-carboxamide HCl (1.25 M solution in MeOH, 3.90 mL, 4.90 mmol) was added to a solution of the compound obtained in step a) (0.68 g, 1.17 mmol) in MeOH (20 mL) and the mixture was stirred at room temperature for 29 h. Volatiles were removed by rotatory evaporation and the residue was slurried with hexanes (10 mL), filtered, slurried with Et$_2$O (10 mL) and filtered. The red solid was crystallized from iPrOH to give the title compound (300 mg with a purity of 9%, 50% yield).

HPLC-MS (Method H): Ret, 9.64 min; ESI$^+$-MS m/z, 485 (M+1).

c) Title Compound

Formaldehyde (37% aqueous solution, 0.16 mL, 1.73 mmol) and AcOH (99 µL, 1.73 mmol) were added to a solution of the compound obtained in step b) (300 mg, 9% purity) in $CH_2Cl_2$ (10 mL). The reaction mixture was stirred at room temperature for 5 min, $NaBH(OAc)_2$ (0.37 g, 1.73 mmol) was added and the suspension was stirred at room temperature for 16 h. The reaction mixture was poured into $NaHCO_3$ (saturated aqueous solution, 15 mL) and the mixture was extracted with $CH_2Cl_2$. The combined organic layers were dried over $Na_2SO_4$ (anhydrous), filtered and concentrated. The crude residue was purified by flash chromatography on $SiO_2$ (3 to 5% $MeOH:CH_2Cl_2$) followed by semipreparative HPLC to give the title compound (colorless oil, 14 mg, 39% yield).

HPLC-MS (Method G): Ret, 16.59 min; $ESI^+$-MS m/z, 499 (M+1).

Example 70. N-(1-Methylpiperidin-4-yl)-N-(1-pyridin-2-yl-1H-pyrazol-3-yl)thiophene-2-carboxamide

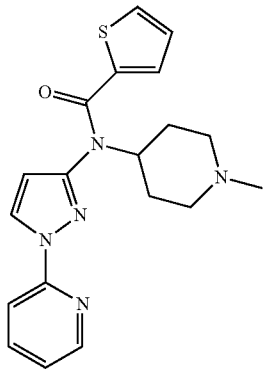

Arylation conditions A: N,N,N',N'-Tetramethylethane-1,2-diamine (21 µL, 0.14 mmol) was added to a suspension of N-(1-methylpiperidin-4-yl)-N-(1H-pyrazol-3-yl)thiophene-2-carboxamide (Intermediate C1, 100 mg, 0.34 mmol), 2-iodopyridine (44 µL, 0.41 mmol) and $Cs_2CO_3$ (235 mg, 0.72 mmol) in MeCN (8 mL). The reaction mixture was deoxygenated, CuI (13 mg, 0.07 mmol) was added and it was heated under reflux for 6 h. It was cooled down to room temperature, poured into $NaHCO_3$ (saturated aqueous solution, 10 mL) and extracted with $CH_2Cl_2$. The combined organic layers were dried over $Na_2SO_4$ (anhydrous), filtered and concentrated. The crude residue was purified by flash chromatography on $SiO_2$ ($CH_2Cl_2$/MeOH/$NH_4OH$ 97:3:1), to afford 118 mg of title compound (beige solid, 93% yield).

HPLC-MS (Method G): Ret, 14.94 min; $ESI^+$-MS m/z, 368 (M+1).

Arylation conditions B: (±)-trans-1,2-diaminocyclohexane was used instead of N,N,N',N'-tetramethylethane-1,2-diamine Arylation conditions C: N,N'-dimethylethane-1,2-diamine was used instead of N,N,N',N'-tetramethylethane-1,2-diamine and $K_3PO_4$ instead of $Cs_2CO_3$.

This method was used for the preparation of examples 71-86 using suitable starting materials and the conditions indicated:

| Ex | Structure/Conditions | Chemical name | Method | Ret (min) | MS (M + H) |
|---|---|---|---|---|---|
| 71 | A | N-(1-Methylpiperidin-4-yl)-N-[1-(pyridin-3-yl)-1H-pyrazol-3-yl]thiophene-2-carboxamide | G | 13.66 | 368 |

-continued
| Ex | Structure/Conditions | Chemical name | Method | Ret (min) | MS (M + H) |
|---|---|---|---|---|---|
| 72 | 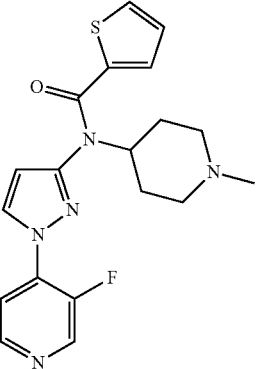 B | N-[1-(3-Fluoropyridin-4-yl)-1H-pyrazol-3-yl]-N-(1-methylpiperidin-4-yl)thiophene-2-carboxamide | G | 14.36 | 386 |
| 73 | 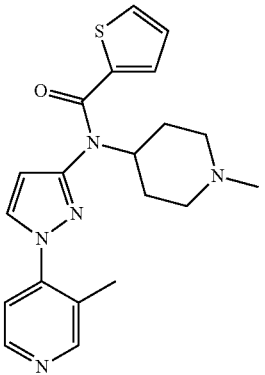 B | N-(1-Methylpiperidin-4-yl)-N-[1-(3-methylpyridin-4-yl)-1H-pyrazol-3-yl]thiophene-2-carboxamide | G | 14.45 | 382 |
| 74 | 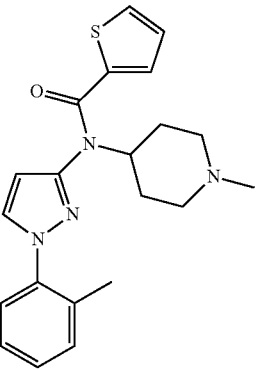 A | N-(1-Methylpiperidin-4-yl)-N-[1-(o-tolyl)-1H-pyrazol-3-yl]thiophene-2-carboxamide | G | 15.97 | 381 |

-continued

| Ex | Structure/Conditions | Chemical name | Method | Ret (min) | MS (M + H) |
|---|---|---|---|---|---|
| 75 | 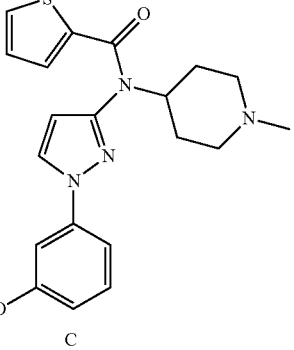 C | N-{1-[3-(2-Methoxyethoxy) phenyl]-1H-pyrazol-3-yl}-N-(1-methylpiperidin-4-yl)thiophene-2-carboxamide | G | 15.78 | 441 |
| 76 | 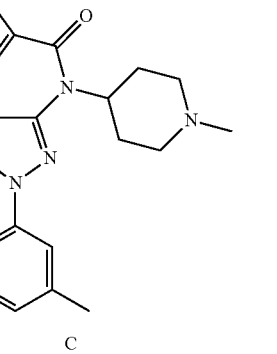 C | N-[1-(3-Methoxy-5-methylphenyl)-1H-pyrazol-3-yl]-N-(1-methylpiperidin-4-yl)thiophene-2-carboxamide | G | 16.96 | 411 |
| 77 | 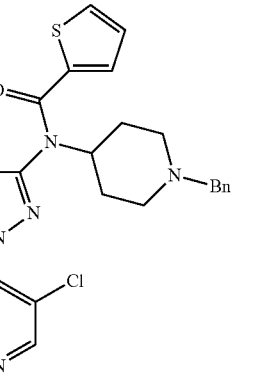 A | N-(1-Benzylpiperidin-4-yl)-N-[1-(3,5-dichloropyridin-4-yl)-1H-pyrazol-3-yl]thiophene-2-carboxamide | K | 17.38 | 512 |
| 78 | 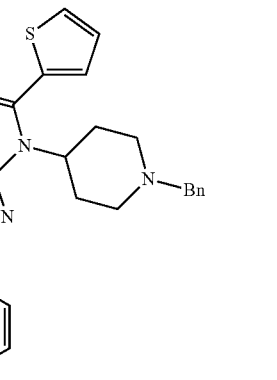 A | N-(1-Benzylpiperidin-4-yl)-N-[1-(pyridin-4-yl)-1H-pyrazol-3-yl]thiophene-2-carboxamide | G | 18.11 | 444 |

| Ex | Structure/Conditions | Chemical name | Method | Ret (min) | MS (M + H) |
|---|---|---|---|---|---|
| 79 | 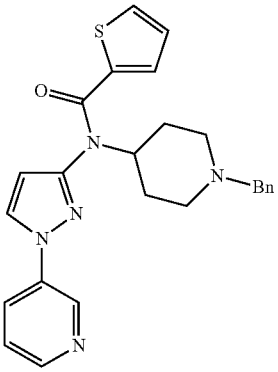 A | N-(1-Benzylpiperidin-4-yl)-N-[1-(pyridin-3-yl)-1H-pyrazol-3-yl]thiophene-2-carboxamide | G | 17.90 | 444 |
| 80 | 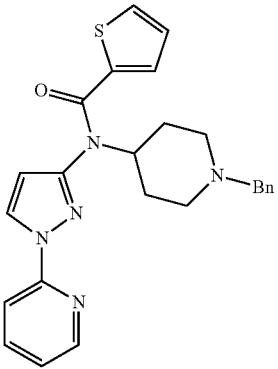 A | N-(1-Benzylpiperidin-4-yl)-N-[1-(pyridin-2-yl)-1H-pyrazol-3-yl]thiophene-2-carboxamide | G | 19.44 | 444 |
| 81 | 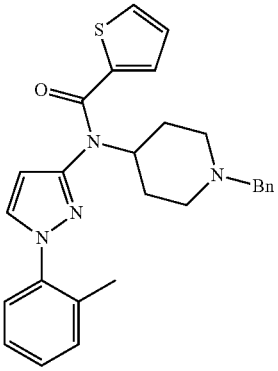 A | N-(1-Benzylpiperidin-4-yl)-N-[1-(o-tolyl)-1H-pyrazol-3-yl]thiophene-2-carboxamide | G | 19.72 | 457 |

-continued
| Ex | Structure/Conditions | Chemical name | Method | Ret (min) | MS (M + H) |
|---|---|---|---|---|---|
| 82 | 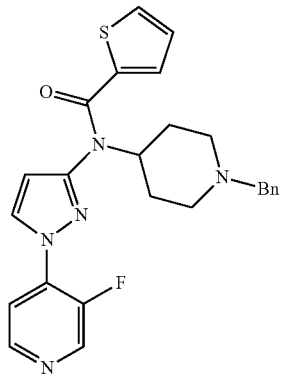<br>B | N-(1-Benzylpiperidin-4-yl)-N-[1-(3-fluoropyridin-4-yl)-1H-pyrazol-3-yl]thiophene-2-carboxamide | G | 18.70 | 462 |
| 83 | 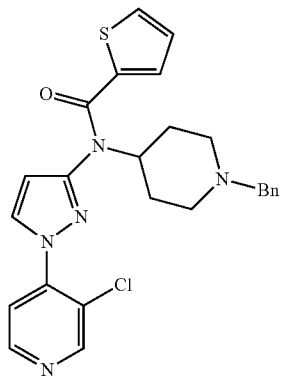<br>B | N-(1-Benzylpiperidin-4-yl)-N-[1-(3-chloropyridin-4-yl)-1H-pyrazol-3-yl]thiophene-2-carboxamide | G | 18.79 | 478 |
| 84 | 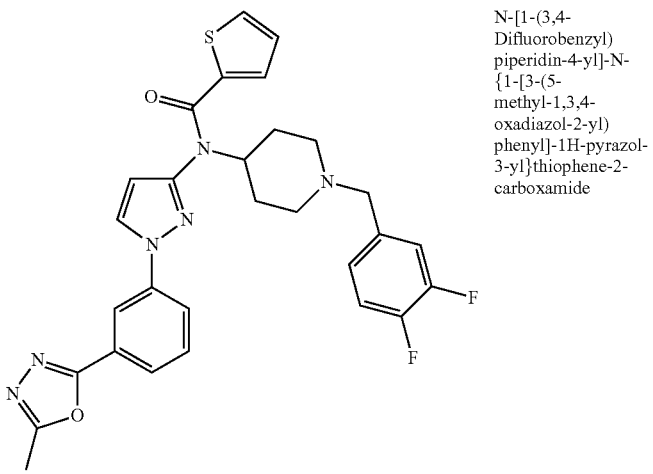<br>C | N-[1-(3,4-Difluorobenzyl)piperidin-4-yl]-N-{1-[3-(5-methyl-1,3,4-oxadiazol-2-yl)phenyl]-1H-pyrazol-3-yl}thiophene-2-carboxamide | G | 19.73 | 561 |

| Ex | Structure/Conditions | Chemical name | Method | Ret (min) | MS (M + H) |
|---|---|---|---|---|---|
| 85 | C | N-{1-[3-(5-Methyl-1,3,4-oxadiazol-2-yl)phenyl]-1H-pyrazol-3-yl}-N-(1-phenethylpiperidin-4-yl)thiophene-2-carboxamide | G | 18.62 | 539 |
| 86 | C | N-{1-[3-(5-Methyl-1,3,4-oxadiazol-2-yl)phenyl]-1H-pyrazol-3-yl}-N-(1-(pyridin-2-ylmethyl)piperidin-4-yl)thiophene-2-carboxamide | G | 17.40 | 526 |

Example 87. N-[1-(4-Ethoxyphenyl)-1H-pyrazol-3-yl]-N-(1-methylpiperidin-4-yl)thiophene-2-carboxamide

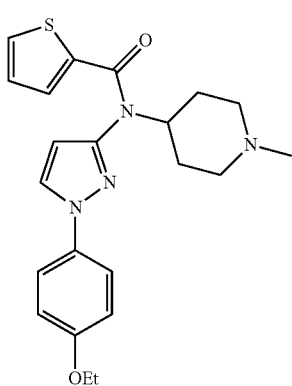 [SMILES: CCOc1ccc(-n2ccc(N(C(=O)c3cccs3)C3CCN(C)CC3)n2)cc1]

Pyridine (0.12 mL, 1.53 mmol) and Cu(OAc)$_2$ (0.19 g, 1.02 mmol) were added to a solution of N-(1-methylpiperidin-4-yl)-N-1H-pyrazol-3-ylthiophene-2-carboxamide (Intermediate C1, 0.15 g, 0.51 mmol) and (4-ethoxyphenyl)boronic acid (0.13 g, 0.77 mmol) in CH$_2$Cl$_2$ (8 mL) and the mixture was stirred at room temperature for 19 h in an open flask. The reaction was diluted with CH$_2$Cl$_2$ (50 mL) and was washed with brine. The organic layer was dried over Na$_2$SO$_4$ (anhydrous), filtered and concentrated. The crude residue was purified by flash chromatography on SiO$_2$ (CH$_2$Cl$_2$/MeOH/NH$_4$OH 97:3:1 to 96:4:1) affording the title compound (pale pink solid, 0.17 g, 81% yield).

HPLC-MS (Method G): Ret, 16.64 min; ESI$^+$-MS m/z, 411 (M+1).

This method was used for the preparation of examples 88-122 using suitable starting materials:

| Ex | Structure | Chemical name | Method | Ret (min) | MS (M + H) |
|---|---|---|---|---|---|
| 88 | 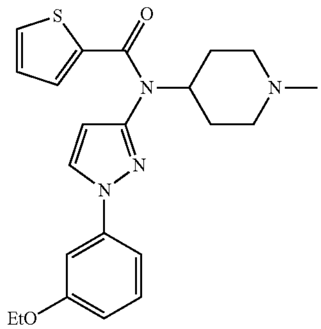 [SMILES: CCOc1cccc(-n2ccc(N(C(=O)c3cccs3)C3CCN(C)CC3)n2)c1] | N-[1-(3-Ethoxyphenyl)-1H-pyrazol-3-yl]-N-(1-methylpiperidin-4-yl)thiophene-2-carboxamide | G | 16.60 | 411 |
| 89 | 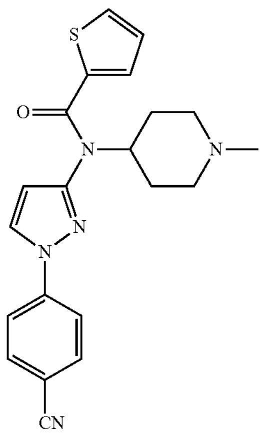 [SMILES: CN1CCC(N(C(=O)c2cccs2)c2ccn(-c3ccc(C#N)cc3)n2)CC1] | N-[1-(4-Cyanophenyl)-1H-pyrazol-3-yl]-N-(1-methylpiperidin-4-yl)thiophene-2-carboxamide | G | 15.36 | 392 |
| 90 | 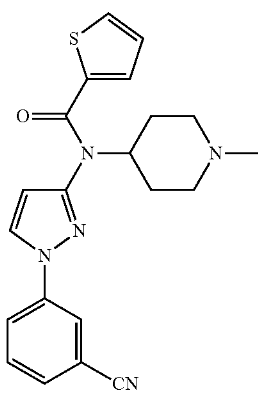 [SMILES: CN1CCC(N(C(=O)c2cccs2)c2ccn(-c3cccc(C#N)c3)n2)CC1] | N-[1-(3-Cyanophenyl)-1H-pyrazol-3-yl]-N-(1-methylpiperidin-4-yl)thiophene-2-carboxamide | G | 15.42 | 392 |
| 91 | 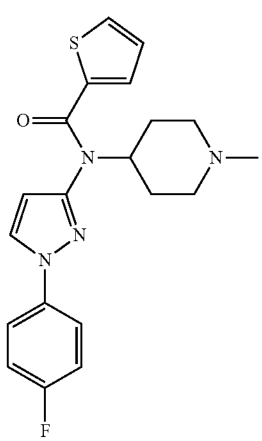 [SMILES: CN1CCC(N(C(=O)c2cccs2)c2ccn(-c3ccc(F)cc3)n2)CC1] | N-[1-(4-Fluorophenyl)-1H-pyrazol-3-yl]-N-(1-methylpiperidin-4-yl)thiophene-2-carboxamide | G | 15.87 | 385 |

| Ex | Structure | Chemical name | Method | Ret (min) | MS (M + H) |
|---|---|---|---|---|---|
| 92 | 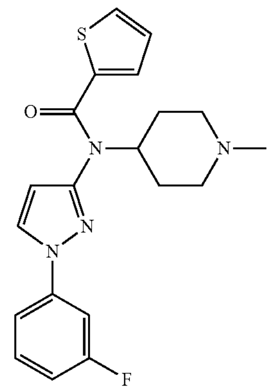 [SMILES: CN1CCC(N(C(=O)c2cccs2)c2ccn(-c3cccc(F)c3)n2)CC1] | N-[1-(3-Fluorophenyl)-1H-pyrazol-3-yl]-N-(1-methylpiperidin-4-yl)thiophene-2-carboxamide | G | 16.14 | 385 |
| 93 | 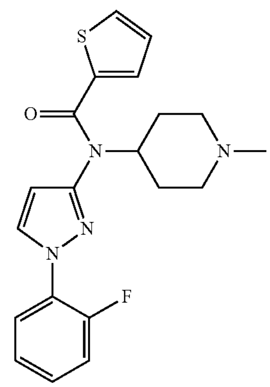 [SMILES: CN1CCC(N(C(=O)c2cccs2)c2ccn(-c3ccccc3F)n2)CC1] | N-[1-(2-Fluorophenyl)-1H-pyrazol-3-yl]-N-(1-methylpiperidin-4-yl)thiophene-2-carboxamide | G | 13.26 | 385 |
| 94 | 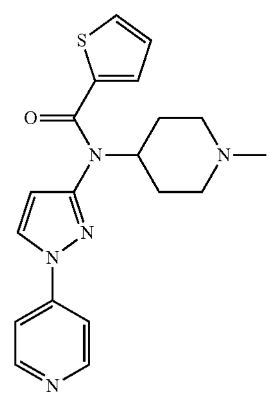 [SMILES: CN1CCC(N(C(=O)c2cccs2)c2ccn(-c3ccncc3)n2)CC1] | N-(1-Methylpiperidin-4-yl)-N-(1-(pyridin-4-yl)-1H-pyrazol-3-yl)thiophene-2-carboxamide | G | 13.79 | 368 |
| 95 | 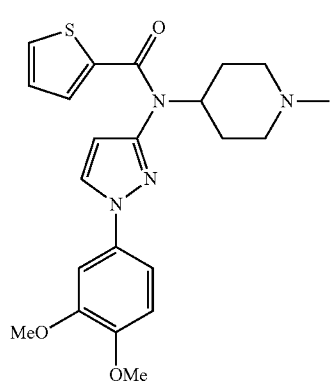 [SMILES: COc1ccc(-n2ccc(N(C(=O)c3cccs3)C3CCN(C)CC3)n2)cc1OC] | N-[1-(3,4-Dimethoxyphenyl)-1H-pyrazol-3-yl]-N-(1-methylpiperidin-4-yl)thiophene-2-carboxamide | G | 14.96 | 427 |

| Ex | Structure | Chemical name | Method | Ret (min) | MS (M + H) |
|---|---|---|---|---|---|
| 96 | 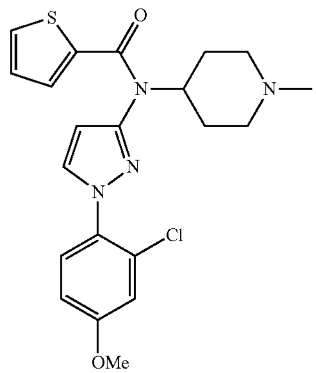 [SMILES: COc1ccc(-n2ccc(N(C(=O)c3cccs3)C3CCN(C)CC3)n2)c(Cl)c1] | N-[1-(2-Chloro-4-methoxyphenyl)-1H-pyrazol-3-yl]-N-(1-methylpiperidin-4-yl)thiophene-2-carboxamide | G | 16.25 | 431 |
| 97 | 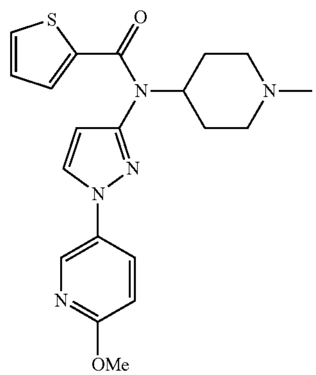 [SMILES: COc1ccc(-n2ccc(N(C(=O)c3cccs3)C3CCN(C)CC3)n2)cn1] | N-[1-(6-Methoxypyridin-3-yl)-1H-pyrazol-3-yl]-N-(1-methylpiperidin-4-yl)thiophene-2-carboxamide | G | 14.87 | 398 |
| 98 | 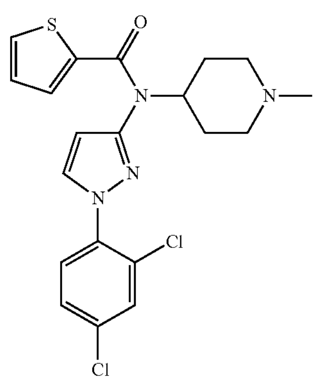 [SMILES: CN1CCC(N(C(=O)c2cccs2)c2ccn(-c3ccc(Cl)cc3Cl)n2)CC1] | N-[1-(2,4-Dichlorophenyl)-1H-pyrazol-3-yl]-N-(1-methylpiperidin-4-yl)thiophene-2-carboxamide | G | 17.24 | 435 |
| 99 | 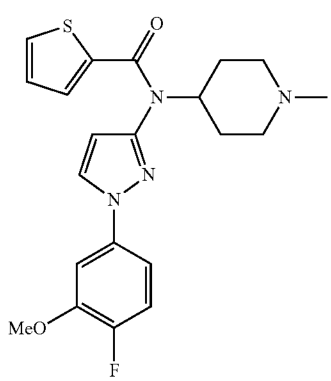 [SMILES: COc1cc(-n2ccc(N(C(=O)c3cccs3)C3CCN(C)CC3)n2)ccc1F] | N-[1-(4-Fluoro-3-methoxyphenyl)-1H-pyrazol-3-yl]-N-(1-methylpiperidin-4-yl)thiophene-2-carboxamide | G | 16.04 | 415 |

| Ex | Structure | Chemical name | Method | Ret (min) | MS (M + H) |
|---|---|---|---|---|---|
| 100 | 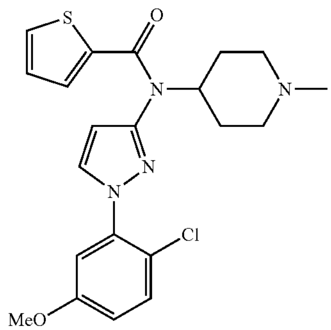 [SMILES: COc1ccc(Cl)c(-n2ccc(N(C(=O)c3cccs3)C3CCN(C)CC3)n2)c1] | N-[1-(2-Chloro-5-methoxyphenyl)-1H-pyrazol-3-yl]-N-(1-methylpiperidin-4-yl)thiophene-2-carboxamide | G | 16.41 | 431 |
| 101 | 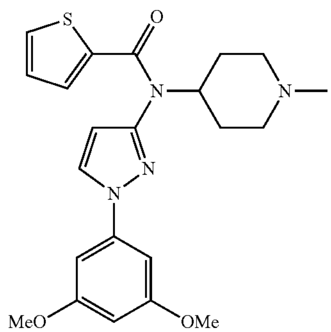 [SMILES: COc1cc(OC)cc(-n2ccc(N(C(=O)c3cccs3)C3CCN(C)CC3)n2)c1] | N-[1-(3,5-Dimethoxyphenyl)-1H-pyrazol-3-yl]-N-(1-methylpiperidin-4-yl)thiophene-2-carboxamide | G | 16.54 | 427 |
| 102 | 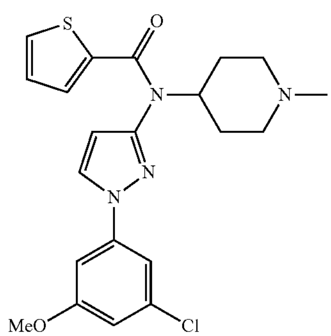 [SMILES: COc1cc(Cl)cc(-n2ccc(N(C(=O)c3cccs3)C3CCN(C)CC3)n2)c1] | N-[1-(3-Chloro-5-methoxyphenyl)-1H-pyrazol-3-yl]-N-(1-methylpiperidin-4-yl)thiophene-2-carboxamide | G | 17.78 | 431 |
| 103 | 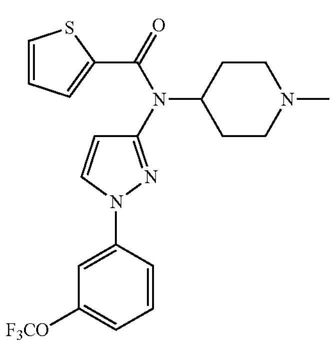 [SMILES: CN1CCC(N(C(=O)c2cccs2)c2ccn(-c3cccc(OC(F)(F)F)c3)n2)CC1] | N-(1-Methylpiperidin-4-yl)-N-{1-[3-(trifluoromethoxy)phenyl]-1H-pyrazol-3-yl}thiophene-2-carboxamide | G | 17.99 | 451 |

-continued

| Ex | Structure | Chemical name | Method | Ret (min) | MS (M + H) |
|---|---|---|---|---|---|
| 104 | 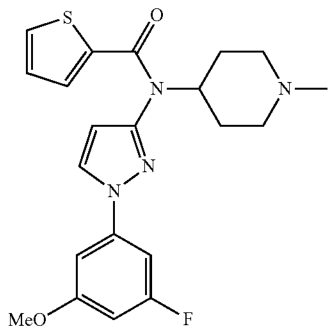 [SMILES: COc1cc(F)cc(-n2ccc(N(C(=O)c3cccs3)C3CCN(C)CC3)n2)c1] | N-[1-(3-Fluoro-5-methoxyphenyl)-1H-pyrazol-3-yl]-N-(1-methylpiperidin-4-yl)thiophene-2-carboxamide | G | 16.89 | 415 |
| 105 | 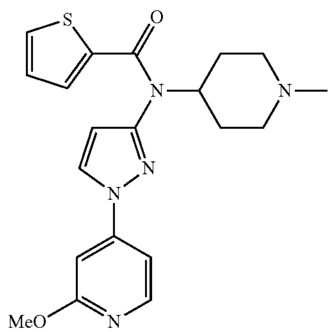 [SMILES: COc1cc(-n2ccc(N(C(=O)c3cccs3)C3CCN(C)CC3)n2)ccn1] | N-[1-(2-Methoxypyridin-4-yl)-1H-pyrazol-3-yl]-N-(1-methylpiperidin-4-yl)thiophene-2-carboxamide | G | 15.29 | 398 |
| 106 | 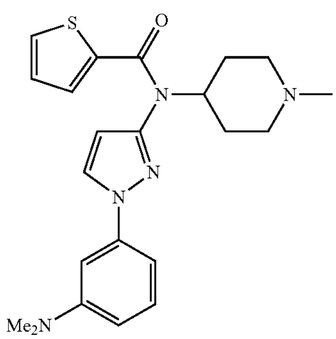 | N-{1-[3-(Dimethylamino)phenyl]-1H-pyrazol-3-yl}-N-(1-methylpiperidin-4-yl)thiophene-2-carboxamide | G | 16.81 | 410 |
| 107 | 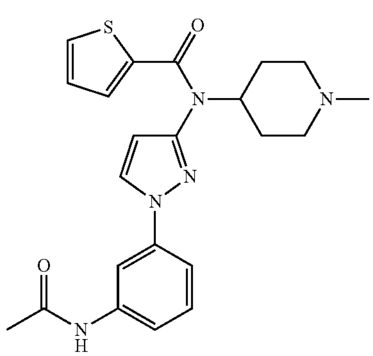 [SMILES: CC(=O)Nc1cccc(-n2ccc(N(C(=O)c3cccs3)C3CCN(C)CC3)n2)c1] | N-[1-(3-Acetamidophenyl)-1H-pyrazol-3-yl]-N-(1-methylpiperidin-4-yl)thiophene-2-carboxamide | G | 14.35 | 424 |

| Ex | Structure | Chemical name | Method | Ret (min) | MS (M + H) |
|---|---|---|---|---|---|
| 108 | 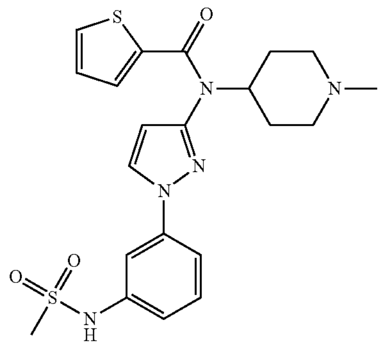 [SMILES: CN1CCC(N(C(=O)c2cccs2)c2ccn(-c3cccc(NS(C)(=O)=O)c3)n2)CC1] | N-(1-Methylpiperidin-4-yl)-N-{1-[3-(methylsulfonamido)phenyl]-1H-pyrazol-3-yl}thiophene-2-carboxamide | G | 14.31 | 460 |
| 109 | 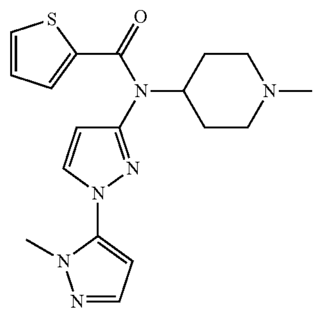 [SMILES: CN1CCC(N(C(=O)c2cccs2)c2ccn(-c3ccnn3C)n2)CC1] | N-(2'-Methyl-2'H-[1,3'-bipyrazol]-3-yl)-N-(1-methylpiperidin-4-yl)thiophene-2-carboxamide | G | 13.68 | 371 |
| 110 | 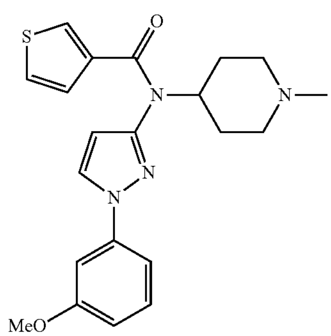 [SMILES: COc1cccc(-n2ccc(N(C(=O)c3ccsc3)C3CCN(C)CC3)n2)c1] | N-[1-(3-Methoxyphenyl)-1H-pyrazol-3-yl]-N-(1-methylpiperidin-4-yl)thiophene-3-carboxamide | G | 15.74 | 397 |
| 111 | 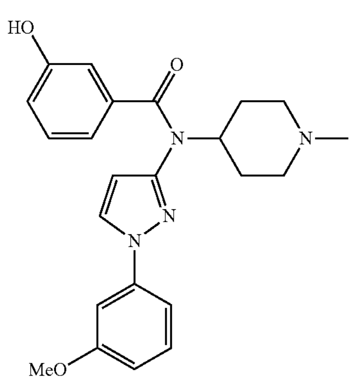 [SMILES: COc1cccc(-n2ccc(N(C(=O)c3cccc(O)c3)C3CCN(C)CC3)n2)c1] | 3-Hydroxy-N-[1-(3-methoxyphenyl)-1H-pyrazol-3-yl]-N-(1-methylpiperidin-4-yl)benzamide | G | 14.44 | 407 |

| Ex | Structure | Chemical name | Method | Ret (min) | MS (M + H) |
|---|---|---|---|---|---|
| 112 | 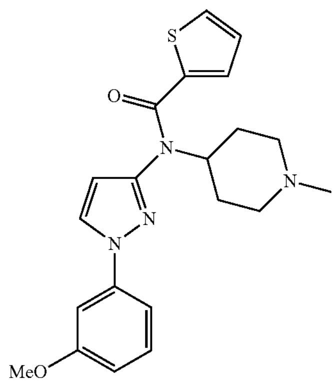 [SMILES: COc1cccc(-n2ccc(N(C(=O)c3cccs3)C3CCN(C)CC3)n2)c1] | N-[1-(3-Methoxyphenyl)-1H-pyrazol-3-yl]-N-(1-methylpiperidin-4-yl)thiophene-2-carboxamide | G | 16.42 | 397 |
| 113 | 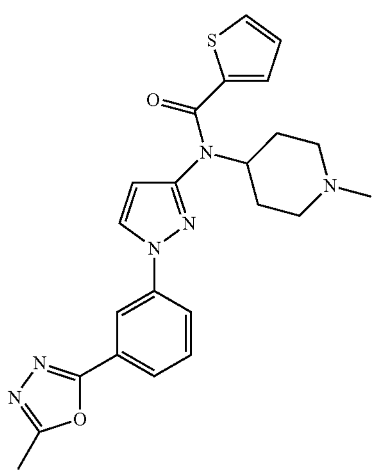 [SMILES: Cc1nnc(-c2cccc(-n3ccc(N(C(=O)c4cccs4)C4CCN(C)CC4)n3)c2)o1] | N-{1-[3-(5-Methyl-1,3,4-oxadiazol-2-yl)phenyl]-1H-pyrazol-3-yl}-N-(1-methylpiperidin-4-yl)thiophene-2-carboxamide | G | 15.58 | 449 |
| 114 | 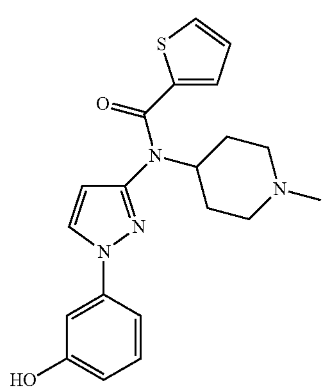 [SMILES: CN1CCC(N(C(=O)c2cccs2)c2ccn(-c3cccc(O)c3)n2)CC1] | N-[1-(3-Hydroxyphenyl)-1H-pyrazol-3-yl]-N-(1-methylpiperidin-4-yl)thiophene-2-carboxamide | G | 14.71 | 383 |

-continued

| Ex | Structure | Chemical name | Method | Ret (min) | MS (M + H) |
|---|---|---|---|---|---|
| 115 | 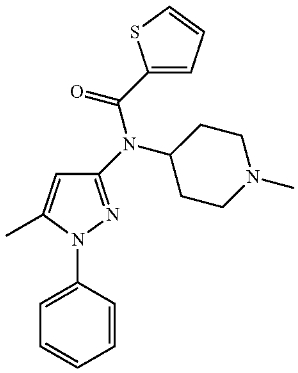 | N-(5-Methyl-1-phenyl-1H-pyrazol-3-yl)-N-(1-methylpiperidin-4-yl)thiophene-2-carboxamide | G | 16.02 | 381 |
| 116 | 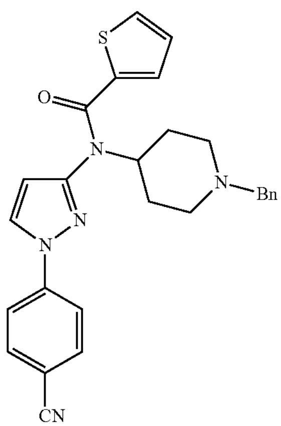 | N-(1-Benzylpiperidin-4-yl)-N-[1-(4-cyanophenyl)-1H-pyrazol-3-yl]thiophene-2-carboxamide | G | 19.21 | 468 |
| 117 | 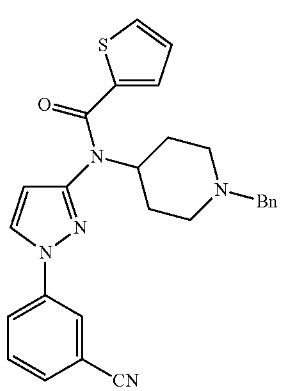 [SMILES: N#Cc1cccc(-n2ccc(N(C(=O)c3cccs3)C3CCN(Cc4ccccc4)CC3)n2)c1] | N-(1-Benzylpiperidin-4-yl)-N-[1-(3-cyanophenyl)-1H-pyrazol-3-yl]thiophene-2-carboxamide | G | 19.23 | 468 |

| Ex | Structure | Chemical name | Method | Ret (min) | MS (M + H) |
|---|---|---|---|---|---|
| 118 | 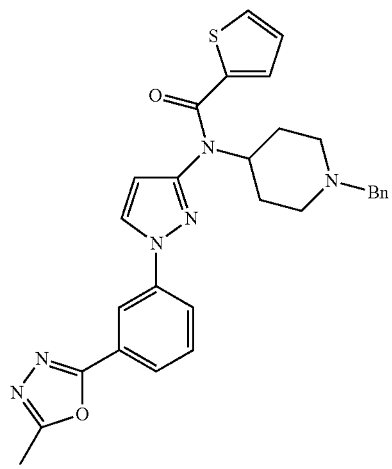 [SMILES: Cc1nnc(-c2cccc(-n3ccc(N(C(=O)c4cccs4)C4CCN(Cc5ccccc5)CC4)n3)c2)o1] | N-(1-Benzylpiperidin-4-yl)-N-{1-[3-(5-methyl-1,3,4-oxadiazol-2-yl)phenyl]-1H-pyrazol-3-yl}-thiophene-2-carboxamide | G | 19.02 | 525 |
| 119 | 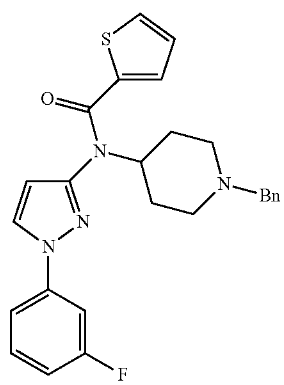 [SMILES: O=C(c1cccs1)N(c1ccn(-c2cccc(F)c2)n1)C1CCN(Cc2ccccc2)CC1] | N-(1-Benzylpiperidin-4-yl)-N-[1-(3-fluorophenyl)-1H-pyrazol-3-yl]thiophene-2-carboxamide | G | 19.99 | 461 |
| 120 | 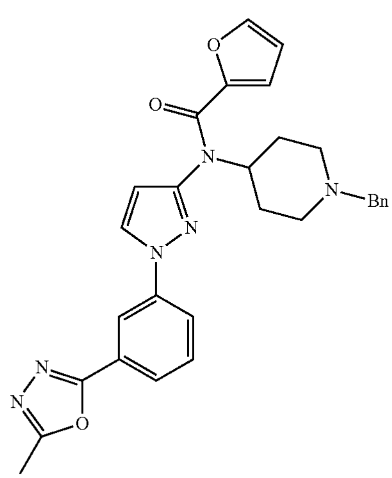 | N-(1-Benzylpiperidin-4-yl)-N-{1-[3-(5-methyl-1,3,4-oxadiazol-2-yl)phenyl]-1H-pyrazol-3-yl}-2-furamide | G | 18.19 | 509 |

| Ex | Structure | Chemical name | Method | Ret (min) | MS (M + H) |
|---|---|---|---|---|---|
| 121 | 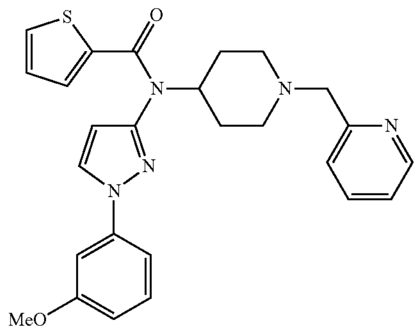 [SMILES: COc1cccc(-n2ccc(N(C(=O)c3cccs3)C3CCN(Cc4ccccn4)CC3)n2)c1] | N-[1-(3-Methoxyphenyl)-1H-pyrazol-3-yl]-N-[1-(pyridin-2-ylmethyl)piperidin-4-yl]thiophene-2-carboxamide | G | 18.33 | 474 |
| 122 | 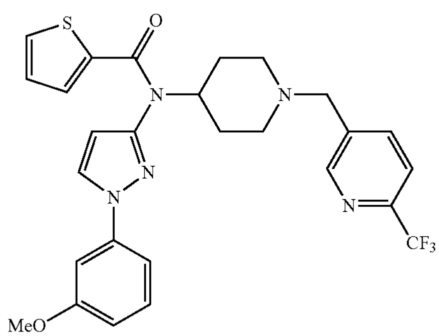 [SMILES: COc1cccc(-n2ccc(N(C(=O)c3cccs3)C3CCN(Cc4ccc(C(F)(F)F)nc4)CC3)n2)c1] | N-[1-(3-Methoxyphenyl)-1H-pyrazol-3-yl]-N-(1-{[6-(trifluoromethyl)pyridin-3-yl]methyl}piperidin-4-yl)thiophene-2-carboxamide | G | 19.75 | 542 |

Example 123. N-[1-(2-Chloro-4-hydroxyphenyl)-1H-pyrazol-3-yl]-N-(1-methylpiperidin-4-yl)thiophene-2-carboxamide

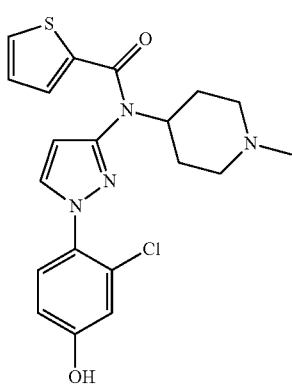 [SMILES: CN1CCC(N(C(=O)c2cccs2)c2ccn(-c3ccc(O)cc3Cl)n2)CC1]

BBr$_2$ (1 M solution in CH$_2$Cl$_2$, 0.85 mL, 0.85 mmol) was added to a solution of N-[1-(2-chloro-4-methoxyphenyl)-1H-pyrazol-3-yl]-N-(1-methylpiperidin-4-yl)thiophene-2-carboxamide (Example 96, 123 mg, 0.29 mmol) in CHCl$_2$ (6 mL) cooled at −5° C. and the mixture was stirred at room temperature for 20 h. NaOH (10% aqueous solution, 5 mL) was added dropwise. After 30 min the mixture was diluted with CH$_2$Cl$_2$ (50 mL) and washed with water. The aqueous layer was extracted with MeTHF and the combined organic layers were dried over Na$_2$SO$_4$ (anhydrous), filtered and concentrated. The residue was slurried with Et$_2$O (5 mL), filtered and vacuum dried to afford the title compound (white solid, 40 mg, 33% yield).

HPLC-MS (Method G): Ret, 14.76 min; ESI$^+$-MS m/z. 417 (M+1).

This method was used for the preparation of examples 124-125 using suitable starting materials:

| Ex | Structure | Chemical name | Method | Ret (min) | MS (M + H) |
|---|---|---|---|---|---|
| 124 | 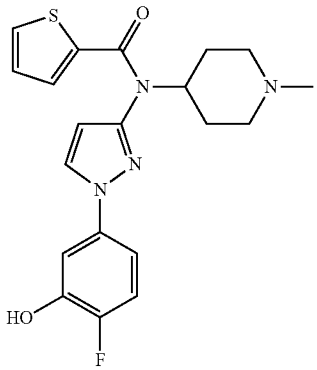 [SMILES: CN1CCC(N(C(=O)c2cccs2)c2ccn(-c3ccc(F)c(O)c3)n2)CC1] | N-[1-(4-Fluoro-3-hydroxyphenyl)-1H-pyrazol-3-yl]-N-(1-methylpiperidin-4-yl)thiophene-2-carboxamide | G | 14.40 | 401 |
| 125 | 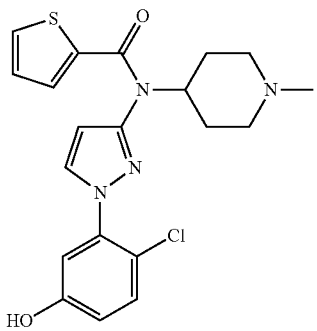 [SMILES: CN1CCC(N(C(=O)c2cccs2)c2ccn(-c3cc(O)ccc3Cl)n2)CC1] | N-[1-(2-Chloro-5-hydroxyphenyl)-1H-pyrazol-3-yl]-N-(1-methylpiperidin-4-yl)thiophene-2-carboxamide | G | 15.17 | 417 |

Example 126. N-(1-Isobutylpiperidin-4-yl)-N-{1-[3-(5-methyl-1,3,4-oxadiazol-2-yl)phenyl]-1H-pyrazol-3-yl}-thiophene-2-carboxamide

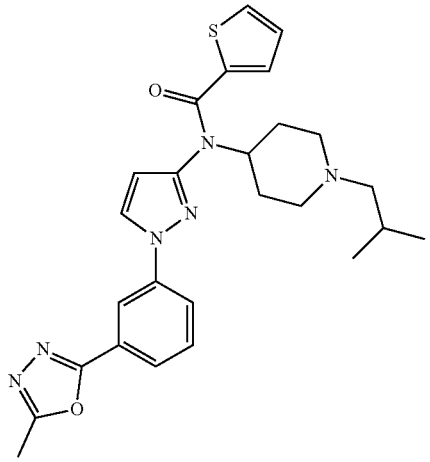 [SMILES: Cc1nnc(-c2cccc(-n3ccc(N(C(=O)c4cccs4)C4CCN(CC(C)C)CC4)n3)c2)o1]

a) N-{1-[3-(5-Methyl-1,34-oxadiazol-2-yl)phenyl]-1H-pyrazol-3-yl}-N-(piperidin-4-yl)thiophene-2-carboxamide 1-Chloroethyl chloroformate (73 µL, 0.66 mmol) was added to a solution of N-(1-benzylpiperidin-4-yl)-N-{1-[3-(5-methyl-1,3,4-oxadiazol-2-yl)phenyl]-1H-pyrazol-3-yl}-thiophene-2-carboxamide (Example 118, 174 mg, 0.33 mmol) in $CH_2Cl_2$ (5 mL) and the mixture was stirred at room temperature for 23 h. The reaction was poured into $NaHCO_3$ (saturated aqueous solution, 20 mL) and extracted with $CH_2Cl_2$. The combined organic layers were dried over $Na_2SO_4$ (anhydrous), filtered and concentrated. The crude residue was dissolved in MeOH (8 mL) and heated under reflux for 18 h. Volatiles were removed by rotatory evaporation and the residue was purified by semipreparative HPLC to afford the title compound (pale yellow solid, 35 mg, 24% yield).

HPLC-MS (Method G): Ret, 14.31 min; $ESI^+$-MS m/z, 435 (M+1).

b) Title Compound

2-Methylpropanal (8 µL, 0.09 mmol) and AcOH (8 µL, 0.14 mmol) were added to a solution of the compound obtained in step a) (20 mg, 0.045 mmol) in $CH_2Cl_2$ (2 mL). The reaction mixture was stirred at room temperature for 5 min, $NaBH(OAc)_3$ (29 mg, 0.14 mmol) was added and the suspension was stirred at room temperature for 16 h. The reaction mixture was poured into $NaHCO_3$ (saturated aqueous solution, 15 mL) and was extracted with EtOAc. The combined organic layers were dried over $Na_2SO_4$ (anhydrous), filtered and concentrated. The crude residue was purified by flash chromatography on $SiO_2$ (7% MeOH/$CH_2Cl_2$) to give the title compound (white solid, 10 mg, 49% yield).

HPLC-MS (Method G): Ret, 17.27 min; $ESI^+$-MS m/z, 491 (M+1).

Example 127. N-[4-(Dimethylamino)cyclohexyl]-N-(1-phenyl-1H-pyrazol-3-yl)thiophene-2-carboxamide

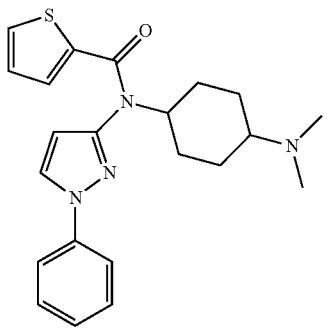 [SMILES: CN(C)C1CCC(N(C(=O)c2cccs2)c2ccn(-c3ccccc3)n2)CC1]

solution of the compound obtained in step a) in CH$_2$Cl$_2$ (12 mL). After 5 min, NaBH(OAc)$_3$ (0.22 g, 1.05 mmol) was added and the mixture was stirred at room temperature for 16 h. The reaction mixture was poured into NaHCO$_3$ (saturated aqueous solution, 25 mL) and was extracted with CH$_2$Cl$_2$. The combined organic layers were dried over Na$_2$SO$_4$ (anhydrous), filtered and concentrated. The crude residue was purified by flash chromatography on SiO$_2$ (CH$_2$Cl$_2$/MeOH/NH$_4$OH from 98:2:1 to 95:5:1) to give the title compound as a mixture of isomers (white solid, 105 mg, 33%).

HPLC-MS (Method G): Ret, 15.86 min and 16.31 min; ESI$^+$-MS m/z, 395 (M+1).

This method was used for the preparation of example 128 using suitable starting materials:

| Ex | Structure | Chemical name | Method | Ret (min) | MS (M + H) |
|---|---|---|---|---|---|
| 128 | (structure shown) | N-{4-[Benzyl(methyl)amino]cyclohexyl}-N-(1-phenyl-1H-pyrazol-3-yl)thiophene-2-carboxamide | M | 13.68 | 471 | a) N-(4-Oxocyclohexyl)-N-(1-phenyl-1H-pyrazol-3-yl)thiophene-2-carboxamide

HCl (10% aqueous solution) was added to a solution of N-(1-phenyl-1H-pyrazol-3-yl)-N-(1,4-dioxaspiro[4.5]decan-8-yl)thiophene-2-carboxamide (Intermediate C14, 0.33 g, 0.81 mmol) in THF (8 mL) and the mixture was stirred at 50° C. for 30 h. The reaction mixture was poured into NaHCO$_3$ (saturated aqueous solution, 15 mL) and was extracted with CH$_2$Cl$_2$. The combined organic layers were dried over Na$_2$SO$_4$ (anhydrous), filtered and concentrated, to give the title compound as a yellowish oil, (0.32 g), which was used in the next step without further purification.

HPLC-MS (Method H): Ret, 10.13 min; ESI$^+$-MS m/z, 366 (M+1).

b) Title Compound

Dimethylamine (2 M solution in THF, 0.49 mL, 0.98 mmol) and AcOH (0.09 mL, 1.62 mmol) were added to a

Example 129. N-[6-(4-Fluorophenyl)pyridin-2-yl]-N-(1-methylpiperidin-4-yl)thiophene-2-carboxamide

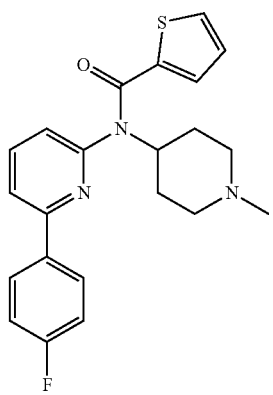 [SMILES: CN1CCC(N(C(=O)c2cccs2)c2cccc(-c3ccc(F)cc3)n2)CC1]

Pd(dppf)Cl$_2$ (27 mg, 0.04 mmol) and Na$_2$CO$_3$ (2 M aqueous solution, 0.36 mL, 0.72 mmol) were added to a degassed solution of N-(6-chloropyridin-2-yl)-N-(1-methylpiperidin-4-yl)thiophene-2-carboxamide (121 mg, 0.36 mmol) and (4-fluorophenyl)boronic acid (76 mg, 0.54 mmol) in dioxane (5 mL). The reaction mixture was heated under reflux for 17 h. The reaction mixture was allowed to cool down to room temperature and concentrated. The residue was diluted with water (50 mL) and extracted with Et$_2$O. The combined organic layers were dried over Na$_2$SO$_4$ (anhydrous), filtered and concentrated. The crude residue was purified by flash chromatography on SiO$_2$ (CH$_2$Cl$_2$/MeOH/NH$_4$OH 95:5:1) followed by medium pressure flash chromatography (Combiflash, 0 to 100% MeOH/H$_2$O) and semipreparative HPLC to give the title compound (cream solid, 76 mg, 53% yield).

HPLC-MS (Method G): Ret, 16.70 min; ESI$^+$-MS m/z, 396 (M+1).

This method was used for the preparation of examples 130-132 using suitable starting materials:

| Ex | Structure | Chemical name | Method | Ret (min) | MS (M + H) |
|---|---|---|---|---|---|
| 130 | 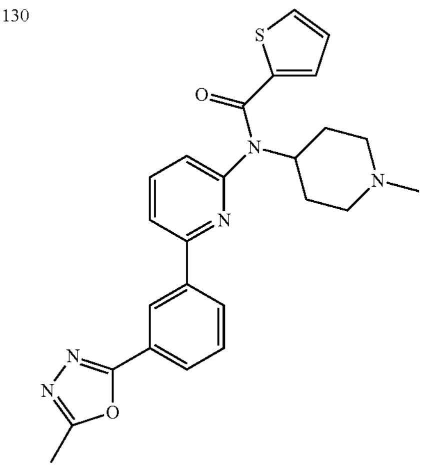 | N-{6-[3-(5-methyl-1,3,4-oxadiazol-2-yl)phenyl]pyridin-2-yl}-N-(1-methylpiperidin-4-yl)thiophene-2-carboxamide | G | 15.68 | 460 |
| 131 | 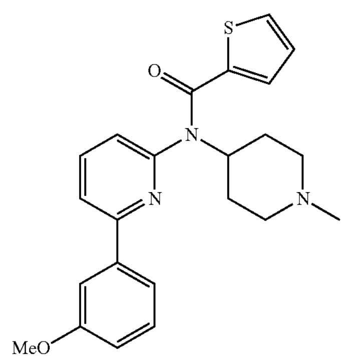 [SMILES: COc1cccc(-c2cccc(N(C(=O)c3cccs3)C3CCN(C)CC3)n2)c1] | 4-[6-(3-Methoxyphenyl)pyridin-2-yl]-N-(1-methylpiperidin-4-yl)thiophene-2-carboxamide | G | 16.51 | 408 |
| 132 | 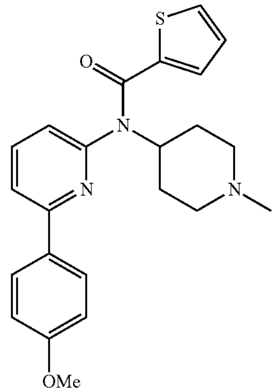 [SMILES: COc1ccc(-c2cccc(N(C(=O)c3cccs3)C3CCN(C)CC3)n2)cc1] | N-[6-(4-Methoxyphenyl)pyridin-2-yl]-N-(1-methylpiperidin-4-yl)thiophene-2-carboxamide | G | 14.17 | 408 |

Example 133. N-[6-(4-Fluorophenyl)pyrazin-2-yl]-N-(piperidin-4-yl)thiophene-2-carboxamide

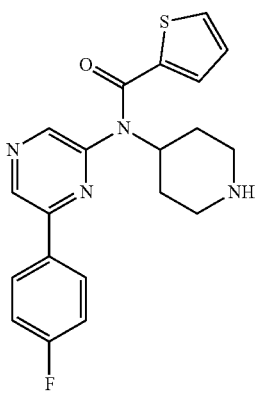 [SMILES: O=C(c1cccs1)N(c1cncc(-c2ccc(F)cc2)n1)C1CCNCC1]

a) tert-Butyl 4-[(6-chloropyrazin-2-yl)amino]piperidine-1-carboxylate

A mixture of 2,6-dichloropyrazine (0.71 g, 4.75 mmol), tert-butyl 4-aminopiperidine-1-carboxylate (1.00 g, 4.99 mmol) and $K_2CO_3$ (1.31 g, 9.50 mmol) in DMF (20 mL) was heated at 90° C. for 4 h. The reaction mixture was allowed to cool down to room temperature, poured into water (60 mL) and extracted with $Et_2O$. The combined organic layers were dried over $Na_2SO_4$ (anhydrous), filtered and concentrated. The crude residue was purified by flash chromatography on $SiO_2$ (5% to 60% EtOAc/hexanes) to give the title compound (pale yellow solid, 0.37 g, 25% yield).

HPLC-MS (Method D): Rot, 10.03 min; ESI⁻-MS m/z, 311 (M−1).

b) N-(6-Chloropyrazin-2-yl)-N-(piperidin-4-yl)thiophene-2-carboxamide

Thiophene-2-carbonyl chloride (0.15 mL, 1.41 mmol) was added to solution of the compound obtained in step a) (0.29 g, 0.94 mmol) in pyridine (1.2 mL). The reaction mixture was heated under MW irradiation at 140° C. for 3 h. The mixture was cooled down to room temperature, diluted with $CH_2Cl_2$ (30 mL) and washed with water and 10% HCl. The organic layer was dried over $Na_2SO_4$ (anhydrous), filtered and concentrated. The crude residue was purified by flash chromatography on $SiO_2$ (7% MeOH/$CH_2Cl_2$) to afford the title compound (brown solid, 0.19 g, 62% yield)

HPLC-MS (Method D): Ret, 9.17 min; ESI⁺-MS m/z, 323 (M+1).

c) N-[6-(4-Fluorophenyl)pyrazin-2-yl]-N-(piperidin-4-yl)thiophene-2-carboxamide $Pd(dppf)Cl_2$ (32 mg, 0.04 mmol) and $Na_2CO_3$ (2 M aqueous solution, 0.55 mL, 1.10 mmol) were added to a degassed solution of the compound obtained in step b) (186 mg, 0.58 mmol) and (4-fluorophenyl)boronic acid (115 mg, 0.83 mmol) in dioxane (15 mL). The reaction mixture was heated under reflux for 15 h and more $Pd(dppf)Cl_2$ (20 mg, 0.02 mmol) and (4-fluorophenyl)boronic acid (50 mg, 0.36 mmol) were added, refluxing continued for 18 h. The reaction mixture was allowed to cool down to room temperature, was poured into water (40 mL) and extracted with $Et_2O$. The organic layer was dried over $Na_2SO_4$ (anhydrous), filtered and concentrated. The crude residue was purified by flash chromatography on $SiO_2$ (EtOAc/iPrOH/hexanes 15:5:20) to give the title compound (pale brown solid, 154 mg, 70% yield).

HPLC-MS (Method G): Ret, 18.50 min; ESI⁺-MS m/z, 383 (M+1).

Example 134. N-[6-(4-Fluorophenyl)pyrazin-2-yl]-N-(1-methylpiperidin-4-yl)thiophene-2-carboxamide

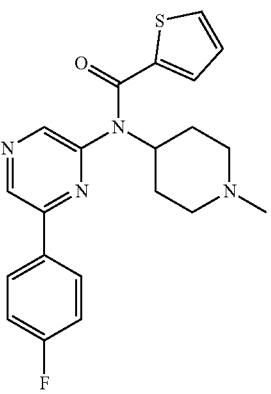 [SMILES: CN1CCC(N(C(=O)c2cccs2)c2cncc(-c3ccc(F)cc3)n2)CC1]

A solution of N-[6-(4-fluorophenyl)pyrazin-2-yl]-N-(piperidin-4-yl)thiophene-2-carboxamide (140 mg, 0.37 mmol) and formaldehyde (37% aqueous solution, 1.36 mL, 18.30 mmol) in $HCO_2H$ (1 mL) was heated at 80° C. for 24 h. The reaction mixture was allowed to cool down to room temperature, was basified with NaOH (10% aqueous solution) and extracted with EtOAc. The organic layer was dried over $Na_2SO_4$ (anhydrous), filtered and concentrated. The crude residue was purified by flash chromatography on $SiO_2$ (2% MeOH/$CH_2Cl_2$) followed by semipreparative HPLC to give the title compound (pale yellow solid, 25 mg, 17% yield).

HPLC-MS (Method G): Ret, 19.15 min; ESI⁺-MS m/z, 397 (M+1).

Example 135. N-(1-benzylpiperidin-4-yl)-N-(1-(4-fluorophenyl)-1H-1,2,3-triazol-4-yl)thiophene-2-carboxamide

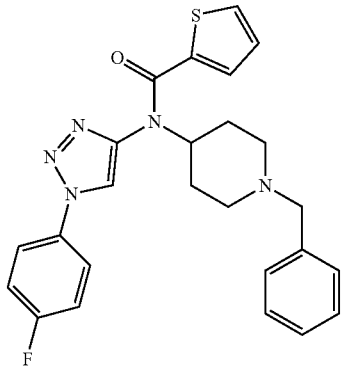 [SMILES: O=C(c1cccs1)N(c1cn(-c2ccc(F)cc2)nn1)C1CCN(Cc2ccccc2)CC1]

A schlenk was charged with N-(1-benzylpiperidin-4-yl)-N-((triisopropylsilyl)ethynyl)thiophene-2-carboxamide (Intermediate E1, 93 mg, 0.193 mmol) evacuated and backfilled with argon. Then dry THF (4 mL) was added and the reaction solution cooled down to 0° C. At this temperature TBAF (1M in thf, 193 μL, 0.193 mmol) was added. The reaction mixture was stirred at 0° C. for 30 min., after which the TIPS deprotection had been completed as judged by TLC analysis. Then 1-azido-4-fluorobenzene (0.5 M in tert-butyl methyl ether, 502 μL, 0.251 mmol) was added, followed by CuI (18.4 mg, 0.097 mmol) and DIPEA (52.9 μL, 0.193 mmol). The reaction mixture was allowed to reach r.t. and stirred for 3 days. The solvent was removed under reduced pressure and the residue directly absorbed onto silica gel. Column purification (SiO$_2$, c-Hex/EA 5-50%, then DCM/MeOH up to 10%) provided the title compound as oil (54 mg, 60%).

HPLC-MS (Method N): Ret, 2.24 min; ESI$^+$-MS m/z, 482 (M+1).

This method was used for the preparation of example 136 using suitable starting materials:

Example 137. N-(1-benzylpiperidin-4-yl)-N-(2-phenyl-2H-1,2,3-triazol-4-yl)thiophene-2-carboxamide

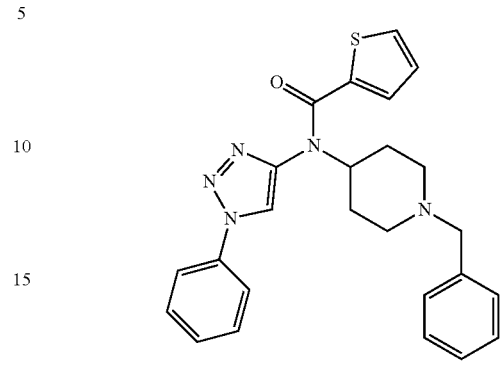

An oven-dried schlenk was charged with [Pd$_2$(dba)$_3$] (2.56 mg, 0.003 mmol) and di-tert-butyl(2',4',6'-triisopropyl-3,4,5,6-tetramethylbiphenyl-2-yl)phosphine (5.59 mg, 0.012 mmol). The schlenk was evacuated and backfilled with argon (three cycles). Dry toluene (0.5 mL) was added. The resulting dark-purple mixture was stirred at 120° C. for 3 min, at this point the color of the mixture turned to dark brown. A second schlenk was charged with N-(1-benzylpiperidin-4-yl)-N-(1H-1,2,3-triazol-4-yl)thiophene-2-carboxamide (57 mg, 0.16 mmol), K$_3$PO$_4$ (65.9 mg, 0.31 mmol) and bromobenzene (29.2 mg, 0.186 mmol) and toluene (4.5 mL) under argon. After cooling down the [Pd$_2$(dba)$_3$]/Phosphine ligand solution, this solution was added to the second schlenk and the reaction mixture subjected to an oil bath at 120° C. overnight. Additional [Pd$_2$(dba)$_3$] (2.56 mg, 0.003 mmol) and di-tert-butyl(2',4',6'-triisopropyl-3,4,5,6-tetramethylbiphenyl-2-yl)phosphine (5.59 mg, 0.012 mmol) were added as well as bromobenzene (29.2 mg, 0.186 mmol) and the reaction mixture was heated for 3 days at 110° C. After cooling to r.t., the solvent was removed under reduced pressure and the residue was purified by combiflash chromatography (SiO$_2$. CH$_2$Cl$_2$/MeOH up to 20%) and semi-preparative HPLC purification to give the title compound (7.58 mg, 11%).

HPLC-MS (Method N): Ret, 2.56 min; ESI$^+$-MS m/z, 444 (M+1).

| Ex | Structure | Chemical name | Method | Ret (min) | MS (M + H) |
|---|---|---|---|---|---|
| 136 | 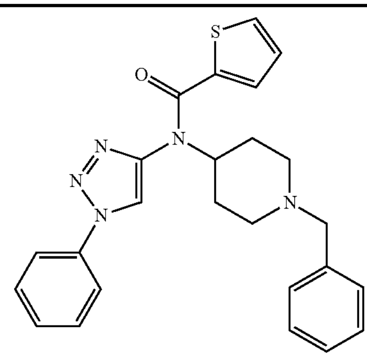 | N-(1-benzylpiperidin-4-yl)-N-(1-phenyl-1H-1,2,3-triazol-4-yl)thiophene-2-carboxamide | N | 2.22 | 444 |

Examples 138-139

Prepared following the procedure described in Example 1 using suitable starting materials:

| Ex | Structure | Chemical name | Method | Ret (min) | MS (M + H) |
|---|---|---|---|---|---|
| 138 | 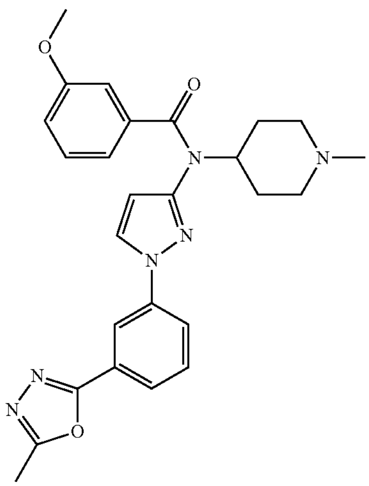 [SMILES: COc1cccc(C(=O)N(c2ccn(-c3cccc(-c4nnc(C)o4)c3)n2)C2CCN(C)CC2)c1] | 3-Methoxy-N-{1-[3-(5-methyl-1,3,4-oxadiazol-2-yl)phenyl]-1H-pyrazol-3-yl}-N-(1-methylpiperidin-4-yl)benzamide | G | 15.31 | 473 |
| 139 | 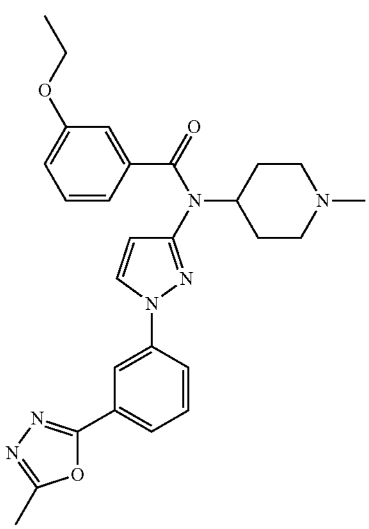 [SMILES: CCOc1cccc(C(=O)N(c2ccn(-c3cccc(-c4nnc(C)o4)c3)n2)C2CCN(C)CC2)c1] | 3-Ethoxy-N-{1-[3-(5-methyl-1,3,4-oxadiazol-2-yl)phenyl]-1H-pyrazol-3-yl}-N-(1-methylpiperidin-4-yl)benzamide | G | 16.25 | 487 |

Example 140

Prepared following the procedure described in Example 50 using suitable starting materials:

| Ex | Structure | Chemical name | Method | Ret (min) | MS (M + H) |
|---|---|---|---|---|---|
| 140 | 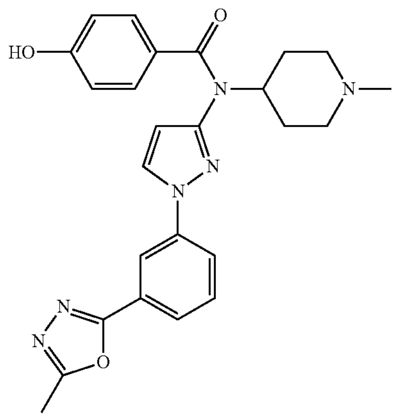 [SMILES: Cc1nnc(-c2cccc(-n3ccc(N(C(=O)c4ccc(O)cc4)C4CCN(C)CC4)n3)c2)o1] | 4-Hydroxy-N-{1-[3-(5-methyl-1,3,4-oxadiazol-2-yl)phenyl]-1H-pyrazol-3-yl}-N-(1-methylpiperidin-4-yl)benzamide | G | 13.80 | 459 |

Example 141. 3-(1H-imidazol-2-yl)-N-{1-[3-(5-methyl-1,3,4-oxadiazol-2-yl)phenyl]-1H-pyrazol-3-yl}-N-(1-methylpiperidin-4-yl)benzamide

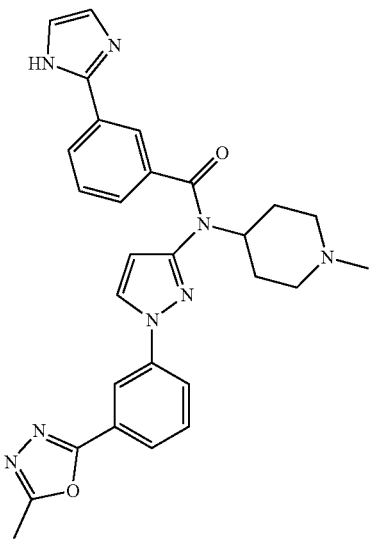 [SMILES: Cc1nnc(-c2cccc(-n3ccc(N(C(=O)c4cccc(-c5ncc[nH]5)c4)C4CCN(C)CC4)n3)c2)o1]

a) 3-Formyl-N-{1-[3-(5-methyl-1,3,4-oxadiazol-2-yl)phenyl]-1H-pyrazol-3-yl}-N-(1-methylpiperidin-4-yl)benzamide The title compound was obtained following the procedure described in Example 1 and using 1-methyl-N-{1-[3-(5-methyl-1,3,4-oxadiazol-2-yl)phenyl]-1H-pyrazol-3-yl})piperidin-4-amine (intermediate B39) and 3-formylbenzoyl chloride as starting materials.

HPLC-MS (Method H): Ret, 8.54 min; ESI$^+$-MS m/z, 471 (M+1).

b) Title Compound

NH$_3$ (7 M solution in MeOH, 0.24 mL, 1.68 mmol) was added to a 0° C. cooled solution of compound obtained in step a) (100 mg, 0.1 mmol) and glyoxal (40% aqueous solution, 24 microL, 0.21 mmol) in a mixture of MeOH (0.5 mL) and water (0.5 mL). The reaction was allowed to reach room temperature and stirred for 17 h. A new charge of NH$_3$ (0.12 mL, 0.84 mmol) and glyoxal (12 microL, 0.11 mmol) was done and stirring continued for additional 7 h. The solvent was concentrated off and the crude residue was purified by flash chromatography on SiO$_2$ (CH$_2$Cl$_2$/MeOH/NH$_4$OH 98:2:1 to 96:4:1) to afford the title compound (pale yellow solid, 26 mg, 24% yield).

HPLC-MS (Method G): Ret, 13.38 min; ESI$^+$-MS m/z, 509 (M+1).

Example 142. N-(1-[3-(5-Methyl-1,3,4-oxadiazol-2-yl)phenyl]-1H-pyrazol-3-yl)-N-(1-methylpiperidin-4-yl)-3-(methylsulfonamido)benzamide

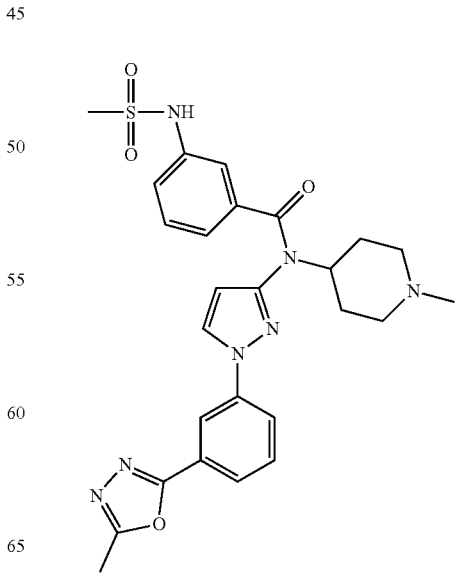

a) 3-Bromo-N-{1-[3-(5-methyl-1,3,4-oxadiazol-2-yl)phenyl]-1H-pyrazol-3-yl}-N-(1-methylpiperidin-4-yl)benzamide The title compound was obtained following the procedure described in Example 1 and using 1-methyl-N-{1-[3-(5-methyl-1,3,4-oxadiazol-2-yl)phenyl]-1H-pyrazol-3-yl}piperidin-4-amine (Intermediate 839) and 3-bromobenzoyl chloride as starting materials.

HPLC-MS (Method H): Ret, 9.59 min; ESI$^+$-MS m/z, 521-523 (M+1).

b) tert-Butyl (3-[{1-[3-(5-methyl-1,3,4-oxadiazol-2-yl)phenyl]-1H-pyrazol-3-yl}(1-methylpiperidin-4-yl)carbamoyl]phenyl)carbamate Pd(OAc)$_2$ (16 mg, 0.07 mmol) was added to a degassed suspension of Cs$_2$CO$_3$ (0.94 g, 2.87 mmol), Xantphos (40 mg, 0.07 mmol), tert-butyl carbamate (0.34 g, 2.87 mmol) and 3-bromo-N-{1-[3-(5-methyl-1,3,4-oxadiazol-2-yl)phenyl]-1H-pyrazol. 3-yl}-N-(1-methylpiperidin-4-yl)benzamide (0.75 g, 1.44 mmol) in 1,4-dioxane (15 mL). The reaction was heated under reflux for 2.5 h and allowed to reach room temperature. Volatiles were removed by rotatory evaporation in the presence of SiO$_2$ and the residue was purified by flash chromatography on SiO$_2$ (CH$_2$Cl$_2$/MeOH/NH$_4$OH 98:2:1 to 96:4:1) to afford 0.51 g of the title compound (pale orange solid, 69% yield).

HPLC-MS (Method H): Ret, 9.50 min; ESI$^+$-MS m/z: 558 (M+1).

c) 3-Amino-N-{1-[3-(5-methyl-1,3,4-oxadiazol-2-yl)phenyl]-1H-pyrazol-3-yl}-N-(1-methylpiperidin-4-yl)benzamide TFA (2.3 mL) was added to a solution tert-butyl (3-[{1-[3-(5-methyl-1,3,4-oxadiazol-2-yl)phenyl]-1H-pyrazol-3-yl}(1-methylpiperidin-4-yl)carbamoyl]phenyl)carbamate (0.48 g, 0.86 mmol) in CH$_2$Cl$_2$ (8 mL). The reaction mixture was stirred at room temperature until full conversion was achieved (5.5 h). The mixture was diluted with CH$_2$Cl$_2$ (30 mL) and was washed with K$_2$CO$_3$ (10% aqueous solution, 40 mL). The organic layer was dried over Na$_3$SO$_4$ (anhydrous), filtered and concentrated to afford 0.35 g of the title compound (yellow foam, 88% yield), which was used without further purification.

HPLC-MS (Method H): Ret, 8.14 min; ESI$^+$-MS m/z: 458 (M+1).

d) Title Compound

Methanesulfonyl chloride (69 μL, 0.89 mmol) was added to a 0° C. cooled solution of 3-amino-N-{1-[3-(5-methyl-1,3,4-oxadiazol-2-yl)phenyl]-1H-pyrazol-3-yl}-N(1-methyl piperidin-4-yl)benzamide (0.34, 0.74 mmol) and Py (119 μL, 1.48 mmol) in CH$_2$Cl$_2$ (10 mL). The reaction mixture was allowed to reach room temperature and stirred for 15 h. Volatiles were removed by rotatory evaporation in the presence of SiO$_2$ and the residue was purified by flash chromatography on SiO$_2$ (CH$_2$Cl$_2$/MeOH/NH$_4$OH 98:2:1 to 90:10:1) to render 0.38 g of a pale yellow oil, which was slurried with Et$_2$O/hexanes (10 mL, 1:1), filtered and vacuum dried to afford the title compound (pale yellow solid, 245 mg, 62% yield).

HPLC-MS (Method G): Ret, 13.47 min; ESI$^+$-MS m/z: 536 (M+1).

Example 143. 3-Hydroxy-N-(1-[3-(5-methyl-1,3,4-oxadiazol-2-yl)phenyl]-1H-pyrazol-3-yl-N-(piperidin-4-yl)benzamide

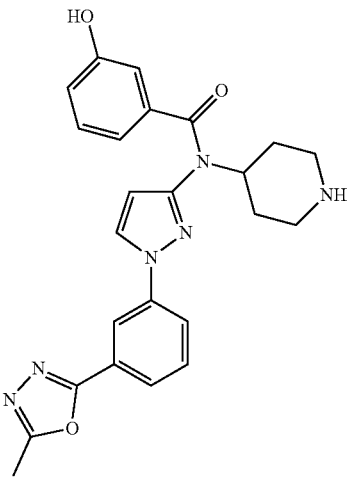 [SMILES: Cc1nnc(-c2cccc(-n3ccc(N(C(=O)c4cccc(O)c4)C4CCNCC4)n3)c2)o1]

A suspension of N-(1-benzylpiperidin-4-yl)-3-hydroxy-N-{1-[3-(5-methyl-1,3,4-oxadiazol-2-yl)phenyl]-1H-pyrazol-3-yl}benzamide (Example 51, 310 mg, 0.58 mmol), and Pd(OH)$_2$/C (20% w/w palladium on activated carbon. 407 mg, 0.58 mmol) in MeOH (15 mL) and AcOH (2 mL) was stirred under H$_2$ atmosphere (balloon) for 16 h. The reaction mixture was filtered through Celite, rinsed with MeOH (3×20 mL) and concentrated. The crude residue was purified by flash chromatography on SiO$_2$ (CH$_2$Cl/MeOH/NH$_4$OH 95:5:1 to 90:10:1) to afford 133 mg of the title compound (white solid, 51% yield).

HPLC-MS (Method P): Ret, 12.56 min; ESI$^+$-MS m/z: 445 (M+1).

This method was used for the preparation of Example 144 using N-[(2S,6R)-1-benzyl-2,6-dimethylpiperidin-4-yl)-3-hydroxy-N-{1-[3-(5-methy-1,3,4-oxadiazol-2-yl)phenyl]-1H-pyrazol-3-yl}benzamide (prepared following a similar route to that of Example 51) as starting material:

| Ex | Structure | Chemical name | Method | Ret (min) | MS (M + H) |
|---|---|---|---|---|---|
| 144 | 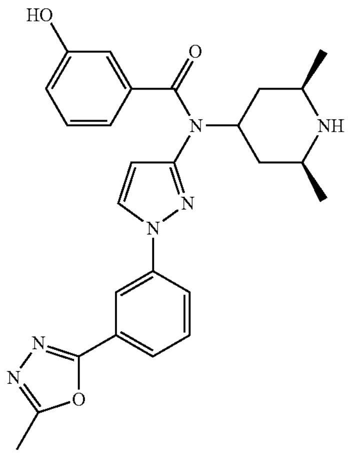 [SMILES: Cc1nnc(-c2cccc(-n3ccc(N(C(=O)c4cccc(O)c4)C4C[C@@H](C)N[C@@H](C)C4)n3)c2)o1] | N-[(2S,6R)-2,6-Dimethylpiperidin-4-yl]-3-hydroxy-N-{1-[3-(5-methyl-1,3,4-oxadiazol-2-yl)phenyl]-1H-pyrazol-3-yl}benzamide | P | 13.21 | 473 |

Example 145. N-[1-(3-Methoxyphenyl)-1H-pyrazol-3-yl]-N-(1-([6-(trifluoromethyl)pyridin-2-yl]methyl)piperidin-4-yl)thiophene-2-carboxamide

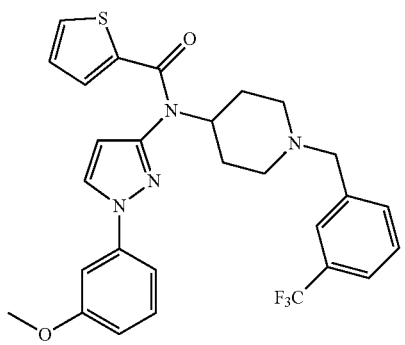 [SMILES: COc1cccc(-n2ccc(N(C(=O)c3cccs3)C3CCN(Cc4cccc(C(F)(F)F)c4)CC3)n2)c1]

a) [6-(Trifluoromethyl)pyridin-2-yl]methanol $NaBH_4$ (67 mg, 1.78 mmol) was added to a 0° C. cooled solution of 6-(trifluoromethyl)picolinaldehyde (260 mg, 1.48 mmol) in MeOH (15 mL); the reaction was allowed to reach room temperature and stirred for 2.5 h. The mixture was poured into water (20 mL) and was extracted with $CH_2Cl_2$ (2×30 mL). The organic layer was dried over $Na_2SO_4$ (anhydrous), filtered and concentrated to give the title compound as a yellow oil, 0.28 g, more than 100% weight. This oil was used in the next step without further purification.

HPLC-MS (Method H): Ret, 7.71 min; ESI$^+$-MS m/z: 178 (M+1).

b) [6-(Trifluoromethyl)pyridin-2-yl]methyl methanesulfonate

Methanesulfonyl chloride (0.15 mL, 1.96 mmol) was added to a 0° C. cooled solution of [6-(trifluoromethyl)pyridin-2-yl]methanol (0.32, 1.78 mmol) and $Et_3N$ (0.30 mL, 2.13 mmol) in $CH_2Cl_2$ (15 mL). The reaction mixture was stirred at room temperature for 22 h and concentrated to dryness, rendering the title compound as a white sticky solid, which was used in the next step without further purification.

HPLC-MS (Method H): Ret, 9.06 min; ESI$^+$-MS m/z: 256 (M+1).

c) 1-{[6-(Trifluormethyl)pyridin-2-yl]methyl}piperidin-4-one $K_2CO_3$ (0.44 g, 3.21 mmol) and [6-(trifluoromethyl)pyridin-2-yl]methyl methanesulfonate (0.30 g, 1.18 mmol) were added to a suspension of piperidin-4-one hydrochloride (0.18 g, 1.07 mmol) in $CH_3CN$ (17 mL) and the mixture was stirred at room temperature for 4 d. The mixture was poured into $H_2O$ (20 mL) and extracted with EtOAc (2×30 mL). The organic layer was washed with $H_2O$ (20 mL), dried over $Na_2SO_4$ (anhydrous), filtered and concentrated to give 0.15 g of the title compound as a yellow oil, 55% yield, which was used in the next step without further purification.

HPLC-MS (Method H): Ret, 9.18 min; ESI$^+$-MS m/z: 259 (M+1).

d) N-(1H-Pyrazol-3-yl)-1-{[6-(rifluoromethyl)pyridin-2-yl]methy}piperidin-4-amine The title compound was obtained following the procedure described in intermediate B1 and using 1H-pyrazol-3-amine and 1-{[6-(trifluoromethyl)pyridin-2-yl]methyl}piperidin-4-one as starting materials.

HPLC-MS (Method H): Ret, 9.00 min; ESI$^+$-MS m/z: 325 (M+1).

e) N-(1H-Pyrazol-3-yl)-N-(1-{[6-(trifluoromethyl)pyridin-2-yl]methyl}piperidin-4-yl)thiophene-2-carboxamide The title compound was obtained following the procedure described in intermediate C1 and using N-(1H-pyrazol-3-yl)-1-{[6-(trifluoromethyl)pyridin-2-yl]methyl}piperidin-4-amine as starting material.

HPLC-MS (Method H): Ret, 9.98 min; ESI$^+$-MS m/z: 436 (M+1), f) N-[1-(3-Methoxyphenyl)-1H-pyrazol-3-yl]-N-(1-{[6-(trifluoromethyl)pyridin-2-yl]methyl}piperidin-4-yl)thiophene-2-carboxamide The title compound was obtained following the procedure described in Example 87 and using N-(1H-pyrazol-3-yl)-N-(1-{[6-(trifluoromethyl)pyridin-2-yl]methy}piperidin-4-yl)thiophene-2-carboxamide and (3-methoxyphenyl)boronic acid as starting materials.

HPLC-MS (Method G): Ret, 19.90 min; ESI$^+$-MS m/z: 542 (M+1).

Example 146. N-{1-[3-(5-Methyl-1,3,4-oxadiazol-2-yl)phenyl]-1H-pyrazol-3-yl}-N-(1-{[6-(trifluoromethyl)pyridin-2-yl]methyl}piperidin-4-yl)thiophene-2-carboxamide

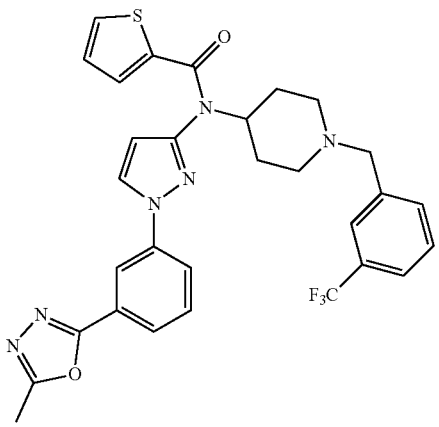 [SMILES: Cc1nnc(-c2cccc(-n3ccc(N(C(=O)c4cccs4)C4CCN(Cc5cccc(C(F)(F)F)c5)CC4)n3)c2)o1]

The title compound was obtained following the procedure described in Example 70, arylation conditions C, and using N-(1H-pyrazol-3-yl)-N-(1-{[6-(trifluoromethyl)pyridin-2-yl]methyl}piperidin-4-yl)thiophene-2-carboxamide and 2-(3-iodophenyl)-5-methyl-1,3,4-oxadiazole as starting materials.

HPLC-MS (Method G): Ret, 19.10 min; ESI$^+$-MS m/z: 594 (M+1).

Example 147. N-[1-(2-Hydroxy-2-phenylethyl)piperidin-4-yl]-N-{1-[3-(5-methyl-1,3,4-oxadiazol-2-yl)phenyl]-1H-pyrazol-3-yl}thiophene-2-carboxamide

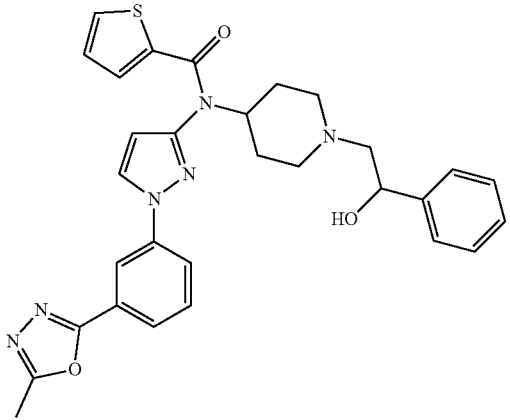 [SMILES: Cc1nnc(-c2cccc(-n3ccc(N(C(=O)c4cccs4)C4CCN(CC(O)c5ccccc5)CC4)n3)c2)o1]

a) 1-(2-Hydroxy-2-phenylethyl)piperidin-4-one $K_2CO_3$ (5.52 g, 40.0 mmol) and 2-phenyloxirane (4.80 g, 40.0 mmol) were added to a suspension of piperidin-4-one hydrochloride (5.42 g, 40.0 mmol) in i-PrOH (30 mL) and the mixture was stirred at 50° C. for 18 h and at 70° C. for 4 h. The reaction was allowed to reach room temperature; volatiles were removed and the residue was dissolved in $CH_2Cl_2$ (100 mL) and washed with water (100 mL) and brine (30 mL). The organic layer was dried over $Na_2SO_4$ (anhydrous), filtered and concentrated. The crude residue was purified by flash chromatography on $SiO_2$ ($CH_2Cl_2$/MeOH/NH$_4$OH 98:2:1 to 94:6:1) to afford the title compound (pale yellow solid, 1.80 g, 17% yield).

HPLC-MS (Method H): Ret, 8.23 min; ESI$^+$-MS m/z: 220 (M+1).

b) N-(1-(2-Hydroxy-2-phenylethyl)piperidin-4-yl)-N-(1H-pyrazol-3-yl)thiophene-2-carboxamide The title compound was obtained following the procedure described in Example 145, steps d) and e), and using 1-(2-hydroxy-2-phenylethyl)piperidin-4-one as starting material.

HPLC-MS (Method H): Ret, 9.14 min; ESI$^+$-MS m/z: 397 (M+1).

c) N-[1-(2-Hydroxy-2-phenylethyl)piperidin-4-yl]-N-{1-[3-(5-methyl-1,3,4-oxadiazol-2-yl)phenyl]-1H-pyrazol-3-yl}thiophene-2-carboxamide The title compound was obtained following the procedure described in Example 70, arylation conditions C, and using N-[1-(2-hydroxy-2-phenylethyl)piperidin-4-yl]-N-(1H-pyrazol-3-yl)thiophene-2-carboxamide and 2-(3-iodophenyl)-5-methyl-1,3,4-oxadiazole as starting materials.

HPLC-MS (Method G): Ret, 17.83 min; ESI$^+$-MS m/z: 555 (M+1).

Example 149. N-[(1r,4r)-4-(Dimethylamino)cyclohexyl]-N-(1-[3-(5-methyl-1,3,4-oxadiazol-2-yl)phenyl]-1H-pyrazol-3-yl)thiophene-2-carboxamide

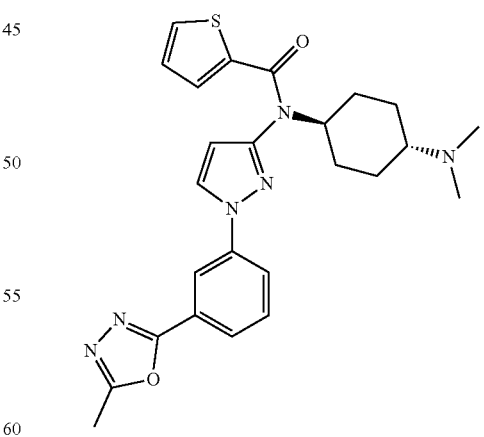

a) 1-[3-(5-Methyl-1,3,4-oxadiazol-2-yl)phenyl]-N-(1,4-dioxaspiro[4.5]decan-8-yl)-1H-pyrazol-3-amine The title compound was obtained following the procedure described in Example 70, arylation conditions C, and using N-(1,4-dioxaspiro[4.5]decan-8-yl)-1H-pyrazol-3-amine (intermediate B31) and 2-(3-iodophenyl)-5-methyl-1,3,4-oxadiazole as starting materials.

HPLC-MS (Method H): Ret, 9.73 min; ESI⁺-MS m/z: 382 (M+1), b) N-(1-[3-(5-Methy-1,3,4-oxadiazol-2-yl)phenyl]-1H-pyrazol-3-yl)-N-(1,4-dioxaspiro[4.5]decan-8-yl)thiophene-2-carboxamide The title compound was obtained following the procedure described in Example 1 and using 1-[3-(5-methyl-1,3,4-oxadiazol-2-yl)phenyl]-N-(1,4-dioxaspiro[4.5]decan-8-yl)-1H-pyrazol-3-amine as starting material.

HPLC-MS (Method H): Ret, 10.05 min; ESI⁺-MS m/z, 492 (M+1).

c) N-[(1r,4r)-4-(Dimethylamino)cyclohexyl]-N-{1-[3-(5-methyl-1,3,4-oxadiazol-2-yl)phenyl]-1H-pyrazol-3-yl}thiophene-2-carboxamide The title compound was obtained following the procedure described in Example 127 and using 1-[3-(5-methyl-1,3,4-oxadiazol-2-yl)phenyl]-N-(1,4-dioxaspiro[4.5]decan-8-yl)-1H-pyrazol-3-amine as starting material.

HPLC-MS (Method P): Ret. 14.61 min; ESI⁺-MS m/z, 477 (M+1).

This method was used for the preparation of examples 150-154 using suitable starting materials:

| Ex | Structure | Chemical name | Method | Ret (min) | MS (M + H) |
|---|---|---|---|---|---|
| 150 | 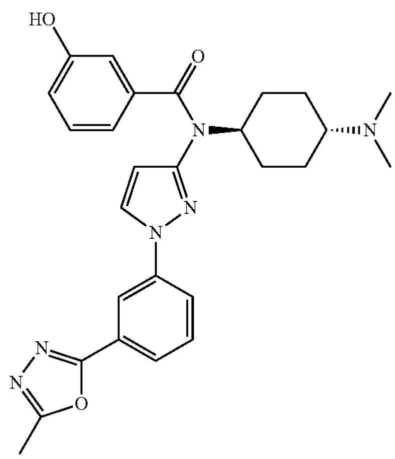 [SMILES: Cc1nnc(-c2cccc(-n3ccc(N(C(=O)c4cccc(O)c4)[C@H]4CC[C@H](N(C)C)CC4)n3)c2)o1] | N-[(1r,4r)-4-(Dimethylamino)cyclohexyl]-3-hydroxy-N-{1-[3-(5-methyl-1,3,4-oxadiazol-2-yl)phenyl]-1H-pyrazol-3-yl}benzamide | P | 13.30 | 487 |
| 151 | 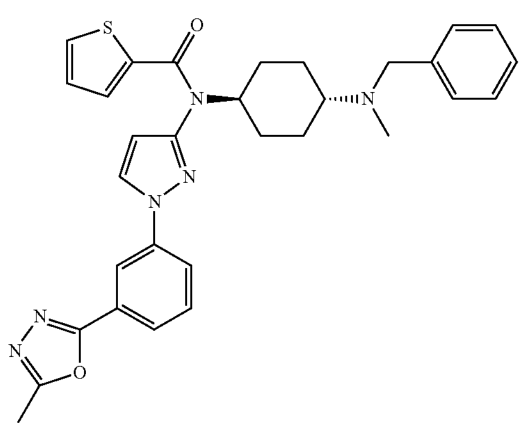 [SMILES: Cc1nnc(-c2cccc(-n3ccc(N(C(=O)c4cccs4)[C@H]4CC[C@H](N(C)Cc5ccccc5)CC4)n3)c2)o1] | N-{(1r,4r)-4-[Benzyl(methyl)amino]cyclohexyl}-N-{1-[3-(5-methyl-1,3,4-oxadiazol-2-yl)phenyl]-1H-pyrazol-3-yl}thiophene-2-carboxamide | P | 18.13 | 553 |

-continued

| Ex | Structure | Chemical name | Method | Ret (min) | MS (M + H) |
|---|---|---|---|---|---|
| 152 | 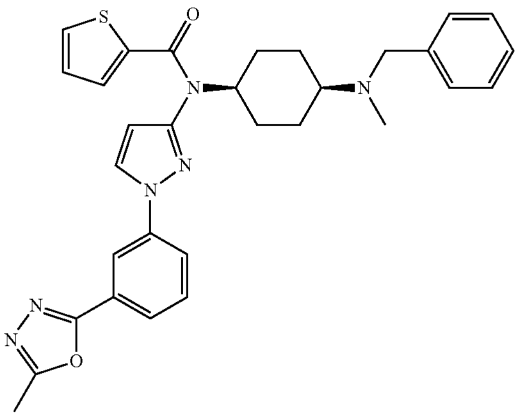 [SMILES: Cc1nnc(-c2cccc(-n3ccc(N(C(=O)c4cccs4)[C@H]4CC[C@@H](N(C)Cc5ccccc5)CC4)n3)c2)o1] | N-{(1s,4s)-4-[Benzyl(methyl)amino]cyclohexyl}-N-{1-[3-(5-methyl-1,3,4-oxadiazol-2-yl)phenyl]-1H-pyrazol-3-yl}thiophene-2-carboxamide | P | 20.45 | 553 |
| 153 | 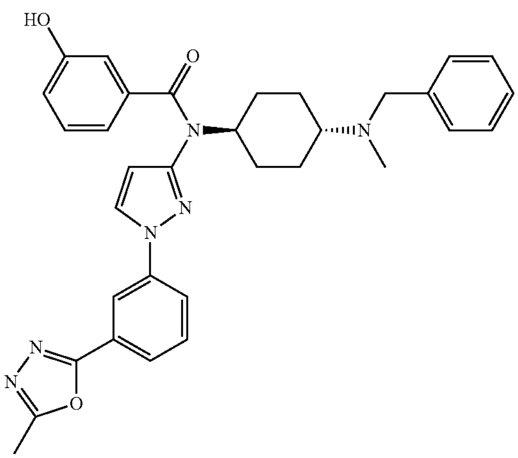 [SMILES: Cc1nnc(-c2cccc(-n3ccc(N(C(=O)c4cccc(O)c4)[C@H]4CC[C@H](N(C)Cc5ccccc5)CC4)n3)c2)o1] | N-{(1r,4r)-4-[Benzyl(methyl)amino]cyclohexyl}-3-hydroxy-N-{1-[3-(5-methyl-1,3,4-oxadiazol-2-yl)phenyl]-1H-pyrazol-3-yl}benzamide | P | 16.88 | 563 |
| 154 | 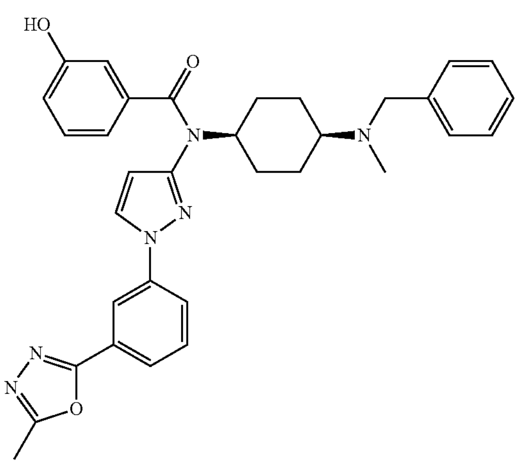 [SMILES: Cc1nnc(-c2cccc(-n3ccc(N(C(=O)c4cccc(O)c4)[C@H]4CC[C@@H](N(C)Cc5ccccc5)CC4)n3)c2)o1] | N-{(1s,4s)-4-[Benzyl(methyl)amino]cyclohexyl}-3-hydroxy-N-{1-[3-(5-methyl-1,3,4-oxadiazol-2-yl)phenyl]-1H-pyrazol-3-yl}benzamide | P | 19.33 | 563 |

Example 155. N-{1-[3-(5-Methyl-1,3,4-oxadiazol-2-yl)phenyl]-1H-pyrazol-4-yl}-N-(1-methylpiperidin-4-yl)thiophene-2-carboxamide

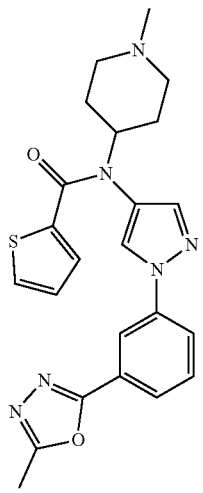 [SMILES: Cc1nnc(-c2cccc(-n3cc(N(C(=O)c4cccs4)C4CCN(C)CC4)cn3)c2)o1]

a) 1H-Pyrazol-4-amine

A suspension of 4-nitro-1H-pyrazole (2.05 g, 18.13 mmol), and Pd/C (10% w/w palladium on activated carbon, 0.96 g, 0.90 mmol) in MeOH (20 mL) was stirred under $H_2$ atmosphere (balloon) for 16 h. The reaction mixture was filtered through Celite, rinsed with MeOH (3×30 mL) and concentrated, affording 1.50 g of 1H-pyrazol-4-amine (pale pink solid, 99% yield).
HPLC-MS (Method H): Ret, 1.16 min; ESI$^+$-MS m/z: 84 (M+1).

b) 1-Methyl-N-(1H-pyrazol-4-yl)piperidin-4-amine

The title compound was obtained following the procedure described in intermediate B1 and using 1H-pyrazol-4-amine and 1-methylpiperidin-4-one as starting materials.
HPLC-MS (Method H): Ret, 1.58 min; ESI$^+$-MS m/z: 181 (M+1).

c) N-(1-Methylpiperidin-4-yl)-N-(1H-pyrazol-4-yl)thiophene-2-carboxamide

The title compound was obtained following the procedure described in intermediate C1 and using 1-methyl-N-(1H-pyrazol-4-yl)piperidin-4-amine as starting material.
HPLC-MS (Method H): Ret, 6.58 min; ESI$^+$-MS m/z: 291 (M+1).

d) N-(1-(3-(5-Methyl-1,3,4-oxadiazol-2-yl)phenyl)-1H-pyrazol-4-yl)-N-(1-methylpiperidin-4-yl)thiophene-2-carboxamide The title compound was obtained following the procedure described in Example 70, arylation conditions C, and using N-(1-methylpiperidin-4-yl)-N-(1H-pyrazol-4-yl)thiophene-2-carboxamide and 2-(3-iodophenyl)-5-methyl-1,3,4-oxadiazole as starting materials.
HPLC-MS (Method G): Ret, 14.85 min; ESI$^+$-MS m/z: 449 (M+1).
This method was used for the preparation of example 156 using suitable starting materials:

| Ex | Structure | Chemical name | Method | Ret (min) | MS (M + H) |
|----|-----------|---------------|--------|-----------|------------|
| 156 | 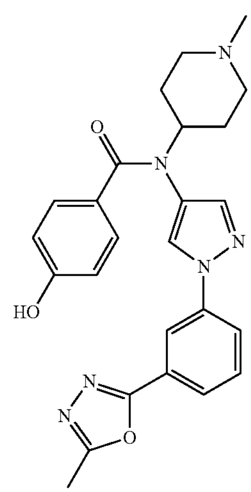 [SMILES: Cc1nnc(-c2cccc(-n3cc(N(C(=O)c4ccc(O)cc4)C4CCN(C)CC4)cn3)c2)o1] | 4-Hydroxy-N-{1-[3-(5-methyl-1,3,4-oxadiazol-2-yl)phenyl]-1H-pyrazol-4-yl}-N-(1-methylpiperidin-4-yl)benzamide | G | 13.70 | 459 |

Example 167. N-[1-(3-Fluoro-5-methoxyphenyl)-1H-pyrazol-4-yl]-N-(1-methylpiperidin-4-yl)thiophene-2-carboxamide

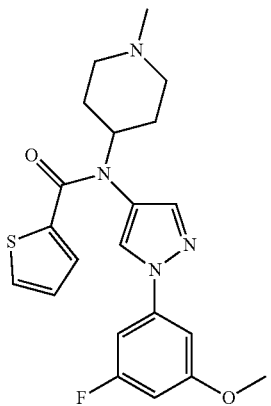 [SMILES: COc1cc(F)cc(-n2cc(N(C(=O)c3cccs3)C3CCN(C)CC3)cn2)c1]

The title compound was obtained following the procedure described in Example 87 and using N-(1-methylpiperidin-4-yl)-N-(1H-pyrazol-4-yl)thiophene-2-carboxamide (Example 155, step c) and (3-fluoro-5-methoxyphenyl)boronic acid as starting materials.

HPLC-MS (Method G): Ret, 16.41 min; ESI$^+$-MS m/z: 415 (M+0.1).

Example 158. N-(1-Benzylpiperidin-4-yl)-N-{1-[3-(5-methyl-1,3,4-oxadiazol-2-yl)phenyl]-1H-pyrazol-4-yl}thiazole-2-carboxamide

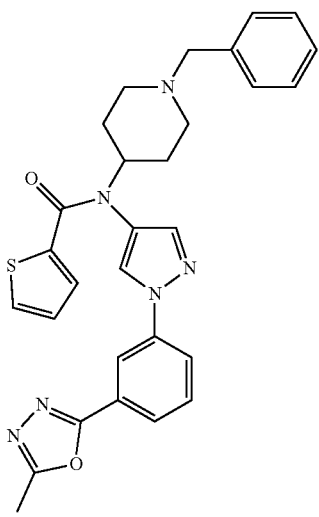 [SMILES: Cc1nnc(-c2cccc(-n3cc(N(C(=O)c4cccs4)C4CCN(Cc5ccccc5)CC4)cn3)c2)o1]

a) 1-Benzyl-N-(1H-pyrazol-4-yl)piperidin-4-amine

The title compound was obtained following the procedure described in intermediate B1 and using 1H-pyrazol-4-amine as starting material.

HPLC-MS (Method H): Ret, 7.44 min; ESI$^+$-MS m/z: 257 (M+1).

b) 1-Benzyl-N-{1-[3-(5-methyl-1,3,4-oxadiazol-2-yl)phenyl]-1H-pyrazol-4-yl}piperidin-4-amine The title compound was obtained following the procedure described in Example 70, arylation conditions C, and using 1-benzyl-N-(1H-pyrazol-4-yl)piperidin-4-amine and 2-(3-iodophenyl)-5-methyl-1,3,4-oxadiazole as starting materials.

HPLC-MS (Method G): Ret, 16.69 min; ESI$^+$-MS m/z: 415 (M+1).

c) N-(1-Benzylpiperidin-4-yl)-N-{1-[3-(5-methyl-1,3,4-oxadiazol-2-yl)phenyl]-1H-pyrazol-4-yl}thiazole-2-carboxamide The title compound was obtained following the procedure described in Example 1 and using 1-benzyl-N-{1-[3-(5-methyl-1,3,4-oxadiazol-2-yl)phenyl]-1H-pyrazol-4-yl}piperidin-4-amine and thiazole-2-carbonyl chloride as starting materials.

HPLC-MS (Method J): Ret, 19.14 min; ESI$^+$-MS m/z: 526 (M+1).

Table of Examples with binding to the μ-opioid Receptor and the α$_2$δ-1Subunit of the Voltage-Gated Calcium Channel:

Biological Activity

Pharmacological Study

Human α$_2$δ-1 Subunit of Ca$_v$2.2 Calcium Channel Assay

Human α$_2$δ-1 enriched membranes (2.5 μg) were incubated with 15 nM of radiolabeled [3H]-Gabapentin in assay buffer containing Hepes-KOH 10 mM, pH 7.4. NSB (non specific binding) was measured by adding 10 μM pregabalin. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 hour and 30 μl of scintillation cocktail were added to each well before radioactivity reading. Readings were performed in a Trilux 1450 Microbeta radioactive counter (Perkin Elmer).

Human μ-Opioid Receptor Radioligand Assay

To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl$_2$ 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the α$_2$δ subunit of voltage-gated calcium channels and the μ-opioid receptor it is a very preferred embodiment in which the compounds are selected which act as dual ligands of the α$_2$δ subunit of voltage-gated calcium channels and the μ-opioid receptor and especially compounds which have a binding expressed as K$_i$ responding to the following scales:

$K_i(\mu)$ is preferably <1000 nM, more preferably <500 nM, even more preferably <100 nM.

$K_i(\alpha_2\delta\text{-}1)$ is preferably <10000 nM, more preferably <5000 nM, even more preferably <500 nM or even more preferably <100 nM.

The following scale has been adopted for representing the binding to i-opioid receptor expressed as $K_i$:

+ $K_i$ (μ)>=500 nM
++ 100 nM<=$K_i$(μ)<500 nM
+++ $K_i$(μ)<100 nM

The following scale has been adopted for representing the binding to the $\alpha_2\delta$-1 subunit of voltage-gated calcium channels expressed as $K_i$:

+ $K_i(\alpha_2\delta\text{-}1)$>=5000 nM
++ 500 nM<=$K_i(\alpha_2\delta\text{-}1)$<5000 nM
+++ 100 nM<=$K_i(\alpha_2\delta\text{-}1)$<500 nM
++++ $K_i(\alpha_2\delta\text{-}1)$<100 nM All compounds prepared in the present application exhibit binding to the $\alpha_2\delta$ subunit of voltage-gated calcium channels and the μ-opioid receptor, in particular the following binding results are shown:

| EX | μ ($K_i$) (nM) | $\alpha_2\delta$ – 1 ($K_i$) (nM) |
|---|---|---|
| 1 | +++ | ++ |
| 2 | +++ | + |
| 3 | ++ | + |
| 4 | +++ | ++ |
| 5 | +++ | ++ |
| 6 | +++ | + |
| 7 | ++ | + |
| 8 | +++ | + |
| 9 | +++ | + |
| 10 | ++ | + |
| 11 | +++ | ++ |
| 12 | +++ | + |
| 13 | +++ | + |
| 14 | +++ | + |
| 15 | +++ | + |
| 16 | +++ | + |
| 17 | +++ | ++ |
| 18 | +++ | ++ |
| 19 | +++ | ++ |
| 20 | ++ | + |
| 21 | + | + |
| 22 | ++ | ++ |
| 23 | ++ | + |
| 24 | ++ | + |
| 25 | ++ | ++ |
| 26 | ++ | + |
| 27 | ++ | +++ |
| 28 | + | + |
| 29 | + | + |
| 30 | + | + |
| 31 | + | + |
| 32 | + | + |
| 33 | + | + |
| 34 | + | + |
| 35 | + | + |
| 36 | ++ | + |
| 37 | + | +++ |
| 39 | + | +++ |
| 40 | ++ | + |
| 41 | + | ++ |
| 43 | ++ | +++ |
| 44 | + | +++ |
| 45 | + | + |
| 46 | + | + |
| 47 | ++ | + |
| 48 | ++ | + |
| 49 | +++ | + |
| 50 | ++ | ++ |
| 51 | +++ | ++ |
| 52 | + | +++ |
| 53 | + | ++ |
| 54 | +++ | ++ |
| 55 | +++ | ++ |
| 56 | +++ | ++ |
| 57 | +++ | ++ |
| 58 | +++ | ++ |
| 59 | ++ | ++ |
| 60 | ++ | ++ |
| 61 | +++ | ++ |
| 62 | +++ | ++ |
| 63 | + | ++ |
| 64 | + | + |
| 65 | + | ++ |
| 66 | ++ | + |
| 67 | + | + |
| 68 | ++ | ++ |
| 69 | + | +++ |
| 70 | ++ | + |
| 71 | + | ++ |
| 72 | + | ++ |
| 73 | + | ++ |
| 74 | + | ++ |
| 75 | + | ++ |
| 76 | + | ++ |
| 77 | + | + |
| 78 | +++ | ++ |
| 79 | +++ | ++ |
| 80 | +++ | ++ |
| 81 | ++ | ++ |
| 82 | +++ | ++ |
| 83 | +++ | ++ |
| 84 | + | +++ |
| 86 | + | +++ |
| 87 | + | + |
| 88 | ++ | ++ |
| 89 | ++ | ++ |
| 90 | + | ++ |
| 91 | + | ++ |
| 92 | + | ++ |
| 93 | + | ++ |
| 94 | + | ++ |
| 95 | + | + |
| 96 | + | + |
| 97 | ++ | + |
| 98 | ++ | ++ |
| 99 | + | ++ |
| 100 | + | + |
| 101 | + | + |
| 102 | + | ++ |
| 103 | ++ | ++ |
| 104 | ++ | +++ |
| 105 | ++ | ++ |
| 106 | + | ++ |
| 107 | + | ++ |
| 108 | + | +++ |
| 109 | + | + |
| 110 | + | ++ |
| 111 | +++ | + |
| 112 | + | +++ |
| 113 | + | ++++ |
| 114 | ++ | ++ |
| 115 | + | + |
| 116 | +++ | + |
| 117 | +++ | ++ |
| 118 | ++ | +++ |
| 119 | +++ | ++ |
| 120 | ++ | +++ |
| 121 | +++ | ++ |
| 122 | ++ | + |
| 123 | + | ++ |
| 124 | + | ++ |
| 125 | + | + |
| 126 | + | ++ |
| 127 | + | + |
| 128 | ++ | + |
| 129 | ++ | ++ |

-continued

| EX | μ (K$_i$) (nM) | α$_2$δ − 1 (K$_i$) (nM) |
|---|---|---|
| 130 | + | +++ |
| 131 | + | ++ |
| 132 | +++ | + |
| 133 | + | + |
| 134 | + | + |
| 135 | +++ | + |
| 136 | +++ | + |
| 137 | +++ | + |
| 138 | + | ++ |
| 139 | + | + |
| 140 | + | + |
| 141 | ++ | + |
| 142 | + | + |
| 143 | + | + |
| 144 | + | ++ |
| 145 | ++ | + |
| 146 | + | ++ |
| 147 | + | + |
| 149 | + | + |
| 150 | + | + |
| 151 | + | + |
| 152 | +++ | + |
| 153 | +++ | + |
| 154 | +++ | + |
| 155 | + | + |
| 156 | + | + |
| 157 | + | + |
| 158 | + | + |

The invention claimed is:

1. A compound of Formula (I):

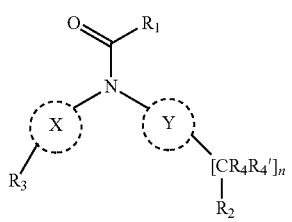

(I)

wherein n is 0, 1, or 2;

X is an unsubstituted aromatic heterocyclyl having one or more nitrogen atoms as the only heteroatom selected from the group consisting of

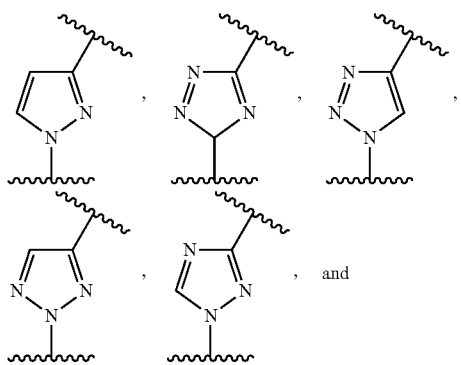

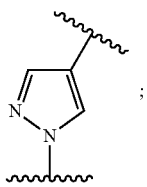

Y is selected from the group consisting of

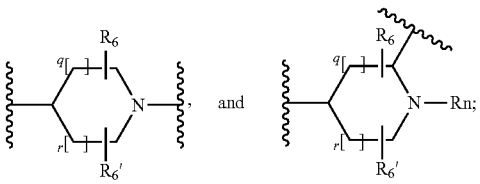

wherein p is 2 or 3;

q is 0 or 1;

r is 0, 1, or 2;

$R_6$ and $R_{6'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

$R_n$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from the group consisting of substituted or unsubstituted monocyclic aryl and substituted or unsubstituted monocyclic aromatic heterocyclyl;

wherein the aryl or aromatic heterocyclyl in $R_1$ if substituted, is substituted with one or more substituent/s selected from the group consisting of halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$, and substituted or unsubstituted five membered aromatic heterocyclyl;

wherein $R_{11}$, $R_{11'}$ and $R_{11''}$ are independently selected from the group consisting of hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;

$R_2$ is selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted monocyclic cycloalkyl, substituted or unsubstituted monocyclic aryl and substituted or unsubstituted monocyclic aromatic heterocyclyl, wherein the cycloalkyl, aryl or aromatic heterocyclyl in $R_2$, if substituted, is substituted with one or more substituent/s selected from the group consisting of halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —C(O)OR$_{12}$, —C(O)NR$_{12}$R$_{12'}$, —OCH$_2$CH$_2$OH, —NR$_{12}$S(O)$_2$NR$_{12}$R$_{12''}$ and C(CH$_3$)$_2$OR$_{12}$;

and wherein the alkyl, alkenyl or alkynyl in R$_2$, if substituted, is substituted with one or more substituent/s selected from the group consisting of —OR$_{12}$, halogen, —CN, haloalkyl, haloalkoxy and —NR$_{12}$R$_{12'''}$;

wherein R$_{12}$, R$_{12'}$ and R$_{12''}$ are independently selected from the group consisting of hydrogen, unsubstituted C$_{1-6}$ alkyl, unsubstituted C$_{2-6}$ alkenyl and unsubstituted C$_{2-6}$ alkynyl;

and wherein R$_{12'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;

R$_3$ is selected from the group consisting of substituted or unsubstituted monocyclic aryl and substituted or unsubstituted monocyclic aromatic heterocyclyl, wherein the aryl or aromatic heterocyclyl in R$_3$, if substituted, is substituted with one or more substituent/s selected from the group consisting of halogen, —R$_{13}$, —OR$_{13}$, —NO$_2$, —NR$_{13}$R$_{13'''}$, NR$_{13}$C(O)R$_{13'}$, —NR$_{13}$S(O)$_2$R$_{13'}$, —S(O)$_2$NR$_{13}$R$_{13'}$, —NR$_{13}$C(O)NR$_{13'}$R$_{13''}$, —SR$_{13}$, —S(O)R$_{13}$, S(O)$_2$R$_{13}$, —CN, haloalkyl, haloalkoxy, —C(O)OR$_{13}$, —C(O)NR$_{13}$R$_{13'}$, —OCH$_2$CH$_2$OCH$_3$, —NR$_{13}$S(O)$_2$NR$_{13'}$R$_{13''}$, C(CH$_3$)$_2$OR$_{13}$ and substituted or unsubstituted five membered aromatic heterocyclyl;

wherein R$_{13}$, R$_{13'}$ and R$_{13''}$ are independently selected from the group consisting of hydrogen, unsubstituted C$_{1-6}$ alkyl, unsubstituted C$_{2-6}$ alkenyl, and unsubstituted C$_{2-6}$ alkynyl;

R$_{13'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;

R$_4$ and R$_{4'}$ are independently selected from the group consisting of hydrogen, —OR$_{14}$, substituted or unsubstituted C$_{1-6}$ alkyl, substituted or unsubstituted C$_{2-6}$ alkenyl and substituted or unsubstituted C$_{2-6}$ alkynyl;

wherein the alkyl, alkenyl or alkynyl, other than those defined in R$_2$, if substituted, is substituted with one or more substituent/s selected from the group consisting of —OR$_{14}$, halogen, —CN, haloalkyl, haloalkoxy and —NR$_{14}$R$_{14'''}$;

wherein R$_{14}$ is selected from the group consisting of hydrogen, unsubstituted C$_{1-6}$ alkyl, unsubstituted C$_{2-6}$ alkenyl, and unsubstituted C$_{2-6}$ alkynyl;

R$_{14'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;

and wherein the aryl, heterocyclyl or cycloalkyl other than those defined in R$_1$, R$_2$ or R$_3$, if substituted, is substituted with one or more substituent/s selected from the group consisting of halogen, —R$_{15}$, —OR$_{15}$, —NO$_2$, —NR$_{15}$R$_{15'''}$, NR$_{15}$C(O)R$_{15'}$, —NR$_{15}$S(O)$_2$R$_{15'}$, —S(O)$_2$NR$_{15}$R$_{15'}$, —NR$_{15}$C(O)NR$_{15'}$R$_{15''}$, —SR$_{15}$, —S(O)R$_{15}$, S(O)$_2$R$_{15}$, —CN, haloalkyl, haloalkoxy, —C(O)OR$_{15}$, —C(O)NR$_{15}$R$_{15'}$, —OCH$_2$CH$_2$OH, —NR$_{15}$S(O)$_2$NR$_{15'}$R$_{15''}$ and C(CH$_3$)$_2$ OR$_{15}$;

wherein R$_{15}$, R$_{15'}$ and R$_{15''}$ are independently selected from the group consisting of hydrogen, unsubstituted C$_{1-6}$ alkyl, unsubstituted C$_{2-6}$ alkenyl, and unsubstituted C$_{2-6}$ alkynyl;

and wherein R$_{15'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;

optionally as a stereoisomer, including enantiomers and diastereomers, a racemate or a mixture of at least two stereoisomers, including enantiomers and/or diastereomers, in any mixing ratio, or a corresponding salt thereof, or a corresponding solvate thereof.

2. The compound according to claim 1, wherein R$_4$ and R$_{4'}$ are independently selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl.

3. The compound according to claim 1, wherein X is selected from the group consisting of:

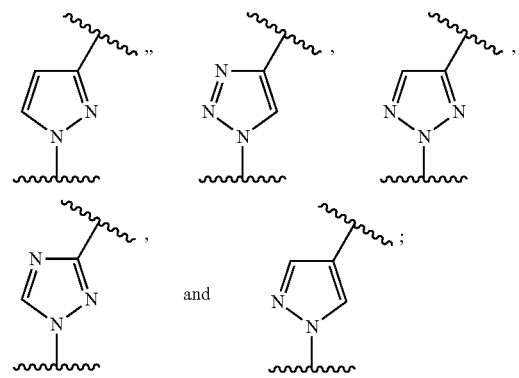

and the compound of Formula (I) is a compound of formula (Ia$_1$), (Ia$_2$), (Ia$_3$), (Ia$_4$) or (Ia$_8$):

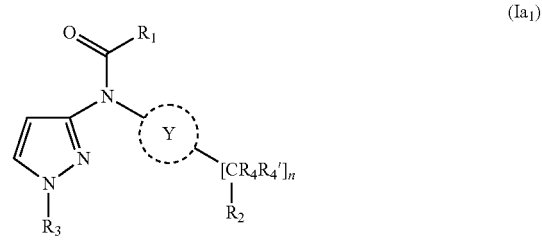
(Ia$_1$)

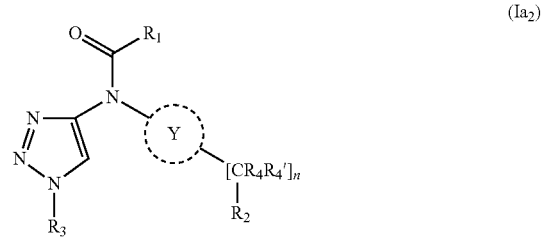
(Ia$_2$)

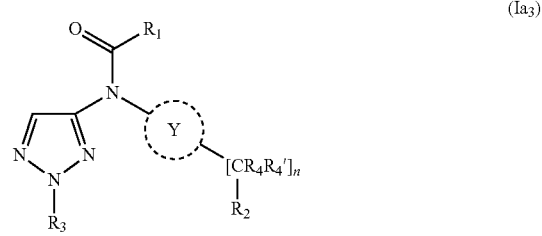
(Ia$_3$)

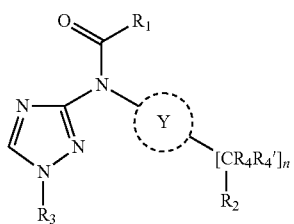

(Ia4)

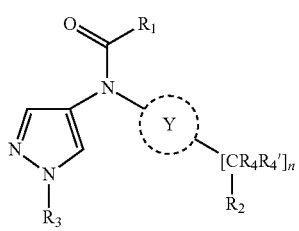

(Ia8)

wherein Y, $R_1$, $R_2$, $R_3$, $R_4$, $R_{4'}$ and n are as defined in claim 1.

4. The compound according to claim 1, wherein Y is selected from the group consisting of:

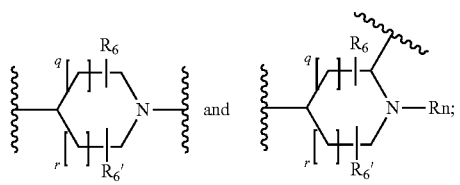

and the compound of Formula (I) is a compound of formula (Ib$_2$) or (Ib$_3$);

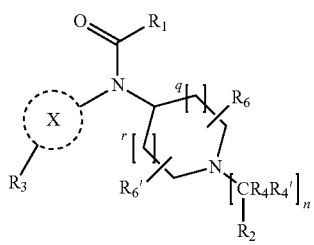

(Ib$_2$)

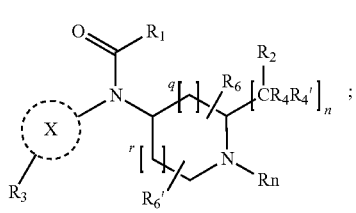

(Ib$_3$)

wherein X, $R_1$, $R_2$, $R_3$, $R_4$, $R_{4'}$, $R_6$, $R_{6'}$, $R_n$, p, q, r and n are as defined in claim 1.

5. The compound according to claim 1, which is a compound of formula (Ib$_{21}$), (Ib$_{22}$), (Ib$_{23}$), (Ib$_{24}$) or (Ib$_{31}$)

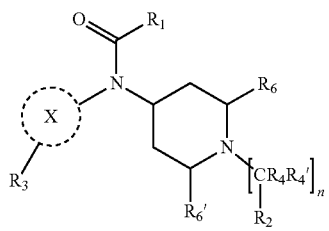

(Ib$_{21}$)

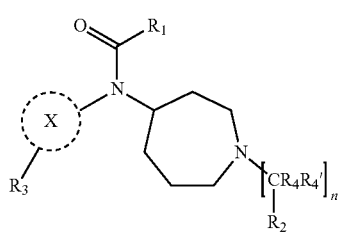

(Ib$_{22}$)

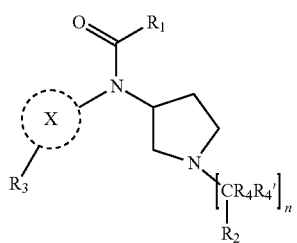

(Ib$_{23}$)

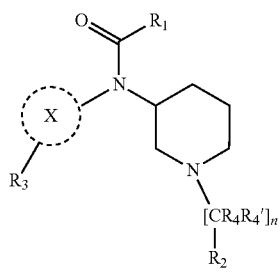

(Ib$_{24}$)

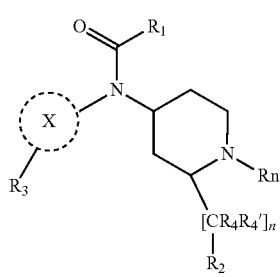

(Ib$_{31}$)

wherein X, $R_1$, $R_2$, $R_3$, $R_4$, $R_{4'}$, $R_6$, $R_{6'}$, $R_n$, p and n are as defined in claim 1.

6. The compound according to claim 1, wherein $R_1$ is a substituted or unsubstituted group selected from the group consisting of phenyl, pyridine, thiophen, furane, isoxazole, thiazole, pyrrole, oxazole and isothiazole.

7. The compound according to claim 1, wherein $R_1$ is a substituted or unsubstituted group selected from:

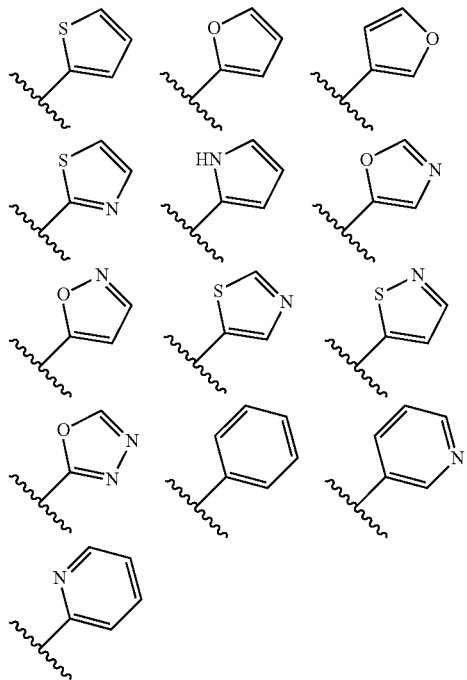

which groups can be unsubstituted or substituted with one or more substituent/s selected from the group consisting of halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ $C(CH_3)_2OR_{11}$ and substituted or unsubstituted five membered aromatic heterocyclyl;

wherein $R_{11}$, $R_{11'}$, $R_{11''}$ and $R_{11'''}$ are as defined in claim 1.

8. The compound according to claim 1, wherein $R_2$ is selected from the group consisting of hydrogen, substituted or unsubstituted $C_{1-6}$ alkyl, substituted or unsubstituted monocyclic aryl and substituted or unsubstituted monocyclic aromatic heterocyclyl, wherein the aryl or aromatic heterocyclyl can be optionally substituted with one or more substituent/s selected from the group consisting of halogen, —$R_{12}$, —$OR_{12}$, —$NO_2$, —$NR_{12}R_{12'''}$, $NR_{12}C(O)R_{12'}$, —$NR_{12}S(O)_2 R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2 OR_{12}$;

and wherein the alkyl, if substituted, is substituted with one or more substituent/s selected from the group consisting of —$OR_{12}$, halogen, —CN, haloalkyl, haloalkoxy and —$NR_{12}R_{12'''}$;

wherein $R_{12}$, $R_{12'}$, $R_{12''}$ and $R_{12'''}$ are as defined in claim 1.

9. The compound according to claim 1, wherein $R_2$ is selected from hydrogen, substituted or unsubstituted methyl, substituted or unsubstituted phenyl and substituted or unsubstituted pyridine;

wherein the phenyl or pyridine can be optionally substituted with one or more substituent/s selected from the group consisting of halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and $C(CH_3)_2OR_{12}$;

and wherein the methyl, if substituted, is substituted with one or more substituent/s selected from —$OR_{12}$, halogen, —CN, haloalkyl, haloalkoxy and —$NR_{12}R_{12'''}$;

wherein $R_{12}$, $R_{12'}$, $R_{12''}$ and $R_{12'''}$ are as defined in claim 1.

10. The compound according to claim 1, wherein $R_3$ is a substituted or unsubstituted group selected from phenyl, pyridine or pyrazole, which groups, if substituted, are substituted with one or more substituent/s selected from the group consisting of halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, $NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OCH_3$, —$NR_{13}S(O)_2NR_{13'}R_{13''}$, $C(CH_3)_2OR_{13}$ and substituted or unsubstituted five membered aromatic heterocyclyl;

wherein $R_{13}$, $R_{13'}$ and $R_{13''}$ are independently selected from the group consisting of hydrogen, unsubstituted $C_{1-6}$ alkyl, unsubstituted $C_{2-6}$ alkenyl, and unsubstituted $C_{2-6}$ alkynyl; and $R_{13'''}$ is selected from hydrogen, unsubstituted $C_{1-6}$ alkyl, unsubstituted $C_{2-6}$ alkenyl, unsubstituted $C_{2-6}$ alkynyl and -Boc.

11. The compound according to claim 1, wherein $R_1$ is substituted or unsubstituted thiophene.

12. The compound according to any one of claim 1, wherein $R_2$ is substituted or unsubstituted phenyl.

13. The compound according to claim 1, wherein $R_3$ is substituted or unsubstituted phenyl.

14. The compound according to claim 1, wherein the compound is selected from the group consisting of:
N-(1-Benzylpiperidin-4-yl)-N-[1-(4-fluorophenyl)-1H-pyrazol-3-yl]thiophene-2-carboxamide,
N-(1-Benzylpiperidin-4-yl)-N-[1-(4-fluorophenyl)-1H-pyrazol-3-yl]furan-2-carboxamide,
N-(1-Benzylpiperidin-4-yl)-N-[1-(4-fluorophenyl)-1H-pyrazol-3-yl]isoxazole-5-carboxamide,
N-(1-Benzylpiperidin-4-yl)-N-[1-(4-fluorophenyl)-1H-pyrazol-3-yl]furan-3-carboxamide,
N-(1-Benzylpiperidin-4-yl)-N-[1-(4-fluorophenyl)-1H-pyrazol-3-yl]thiazole-2-carboxamide,
N-(1-Benzylpiperidin-4-yl)-N-[1-(4-fluorophenyl)-1H-pyrazol-3-yl]-1-methyl-1H-pyrrole-2-carboxamide,
N-(1-Benzylpiperidin-4-yl)-N-[1-(4-fluorophenyl)-1H-pyrazol-3-yl)]oxazole-5-carboxamide,
N-[1-(4-Fluorophenyl)-1H-pyrazol-3-yl]-N-(1-phenethylpiperidin-4-yl)thiophene-2-carboxamide,
N-[1-(4-Fluorophenyl)-1H-pyrazol-3-yl]-N-(1-phenethylpiperidin-4-yl)isoxazole-5-carboxamide,
N-(1-Benzylpiperidin-4-yl)-N-[1-(4-ethoxyphenyl)-1H-pyrazolyl]thiophene-2-carboxamide,
N-(1-Benzylpiperidin-4-yl)-N-[1-(4-ethoxyphenyl)-1H-pyrazolyl]thiazole-2-carboxamide,
N-(1-Phenethylpiperidin-4-yl)-N-(1-phenyl-1H-pyrazol-3-yl)thiophene-2-carboxamide,
N-(1-Benzylpiperidin-4-yl)-N-(1-phenyl-1H-pyrazol-3-yl)thiophene-2-carboxamide,
N-(1-Benzylpiperidin-4-yl)-N-(1-phenyl)-1H-pyrazol-3-yl)furanol-2-carboxamide, N-(1-Benzylpiperidin-4-yl)-N-(1-phenyl-1H-pyrazol-3-yl)thiazole-2-carboxamide,
N-(1-Benzylpiperidin-4-yl)-N-(1-phenyl-1H-pyrazol-3-yl)picolinamide,
N-(1-Benzylpiperidin-4-yl)-N-(1-phenyl-1H-pyrazol-3-yl)thiazole-carboxamide,
N-(1-Benzylpiperidin-4-yl)-5-fluoro-N-(1-phenyl-1H-pyrazol-3-yl)thiophene-2-carboxamide,
N-(1-Benzylpiperidin-4-yl)-5-chloro-N(1-phenyl-1H-pyrazol-3-yl)thiophene-2-carboxamide,
N-(1-Benzylpiperidin-4-yl)-3-chloro-N-(1-phenyl-1H-pyrazol-3-yl)thiophene-2-carboxamide,
N-(1-Benzylpiperidin-4-yl)-N-(1-phenyl-1H-pyrazol-3-yl)isothiazole-5-carboxamide,
N-(1-Benzylpiperidin-4-yl)-4-methoxy-N-(1-phenyl-1H-pyrazol-3-yl)benzamide,
N-(1-Methylpiperidin-4-yl)-N-(1-phenyl-1H-pyrazol-3-yl)thiophene-2-carboxamide,
3-Methoxy-N-(1-methyl-piperidin-4-yl)-N-(1-phenyl-1H-pyrazol-3-yl)-benzamide,
3-(5-Methyl-[1,3,4]oxadiazol-2-yl)-N-(1-methyl-piperidin-4-yl)-N-(1-phenyl-1H-pyrazol-3-yl)-benzamide,
N-(1-Methylpiperidin-4-yl)-N-(1-phenyl-1H-pyrazol-3-yl)benzamide,
2-Methoxy-N-(1-methylpiperidin-4-yl)-N-(1-phenyl-1H-pyrazol-3-yl)benzamide,
3-Fluoro-N-(1-methylpiperidin-4-yl)-N-1-phenyl-1H-pyrazol-3-yl)picolinamide,
N-(1-Methylpiperidin-4-yl)-N-(1-phenyl-1H-pyrazol-3-yl)nicotinamide,
2-Fluoro-6-methyl-N-(1-methylpiperidin-4-yl)-N-(1-phenyl-1H-pyrazol-3-yl)benzamide,
4-Methyl-N-(1-methylpiperidin-4-yl)-N-(1-phenyl-1H-pyrazol-3-yl)thiazole-2-carboxamide,
6-Methyl-N-(1-methylpiperidin-4-yl)-N-(1-phenyl-1H-pyrazol-3-yl)nicotinamide,
N-(1-Methylpiperidin-4-yl)-N-(1-phenyl-1H-pyrazol-3-yl)-1H-pyrrole-2-carboxamide,
N-(1-Methylpyrrolidin-3-yl)-N-(1-phenyl-1H-pyrazol-3-yl)thiophene-2-carboxamide,
N-(1-Methylazepan-4-yl)-N-(1-phenyl-1H-pyrazol-3-yl)thiophene-2-carboxamide,
N-(1-Benzyl-2,6-dimethylpiperidin-4-yl)-N-(1-phenyl-1H-pyrazol-3-yl)thiophene-2-carboxamide,
N-(1-Phenyl-1H-pyrazol-3-yl)-N-(1,2,6-trimethylpiperidin-4-yl)thiophene-2-carboxamide,
N-[1-(3,4-Dichlorophenyl)-1H-pyrazol-3-yl]-N-(1-phenethyl piperidin-4-yl)furan-2-carboxamide,
N-(1-Benzylpiperidin-4-yl)-N-{1-[3-(5-methyl-1,3,4-oxadiazol-2-yl)phenyl]-1H-pyrazol-3-yl}-1,3-thiazole-2-carboxamide,
N-(1-Benzylpiperidin-4-yl)-N-{1-[3-(5-methyl-1,3,4-oxadiazol-2-yl)phenyl]-1H-pyrazol-3-yl}-isothiazole-5-carboxamide,
N-{1-[3-(5-Methyl-1,3,4-oxadiazol-2-yl)phenyl]-1H-pyrazol-3-yl}-N-{1-[2-(pyridin-2-yl)ethyl]piperidin-4-yl}thiophene-2-carboxamide,
N-[1-(3-Methoxyphenyl)-1H-pyrazol-3-yl]-N-[1-(pyridin-3-ylmethyl)piperidin-4-yl]thiophene-2-carboxamide,
N-(1-benzylpiperidin-4-yl)-N-(1-phenyl-1H-1,2,4-triazol-3-yl)thiophene-2-carboxamide,
N-(1-benzylpiperidin-4-yl)-N-(1-phenyl-1H-1,2,4-triazol-3-yl)furan-2-carboxamide,
N-(1-phenethylpiperidin-4-yl)-N-(1-phenyl-1H-1,2,4-triazol-3-yl)thiophene-2-carboxamide,
3-Hydroxy-N-{1-[3-(5-methyl-1,3,4-oxadiazol-2-yl)phenyl]-1H-pyrazol-3-yl}-N-(1-methylpiperidin-4-yl)benzamide,
N-(1-Benzylpiperidin-4-yl)-3-hydroxy-N-{1-[3-(5-methyl-1,3,4-oxadiazol-2-yl)phenyl]-1H-pyrazol-3-yl}benzamide,
N-(1-Phenyl-1H-pyrazol-3-yl)-N-piperidin-4-ylthiophene-2 carboxamide,
N-(1-Phenyl-1H-pyrazol-3-yl)-N-(piperidin-3-yl)thiophene-2-carboxamide,
N-(2-Benzylpiperidin-4-yl)-N-(1-phenyl-1H-pyrazol-3-yl)thiophene-2-carboxamide,
N-(1-Isobutylpiperidin-4-yl)-N-(1-phenyl-1H-pyrazol-3-yl)thiophene-2-carboxamide,
N-(1-Ethylpiperidin-4-yl)-N-(1-phenyl-1H-pyrazol-3-yl)thiophene-2-carboxamide,
N-(1-Isopropylpiperidin-4-yl)-N-(1-phenyl-1H-pyrazol-3-yl)thiophene-2-carboxamide,
N-(1-Methylpiperidin-3-yl)-N-(1-phenyl-1H-pyrazol-3-yl)thiophene-2-carboxamide,
N-(1-Methylpiperidin-4-yl)-N-(1-pyridin-2-yl-1H-pyrazol-3-yl)thiophene-2-carboxamide,
N-(1-Methylpiperidin-4-yl)-N-[1-(pyridin-3-yl)-1H-pyrazol-3-yl]thiophene-2-carboxamide,
N-[1-(3-Fluoropyridin-4-yl)-1H-pyrazol-3-yl]-N-(1-methylpiperidin-4-yl)thiophene-2-carboxamide,
N-(1-Methylpiperidin-4-yl)-N-[1-(3-methylpyridin-4-yl)-1H-pyrazol-3-yl]thiophene-2-carboxamide,
N-(1-Methylpiperidin-4-yl)-N-[1-(o-tolyl)-1H-pyrazol-3-yl]thiophene-2-carboxamide,
N-{1-[3-(2-Methoxyethoxy)phenyl]-1H-pyrazol-3-yl}-N-(1-methylpiperidin-4-yl)thiophene-2-carboxamide,
N-[1-(3-Methoxy-5-methylphenyl)-1H-pyrazol-3-yl]-N-(1-methylpiperidin-4-yl)thiophene-2-carboxamide,
N-(1-Benzylpiperidin-4-yl)-N-[1-(3,5-dichloropyridin-4-yl)-1H-pyrazol-3-yl]thiophene-2-carboxamide,
N-(1-Benzylpiperidin-4-yl)-N-[1-(pyridin-4-yl)-1H-pyrazol-3-yl]thiophene-2-carboxamide,
N-(1-Benzylpiperidin-4-yl)-N-[1-(pyridin-3-yl)-1H-pyrazol-3-yl]thiophene-2-carboxamide,
N-(1-Benzylpiperidin-4-yl)-N-[1-(pyridin-2-yl)-1H-pyrazol-3-yl]thiophene-2-carboxamide,
N-(1-Benzylpiperidin-4-yl)-N-[1-(o-tolyl)-1H-pyrazol-3-yl]thiophene-2-carboxamide,
N-(1-Benzylpiperidin-4-yl)-N-[1-(3-fluoropyridin-4-yl)-1H-pyrazol-3-yl]thiophene-2-carboxamide,
N-(1-Benzylpiperidin-4-yl)-N-[1-(3-chloropyridin-4-yl)-1H-pyrazol-3-yl]thiophene-2-carboxamide,
N-[1-(3,4-Difluorobenzyl)piperidin-4-yl]-N-{1-[3-(5-methyl-1,3,4-oxadiazol-2-yl)phenyl]-1H-pyrazol-3-yl}thiophene-2-carboxamide,
N-{1-[3-(5-Methyl-1,3,4-oxadiazol-2-yl)phenyl]-1H-pyrazol-3-yl}-N-(1-phenethylpiperidin-4-yl)thiophene-2-carboxamide,
N-{1-[3-(5-Methyl-1,3,4-oxadiazol-2-yl)phenyl]-1H-pyrazol-3-yl}-N-(1-(pyridin-2-ylmethyl)piperidin-4-yl)thiophene-2-carboxamide,
N-[1-(4-Ethoxyphenyl)-1H-pyrazol-3-yl]-N-(1-methylpiperidin-4-yl)thiophene-2-carboxamide,
N-[1-(3-Ethoxyphenyl)-1H-pyrazol-3-yl]-N-(1-methylpiperidin-4-yl)thiophene-2-carboxamide,
N-[1-(4-Cyanophenyl)-1H-pyrazol-3-yl]-N-(1-methylpiperidin-4-yl)thiophene-2-carboxamide,
N-[1-(3-Cyanophenyl)-1H-pyrazol-3-yl]-N-(1-methylpiperidin-4-yl)thiophene-2-carboxamide,
N-[1-(4-Fluorophenyl)-1H-pyrazol-3-yl]-N-(1-methylpiperidin-4-yl)thiophene-2-carboxamide, N-[1-(3-Fluorophenyl)-1H-pyrazol-3-yl]-N-(1-methylpiperidin-4-yl)thiophene-2-carboxamide,
N-[1-(2-Fluorophenyl)-1H-pyrazol-3-yl]-N-(1-methylpiperidin-4-yl)thiophene-2-carboxamide,
N-(1-Methylpiperidin-4-yl)-N-[1-(pyridin-4-yl)-1H-pyrazol-3-yl]thiophene-2-carboxamide,
N-[1-(3,4-Dimethoxyphenyl)-1H-pyrazol-3-yl]-N-(1-methylpiperidin-4-yl)thiophene-2-carboxamide,
N-[1-(2-Chloro-4-methoxyphenyl)-1H-pyrazol-3-yl]-N-(1-methylpiperidin-4-yl)thiophene-2-carboxamide,
N-[1-(6-Methoxypyridin-3-yl)-1H-pyrazol-3-yl]-N-(1-methylpiperidin-4-yl)thiophene-2-carboxamide,
N-[1-(2,4-Dichlorophenyl)-1H-pyrazol-3-yl]-N-(1-methylpiperidin-4-yl)thiophene-2-carboxamide,
N-[1-(4-Fluoro-3-methoxyphenyl)-1H-pyrazol-3-yl]-N-(1-methylpiperidin-4-yl)thiophene-2-carboxamide,
N-[1-(2-Chloro-5-methoxyphenyl)-1H-pyrazol-3-yl]-N-(1-methylpiperidin-4-yl)thiophene-2-carboxamide,
N-[1-(3,5-Dimethoxyphenyl)-1H-pyrazol-3-yl]-N-(1-methylpiperidin-4-yl)thiophene-2-carboxamide,
N-[1-(3-Chloro-5-methoxyphenyl)-1H-pyrazol-3-yl]-N-(1-methylpiperidin-4-yl)thiophene-2-carboxamide,
N-(1-Methylpiperidin-4-yl)-N-{1-[3-(trifluoromethoxy)phenyl]-1H-pyrazol-3-yl}thiophene-2-carboxamide,
N-[1-(3-Fluoro-5-methoxyphenyl)-1H-pyrazol-3-yl]-N-(1-methylpiperidin-4-yl)thiophene-2-carboxamide,
N-[1-(2-Methoxypyridin-4-yl)-1H-pyrazol-3-yl]-N-(1-methylpiperidin-4-yl)thiophene-2-carboxamide,
N-{1-[3-(Dimethylamino)phenyl]-1H-pyrazol-3-yl}-N-(1-methylpiperidin-4-yl)thiophene-2-carboxamide,
N-[1-(3-Acetamidophenyl)-1H-pyrazol-3-yl]-N-(1-methylpiperidin-4-yl)thiophene-2-carboxamide,
N-(1-Methylpiperidin-4-yl)-N-{1-[3-(methylsulfonamido)phenyl]-1H-pyrazol-3-yl}thiophene-2-carboxamide,
N-(2'-Methyl-2'H-[1,3'-bipyrazol]-3-yl)-N-(1-methylpiperidin-4-yl)thiophene-2-carboxamide,
N-[1-(3-Methoxyphenyl)-1H-pyrazol-3-yl]-N-(1-methylpiperidin-4-yl)thiophene-3-carboxamide,
3-Hydroxy-N-[1-(3-methoxyphenyl)-1H-pyrazol-3-yl]-N-(1-methylpiperidin-4-yl)benzamide,
N-[1-(3-Methoxyphenyl)-1H-pyrazol-3-yl]-N-(1-methylpiperidin-4-yl)benzamide,
N-{1-[3-(5-Methyl-1,3,4-oxadiazol-2-yl)phenyl]-1H-pyrazol-3-yl}-N(1-methylpiperidin-4-yl)thiophene-2-carboxamide,
N-[1-(3-Hydroxyphenyl)-1H-pyrazol-3-yl]-N-(1-methylpiperidin-4-yl)thiophene-2-carboxamide,
N-(1-Benzylpiperidin-4-yl)-N-[1-(4-cyanophenyl)-1H-pyrazol-3-yl]thiophene-2-carboxamide,
N-(1-Benzylpiperidin-4-yl)-N-[1-(3-cyanophenyl)-1H-pyrazol-3-yl]thiophene-2-carboxamide,
N-(1-Benzylpiperidin-4-yl)-N-{1-[3-(5-methyl-1,3,4-oxadiazol-2-yl)phenyl]-1H-pyrazol-3-yl}-thiophene-2-carboxamide,
N-(1-Benzylpiperidin-4-yl)-N-[1-(3-fluorophenyl)-1H-pyrazol-3-yl]thiophene-2-carboxamide,
N-(1-Benzylpiperidin-4-yl)-N-{1-[3-(5-methyl-1,3,4-oxadiazol-2-yl)phenyl]-1H-pyrazol-3-yl}-2-furamide,
N-[1-(3-Methoxyphenyl)-1H-pyrazol-3-yl]-N-[1-(pyridin-2-ylmethyl)piperidin-4-yl]thiophene-2-carboxamide,
N-[1-(3-Methoxyphenyl)-1H-pyrazol-3-yl]-N-(1-{[6-(trifluoromethyl)pyridin-3-yl]methyl}piperidin-4-yl)thiophene-2-carboxamide,
N-[1-(2-Chloro-4-hydroxyphenyl)-1H-pyrazol-3-yl]-N-(1-methylpiperidin-4-yl)thiophene-2-carboxamide,
N-[1-(4-Fluoro-3-hydroxyphenyl)-1H-pyrazol-3-yl]-N-(1-methylpiperidin-4-yl)thiophene-2-carboxamide,
N-[1-(2-Chloro-5-hydroxyphenyl)-1H-pyrazol-3-yl]-N-(1-methylpiperidin-4-yl)thiophene-2-carboxamide,
N-(1-benzylpiperidin-4-yl)-N-(1-(4-fluorophenyl)-1H-1,2,3-triazol-4-yl)thiophene-2-carboxamide,
N-(1-benzylpiperidin-4-yl)-N-(1-phenyl-1H-1,2,3-triazol-4-yl)thiophene-2-carboxamide,
N-(1-benzylpiperidin-4-yl)-N-(2-phenyl-2H-1,2,3-triazol-4-yl)thiophene-2-carboxamide,
3-Methoxy-N-{1-[3-(5-methyl-1,3,4-oxadiazol-2-yl)phenyl]-1H-pyrazol-3-yl}-N-(1-methylpiperidin-4-yl)benzamide,
3-Ethoxy-N-{1-[3-(5-methyl-1,3,4-oxadiazol-2-yl)phenyl]-1H-pyrazol-3-yl}-N-(1-methylpiperidin-4-yl)benzamide,
4-Hydroxy-N-{1-[3-(5-methyl-1,3,4-oxadiazol-2-yl)phenyl]-1H-pyrazol-3-yl}-N-(1-methylpiperidin-4-yl)benzamide,
3-(1H-Imidazol-2-yl)-N-{1-[3-(5-methyl-1,3,4-oxadiazol-2-yl)phenyl]-1H-pyrazol-3-yl}-N-(1-methylpiperidin-4-yl)benzamide,
N-{1-[3-(5-Methyl-1,3,4-oxadiazol-2-yl)phenyl]-1H-pyrazol-3-yl}-N-(1-methylpiperidin-4-yl)-3-(ethylsulfonamido)benzamide,
3-Hydroxy-N-{1-[3-(5-methyl-1,3,4-oxadiazol-2-yl)phenyl]-1H-pyrazol-3-yl}-N-(piperidin-4-yl)benzamide,
N-[(2S,6R)-2,6-Dimethylpiperidin-4-yl]-3-hydroxy-N-{1-[3-(5-methyl-1,3,4-oxadiazol-2-yl)phenyl]-1H-pyrazol-3-yl}benzamide,
N-[1-(3-Methoxyphenyl)-1H-pyrazol-3-yl]-N-(1-{[6-(trifluoromethyl)pyridin-2-yl]methyl}piperidin-4-yl)thiophene-2-carboxamide,
N-{1-[3-(5-Methyl-1,3,4-oxadiazol-2-yl)phenyl]-1H-pyrazol-3-yl}-N-(1-{[6-(trifluoromethyl)pyridin-2-yl]methyl}piperidin-4-yl)thiophene-2-carboxamide,
N-[1-(2-Hydroxy-2-phenylethyl)piperidin-4-yl]-N-{1-[3-(5-methyl-1,3,4-oxadiazol-2-yl)phenyl]-1H-pyrazol-3-yl}thiophene-2-carboxamide,
N-{1-[3-(5-Methyl-1,3,4-oxadiazol-2-yl)phenyl]-1H-pyrazol-4-yl}-N-(1-methylpiperidin-4-yl)thiophene-2-carboxamide,
4-Hydroxy-N-{1-[3-(5-methyl-1,3,4-oxadiazol-2-yl)phenyl]-1H-pyrazol-4-yl}-N-(1-methylpiperidin-4-yl)benzamide,
N-[1-(3-Fluoro-5-methoxyphenyl)-1H-pyrazol-4-yl]-N-(1-methylpiperidin-4-yl)thiophene-2-carboxamide, and
N-(1-Benzylpiperidin-4-yl)-N-{1-[3-(5-methyl-1,3,4-oxadiazol-2-yl)phenyl]-1H-pyrazol-4-yl}thiazole-2-carboxamide.

15. A process for the preparation of the compound of Formula (I) according to claim 1,

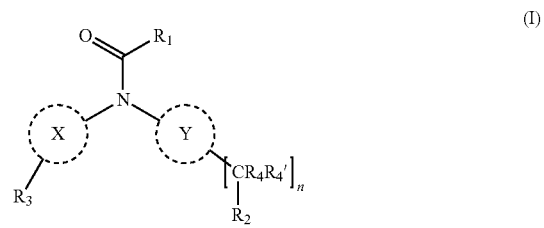

which process comprises acylation of a compound of formula IVb

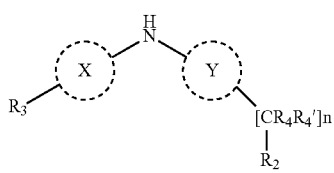

with an acyl halide of formula V

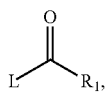

or
alkylation of a compound of Formula Ib,

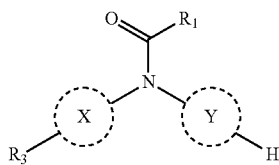

with a compound of formula VIIa,

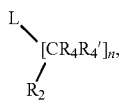

or
a reductive amination reaction between a compound of formula Ib,

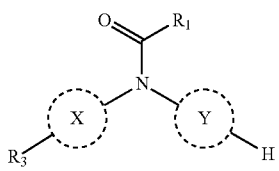

and a compound of formula VIIb,

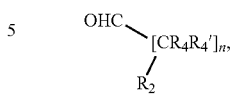

or
a coupling reaction between a compound of formula XIb

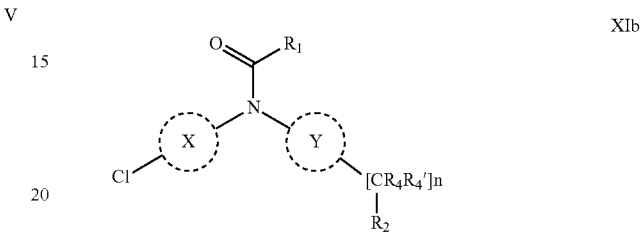

and a compound of formula IX

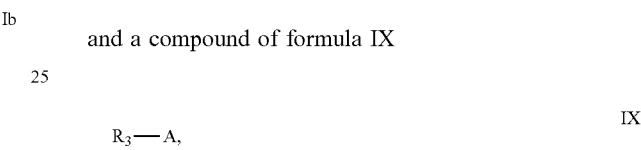

wherein L is a leaving group, including halogen, mesylate and tosylate, A is $(BOH)_2$ or a suitable leaving group, and X, Y, $R_1$, $R_2$, $R_3$, $R_4$, $R_{4'}$ and n are as defined in claim 1.

16. A pharmaceutical composition which comprises the compound according to claim 1, or a pharmaceutically acceptable salt thereof, and a pharmaceutically acceptable carrier, adjuvant or vehicle.

17. A method of treating pain in a subject in need thereof, comprising administration of an effective amount of the compound according to claim 1.

18. The method according to claim 17, wherein the pain is selected from the group consisting of medium to severe pain, visceral pain, chronic pain, cancer pain, migraine, inflammatory pain, acute pain or neuropathic pain, allodynia and hyperalgesia.

19. A compound which is N-(5-Methyl-1-phenyl-1H-pyrazol-3-yl)-N-(1-methylpiperidin-4-yl)thiophene-2-carboxamide, optionally as a stereoisomer, including enantiomers and diastereomers, a racemate or a mixture of at least two stereoisomers, including enantiomers and/or diastereomers, in any mixing ratio, or a corresponding salt thereof, or a corresponding solvate thereof.

* * * * *

UNITED STATES PATENT AND TRADEMARK OFFICE
CERTIFICATE OF CORRECTION

PATENT NO. : 10,577,360 B2
APPLICATION NO. : 16/090403
DATED : March 3, 2020
INVENTOR(S) : Pilar Goya et al.

It is certified that error appears in the above-identified patent and that said Letters Patent is hereby corrected as shown below:

In the Claims

Claim 9, Column 264, Line 5: "$NR_{12}R_{12}$" should read -- $NR_{12'}R_{12''}$ --.

Claim 14, Column 264, Line 59: "pyrazolel]" should read -- pyrazol-3-yl] --.
        Line 61: "pyrazolel]" should read -- pyrazol-3-yl] --.
        Line 67: "furanol" should read -- furan --.

Column 265, Line 6: "thiazole-" should read -- thiazole-5- --.

Column 268, Line 5: The entire line should read -- N-(1-Isobutylpiperidin-4-yl)-*N*-{1-[3-(5-methyl-1,3,4-oxadiazol-2-yl)phenyl]-1*H*-pyrazol-3-yl}-thiophene-2-carboxamide, --.
        Line 25: "(ethylsul-" should read -- methylsul- --.

Claim 15, Column 269, Line 31: "Vila" should read -- VIIa --.

Signed and Sealed this
Twenty-third Day of June, 2020

Andrei Iancu
*Director of the United States Patent and Trademark Office*